US007960348B2

(12) United States Patent
Asami et al.

(10) Patent No.: US 7,960,348 B2
(45) Date of Patent: Jun. 14, 2011

(54) METASTIN DERIVATIVES AND USE THEREOF

(75) Inventors: Taiji Asami, Ibaraki (JP); Naoki Nishizawa, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 508 days.

(21) Appl. No.: 12/158,251

(22) PCT Filed: Dec. 21, 2006

(86) PCT No.: PCT/JP2006/326176
§ 371 (c)(1),
(2), (4) Date: Jun. 19, 2008

(87) PCT Pub. No.: WO2007/072997
PCT Pub. Date: Jun. 28, 2007

(65) Prior Publication Data
US 2010/0331520 A1    Dec. 30, 2010

(30) Foreign Application Priority Data

Dec. 22, 2005  (JP) ................................ 2005-370388
Oct. 6, 2006  (JP) ................................ 2006-275843

(51) Int. Cl.
*A61K 38/08*    (2006.01)
*C07K 7/04*    (2006.01)
(52) U.S. Cl. ...................................... 514/19.8; 530/328
(58) Field of Classification Search .................. None
See application file for complete search history.

(56) References Cited

U.S. PATENT DOCUMENTS

| 6,699,965 | B1 | 3/2004 | Watanabe et al. |
| 7,725,869 | B1 | 5/2010 | Kitada et al. |
| 7,754,220 | B2 | 7/2010 | Ohtaki et al. |
| 2003/0096956 | A1 | 5/2003 | Suenaga et al. |
| 2004/0185525 | A1 | 9/2004 | Nishimura et al. |
| 2004/0236077 | A1 | 11/2004 | Matsumoto et al. |
| 2005/0176091 | A1 | 8/2005 | Yamada et al. |
| 2005/0240008 | A1 | 10/2005 | Ohtaki et al. |
| 2006/0241051 | A1 | 10/2006 | Kitada et al. |
| 2006/0287227 | A1 | 12/2006 | Ohtaki et al. |
| 2009/0093615 | A1 | 4/2009 | Asami et al. |
| 2009/0099334 | A1 | 4/2009 | Asami et al. |
| 2009/0105152 | A1 | 4/2009 | Asami et al. |

FOREIGN PATENT DOCUMENTS

| EP | 0162575 A | 11/1985 |
| EP | 0472220 A1 | 2/1992 |
| EP | 1126028 | 8/2001 |
| EP | 1577323 | 9/2005 |
| EP | 1604682 | 12/2005 |
| JP | 9-169735 | 6/1997 |
| JP | 2002-320496 | 11/2002 |
| JP | 2003-26601 | 1/2003 |
| JP | 2003300906 | 10/2003 |
| JP | 2004217651 | 8/2004 |
| RU | 2002102081 | 9/2003 |
| RU | 2005135739 A | 3/2006 |
| RU | 2306147 C2 | 9/2007 |
| RU | 2311920 C2 | 12/2007 |
| RU | 2006/145886 A | 6/2008 |
| RU | 2333221 C2 | 9/2008 |
| RU | 2344831 C2 | 1/2009 |
| RU | 2008125063 A | 12/2009 |
| WO | WO-97/14682 | 4/1997 |
| WO | WO-97/40071 | 10/1997 |
| WO | WO-98/39448 | 9/1998 |
| WO | WO-00/24890 | 5/2000 |
| WO | 0100228 | 1/2001 |
| WO | 019286 A1 | 2/2001 |
| WO | WO-01/44469 | 6/2001 |
| WO | 0172295 | 10/2001 |
| WO | WO-01/74377 | 10/2001 |
| WO | WO-01/75104 | 10/2001 |
| WO | WO-02/085399 | 10/2002 |
| WO | WO-02/092829 | 11/2002 |
| WO | WO-03/027149 | 4/2003 |
| WO | WO-03/060125 | 7/2003 |
| WO | WO-2004/038021 | 5/2004 |
| WO | WO-2004/060264 | 7/2004 |
| WO | WO-2004/063221 | 7/2004 |
| WO | 2004073730 A1 | 9/2004 |
| WO | WO-2004/080479 | 9/2004 |
| WO | WO-2004/087622 | 10/2004 |

(Continued)

OTHER PUBLICATIONS

Search Report with English translation form corresponding Georgian Patent Application No. AP 2006 010770 issued on Nov. 30, 2009.
analogs with maintenance of high GPR54 agonistic activity," Bioorganic & Medicinal Chemistry Letters (2006) 16:134-137.
Tomita et al., "Structure-activity relationship study on small peptidic GPR54 agonists," Bioorganic & Medicinal Chemistry (2006) 14:7595-7603.
Venkatesan et al., "Synthesis and Enzyme Inhibitory Activities of Novel Peptide Isosteres," Current Medicinal Chemistry (2002) 9:2242-2270.
Search Report of Corresponding Georgian Patent Application No. 2005 010294, Issued on Dec. 8, 2008.
Official Action of Corresponding Japanese Patent Application No. 2008-245073, Issued on Mar. 31, 2009.

(Continued)

*Primary Examiner* — Andrew D Kosar
(74) *Attorney, Agent, or Firm* — Edwards Angell Palmer & Dodge LLP; David G. Conlin, Esq.; Peter C. Lauro, Esq.

(57) ABSTRACT

The present invention provides stable metastin derivatives having excellent biological activities (a cancer metastasis suppressing activity, a cancer growth suppressing activity, a gonadotropic hormone secretion stimulating activity, sex hormone secretion stimulating activity, etc.). By substituting the constituent amino acids of metastin with specific amino acids in the metastin derivative of the present invention, blood stability, solubility, etc. are more improved, gelation tendency is reduced, pharmacokinetics are also improved, and an excellent cancer metastasis suppressing activity or a cancer growth suppressing activity is exhibited. Furthermore, the metastin derivative of the present invention has the effects of suppressing gonadotropic hormone secretion, suppressing sex hormone secretion, etc.

2 Claims, No Drawings

FOREIGN PATENT DOCUMENTS

| WO | 2004093894 A2 | 11/2004 |
|---|---|---|
| WO | WO-2004/096855 | 11/2004 |
| WO | WO-2004/101747 | 11/2004 |
| WO | WO-2004/106289 | 12/2004 |
| WO | 2005042744 A1 | 5/2005 |
| WO | WO-2005/095973 | 10/2005 |
| WO | WO-2006/001499 | 1/2006 |
| WO | WO-2007/072997 | 6/2007 |
| WO | WO-2007/084211 | 7/2007 |
| WO | 2008050897 | 5/2008 |

OTHER PUBLICATIONS

Niida et al., "Design and synthesis of downsized metastin (45-54)
Dutta et al., "Polypeptides. Part 15. Synthesis and Biological Acitvity of α-Aza-analogues of Luliberin modified in Positions 6 and 10," J. Chemical Society, Perkin Transactions (1979) vol. 1, No. 2, pp. 379-388.
Ohtaki et al., "Metastasis suppressor gene KiSS-1 encodes peptide ligand of a G-protein-coupled receptor," Nature (2001), vol. 411, pp. 613-617.
Kotani et al., "The Metastasis Suppressor Gene KiSS Encodes Kisspeptins, the Natural Ligands of the Orphan G Protein-coupled Receptor GPR54," J. of Biol. Chem. (2001), vol. 276, pp. 34631-34636.
Ringel et al., "Metastin Receptor is Overexpressed in Papillary Thyroid Cancer and Activates MAP Kinase in Thyroid Cancer Cells," J. of Clin. Endocrinology & Metabolism (2002), vol. 87, pp. 2399-2402.
Han et al., "Orphan G protein-coupled receptors MrgA1 and MrgC11 are distinctively activated by RF-amide-related peptides through the $G\alpha_{q/11}$ pathway," Proc. Natl. Acad. Sci. USA (2002), vol. 99, pp. 14740-14745.
Horikoshi et al., "Dramatic Elevation of Plasma Metastin Concentrations in Human Pregnancy: Metastin as a Novel Placenta-Derived Hormone in Humans," J. of Clin. Endocrinology & Metabolism (2003), vol. 88, pp. 914-919.
53rd, Nihon Yakugaku Kai, Kinki Shibu Sokai, Taikai Koen Yoshishu (2003) Yuki 2B-13-2 (Japanese language, translation enclosed).
Masui et al., "Metastin and its variant forms suppress migration of pancreatic cancer cells," BBRC (2004), vol. 315, pp. 85-92.
Terao et al., "Expression of KiSS-1, a metastasis suppressor gene in trophoblast giant cells of the rat placenta," Biochimica et Biophysica Acta (2004), vol. 1678, pp. 102-110.
Gottsch et al., "A Role for Kisspeptins in the Regulation of Gonadotropin Secretion in the Mouse," Endocrinology (2004), vol. 145, pp. 4073-4077.
S. Hinuma et al., "A prolactin-releasing peptide in the brain", Nature, vol. 393, pp. 272-276 (1998).
J.C. Meunier et al. "Molecular Neuroendocrinology: Working backwards to find answers", Nature, vol. 393, pp. 211-212 (1998).
H. Satake et al., "Characterization of a cDNA encoding a novel avian hypothalamic neuropepetide exerting an inhibitory effect on gonadotropin release", Biochem. J., vol. 354, pp. 379-385 (2001).
Muir et al., "AXOR12, a Novel Human G Protein-coupled Receptor, Activated by the Peptide KiSS-1," Journal of Biological Chemistry (2001), 276(31):28969-28975.
Supplementary European Search Report for corresponding European application EP04719659, dated May 26, 2009.
EPO Form 1507N, Jun. 10, 2010, European Search Report for EP 09075257.7.
Bruehlmeier M, et al, Nuclear Medicine and Biology, vol. 29, No. 3, Apr. 1, 2002, pp. 321-327.
Cudic M, et al, Peptides, Elsevier, vol. 23, Jan. 1, 2002, pp. 2071-2083.
Georgian Srch Rpt, Nov. 16, 2010, Srch Rpt for Georgian patent appln AP2007011265.

METASTIN DERIVATIVES AND USE THEREOF

This application is a US National Phase application of PCT/JP2006/326176 filed on Dec. 21, 2006 which claims priority to Japanese Patent Applications 2005-370388 filed on Dec. 21, 2005 and 2006-275843. Each of the applications is hereby incorporated by reference in its entirety.

That is, the present invention provides the following features, and so on.

(1) A metastin derivative represented by formula:

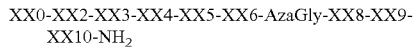

(wherein:

XX0 represents formyl, a $C_{1-20}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl, 6-aminocaproyl, 6-acetylaminocaproyl, 4-[bis-(2-pyridylmethyl)aminomethyl]benzoyl or 4-ureidobenzoyl;

XX2 represents Tyr, D-Tyr, D-Ala, D-Leu, D-Phe, D-Lys, D-Trp or a chemical bond;

XX3 represents:
i) an amino acid selected from Ala, Arg, Asn, Asp, Cys, Gln, Glu, Gly, His, Ile, Leu, Lys, Met, Phe, Ser, Thr, Trp, Tyr and Val wherein the α-amino group may optionally be methylated;
ii) a cyclic amino acid selected from Pro, Aze(2), Aze(3), Pic(2), Pic(3), Hyp, Thz, Abz(2), Abz(3), Pzc(2), Pro(4NH$_2$), Hyp(Bzl), cisHyp, Pro(4F) and Izc;
iii) an amino acid selected from D-Dap, D-Pya(4), DL-Ala(Pip), Orn, Aib and Tyr(PO$_3$H$_2$); or,
iv) a chemical bond;

XX4 represents Asn, 2-amino-3-ureidopropionic acid, N$^\beta$-formyl-β-diaminopropionic acid, N$^\beta$-acetyl-β-diaminopropionic acid, N$^\omega$-pentylasparagine, N$^\omega$-cyclopropylasparagine, N$^\omega$-benzylasparagine, 2,4-diaminobutanoic acid, 2,3-diaminopropionic acid, His, Gln, Gly, Arg, Cit, Nva, D-Asn or a chemical bond;

XX5 represents Ser, Thr, Val, NMeSer, Gly, Ala, Hyp, D-Ala, D-Thr, D-Pro or a chemical bond;

XX6 represents-Phe, Tyr, Trp, Tyr(Me), Thi, Nal(2), Cha, Pya(4), threo-Ser(3Phenyl), erythro-Ser(3Phenyl), or optionally substituted phenylalanine;

AzaGly represents azaglycine,

XX8 represents Leu, Nva, Val or Ala(cPr);

XX9 represents optionally substituted arginine, optionally substituted lysine or optionally substituted ornithine; and, XX10 represents 2-naphthylalanine, 2-thienylalanine, tyrosine, optionally substituted phenylalanine or optionally substituted tryptophan); or a salt thereof.

(2) A metastin derivative represented by formula:

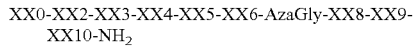

(wherein:

XX0 represents formyl, a $C_{1-20}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl, 6-aminocaproyl, 6-acetylaminocaproyl, 4-[bis-(2-pyridylmethyl)aminomethyl]benzoyl or 4-ureidobenzoyl;

XX2 represents Tyr, D-Tyr, D-Ala, D-Leu, D-Phe, D-Lys, D-Trp or a chemical bond;

XX3 represents D-Asp, D-Dap, D-Ser, D-Gln, D-His, D-Trp, D-Tyr, D-Pya(4), D-NMeAla, D-NMePhe, Aze(2), Aze(3), Pic(2), Pic(3), Hyp, Thz, Gly, Aib, Abz(2), Abz(3), Sar, Izc, Leu, Lys, Glu, Thr, Trp, Ser, Ala, NMeAla, β-alanine, DL-Ala(Pip), Pzc(2), Orn, His(3Me), Tyr(PO$_3$H$_2$), Pro (4NH$_2$), Hyp(Bzl), cisHyp, Pro(4F) or a chemical bond;

XX4 represents Asn, 2-amino-3-ureidopropionic acid, N$^\beta$-formyl-β-diaminopropionic acid, N$^\beta$-acetyl-β-diaminopropionic acid, N$^\omega$-pentylasparagine, N$^\omega$-cyclopropylasparagine, N$^\omega$-benzylasparagine, 2,4-diaminobutanoic acid, 2,3-diaminopropionic acid, His, Gln, Gly, Arg, Cit, Nva, D-Asn or a chemical bond;

XX5 represents Ser, Thr, Val, NMeSer, Gly, Ala, Hyp, D-Ala, D-Thr, D-Pro or a chemical bond;

XX6 represents Phe, Tyr, Trp, Tyr(Me), Thi, Nal(2), Cha, Pya(4), Phe(2F), Phe(3F), Phe(4F), Phe(4Cl), αMePhe, Phe (2Me), Phe(3Me), Phe(4Me), threo-Ser(3Phenyl), erythro-Ser(3Phenyl) or D-Phe;

AzaGly represents azaglycine;

XX8 represents Leu, Nva, Val or Ala(cPr);

XX9 represents Arg, Orn, Arg(Me), D-Arg or Arg (asymMe$_2$), and,

XX10 represents Phe, Trp, 2-naphthylalanine, 2-thienylalanine, tyrosine or 4-fluorophenylalanine); or a salt thereof.

(3) A metastin derivative represented by formula:

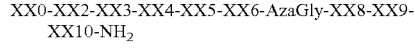

(wherein:

XX0 represents formyl, a $C_{1-20}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl or 6-aminocaproyl;

XX2 represents Tyr, D-Tyr, D-Ala, D-Leu, D-Phe, D-Lys, D-Trp or a chemical bond;

XX3 represents D-Asp, D-Dap, D-Ser, D-Gln, D-His, D-NMeAla, D-NMePhe, Aze(2), Pic(2), Pic(3), Hyp, Thz, NMeAla, Gly, Aib, Abz(2), Abz(3), Sar, Leu, Lys, Glu, β-alanine, Pzc(2), Orn, His(3Me), Tyr(PO$_3$H$_2$), Pro(4NH$_2$) or Hyp (Bzl);

XX4 represents Asn, 2-amino-3-ureidopropionic acid, N$^\beta$-formyl-β-diaminopropionic acid, N$^\beta$-acetyl-β-diaminopropionic acid, N$^\omega$-pentylasparagine, N$^\omega$-cyclopropylasparagine, N$^\omega$-benzylasparagine, 2,4-diaminobutanoic acid, His, Gln, Cit or D-Asn;

XX5 represents Ser, Thr, Val, NMeSer, Gly, Ala, Hyp, D-Ala or D-Thr;

XX6 represents Phe, Tyr, Trp, Tyr(Me), Thi, Nal(2), Cha, Pya(4), Phe(2F), Phe(3F), Phe(4F), Phe(4Cl) or D-Phe;

AzaGly represents azaglycine;

XX8 represents Leu, Nva or Val;

XX9 represents Arg, Orn, Arg(Me) or Arg(asymMe$_2$); and,

XX10 represents Phe, Trp, 2-naphthylalanine, 2-thienylalanine, tyrosine or 4-fluorophenylalanine); or a salt thereof.

(4) A metastin derivative represented by formula:

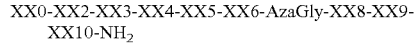

(wherein:

XX0 represents formyl, a $C_{1-12}$ alkanoyl, cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl or 6-aminocaproyl;

XX2 represents Tyr, D-Tyr, D-Ala, D-Leu, D-Phe, D-Lys, D-Trp or a chemical bond;

XX3 represents D-Asp, D-Dap, D-Ser, D-Gln, D-His, D-NMeAla, D-NMePhe, Aze(2), Pic(2), Pic(3), Hyp, Thz, NMeAla, Gly, Aib, Abz(2), Abz(3), Sar, Leu, Lys, Glu, β-alanine, Pzc(2), Orn, His(3Me), Tyr(PO$_3$H$_2$), Pro(4NH$_2$) or Hyp (Bzl);

XX4 represents Asn, 2-amino-3-ureidopropionic acid, N$^β$-formyldiaminopropionic acid, N$^β$-acetyldiaminopropionic acid, N$^ω$-pentylasparagine, N$^ω$-cyclopropylasparagine, N$^ω$-benzylasparagine or 2,4-diaminobutanoic acid;

XX5 represents Ser, Thr or Val;

XX6 represents Phe, Tyr, Trp, Tyr(Me), Thi, Nal(2), Cha, Pya(4), Phe(2F), Phe(3F), Phe(4F) or Phe(4Cl);

AzaGly represents azaglycine;

XX8 represents Leu, Nva or Val;

XX9 represents Arg, Orn, Arg(Me) or Arg(asymMe$_2$); and,

XX10 represents Phe, Trp, 2-naphthylalanine, 2-thienylalanine, tyrosine or 4-fluorophenylalanine); or a salt thereof.

(5) The metastin derivative or a salt thereof according to (1), wherein:

XX0 represents a C$_{1-12}$ alkanoyl, 6-aminocaproyl, 6-acetylaminocaproyl, glycoloyl, 4-[bis-(2-pyridylmethyl)aminomethyl]benzoyl, 4-ureidobenzoyl, 3-(4-hydroxyphenyl)propionyl or pyroglutamyl;

XX2 represents D-Tyr, Tyr or a chemical bond;

XX3 represents D-Asp, D-Dap, D-Ser, D-Gln, D-His, D-Trp, D-Tyr, D-Pya(4) D-NMeAla, D-NMePhe, Aze(2), Aze(3), Pic(2), Pic(3), Hyp, Thz, Gly, Aib, Abz(2), Sar, Izc, Leu, Lys, Glu, Thr, Trp, Ser, Ala, NMeAla, β-alanine, DL-Ala (Pip), Pzc(2), Orn, His(3Me), Tyr(PO$_3$H$_2$), Pro(4NH$_2$), Hyp (Bzl), cisHyp, Pro(4F) or a chemical bond;

XX4 represents Asn, 2-amino-3-ureidopropionic acid, N$^ω$-pentylasparagine, N$^ω$-cyclopropylasparagine, N$^ω$-benzylasparagine, 2,4-diaminobutanoic acid, 2,3-diaminopropionic acid, His, Gln, Gly, Arg, Cit, Nva, D-Asn or a chemical bond;

XX5 represents Thr, NMeSer, Gly, Ala, Hyp, D-Ala, D-Thr, D-Pro or a chemical bond;

XX6 represents Phe, Phe(2F), Phe(3F), Phe(4F), Phe(4Cl), αMePhe, Phe(2Me), Phe(3Me), Phe(4Me), threo-Ser(3Phenyl), erythro-Ser(3Phenyl) or D-Phe;

XX8 represents Leu or Ala(cPr);

XX9 represents Arg, Arg(Me) or D-Arg; and,

XX10 represents Trp.

(6) The metastin derivative according to (1), which is represented by formula:

XX0-XX2-XX3-XX4-XX5-XX6-AzaGly-XX8-XX9-XX10-NH$_2$ (wherein:
XX0 represents formyl, a C$_{1-6}$ alkanoyl or glycoloyl;
XX2 represents D-Tyr or a chemical bond;
XX3 represents Aze(2), Hyp, Gly, Aib, Leu, Lys, Glu, His(3Me), Tyr(PO$_3$H$_2$), Hyp(Bzl), cisHyp or Pro(4F);
XX4 represents Asn or 2-amino-3-ureidopropionic acid;
XX5 represents Ser, Thr or Ala;
XX6 represents Phe, Cha, Phe(2F), Phe(3F), Phe(4F), Phe(4Cl), Phe(2Me), Phe(3Me), Phe(4Me), threo-Ser(3Phenyl) or erythro-Ser(3Phenyl);
AzaGly represents azaglycine;
XX8 represents Leu or Ala(cPr);
XX9 represents Arg or Arg(Me); and,
XX10 represents Phe or Trp); or a salt thereof.

(7) Ac-D-Tyr-D-Trp-Asn-Thr-Phe-AzaGly-Leu-D-Arg-Trp-NH$_2$ (Compound No. 708),
Ac-Asn-Thr-Phe-AzaGly-Leu-Arg(Me)-Trp-NH$_2$ (SEQ ID NO: 23) (Compound No. 709),
Decanoyl-Asn-Thr-Phe-AzaGly-Leu-Arg(Me)-Trp-NH$_2$ (SEQ ID NO: 24) (Compound No. 710),
Acp-Asn-Thr-Phe-AzaGly-Leu-Arg(Me)-Trp-NH$_2$ (SEQ ID NO: 25) (Compound No. 712),
Ac-Acp-Asn-Thr-Phe-AzaGly-Leu-Arg(Me)-Trp-NH$_2$ (SEQ ID NO: 26) (Compound No. 713),
Ac-D-Tyr-D-Trp-Asp(NHPen)-Thr-Phe-AzaGly-Leu-Arg(Me)-Trp-NH$_2$ (Compound No. 714),
Ac-D-Tyr-D-Trp-Asp(NHcPr)-Thr-Phe-AzaGly-Leu-Arg(Me)-Trp-NH$_2$ (Compound No. 715),
Ac-D-Tyr-D-Trp-Asp(NHBzl)-Thr-Phe-AzaGly-Leu-Arg(Me)-Trp-NH$_2$ (Compound No. 716),
Ac-D-Tyr-D-Trp-Alb-Thr-Phe-AzaGly-Leu-Arg(Me)-Trp-NH$_2$ (Compound No. 717),
Ac-D-Tyr-D-Pya(4)-Alb-Thr-Phe-AzaGly-Leu-Arg(Me)-Trp-NH$_2$ (Compound No. 718),
Ac-D-Tyr-D-Trp-Asn-D-Pro-Phe-AzaGly-Leu-Arg(Me)-Trp-NH$_2$ (Compound No. 719),
Ac-D-Tyr-Aze(2)-Asn-Thr-Phe-AzaGly-Leu-Arg(Me)-Trp-NH$_2$ (Compound No. 720),
Ac-D-Tyr-Pic(2)-Asn-Thr-Phe-AzaGly-Leu-Arg(Me)-Trp-NH$_2$ (Compound No. 721),
Ac-D-Tyr-Pic(3)-Asn-Thr-Phe-AzaGly-Leu-Arg(Me)-Trp-NH$_2$ (Compound No. 722)
Ac-D-Tyr-Hyp-Asn-Thr-Phe-AzaGly-Leu-Arg(Me)-Trp-NH$_2$ (Compound No. 723),
Ac-D-Tyr-Thz-Asn-Thr-Phe-AzaGly-Leu-Arg(Me)-Trp-NH$_2$ (Compound No. 724),
Ac-D-Tyr-NMeAla-Asn-Thr-Phe-AzaGly-Leu-Arg(Me)-Trp-NH$_2$ (Compound No. 725).
Ac-D-Tyr-Gly-Asn-Thr-Phe-AzaGly-Leu-Arg(Me)-Trp-NH$_2$ (Compound No. 726)
Ac-D-Tyr-Aib-Asn-Thr-Phe-AzaGly-Leu-Arg(Me)-Trp-NH$_2$ (Compound No. 727),
Ac-D-Tyr-Abz(2)-Asn-Thr-Phe-AzaGly-Leu-Arg(Me)-Trp-NH$_2$ (Compound No. 728)
Ac-D-Tyr-Aze(3)-Asn-Thr-Phe-AzaGly-Leu-Arg(Me)-Trp-NH$_2$ (Compound No. 730)
Ac-D-Tyr-Sar-Asn-Thr-Phe-AzaGly-Leu-Arg(Me)-Trp-NH$_2$ (Compound No. 731)
Ac-D-Tyr-D-NMeAla-Asn-Thr-Phe-AzaGly-Leu-Arg(Me)-Trp-NH$_2$ (Compound No. 732),
Ac-D-Tyr-Izc-Asn-Thr-Phe-AzaGly-Leu-Arg(Me)-Trp-NH$_2$ (Compound No. 734),
Ac-D-Tyr-D-Asp-Asn-Thr-Phe-AzaGly-Leu-Arg(Me)-Trp-NH$_2$ (Compound No. 735),
Ac-D-Tyr-D-Dap-Asn-Thr-Phe-AzaGly-Leu-Arg(Me)-Trp-NH$_2$ (Compound No. 736),
Ac-D-Tyr-D-Ser-Asn-Thr-Phe-AzaGly-Leu-Arg(Me)-Trp-NH$_2$ (Compound No. 737),
Ac-D-Tyr-D-Gln-Asn-Thr-Phe-AzaGly-Leu-Arg(Me)-Trp-NH$_2$ (Compound No. 738),
Ac-D-Tyr-D-His-Asn-Thr-Phe-AzaGly-Leu-Arg(Me)-Trp-NH$_2$ (Compound No. 739),
Ac-D-Tyr-D-Trp-Dab-Thr-Phe-AzaGly-Leu-Arg(Me)-Trp-NH$_2$ (Compound No. 740),
Ac-D-Tyr-Ala-Asn-Thr-Phe-AzaGly-Leu-Arg(Me)-Trp-NH$_2$ (Compound No. 742),
Ac-D-Tyr-Leu-Asn-Thr-Phe-AzaGly-Leu-Arg(Me)-Trp-NH$_2$ (Compound No. 743),
Ac-D-Tyr-Ser-Asn-Thr-Phe-AzaGly-Leu-Arg(Me)-Trp-NH$_2$ (Compound No. 744), Ac-D-Tyr-Lys-Asn-Thr-Phe-AzaGly-Leu-Arg(Me)-Trp-NH$_2$ (Compound No. 745),
Ac-D-Tyr-Glu-Asn-Thr-Phe-AzaGly-Leu-Arg(Me)-Trp-NH$_2$ (Compound No. 746),
Ac-D-Tyr-β-Ala-Asn-Thr-Phe-AzaGly-Leu-Arg(Me)-Trp-NH$_2$ (Compound No. 747),
Ac-D-Tyr-D-Trp-Asn-Thr-Phe(4Cl)-AzaGly-Leu-Arg(Me)-Trp-NH$_2$ (Compound No. 748),
Ac-D-Tyr-D-Trp-Asn-Thr-Phe(2F)-AzaGly-Leu-Arg(Me)-Trp-NH$_2$ (Compound No. 749),
Ac-D-Tyr-D-Trp-Asn-Thr-Phe(3F)-AzaGly-Leu-Arg(Me)-Trp-NH$_2$ (Compound No. 750),
Ac-D-Tyr-Lys-Asn-Thr-Phe(2F)-AzaGly-Leu-Arg(Me)-Trp-NH$_2$ (Compound No. 754),
Ac-D-Tyr-Glu-Asn-Thr-Phe(2F)-AzaGly-Leu-Arg(Me)-Trp-NH$_2$ (Compound No. 755),
Ac-D-Tyr-Lys-Asn-Thr-Phe(3F)-AzaGly-Leu-Arg(Me)-Trp-NH$_2$ (Compound No. 756),
Ac-D-Tyr-Glu-Asn-Thr-Phe(3F)-AzaGly-Leu-Arg(Me)-Trp-NH$_2$ (Compound No. 757),
Ac-D-Tyr-Lys-Asn-Thr-Phe(4Cl)-AzaGly-Leu-Arg(Me)-Trp-NH$_2$ (Compound No. 758),
Ac-D-Tyr-Glu-Asn-Thr-Phe(4Cl)-AzaGly-Leu-Arg(Me)-Trp-NH$_2$ (Compound No. 759),
Ac-D-Tyr-Pzc(2)-Asn-Thr-Phe-AzaGly-Leu-Arg(Me)-Trp-NH$_2$ (Compound No. 760),
Ac-D-Tyr-Hyp-Asn-Thr-Phe(2F)-AzaGly-Leu-Arg(Me)-Trp-NH$_2$ (Compound No. 763),
Ac-D-Tyr-Trp-Asn-Thr-Phe(2F)-AzaGly-Leu-Arg(Me)-Trp-NH$_2$ (Compound No. 764),
Ac-D-Tyr-Hyp-Asn-Thr-Phe(3F)-AzaGly-Leu-Arg(Me)-Trp-NH$_2$ (Compound No. 765),
Ac-D-Tyr-Trp-Asn-Thr-Phe(3F)-AzaGly-Leu-Arg(Me)-Trp-NH$_2$ (Compound No. 766),
Ac-D-Tyr-Hyp-Asn-Thr-Phe(4Cl)-AzaGly-Leu-Arg(Me)-Trp-NH$_2$ (Compound No. 767),
Ac-D-Tyr-Trp-Asn-Thr-Phe(4Cl)-AzaGly-Leu-Arg(Me)-Trp-NH$_2$ (Compound No. 768),
Ac-D-Tyr-Gly-Asn-Thr-Phe(4Cl)-AzaGly-Leu-Arg(Me)-Trp-NH$_2$ (Compound No. 769),
Ac-D-Tyr-Aib-Asn-Thr-Phe(4Cl)-AzaGly-Leu-Arg(Me)-Trp-NH$_2$ (Compound No. 770),
Ac-D-Tyr-Orn-Asn-Thr-Phe-AzaGly-Leu-Arg(Me)-Trp-NH$_2$ (Compound No. 771),
Ac-D-Tyr-Thr-Asn-Thr-Phe-AzaGly-Leu-Arg(Me)-Trp-NH$_2$ (Compound No. 772),
Ac-D-Tyr-His(3Me)-Asn-Thr-Phe-AzaGly-Leu-Arg(Me)-Trp-NH$_2$ (Compound No. 773),
Ac-D-Tyr-DL-Ala(Pip)-Asn-Thr-Phe-AzaGly-Leu-Arg(Me)-Trp-NH$_2$ (Compound No. 774),
Ac-D-Tyr-Tyr(PO$_3$H$_2$)-Asn-Thr-Phe-AzaGly-Leu-Arg(Me)-Trp-NH$_2$ (Compound No. 775),
Glycoloyl-D-Tyr-Hyp-Asn-Thr-Phe-AzaGly-Leu-Arg(Me)-Trp-NH$_2$ (Compound No. 776)
Ac-D-Tyr-Asn-Thr-Phe-AzaGly-Leu-Arg(Me)-Trp-NH$_2$ (Compound No. 777),
Ac-D-Tyr-Pro(4NH$_2$)-Asn-Thr-Phe-AzaGly-Leu-Arg(Me)-Trp-NH$_2$ (Compound No. 780),
Ac-D-Tyr-Hyp(Bzl)-Asn-Thr-Phe-AzaGly-Leu-Arg(Me)-Trp-NH$_2$ (Compound No. 781),
Ac-D-Tyr-D-NMePhe-Asn-Thr-Phe-AzaGly-Leu-Arg(Me)-Trp-NH$_2$ (Compound No. 782),
Ac-D-Tyr-Gly-Asn-Thr-Phe(2F)-AzaGly-Leu-Arg(Me)-Trp-NH$_2$ (Compound No. 783),
Ac-D-Tyr-Aib-Asn-Thr-Phe(2F)-AzaGly-Leu-Arg(Me)-Trp-NH$_2$ (Compound No. 784),
Ac-D-Tyr-Gly-Asn-Thr-Phe(3F)-AzaGly-Leu-Arg(Me)-Trp-NH$_2$ (Compound No. 785),
Ac-D-Tyr-Aib-Asn-Thr-Phe(3F)-AzaGly-Leu-Arg(Me)-Trp-NH$_2$ (Compound No. 786),
Ac-D-Tyr-Hyp-Asn-Thr-Phe(4F)-AzaGly-Leu-Arg(Me)-Trp-NH$_2$ (Compound No. 787),
Ac-D-Tyr-Glu-Asn-Thr-Phe(4F)-AzaGly-Leu-Arg(Me)-Trp-NH$_2$ (Compound No. 788),
Ac-D-Tyr-Lys-Asn-Thr-Phe(4F)-AzaGly-Leu-Arg(Me)-Trp-NH$_2$ (Compound No. 789),
Ac-D-Tyr-Gly-Asn-Thr-Phe(4F)-AzaGly-Leu-Arg(Me)-Trp-NH$_2$ (Compound No. 790),
Ac-D-Tyr-Aib-Asn-Thr-Phe(4F)-AzaGly-Leu-Arg(Me)-Trp-NH$_2$ (Compound No. 791),
Ac-D-Tyr-Hyp-Asn-Thr-D-Phe-AzaGly-Leu-Arg(Me)-Trp-NH$_2$ (Compound No. 794),
Ac-D-Tyr-Hyp-Asn-Thr-Phe-AzaGly-Leu-Arg-Trp-NH$_2$ (Compound No. 797),
Ac-D-Tyr-Hyp-Alb-Thr-Phe-AzaGly-Leu-Arg(Me)-Trp-NH$_2$ (Compound No. 800),
4-[Bis-(2-Pyridylmethyl)aminomethyl]benzoyl-Phe-AzaGly-Leu-Arg(Me)-Trp-NH$_2$ (SEQ ID NO: 27) (Compound No. 801),
Ac-D-Tyr-Hyp-Asn-NMeSer-Phe-AzaGly-Leu-Arg(Me)-Trp-NH$_2$ (Compound No. 809),
Ac-D-Tyr-Hyp-Asn-Hyp-Phe-AzaGly-Leu-Arg(Me)-Trp-NH$_2$ (Compound No. 810),
Ac-D-Tyr-Hyp-Asn-Gly-Phe-AzaGly-Leu-Arg(Me)-Trp-NH$_2$ (Compound No. 813),
Ac-D-Tyr-Hyp-Asn-Ala-Phe-AzaGly-Leu-Arg(Me)-Trp-NH$_2$ (Compound No. 814),
Ac-D-Tyr-Hyp-Asn-D-Ala-Phe-AzaGly-Leu-Arg(Me)-Trp-NH$_2$ (Compound No. 815),
Ac-D-Tyr-Hyp-His-Thr-Phe-AzaGly-Leu-Arg(Me)-Trp-NH$_2$ (Compound No. 816),
Ac-D-Tyr-Hyp-Gln-Thr-Phe-AzaGly-Leu-Arg(Me)-Trp-NH$_2$ (Compound No. 843),
Ac-D-Tyr-Hyp-D-Asn-Thr-Phe-AzaGly-Leu-Arg(Me)-Trp-NH$_2$ (Compound No. 844),
Ac-D-Tyr-Hyp-Cit-Thr-Phe-AzaGly-Leu-Arg(Me)-Trp-NH$_2$ (Compound No. 845),
Ac-D-Tyr-Hyp-Asn-D-Thr-Phe-AzaGly-Leu-Arg(Me)-Trp-NH$_2$ (Compound No. 846),
Ac-D-Tyr-Hyp-Asn-Thr-Phe-AzaGly-Ala(cPr)-Arg(Me)-Trp-NH$_2$ (Compound No. 856),
4-Ureidobenzoyl-Phe-AzaGly-Leu-Arg(Me)-Trp-NH$_2$ (SEQ ID NO: 28) (Compound No. 860),
Ac-D-Tyr-Hyp-Arg-Thr-Phe-AzaGly-Leu-Arg(Me)-Trp-NH$_2$ (Compound No. 861),
Ac-D-Tyr-Hyp-Gly-Thr-Phe-AzaGly-Leu-Arg(Me)-Trp-NH$_2$ (Compound No. 862),
Ac-D-Tyr-Hyp-Dap-Thr-Phe-AzaGly-Leu-Arg(Me)-Trp-NH$_2$ (Compound No. 863),
Ac-D-Tyr-Hyp-Dab-Thr-Phe-AzaGly-Leu-Arg(Me)-Trp-NH$_2$ (Compound No. 864),
Ac-D-Tyr-Hyp-Asn-Thr-αMePhe-AzaGly-Leu-Arg(Me)-Trp-NH$_2$ (Compound No. 868),
Ac-D-Tyr-Hyp-Asn-Thr-Phe(2Me)-AzaGly-Leu-Arg(Me)-Trp-NH$_2$ (Compound No. 870),
Ac-D-Tyr-Hyp-Asn-Thr-Phe(3Me)-AzaGly-Leu-Arg(Me)-Trp-NH$_2$ (Compound No. 872),
Ac-D-Tyr-Hyp-Asn-Thr-Phe(4Me)-AzaGly-Leu-Arg(Me)-Trp-NH$_2$ (Compound No. 874),
Ac-D-Tyr-Hyp-Asn-Thr-threo-Ser(3Phenyl)-AzaGly-Leu-Arg(Me)-Trp-NH$_2$ (Compound No. 877),
Ac-D-Tyr-Hyp-Asn-Thr-erythro-Ser(3Phenyl)-AzaGly-Leu-Arg(Me)-Trp-NH$_2$ (Compound No. 882), Ac-D-Tyr-Hyp-Nva-Thr-Phe-AzaGly-Leu-Arg(Me)-Trp-NH$_2$ (Compound No. 886),
Ac-Hyp-Asn-Thr-Phe-AzaGly-Leu-Arg(Me)-Trp-NH$_2$ (SEQ ID NO: 29) (Compound No. 887),
3-(p-Hydroxyphenyl)propionyl-Hyp-Asn-Thr-Phe-AzaGly-Leu-Arg(Me)-Trp-NH$_2$ (SEQ ID NO: 30) (Compound No. 888),
pGlu-Asn-Thr-Phe-AzaGly-Leu-Arg(Me)-Trp-NH$_2$ (SEQ ID NO: 31) (Compound No. 889),
Ac-D-Tyr-cisHyp-Asn-Thr-Phe-AzaGly-Leu-Arg(Me)-Trp-NH$_2$ (Compound No. 896),
Ac-D-Tyr-Pro(4F)-Asn-Thr-Phe-AzaGly-Leu-Arg(Me)-Trp-NH$_2$ (Compound No. 897),
Ac-Tyr-Hyp-Asn-Thr-Phe-AzaGly-Leu-Arg(Me)-Trp-NH$_2$ (SEQ ID NO: 32) (Compound No. 899),
or a salt thereof.

(8) Ac-D-Tyr-D-Trp-Asp(NHPen)-Thr-Phe-AzaGly-Leu-Arg(Me)-Trp-NH$_2$ (Compound No. 714),
Ac-D-Tyr-D-Trp-Asp(NHcPr)-Thr-Phe-AzaGly-Leu-Arg(Me)-Trp-NH$_2$ (Compound No. 715),
Ac-D-Tyr-D-Trp-Asp(NHBzl)-Thr-Phe-AzaGly-Leu-Arg(Me)-Trp-NH$_2$ (Compound No. 716),
Ac-D-Tyr-D-Trp-Alb-Thr-Phe-AzaGly-Leu-Arg(Me)-Trp-NH$_2$ (Compound No. 717),
Ac-D-Tyr-D-Pya(4)-Alb-Thr-Phe-AzaGly-Leu-Arg(Me)-Trp-NH$_2$ (Compound No. 718),
Ac-D-Tyr-Aze(2)-Asn-Thr-Phe-AzaGly-Leu-Arg(Me)-Trp-NH$_2$ (Compound No. 720),
Ac-D-Tyr-Pic(2)-Asn-Thr-Phe-AzaGly-Leu-Arg(Me)-Trp-NH$_2$ (Compound No. 721),
Ac-D-Tyr-Hyp-Asn-Thr-Phe-AzaGly-Leu-Arg(Me)-Trp-NH$_2$ (Compound No. 723),
Ac-D-Tyr-Thz-Asn-Thr-Phe-AzaGly-Leu-Arg(Me)-Trp-NH$_2$ (Compound No. 724),
Ac-D-Tyr-Gly-Asn-Thr-Phe-AzaGly-Leu-Arg(Me)-Trp-NH$_2$ (Compound No. 726)
Ac-D-Tyr-Aib-Asn-Thr-Phe-AzaGly-Leu-Arg(Me)-Trp-NH$_2$ (Compound No. 727),
Ac-D-Tyr-D-NMeAla-Asn-Thr-Phe-AzaGly-Leu-Arg(Me)-Trp-NH$_2$ (Compound No. 732),
Ac-D-Tyr-D-Gln-Asn-Thr-Phe-AzaGly-Leu-Arg(Me)-Trp-NH$_2$ (Compound No. 738),
Ac-D-Tyr-D-His-Asn-Thr-Phe-AzaGly-Leu-Arg(Me)-Trp-NH$_2$ (Compound No. 739),
Ac-D-Tyr-D-Trp-Dab-Thr-Phe-AzaGly-Leu-Arg(Me)-Trp-NH$_2$ (Compound No. 740),
Ac-D-Tyr-Ala-Asn-Thr-Phe-AzaGly-Leu-Arg(Me)-Trp-NH$_2$ (Compound No. 742),
Ac-D-Tyr-Leu-Asn-Thr-Phe-AzaGly-Leu-Arg(Me)-Trp-NH$_2$ (Compound No. 743),
Ac-D-Tyr-Ser-Asn-Thr-Phe-AzaGly-Leu-Arg(Me)-Trp-NH$_2$ (Compound No. 744),
Ac-D-Tyr-Lys-Asn-Thr-Phe-AzaGly-Leu-Arg(Me)-Trp-NH$_2$ (Compound No. 745),
Ac-D-Tyr-Glu-Asn-Thr-Phe-AzaGly-Leu-Arg(Me)-Trp-NH$_2$ (Compound No. 746),
Ac-D-Tyr-D-Trp-Asn-Thr-Phe(4Cl)-AzaGly-Leu-Arg(Me)-Trp-NH$_2$ (Compound No. 748),
Ac-D-Tyr-D-Trp-Asn-Thr-Phe(2F)-AzaGly-Leu-Arg(Me)-Trp-NH$_2$ (Compound No. 749),
Ac-D-Tyr-D-Trp-Asn-Thr-Phe(3F)-AzaGly-Leu-Arg(Me)-Trp-NH$_2$ (Compound No. 750),
Ac-D-Tyr-Lys-Asn-Thr-Phe(2F)-AzaGly-Leu-Arg(Me)-Trp-NH$_2$ (Compound No. 754),
Ac-D-Tyr-Glu-Asn-Thr-Phe(2F)-AzaGly-Leu-Arg(Me)-Trp-NH$_2$ (Compound No. 755),
Ac-D-Tyr-Lys-Asn-Thr-Phe(3F)-AzaGly-Leu-Arg(Me)-Trp-NH$_2$ (Compound No. 756),
Ac-D-Tyr-Glu-Asn-Thr-Phe(3F)-AzaGly-Leu-Arg(Me)-Trp-NH$_2$ (Compound No. 757),
Ac-D-Tyr-Lys-Asn-Thr-Phe(4Cl)-AzaGly-Leu-Arg(Me)-Trp-NH$_2$ (Compound No. 758),
Ac-D-Tyr-Glu-Asn-Thr-Phe(4Cl)-AzaGly-Leu-Arg(Me)-Trp-NH$_2$ (Compound No. 759),
Ac-D-Tyr-Pzc(2)-Asn-Thr-Phe-AzaGly-Leu-Arg(Me)-Trp-NH$_2$ (Compound No. 760),
Ac-D-Tyr-Hyp-Asn-Thr-Phe(2F)-AzaGly-Leu-Arg(Me)-Trp-NH$_2$ (Compound No. 763),
Ac-D-Tyr-Trp-Asn-Thr-Phe(2F)-AzaGly-Leu-Arg(Me)-Trp-NH$_2$ (Compound No. 764),
Ac-D-Tyr-Hyp-Asn-Thr-Phe(3F)-AzaGly-Leu-Arg(Me)-Trp-NH$_2$ (Compound No. 765),
Ac-D-Tyr-Trp-Asn-Thr-Phe(3F)-AzaGly-Leu-Arg(Me)-Trp-NH$_2$ (Compound No. 766),
Ac-D-Tyr-Hyp-Asn-Thr-Phe(4Cl)-AzaGly-Leu-Arg(Me)-Trp-NH$_2$ (Compound No. 767),
Ac-D-Tyr-Trp-Asn-Thr-Phe(4Cl)-AzaGly-Leu-Arg(Me)-Trp-NH$_2$ (Compound No. 768),
Ac-D-Tyr-Gly-Asn-Thr-Phe(4Cl)-AzaGly-Leu-Arg(Me)-Trp-NH$_2$ (Compound No. 769),
Ac-D-Tyr-Aib-Asn-Thr-Phe(4Cl)-AzaGly-Leu-Arg(Me)-Trp-NH$_2$ (Compound No. 770),
Ac-D-Tyr-Orn-Asn-Thr-Phe-AzaGly-Leu-Arg(Me)-Trp-NH$_2$ (Compound No. 771),
Ac-D-Tyr-Thr-Asn-Thr-Phe-AzaGly-Leu-Arg(Me)-Trp-NH$_2$ (Compound No. 772),
Ac-D-Tyr-His(3Me)-Asn-Thr-Phe-AzaGly-Leu-Arg(Me)-Trp-NH$_2$ (Compound No. 773),
Ac-D-Tyr-Tyr(PO$_3$H$_2$)-Asn-Thr-Phe-AzaGly-Leu-Arg(Me)-Trp-NH$_2$ (Compound No. 775),
Glycoloyl-D-Tyr-Hyp-Asn-Thr-Phe-AzaGly-Leu-Arg(Me)-Trp-NH$_2$ (Compound No. 776),
Ac-D-Tyr-Pro(4NH$_2$)-Asn-Thr-Phe-AzaGly-Leu-Arg(Me)-Trp-NH$_2$ (Compound No. 780),
Ac-D-Tyr-Hyp(Bzl)-Asn-Thr-Phe-AzaGly-Leu-Arg(Me)-Trp-NH$_2$ (Compound No. 781),
Ac-D-Tyr-D-NMePhe-Asn-Thr-Phe-AzaGly-Leu-Arg(Me)-Trp-NH$_2$ (Compound No. 782),
Ac-D-Tyr-Gly-Asn-Thr-Phe(2F)-AzaGly-Leu-Arg(Me)-Trp-NH$_2$ (Compound No. 783),
Ac-D-Tyr-Aib-Asn-Thr-Phe(2F)-AzaGly-Leu-Arg(Me)-Trp-NH$_2$ (Compound No. 784),
Ac-D-Tyr-Gly-Asn-Thr-Phe(3F)-AzaGly-Leu-Arg(Me)-Trp-NH$_2$ (Compound No. 785),
Ac-D-Tyr-Aib-Asn-Thr-Phe(3F)-AzaGly-Leu-Arg(Me)-Trp-NH$_2$ (Compound No. 786),
Ac-D-Tyr-Hyp-Asn-Thr-Phe(4F)-AzaGly-Leu-Arg(Me)-Trp-NH$_2$ (Compound No. 787),
Ac-D-Tyr-Glu-Asn-Thr-Phe(4F)-AzaGly-Leu-Arg(Me)-Trp-NH$_2$ (Compound No. 788),
Ac-D-Tyr-Lys-Asn-Thr-Phe(4F)-AzaGly-Leu-Arg(Me)-Trp-NH$_2$ (Compound No. 789),
Ac-D-Tyr-Gly-Asn-Thr-Phe(4F)-AzaGly-Leu-Arg(Me)-Trp-NH$_2$ (Compound No. 790),
Ac-D-Tyr-Aib-Asn-Thr-Phe(4F)-AzaGly-Leu-Arg(Me)-Trp-NH$_2$ (Compound No. 791),
Ac-D-Tyr-Hyp-Asn-Thr-D-Phe-AzaGly-Leu-Arg(Me)-Trp-NH$_2$ (Compound No. 794),
Ac-D-Tyr-Hyp-Asn-Thr-Phe-AzaGly-Leu-Arg-Trp-NH$_2$ (Compound No. 797),
Ac-D-Tyr-Hyp-Alb-Thr-Phe-AzaGly-Leu-Arg(Me)-Trp-NH$_2$ (Compound No. 800), 4-[Bis-(2-Pyridylmethyl)aminomethyl]benzoyl-Phe-Aza-Gly-Leu-Arg(Me)-Trp-NH$_2$ (SEQ ID NO: 27) (Compound No. 801),
Ac-D-Tyr-Hyp-Asn-NMeSer-Phe-AzaGly-Leu-Arg(Me)-Trp-NH$_2$ (Compound No. 809),
Ac-D-Tyr-Hyp-Asn-Hyp-Phe-AzaGly-Leu-Arg(Me)-Trp-NH$_2$ (Compound No. 810),
Ac-D-Tyr-Hyp-Asn-Gly-Phe-AzaGly-Leu-Arg(Me)-Trp-NH$_2$ (Compound No. 813),
Ac-D-Tyr-Hyp-Asn-Ala-Phe-AzaGly-Leu-Arg(Me)-Trp-NH$_2$ (Compound No. 814),
Ac-D-Tyr-Hyp-Asn-D-Ala-Phe-AzaGly-Leu-Arg(Me)-Trp-NH$_2$ (Compound No. 815),
Ac-D-Tyr-Hyp-His-Thr-Phe-AzaGly-Leu-Arg(Me)-Trp-NH$_2$ (Compound No. 816),
Ac-D-Tyr-Hyp-Gln-Thr-Phe-AzaGly-Leu-Arg(Me)-Trp-NH$_2$ (Compound No. 843),
Ac-D-Tyr-Hyp-D-Asn-Thr-Phe-AzaGly-Leu-Arg(Me)-Trp-NH$_2$ (Compound No. 844),
Ac-D-Tyr-Hyp-Cit-Thr-Phe-AzaGly-Leu-Arg(Me)-Trp-NH$_2$ (Compound No. 845),
Ac-D-Tyr-Hyp-Asn-D-Thr-Phe-AzaGly-Leu-Arg(Me)-Trp-NH$_2$ (Compound No. 846),
Ac-D-Tyr-Hyp-Asn-Thr-Phe-AzaGly-Ala(cPr)-Arg(Me)-Trp-NH$_2$ (Compound No. 856),
4-Ureidobenzoyl-Phe-AzaGly-Leu-Arg(Me)-Trp-NH$_2$ (SEQ ID NO: 28) (Compound No. 860),
Ac-D-Tyr-Hyp-Arg-Thr-Phe-AzaGly-Leu-Arg(Me)-Trp-NH$_2$ (Compound No. 861),
Ac-D-Tyr-Hyp-Gly-Thr-Phe-AzaGly-Leu-Arg(Me)-Trp-NH$_2$ (Compound No. 862),
Ac-D-Tyr-Hyp-Dap-Thr-Phe-AzaGly-Leu-Arg(Me)-Trp-NH$_2$ (Compound No. 863),
Ac-D-Tyr-Hyp-Dab-Thr-Phe-AzaGly-Leu-Arg(Me)-Trp-NH$_2$ (Compound No. 864),
Ac-D-Tyr-Hyp-Asn-Thr-αMePhe-AzaGly-Leu-Arg(Me)-Trp-NH$_2$ (Compound No. 868),
Ac-D-Tyr-Hyp-Asn-Thr-Phe(2Me)-AzaGly-Leu-Arg(Me)-Trp-NH$_2$ (Compound No. 870),
Ac-D-Tyr-Hyp-Asn-Thr-Phe(3Me)-AzaGly-Leu-Arg(Me)-Trp-NH$_2$ (Compound No. 872),
Ac-D-Tyr-Hyp-Asn-Thr-Phe(4Me)-AzaGly-Leu-Arg(Me)-Trp-NH$_2$ (Compound No. 874),
Ac-D-Tyr-Hyp-Asn-Thr-threo-Ser(3 Phenyl)-AzaGly-Leu-Arg(Me)-Trp-NH$_2$ (Compound No. 877),
Ac-D-Tyr-Hyp-Asn-Thr-erythro-Ser(3Phenyl)-AzaGly-Leu-Arg(Me)-Trp-NH$_2$ (Compound No. 882),
Ac-D-Tyr-Hyp-Nva-Thr-Phe-AzaGly-Leu-Arg(Me)-Trp-NH$_2$ (Compound No. 886),
3-(p-Hydroxyphenyl)propionyl-Hyp-Asn-Thr-Phe-AzaGly-Leu-Arg(Me)-Trp-NH$_2$ (SEQ ID NO: 30) (Compound No. 888),
Ac-D-Tyr-cisHyp-Asn-Thr-Phe-AzaGly-Leu-Arg(Me)-Trp-NH$_2$ (Compound No. 896),
Ac-D-Tyr-Pro(4F)-Asn-Thr-Phe-AzaGly-Leu-Arg(Me)-Trp-NH$_2$ (Compound No. 897),
Ac-Tyr-Hyp-Asn-Thr-Phe-AzaGly-Leu-Arg(Me)-Trp-NH$_2$ (Compound No. 899),
or a salt thereof.
(9) A prodrug of the metastin derivative according to (1), or a salt thereof.
(10) A prodrug of the metastin derivative according to (7), or a salt thereof.
(11) A medicament comprising the metastin derivative according to (1) through (8), a salt thereof or a prodrug thereof.

(12) The medicament according to (11), which is an agent for suppressing cancer metastasis or an agent for suppressing cancer growth.
(13) The medicament according to (11), which is an agent for preventing or treating cancer.
(14) The medicament according to (11), which is an agent for controlling placental function.
(15) The medicament according to (11), which is an agent for preventing or treating choriocarcinoma, hydatid mole, invasive mole, miscarriage, fetal hypoplasia, abnormal glucose metabolism, abnormal lipid metabolism or induction of delivery.
(16) The medicament according to (11), which is an agent for improving gonadal function.
(17) The medicament according to (11), which is an agent for preventing or treating hormone-dependent cancer, infertility, endometriosis, early puberty or myoma of the uterus.
(18) The medicament according to (11), which is an agent for inducing or stimulating ovulation.
(19) The medicament according to (11), which is a gonadotropic hormone secretagogue agent or a sex hormone secretagogue agent.
(20) The medicament according to (11), which is an agent for preventing or treating Alzheimer's disease, Autism or moderate cognitive impairment.
(21) A method for suppressing cancer metastasis or cancer growth, which comprises administering to a mammal an effective dose of the metastin derivative according to (1) through (8), a salt thereof, or a prodrug thereof.
(22) A method of preventing or treating cancer, which comprises administering to a mammal an effective dose of the metastin derivative according to (1) through (8) or a salt thereof, or a prodrug thereof.
(23) A method for controlling placental function, which comprises administering to a mammal an effective dose of the metastin derivative according to (1) through (8) or a salt thereof, or a prodrug thereof.
(24) A method for preventing or treating choriocarcinoma, hydatid mole, invasive mole, miscarriage, fetal hypoplasia, abnormal glucose metabolism, abnormal lipid metabolism or induction of delivery, which comprises administering to a mammal an effective dose of the metastin derivative according to (1) through (8) or a salt thereof, or a prodrug thereof.
(25) A method for improving gonadal function, which comprises administering to a mammal an effective dose of the metastin derivative according to (1) through (8) or a salt thereof, or a prodrug thereof.
(26) A method for preventing or treating hormone-dependent cancer, infertility, endometriosis, early puberty or myoma of the uterus, which comprises administering to a mammal an effective dose of the metastin derivative according to (1) through (8) or a salt thereof, or a prodrug thereof.
(27) A method for inducing or stimulating ovulation, which comprises administering to a mammal an effective dose of the metastin derivative according to (1) through (8) or a salt thereof, or a prodrug thereof.
(28) A method for promoting gonadotropic hormone secretion or promoting sex hormone secretion, which comprises administering to a mammal an effective dose of the metastin derivative according to (1) or a salt thereof, or a prodrug thereof.
(29) A method for preventing or treating Alzheimer's disease, Autism or moderate cognitive impairment, which comprises administering to a mammal an effective dose of the metastin derivative according to (1) through (8) or a salt thereof, or a prodrug thereof.

(30) The medicament according to (11), which is a down-regulating agent for gonadotropic hormone or sex hormone.

(31) The medicament according to (11), which is a down-regulating agent for human OT7T175 (metastin receptor) protein consisting of the amino acid sequence represented by SEQ ID NO: 9.

(32) The agent according to (30) or (31), which is an agent for preventing or treating hormone-dependent cancer.

(33) A method for down-regulating gonadotropic hormone or sex hormone, which comprises administering to a mammal an effective dose of the metastin derivative according to (1) through (8) or a salt thereof, or a prodrug thereof.

(34) A method for down-regulating human OT7T175 (metastin receptor) protein consisting of the amino acid sequence represented by SEQ ID NO: 9, which comprises administering to a mammal an effective dose of the metastin derivative according to (1) through (8) or a salt thereof, or a prodrug thereof.

(35) A method for preventing or treating hormone-dependent cancer, which comprises administering to a mammal an effective dose of the metastin derivative according to (1) through (8) or a salt thereof, or a prodrug thereof.

The present invention further provides the following features, and so on.

(36) Use of the metastin derivative according to (1) through (8) or a salt thereof, or a prodrug thereof to manufacture an agent for suppressing cancer metastasis or an agent for suppressing cancer growth.

(37) Use of the metastin derivative according to (1) through (8) or a salt thereof, or a prodrug thereof to manufacture an agent for preventing or treating cancer.

(38) Use of the metastin derivative according to (1) through (8) or a salt thereof, or a prodrug thereof to manufacture an agent for controlling placental function.

(39) Use of the metastin derivative according to (1) through (8) or a salt thereof, or a prodrug thereof to manufacture an agent for preventing or treating choriocarcinoma, hydatid mole, invasive mole, miscarriage, fetal hypoplasia, abnormal glucose metabolism, abnormal lipid metabolism or induction of delivery.

(40) Use of the metastin derivative according to (1) through (8) or a salt thereof, or a prodrug thereof to manufacture an agent for improving gonadal function.

(41) Use of the metastin derivative according to (1) through (8) or a salt thereof, or a prodrug thereof to manufacture an agent for preventing or treating hormone-dependent cancer, infertility, endometriosis, early puberty or myoma of the uterus.

(42) Use of the metastin derivative according to (1) through (8), or a salt thereof, or a prodrug thereof to manufacture an agent for inducing or stimulating ovulation.

(43) Use of the metastin derivative according to (1) through (8), or a salt thereof, or a prodrug thereof to manufacture a gonadotropic hormone secretagogue agent or a sex hormone secretagogue agent.

(44) Use of the metastin derivative according to (1) through (8), or a salt thereof, or a prodrug thereof to manufacture an agent for preventing or treating Alzheimer's disease, Autism or moderate cognitive impairment.

In the present invention, Tyr-Asn-Trp-Asn-Ser-Phe-Gly-Leu-Arg-Phe-NH$_2$ (SEQ ID NO: 16) is referred to as metastin 10 (Metastin 10), i.e., MS10.

Herein, the N-terminal Tyr and the C-terminal Phe in MS10 are counted as the 1- and 10-positions, respectively.

(SEQ ID NO: 16)
Tyr-Asn-Trp-Asn-Ser-Phe-Gly-Leu-Arg-Phe-NH$_2$
 1   2   3   4   5   6   7   8   9  10

For example, [Hph10]MS10 means a peptide wherein Phe at the C terminus (10-position) of MS10 is substituted with Hph.

For example, des(1)-MS10 means a peptide wherein Tyr at the N terminus (1-position) of MS10 is deleted.

For example, des(1-3)-Fmoc-MS10 means a peptide wherein Tyr-Asn-Trp at the N terminus (1 to 3-positions) is deleted and the amino group of Asn at the 4-position is modified with Fmoc.

For example, des(1)-Ac-[D-Tyr2,D-Trp3,Thr5,AzaGly7,D-Arg9,Trp10] MS10 of Compound No. 708 means a peptide wherein the amino end of MS10 is modified with Ac, Tyr at the N terminus (1-position) is deleted, Asn at the 2-position is substituted with D-Tyr, Trp at the 3-position is substituted with D-Trp, Ser at the 5-position is substituted with Thr, Gly at the 7-position is substituted with AzaGly, Arg at the 9-position is substituted with D-Arg and Phe at the 10-position is substituted with Trp, i.e., Ac-D-Tyr-D-Trp-Asn-Thr-Phe-AzaGly-Leu-D-Arg-Trp-NH$_2$.

In the formulae described above, XX0 represents a modifying group at the amino end; and each of XX2, XX3, XX4, XX5, XX6, XX8, XX9 and XX10 represents 2-, 3-, 4-, 5-, 6-, 8-, 9- and 10-positions of MS10 described above, respectively.

Each chemical bond "-" between XX0, XX2, XX3, XX4, XX5, XX6, AzaGly, XX8, XX9 and XX10 and NH$_2$ in the formula: "XX0-XX2-XX3-XX4-XX5-XX6-AzaGly-XX8-XX9-XX10-NH$_2$" represents the following meanings.

The chemical bond "-" in the formula "XX0-XX2" means a bond between the group represented by XX0 and the amino group (α-amino group) containing in XX2. More specifically, formula "XX0-XX2" represents the hydrogen atom in the amino group (NH$_2$) contained in XX2 is substituted with a group represented by XX0.

The chemical bond "-" in the formula "XX2-XX3" means that the carboxyl group (α-carboxyl group) contained in XX2 is bound to the amino group (α-amino group) in XX3 through an amide bond. The chemical bonds "-" in the formulae "XX3-XX4," "XX4-XX5," "XX5-XX6," "XX8-XX9" and "XX9-XX10" have the same significance as described above.

The chemical bond "-" in the formula "XX6-AzaGly" means that the carboxyl group (α-carboxyl group) contained in XX6 is bound to the amino group (α-amino group) in AzaGly [azaglycine] through an amide bond.

The chemical bond "-" in the formula "AzaGly-XX8" means that the carboxyl group (α-carboxyl group) contained in AzaGly is bound to the amino group (α-amino group) in XX8 through an amide bond.

The chemical bond "-" in the formula "XX10-NH$_2$" represents the bond between the carboxyl group (α-carboxyl group) and —NH$_2$. More specifically, the formula "XX10-NH$_2$" indicates that —OH in the carboxyl group (—COOH) contained XX10 is substituted with —NH$_2$.

Where XX2, XX3, XX4 or/and XX5 represent the chemical bonds "-," these chemical bonds "-" have the same significance as described above.

Specific examples of these chemical bonds include the bonds represented by the structural formulae shown in TABLE 1B later described, and so on.

In the formula described above, XX0 represents formyl, a $C_{1-20}$ alkanoyl (e.g., acetyl, propionyl, butyryl, hexanoyl, decanoyl, etc.; preferably represents a $C_{1-6}$ alkanoyl such as acetyl, propionyl, butyryl, etc.; more preferably, acetyl, etc.), cyclopropanecarbonyl, 6-(acetyl-D-arginylamino)caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl, 6-aminocaproyl, 6-acetylaminocaproyl, 4-[bis-(2-pyridylmethyl)aminomethyl]benzoyl or 4-ureidobenzoyl, preferably, represents a $C_{1-12}$ alkanoyl, 6-aminocaproyl, 6-acetylaminocaproyl, glycoloyl, 4-[bis-(2-pyridylmethyl)aminomethyl]benzoyl, 4-ureidobenzoyl, 3-(4-hydroxyphenyl)propionyl or pyroglutamyl, more preferably, represents formyl, a $C_{1-6}$ alkanoyl or glycoloyl, much more preferably, represents a $C_{1-6}$ alkanoyl or glycoloyl, and most preferably, represents acetyl or glycoloyl. Also preferably, XX0 is formyl, a $C_{1-20}$ alkanoyl, cyclopropanecarbonyl, 6-(acetyl-D-arginylamino) caproyl, 6-((R)-2,3-diaminopropionylamino)caproyl, 6-(D-norleucylamino)caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl or 6-aminocaproyl; also preferred are formyl, a $C_{1-12}$ alkanoyl, cyclopropanecarbonyl, 6-(acetyl-D-arginylamino)caproyl, 6-((R)-2,3-diaminopropionylamino)caproyl, 6-(D-norleucylamino) caproyl, 4-(D-arginylamino)butyryl, 3-(4-hydroxyphenyl)propionyl, glycyl, tyrosyl, acetylglycyl, acetyltyrosyl, D-tyrosyl, acetyl-D-tyrosyl, pyroglutamyl, 3-(pyridin-3-yl)propionyl, adipoyl, glycoloyl and 6-aminocaproyl.

In the formula above, XX2 represents Tyr, D-Tyr, D-Ala, D-Leu, D-Phe, D-Lys, D-Trp or the chemical bond; preferably represents D-Tyr, Tyr or the chemical bond; more preferably represents D-Tyr or the chemical bond; and most preferably represents D-Tyr.

In the formula above, XX3 represents (i) an amino acid wherein α-amino group may optionally be methylated (an amino acid selected from the group consisting of Ala [alanine], Arg [arginine], Asn [asparagine], Asp [aspartic acid], Cys [cysteine], Gln [glutamine], Glu [glutamic acid], Gly [glycine], His [histidine], Ile [isoleucine], Leu [leucine], Lys [lysine], Met [methionine], Phe [phenylalanine], Ser [serine], Thr [threonine], Trp [tryptophan], Tyr [tyrosine] and Val [valine]), (ii) a cyclic amino acid (a cyclic amino acid selected from Pro [proline], Aze(2), Aze(3), Pic(2), Pic(3), Hyp, Thz, Abz(2), Abz(3), Pzc(2), Pro(4NH$_2$), Hyp(Bzl), cisHyp, Pro (4F) and Izc)), (iii) an amino acid selected from D-Dap, D-Pya(4), DL-Ala(Pip), Orn, Aib and Tyr(PO$_3$H$_2$), or (iv) the chemical bond.

Herein, Aze(2) represents [azetidine-2-carboxylic acid], Aze(3) represents [azetidine-3-carboxylic acid], Pic(2) represents [pipecolinic acid], Pic(3) represents [3-piperidinecarboxylic acid], D-Dap represents [D-2,3-diaminopropionic acid], D-Pya(4) represents [4-pyridyl-D-alanine], Hyp represents [trans-4-hydroxyproline], Thz represents [thioproline], Aib represents [α-aminoisobutanoic acid], Abz(2) represents [2-aminobenzoic acid], Abz(3) represents [3-aminobenzoic acid], Izc represents [imidazolidine-2-carboxylic acid], DL-Ala(Pip) represents [DL-(4-piperidin-1-yl)alanine], Pzc(2) represents [piperazine-2-carboxylic acid], Orn represents [ornithine], Tyr(PO$_3$H$_2$) represents [O-phosphotyrosine], Pro (4NH$_2$) represents [cis-4-aminoproline], Hyp(Bzl) represents [trans-4-benzyloxyproline], cisHyp represents [cis-4-hydroxyproline], and Pro(4F) represents [trans-4-fluoroproline].

Herein, the amino acid may be either an L-amino acid or a D-amino acid. Alanine may be α-alanine or β-alanine unless otherwise indicated. Preferably, XX3 is D-Asp, D-Dap [D-2, 3-diaminopropionic acid], D-Ser, D-Gln, D-His, D-Trp, D-Tyr, D-Pya(4), D-NMeAla [D-N$^\alpha$-methylalanine], D-NMePhe [D-N$^\alpha$-methylphenylalanine], Aze(2), Aze(3) [azetidine-3-carboxylic acid], Pic(2), Pic(3), Hyp, Thz, NMeAla, Gly, Aib, Abz(2), Abz(3), Sar, Izc, Leu, Lys, Glu, Thr, Trp, Ser, Ala, NMeAla, β-alanine, Pzc(2), Orn, His(3Me) [3-methylhistidine], Tyr(PO$_3$H$_2$), Pro(4NH$_2$), Hyp(Bzl), cisHyp, Pro(4F) or the chemical bond; more preferably represents D-Asp, D-Dap, D-Ser, D-Gln, D-His, D-Trp, D-Tyr, D-Pya(4) D-NMeAla, D-NMePhe, Aze(2), Aze(3), Pic(2), Pic(3), Hyp, Thz, Gly, Aib, Abz(2), Sar, Izc, Leu, Lys, Glu, Thr, Trp, Ser, Ala, NMeAla, β-alanine, DL-Ala(Pip), Pzc(2), Orn, His(3Me), Tyr(PO$_3$H$_2$), Pro(4NH$_2$), Hyp(Bzl), cisHyp, Pro(4F) or the chemical bond; particularly preferably represents D-Gln, D-His, Aze(2), Pic(2), Hyp, Thz, Gly, Aib, D-NMeAla, Leu, Lys, Glu, Orn, His(3Me), Tyr(PO$_3$H$_2$), Pro (4NH$_2$), D-NMePhe, Hyp(Bzl), cisHyp or Pro(4F), much more preferably represents Aze(2), Hyp, Gly, Aib, Leu, Lys, Glu, His(3Me), Tyr(PO$_3$H$_2$), Hyp(Bzl), cisHyp or Pro(4F), and most preferably represents Hyp, Glu, Hyp(Bzl) or Pro (4F). As XX3, D-Asp, D-Dap, D-Ser, D-Gln, D-His, D-NMeAla, D-NMePhe, Aze(2), Pic(2), Pic(3), Hyp, Thz, NMeAla, Gly, Aib, Abz(2), Abz(3), Sar, Leu, Lys, Glu, β-alanine, Pzc(2), Orn, His(3Me), Tyr(PO$_3$H$_2$), Pro(4NH$_2$) or Hyp (Bzl) is also preferred.

In the formula above, XX4 represents Asn, 2-amino-3-ureidopropionic acid, N$^\beta$-formyl-β-diaminopropionic acid, N$^\beta$-acetyl-β-diaminopropionic acid, N$^\omega$-pentylasparagine, N$^\omega$-cyclopropylasparagine, N$^\omega$-benzylasparagine, 2,4-diaminobutanoic acid, 2,3-diaminopropionic acid, His, Gln, Gly, Arg, Cit, Nva, D-Asn or the chemical bond; preferably represents Asn, 2-amino-3-ureidopropionic acid, N$^\omega$-pentylasparagine, N$^\omega$-cyclopropylasparagine, N$^\omega$-benzylasparagine, 2,4-diaminobutanoic acid, 2,3-diaminopropionic acid, His, Gln, Gly, Arg, Cit, Nva, D-Asn or the chemical bond; more preferably represents Asn or 2-amino-3-ureidopropionic acid. Also preferably, XX4 represents Asn, 2-amino-3-ureidopropionic acid, N$^\beta$-formyl-β-diaminopropionic acid, N$^\beta$-acetyl-β-diaminopropionic acid, N$^\omega$-pentylasparagine, N$^\omega$-cyclopropylasparagine, N$^\omega$-benzylasparagine, 2,4-diaminobutanoic acid, His, Gln, Cit or D-Asn; or, Asn, 2-amino-3-ureidopropionic acid, N$^\beta$-formyldiaminopropionic acid, N$^\beta$-acetyldiaminopropionic acid, N$^\omega$-pentylasparagine, N$^\omega$-cyclopropylasparagine, N$^\omega$-benzylasparagine or 2,4-diaminobutanoic acid is also preferred.

In the formula described above, XX5 represents Ser, Thr, Val, NMeSer, Gly, Ala, Hyp, D-Ala, D-Thr, D-Pro or the chemical bond; preferably represents Thr, NMeSer, Gly, Ala, Hyp, D-Ala, D-Thr, D-Pro or the chemical bond; more preferably represents Ser, Thr or Ala, and most preferably represents Thr. Also preferably, XX5 is Ser, Thr, Val, NMeSer, Gly, Ala, Hyp, D-Ala or D-Thr; or, Ser, Thr or Val is also preferred.

In the formula described above, XX6 represents Phe, Tyr, Trp, Tyr(Me), Thi, Nal(2), Cha, Pya(4), threo-Ser(3Phenyl), erythro-Ser(3Phenyl) or an optionally substituted phenylalanine. Herein, the substituent in the optionally substituted phenylalanine includes, for example, oxo, a halogen atom (e.g., fluorine, chlorine, bromine, iodine, etc.), a $C_{1-3}$ alkylenedioxy (e.g., methylenedioxy, ethylenedioxy, etc.), nitro, cyano, an optionally substituted $C_{1-6}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted $C_{7-16}$ aralkyl, an optionally substituted $C_{1-6}$ alkoxy, hydroxy, an optionally substituted C$_{6-14}$ aryloxy, an optionally substituted C$_{7-16}$ aralkyloxy, mercapto, an optionally substituted C$_{1-6}$ alkylthio, an optionally substituted C$_{6-14}$ arylthio, an optionally substituted C$_{7-16}$ aralkylthio, an optionally substituted amino [amino, an optionally substituted mono- or di-C$_{1-6}$ alkylamino (e.g., methylamino, dimethylamino, ethylamino, diethylamino, propylamino, isopropylamino, etc.), an optionally substituted mono- or di-C$_{2-6}$ alkenyl-amino (e.g., vinylamino, propenylamino, isopropenylamino), an optionally substituted C$_{2-6}$ alkynyl-amino (e.g., 2-butyn-1-yl-amino, 4-pentyn-1-yl-amino, 5-hexyn-1-yl-amino), an optionally substituted mono- or di-C$_{3-8}$ cycloalkyl-amino (e.g., cyclopropylamino, cyclohexylamino), an optionally substituted C$_{6-14}$ aryl-amino (e.g., phenylamino, diphenylamino, naphthylamino), an optionally substituted C$_{1-6}$ alkoxy-amino (e.g., methoxyamino, ethoxyamino, propoxyamino, isopropoxyamino), formylamino, an optionally substituted C$_{1-6}$ alkyl-carbonylamino (e.g., acetylamino, propionylamino, pivaloylamino, etc.), an optionally substituted C$_{3-8}$ cycloalkyl-carbonylamino (e.g., cyclopropylcarbonylamino, cyclopentylcarbonylamino, cyclohexylcarbonylamino, etc.), an optionally substituted C$_{6-14}$ aryl-carbonylamino (e.g., benzoylamino, naphthoylamino, etc.), an optionally substituted C$_{1-6}$ alkoxy-carbonylamino (e.g., methoxycarbonylamino, ethoxycarbonylamino, propoxycarbonylamino, butoxycarbonylamino, etc.), an optionally substituted C$_{1-6}$ alkylsulfonylamino (e.g., methylsulfonylamino, ethylsulfonylamino, etc.), an optionally substituted C$_{6-14}$ arylsulfonylamino (e.g., phenylsulfonylamino, 2-naphthylsulfonylamino, 1-naphthylsulfonylamino, etc.)], formyl, carboxy, an optionally substituted C$_{1-6}$ alkyl-carbonyl (e.g., acetyl, propionyl, pivaloyl, etc.), an optionally substituted C$_{3-8}$ cycloalkyl-carbonyl (e.g., cyclopropylcarbonyl, cyclopentylcarbonyl, cyclohexylcarbonyl, 1-methylcyclohexyl-carbonyl, etc.), an optionally substituted C$_{6-14}$ aryl-carbonyl (e.g., benzoyl, 1-naphthoyl, 2-naphthoyl, etc.), an optionally substituted C$_{7-16}$ aralkyl-carbonyl (e.g., phenylacetyl, 3-phenylpropionyl, etc.), an optionally substituted 5- to 7-membered heterocyclic carbonyl containing 1 to 4 hetero atoms of 1 or 2 species selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), an optionally esterified carboxyl, an optionally substituted carbamoyl group, an optionally substituted C$_{1-6}$ alkylsulfonyl (e.g., methylsulfonyl, ethylsulfonyl, etc.), an optionally substituted C$_{1-6}$ alkylsulfinyl (e.g., methylsulfinyl, ethylsulfinyl, etc.), an optionally substituted C$_{6-14}$ arylsulfonyl (e.g., phenylsulfonyl, 1-naphthylsulfonyl, 2-naphthylsulfonyl, etc.), an optionally substituted C$_{6-14}$ arylsulfinyl (e.g., phenylsulfinyl, 1-naphthylsulfinyl, 2-naphthylsulfinyl, etc.), an optionally substituted C$_{1-6}$ alkyl-carbonyloxy (e.g., acetoxy, propionyloxy, etc.), an optionally substituted C$_{6-14}$ aryl-carbonyloxy (e.g., benzoyloxy, naphthylcarbonyloxy, etc.), an optionally substituted C$_{1-6}$ alkoxy-carbonyloxy (e.g., methoxycarbonyloxy, ethoxycarbonyloxy, propoxycarbonyloxy, butoxycarbonyloxy, etc.), an optionally substituted mono-C$_{1-6}$ alkylcarbamoyloxy (e.g., methylcarbamoyloxy, ethylcarbamoyloxy, etc.), an optionally substituted di-C$_{1-6}$ alkylcarbamoyloxy (e.g., dimethylcarbamoyloxy, diethylcarbamoyloxy, etc.), an optionally substituted mono- or di-C$_{6-14}$ arylcarbamoyloxy (e.g., phenylcarbamoyloxy, naphthylcarbamoyloxy, etc.), an optionally substituted heterocyclic group, sulfo, sulfamoyl, sulfinamoyl, sulfenamoyl, or a group of 2 or more (e.g., 2 or 3) of these substituents combined, and the like (Substituent Group A). The number of the substituents is not particularly limited but these groups may have 1 to 5, preferably 1 to 3 substituents in substitutable positions, and when there are two or more substituents, each substituent may be the same or different.

The "optionally esterified carboxyl group" in the Substituent Group A includes, for example, an optionally substituted C$_{1-6}$ alkoxy-carbonyl (e.g., methoxycarbonyl, ethoxycarbonyl, propoxycarbonyl, tert-butoxycarbonyl, etc.), an optionally substituted C$_{6-14}$ aryloxy-carbonyl (e.g., phenoxycarbonyl, etc.), an optionally substituted C$_{7-16}$ aralkyloxy-carbonyl (e.g., benzyloxycarbonyl, phenethyloxycarbonyl, etc.), and the like.

The "C$_{1-6}$ alkyl" in the "optionally substituted C$_{1-6}$ alkyl" in the Substituent Group A includes, for example, methyl, ethyl, propyl, isopropyl, butyl, isobutyl, sec-butyl, tert-butyl, pentyl, isopentyl, neopentyl, hexyl, etc.

The "C$_{2-6}$ alkenyl" in the "optionally substituted C$_{2-6}$ alkenyl" in the Substituent Group A includes, for example, vinyl, propenyl, isopropenyl, 2-buten-1-yl, 4-penten-1-yl, 5-hexen-1-yl, etc.

The "C$_{2-6}$ alkynyl" in the "optionally substituted C$_{2-6}$ alkynyl" in the Substituent Group A includes, for example, 2-butyn-1-yl, 4-pentyn-1-yl, 5-hexyn-1-yl, etc.

The "C$_{3-8}$ cycloalkyl" in the "optionally substituted C$_{3-8}$ cycloalkyl" in the Substituent Group A includes, for example, cyclopropyl, cyclobutyl, cyclopentyl, cyclohexyl, etc.

The "C$_{6-14}$ aryl" in the "optionally substituted C$_{6-14}$ aryl" in the Substituent Group A includes, for example, phenyl, 1-naphthyl, 2-naphthyl, 2-biphenylyl, 3-biphenylyl, 4-biphenylyl, 2-anthryl, etc.

The "C$_{7-16}$ aralkyl" in the "optionally substituted C$_{7-16}$ aralkyl" in the Substituent Group A includes, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl), etc.

The "C$_{1-6}$ alkoxy" in the "optionally substituted C$_{1-6}$ alkoxy" in the Substituent Group A includes, for example, methoxy, ethoxy, propoxy, isopropoxy, butoxy, isobutoxy, sec-butoxy, pentyloxy, hexyloxy, etc.

The "C$_{6-14}$ aryloxy" in the "optionally substituted C$_{6-14}$ aryloxy" in the Substituent Group A includes, for example, phenyloxy, 1-naphthyloxy, 2-naphthyloxy, etc.

The "C$_{7-16}$ aralkyloxy" in the "optionally substituted C$_{7-16}$ aralkyloxy" in the Substituent Group A includes, for example, benzyloxy, phenethyloxy, etc.

The "C$_{1-6}$ alkylthio" in the "optionally substituted C$_{1-6}$ alkylthio" in the Substituent Group A includes, for example, methylthio, ethylthio, propylthio, isopropylthio, butylthio, sec-butylthio, tert-butylthio, etc.

The "C$_{6-14}$ arylthio" in the "optionally substituted C$_{6-14}$ arylthio" in the Substituent Group A includes, for example, phenylthio, 1-naphthylthio, 2-naphthylthio, etc.

The "C$_{7-16}$ aralkylthio" in the "optionally substituted C$_{7-16}$ aralkylthio" in the Substituent Group A includes, for example, benzylthio, phenethylthio, etc.

The substituents for these "C$_{1-6}$ alkoxy-carbonyl," "C$_{1-6}$ alkyl group," "C$_{2-6}$ alkenyl," "C$_{2-6}$ alkynyl," "C$_{1-6}$ alkoxy," "C$_{1-6}$ alkylthio," "C$_{1-6}$ alkyl-amino," "C$_{2-6}$ alkenyl-amino," "C$_{2-6}$ alkynyl-amino," "C$_{1-6}$ alkoxy-amino," "C$_{1-6}$ alkyl-carbonyl," "C$_{1-6}$ alkylsulfonyl," "C$_{1-6}$-alkylsulfinyl," "C$_{1-6}$ alkyl-carbonylamino," "C$_{1-6}$ alkoxy-carbonylamino," "C$_{1-6}$ alkylsulfonylamino," "C$_{1-6}$ alkyl-carbonyloxy," "C$_{1-6}$ alkoxy-carbonyloxy," "mono-C$_{1-6}$ alkylcarbamoyloxy" and "di-C$_{1-6}$ alkylcarbamoyloxy" in the Substituent Group A include, for example, 1 to 5 substituents selected from, for example, a halogen atom (e.g., fluorine atom, chlorine atom, bromine atom, iodine atom), carboxy, hydroxy, amino, a mono- or di-$C_{1-6}$ alkylamino, a mono- or di-$C_{6-14}$ arylamino, a $C_{3-8}$ cycloalkyl, a $C_{1-6}$ alkoxy, a $C_{1-6}$ alkoxy-carbonyl, a $C_{1-6}$ alkylthio, a $C_{1-6}$ alkylsulfinyl, a $C_{1-6}$ alkylsulfonyl, the optionally esterified carboxyl described above, carbamoyl, thiocarbamoyl, a mono-$C_{1-6}$ alkylcarbamoyl (e.g., methylcarbamoyl, ethylcarbamoyl, etc.), a di-$C_{1-6}$ alkylcarbamoyl (e.g., dimethylcarbamoyl, diethylcarbamoyl, ethylmethylcarbamoyl, etc.), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), and the like.

The substituents for the "$C_{6-14}$ aryloxy-carbonyl," "$C_{7-16}$ aralkyloxy-carbonyl," "$C_{3-8}$ cycloalkyl," "$C_{6-14}$ aryl," "$C_{7-16}$ aralkyl," "$C_{6-14}$ aryloxy," "$C_{7-16}$ aralkyloxy," "$C_{6-14}$ arylthio," "$C_{7-16}$ aralkylthio," "$C_{3-8}$ cycloalkyl-amino," "$C_{6-14}$ arylamino," "$C_{3-8}$ cycloalkyl-carbonyl," "$C_{6-14}$ aryl-carbonyl," "$C_{7-16}$ aralkyl-carbonyl," "5- to 7-membered heterocyclic carbonyl containing 1 to 4 hetero atoms of 1 or 2 species selected from nitrogen, sulfur and oxygen atoms in addition to carbon atoms," "$C_{6-14}$ arylsulfonyl," "$C_{6-14}$ arylsulfinyl," "$C_{3-8}$ cycloalkyl-carbonylamino," "$C_{6-14}$ aryl-carbonylamino," "$C_{6-14}$ arylsulfonylamino," "$C_{6-14}$ aryl-carbonyloxy" and "mono- or di-$C_{6-14}$ aryl-carbamoyloxy" in the Substituent Group A include, for example, 1 to 5 substituents selected from, for example, a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{1-6}$ alkoxy described above, the optionally substituted $C_{1-6}$ alkylthio described above, the optionally substituted $C_{1-6}$ alkylsulfinyl described above, the optionally substituted $C_{1-6}$ alkylsulfonyl described above, the optionally esterified carboxyl described above, carbamoyl, thiocarbamoyl, a mono-$C_{1-6}$ alkylcarbamoyl, a di-$C_{1-6}$ alkylcarbamoyl, a mono- or di-$C_{6-14}$ arylcarbamoyl, a mono- or di-5- to 7-membered heterocyclic carbamoyl containing 1 to 4 hetero atoms of 1 or 2 species selected from nitrogen, sulfur and oxygen atoms in addition to carbon atoms, and the like.

The "optionally substituted heterocyclic group" in the Substituent Group A includes, for example, a 5- to 14-membered (monocyclic, bicyclic or tricyclic) heterocyclic group containing 1 to 4 hetero atoms of 1 or 2 species selected from nitrogen, sulfur and oxygen atoms in addition to carbon atoms, which may optionally be substituted with a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, the optionally substituted $C_{1-6}$ alkylthio described above, the optionally substituted $C_{6-14}$ arylthio described above, the optionally substituted $C_{7-16}$ aralkylthio described above, the optionally substituted $C_{1-6}$ alkylsulfinyl described above, the optionally substituted $C_{6-14}$ arylsulfinyl described above, the optionally substituted $C_{1-6}$ alkylsulfonyl described above, the optionally substituted $C_{6-14}$ arylsulfonyl described above, the optionally esterified carboxyl described above, carbamoyl, thiocarbamoyl, a mono-$C_{1-6}$ alkylcarbamoyl, a di-lower alkylcarbamoyl, a mono- or di-$C_{6-14}$ arylcarbamoyl, a mono- or di-5- or 7-membered heterocyclic carbamoyl containing 1 to 4 hetero atoms of 1 or 2 species selected from nitrogen, sulfur and oxygen atoms in addition to carbon atoms, or the like; preferably (i) a 5- to 14-membered (preferably, 5- to 10-membered) aromatic heterocyclic group, (ii) a 5- to 10-membered non-aromatic heterocyclic group or (iii) a monovalent group formed by one optional hydrogen atom from 7- to 10-membered bridged-hetero ring, and the like, are employed; among them, preferably used is a 5-membered aromatic heterocyclic group. Specifically used are an aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl), etc., a non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The "optionally substituted carbamoyl group" in the Substituent Group A includes a carbamoyl group, which may optionally be substituted with the optionally substituted $C_{1-6}$ alkyl, optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted heterocyclic group described above, etc., and specific examples are carbamoyl, thiocarbamoyl, a mono-$C_{1-6}$ alkylcarbamoyl (e.g., methylcarbamoyl, ethylcarbamoyl, etc.), a di-$C_{1-6}$ alkylcarbamoyl (e.g., dimethylcarbamoyl, diethylcarbamoyl, ethylmethylcarbamoyl, etc.), a $C_{1-6}$ alkyl ($C_{1-6}$ alkoxy)carbamoyl (e.g., methyl(methoxy)carbamoyl, ethyl(methoxy)carbamoyl), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), a 5- to 7-membered cyclic carbamoyl (e.g., 1-pyrrolidinylcarbonyl, 1-piperidinylcarbonyl, hexamethyleneiminocarbonyl), and the like.

The "optionally substituted amino" in the Substituent Group A includes an amino, which may optionally be substituted with 1 or 2 groups selected from the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, formyl, the optionally substituted $C_{1-6}$ alkyl-carbonyl described above, the optionally substituted $C_{3-8}$ cycloalkyl-carbonyl described above, the optionally substituted $C_{6-14}$ aryl-carbonyl described above, the optionally substituted $C_{1-6}$ alkoxy-carbonyl described above, the optionally substituted $C_{1-6}$ alkylsulfonyl described above, the optionally substituted $C_{6-14}$ arylsulfonyl), and the like.

More preferably, the substituents are a halogen atom, hydroxy, a $C_{1-6}$ alkoxy, an optionally halogenated $C_{1-6}$ alkyl, an optionally halogenated $C_{1-6}$ alkoxy, amino, nitro, cyano, etc.

XX6 preferably represents Phe, Tyr, Trp, Tyr(Me) [O-methyltyrosine], Thi [2-thienylalanine], Nal(2) [2-naphthylalanine], Cha [cyclohexylalanine], Pya(4) [4-pyridylalanine], Phe(2F) [2-fluorophenylalanine], Phe(3F) [3-fluorophenylalanine], Phe(4F) [4-fluorophenylalanine], Phe(4Cl) [4-chlorophenylalanine], αMePhe [α-methylphenylalanine], Phe (2Me), Phe(3Me), Phe(4Me), threo-Ser(3Phenyl), erythro-Ser(3Phenyl) or D-Phe, more preferably represents Phe, Cha, Phe(2F), Phe(3F), Phe(4F), Phe(4Cl), αMePhe, Phe(2Me), Phe(3Me), Phe(4Me), threo-Ser(3Phenyl), erythro-Ser (3Phenyl) or D-Phe, further more preferably represents Phe, Phe(2F), Phe(3F), Phe(4F), Phe(4Cl), αMePhe, Phe(2Me), Phe(3Me), Phe(4Me), threo-Ser(3Phenyl), erythro-Ser (3Phenyl) or D-Phe, much more preferably represents Phe, Cha, Phe(2F), Phe(3F), Phe(4F), Phe(4Cl), Phe(2Me), Phe (3Me), Phe(4Me), threo-Ser(3Phenyl) or erythro-Ser(3Phenyl), and most preferably represents Phe, Cha, Phe(3F) or Phe(4F). As XX6, Phe, Tyr, Trp, Tyr(Me), Thi, Nal(2), Cha, Pya(4), Phe(2F), Phe(3F), Phe(4F), Phe(4Cl) or D-Phe; or Phe, Tyr, Trp, Tyr(Me), Thi, Nal(2), Cha, Pya(4), Phe(2F), Phe(3F), Phe(4F) or Phe(4Cl) is also preferred.

In the formula described above, AzaGly represents azaglycine.

In the formula described above, XX8 represents Leu, Nva [norvaline], Val or Ala(cPr) [cyclopropylalanine], and preferably represents Leu or Ala(cPr). As XX8, Leu, Nva or Val is also preferred.

In the formula described above, XX9 represents an optionally substituted arginine, an optionally substituted lysine or an optionally substituted ornithine. Herein, substituents for the optionally substituted arginine, the optionally substituted lysine or the optionally substituted ornithine are 1 or substitutable number of $C_{1-6}$ alkyl (e.g., methyl, ethyl, propyl, isopropyl, butyl, etc.), $C_{1-6}$ acyl (e.g., acetyl, propionyl, etc.). XX9 preferably represents Arg, Orn [ornithine], Arg(Me) [$N^\omega$-methylarginine], D-Arg or Arg (asymMe$_2$) [asymmetric-$N^{\omega,\omega}$-dimethylarginine], more preferably represents Arg, Arg(Me) or D-Arg, further more preferably represents Arg or Arg(Me). As XX9, Arg, Orn, Arg (Me) or Arg (asymMe$_2$) is also preferred.

In the formula described above, XX10 represents 2-naphthylalanine, 2-thienylalanine, tyrosine, an optionally substituted phenylalanine, or an optionally substituted tryptophan. Herein, the substituents in the optionally substituted phenylalanine and the optionally substituted tryptophan include, for example, oxo, a halogen atom (e.g., fluorine, chlorine, bromine, iodine, etc.), a $C_{1-3}$ alkylenedioxy (e.g., methylenedioxy, ethylenedioxy, etc.), nitro, cyano, an optionally substituted $C_{1-6}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted $C_{7-16}$ aralkyl, an optionally substituted $C_{1-6}$ alkoxy, hydroxy, an optionally substituted $C_{6-14}$ aryloxy, an optionally substituted $C_{7-16}$ aralkyloxy, mercapto, an optionally substituted $C_{1-6}$ alkylthio, an optionally substituted $C_{6-14}$ arylthio, an optionally substituted $C_{7-16}$ aralkylthio, an optionally substituted amino [amino, an optionally substituted mono- or di-$C_{1-6}$ alkyl-amino (e.g., methylamino, dimethylamino, ethylamino, diethylamino, propylamino, isopropylamino, etc.), an optionally substituted mono- or di-$C_{2-6}$ alkenyl-amino (e.g., vinylamino, propenylamino, isopropenylamino), an optionally substituted $C_{2-6}$ alkynyl-amino (e.g., 2-butyn-1-yl-amino, 4-pentyn-1-yl-amino, 5-hexyn-1-yl-amino), an optionally substituted mono- or di-$C_{3-8}$ cycloalkyl-amino (e.g., cyclopropylamino, cyclohexylamino), an optionally substituted $C_{6-14}$ aryl-amino (e.g., phenylamino, diphenylamino, naphthylamino), an optionally substituted $C_{1-6}$ alkoxy-amino (e.g., methoxyamino, ethoxyamino, propoxyamino, isopropoxyamino), formylamino, an optionally substituted $C_{1-6}$ alkyl-carbonylamino (e.g., acetylamino, propionylamino, pivaloylamino, etc.), an optionally substituted $C_{3-8}$ cycloalkyl-carbonylamino (e.g., cyclopropylcarbonylamino, cyclopentylcarbonylamino, cyclohexylcarbonylamino, etc.), an optionally substituted $C_{6-14}$ aryl-carbonylamino (e.g., benzoylamino, naphthoylamino, etc.), an optionally substituted $C_{1-6}$ alkoxy-carbonylamino (e.g., methoxycarbonylamino, ethoxycarbonylamino, propoxycarbonylamino, butoxycarbonylamino, etc.), an optionally substituted $C_{1-6}$ alkylsulfonylamino (e.g., methylsulfonylamino, ethylsulfonylamino, etc.), an optionally substituted $C_{6-14}$ arylsulfonylamino (e.g., phenylsulfonylamino, 2-naphthylsulfonylamino, 1-naphthylsulfonylamino, etc.)], formyl, carboxy, an optionally substituted $C_{1-6}$ alkyl-carbonyl (e.g., acetyl, propionyl, pivaloyl, etc.), an optionally substituted $C_{3-8}$ cycloalkyl-carbonyl (e.g., cyclopropylcarbonyl, cyclopentylcarbonyl, cyclohexylcarbonyl, 1-methylcyclohexyl-carbonyl, etc.), an optionally substituted $C_{6-14}$ arylcarbonyl (e.g., benzoyl, 1-naphthoyl, 2-naphthoyl, etc.), an optionally substituted $C_{7-16}$ aralkyl-carbonyl (e.g., phenylacetyl, 3-phenylpropionyl, etc.), an optionally substituted 5- to 7-membered heterocyclic carbonyl containing 1 to 4 hetero atoms of 1 or 2 species selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), an optionally esterified carboxyl, an optionally substituted carbamoyl group, an optionally substituted $C_{1-6}$ alkylsulfonyl (e.g., methylsulfonyl, ethylsulfonyl, etc.), an optionally substituted $C_{1-6}$ alkylsulfinyl (e.g., methylsulfinyl, ethylsulfinyl, etc.), an optionally substituted $C_{6-14}$ arylsulfonyl (e.g., phenylsulfonyl, 1-naphthylsulfonyl, 2-naphthylsulfonyl, etc.), an optionally substituted $C_{6-14}$ arylsulfinyl (e.g., phenylsulfinyl, 1-naphthylsulfinyl, 2-naphthylsulfinyl, etc.), an optionally substituted $C_{1-6}$ alkyl-carbonyloxy (e.g., acetoxy, propionyloxy, etc.), an optionally substituted $C_{6-14}$ aryl-carbonyloxy (e.g., benzoyloxy, naphthylcarbonyloxy, etc.), an optionally substituted $C_{1-6}$ alkoxy-carbonyloxy (e.g., methoxycarbonyloxy, ethoxycarbonyloxy, propoxycarbonyloxy, butoxycarbonyloxy, etc.), an optionally substituted mono-$C_{1-6}$ alkylcarbamoyloxy (e.g., methylcarbamoyloxy, ethylcarbamoyloxy, etc.), an optionally substituted di-$C_{1-6}$ alkylcarbamoyloxy (e.g., dimethylcarbamoyloxy, diethylcarbamoyloxy, etc.), an optionally substituted mono- or di-$C_{6-14}$ arylcarbamoyloxy (e.g., phenylcarbamoyloxy, naphthylcarbamoyloxy, etc.), an optionally substituted heterocyclic group, sulfo, sulfamoyl, sulfinamoyl, sulfenamoyl, or a group of 2 or more (e.g., 2 or 3) of these substituents combined, and the like (Substituent Group A). The number of the substituents is not particularly limited but these groups may have 1 to 5, preferably 1 to 3 substituents in substitutable positions, and when there are two or more substituents, each substituent may be the same or different.

The "optionally esterified carboxyl group" in the Substituent Group A includes, for example, an optionally substituted $C_{1-6}$ alkoxy-carbonyl (e.g., methoxycarbonyl, ethoxycarbonyl, propoxycarbonyl, tert-butoxycarbonyl, etc.), an optionally substituted $C_{6-14}$ aryloxy-carbonyl (e.g., phenoxycarbonyl, etc.), an optionally substituted $C_{7-16}$ aralkyloxy-carbonyl (e.g., benzyloxycarbonyl, phenethyloxycarbonyl, etc.), and the like.

The "$C_{1-6}$ alkyl" in the "optionally substituted $C_{1-6}$ alkyl" in the Substituent Group A includes, for example, methyl, ethyl, propyl, isopropyl, butyl, isobutyl, sec-butyl, tert-butyl, pentyl, isopentyl, neopentyl, hexyl, etc.

The "$C_{2-6}$ alkenyl" in the "optionally substituted $C_{2-6}$ alkenyl" in the Substituent Group A includes, for example, vinyl, propenyl, isopropenyl, 2-buten-1-yl, 4-penten-1-yl, 5-hexen-1-yl, etc.

The "$C_{2-6}$ alkynyl" in the "optionally substituted $C_{2-6}$ alkynyl" in the Substituent Group A includes, for example, 2-butyn-1-yl, 4-pentyn-1-yl, 5-hexyn-1-yl, etc.

The "$C_{3-8}$ cycloalkyl" in the "optionally substituted $C_{3-8}$ cycloalkyl" in the Substituent Group A includes, for example, cyclopropyl, cyclobutyl, cyclopentyl, cyclohexyl, etc.

The "$C_{6-14}$ aryl" in the optionally substituted $C_{6-14}$ aryl in the Substituent Group A includes, for example, phenyl, 1-naphthyl, 2-naphthyl, 2-biphenylyl, 3-biphenylyl, 4-biphenylyl, 2-anthryl, etc.

The "$C_{7-16}$ aralkyl" in the "optionally substituted $C_{7-16}$ aralkyl" in the Substituent Group A includes, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl), etc.

The "$C_{1-6}$ alkoxy" in the "optionally substituted $C_{1-6}$ alkoxy" in the Substituent Group A includes, for example, methoxy, ethoxy, propoxy, isopropoxy, butoxy, isobutoxy, sec-butoxy, pentyloxy, hexyloxy, etc.

The "$C_{6-14}$ aryloxy" in the "optionally substituted $C_{6-14}$ aryloxy" in the Substituent Group A includes, for example, phenyloxy, 1-naphthyloxy, 2-naphthyloxy, etc.

The "$C_{7-16}$ aralkyloxy" in the "optionally substituted $C_{7-16}$ aralkyloxy" in the Substituent Group A includes, for example, benzyloxy, phenethyloxy, etc.

The "$C_{1-6}$ alkylthio" in the "optionally substituted $C_{1-6}$ alkylthio" in the Substituent Group A includes, for example, methylthio, ethylthio, propylthio, isopropylthio, butylthio, sec-butylthio, tert-butylthio, etc.

The "$C_{6-14}$ arylthio" in the "optionally substituted $C_{6-14}$ arylthio" in the Substituent Group A includes, for example, phenylthio, 1-naphthylthio, 2-naphthylthio, etc.

The "$C_{7-16}$ aralkylthio" in the "optionally substituted $C_{7-16}$ aralkylthio" in the Substituent Group A includes, for example, benzylthio, phenethylthio, etc.

The substituents for these "$C_{1-6}$ alkoxy-carbonyl," "$C_{1-6}$ alkyl group," "$C_{2-6}$ alkenyl," "$C_{2-6}$ alkynyl," "$C_{1-6}$ alkoxy," "$C_{1-6}$ alkylthio," "$C_{1-6}$ alkyl-amino," "$C_{2-6}$ alkenyl-amino," "$C_{2-6}$ alkynyl-amino," "$C_{1-6}$ alkoxy-amino," "$C_{1-6}$ alkyl-carbonyl," "$C_{1-6}$ alkylsulfonyl," "$C_{1-6}$ alkylsulfinyl," "$C_{1-6}$ alkylcarbonylamino," "$C_{1-6}$ alkoxy-carbonylamino," "$C_{1-6}$ alkylsulfonylamino," "$C_{1-6}$ alkyl-carbonyloxy," "$C_{1-6}$ alkoxy-carbonyloxy," "mono-$C_{1-6}$ alkylcarbamoyloxy" and "di-$C_{1-6}$ alkylcarbamoyloxy" include 1 to 5 substituents selected from, for example, a halogen atom (e.g., fluorine atom, chlorine atom, bromine atom, iodine atom), carboxy, hydroxy, amino, a mono- or di-$C_{1-6}$ alkylamino, a mono- or di-$C_{6-14}$ arylamino, a $C_{3-8}$ cycloalkyl, a $C_{1-6}$ alkoxy, a $C_{1-6}$ alkoxy-carbonyl, a $C_{1-6}$ alkylthio, a $C_{1-6}$ alkylsulfinyl, a $C_{1-6}$ alkylsulfonyl, the optionally esterified carboxyl described above, carbamoyl, thiocarbamoyl, a mono-$C_{1-6}$ alkylcarbamoyl (e.g., methylcarbamoyl, ethylcarbamoyl, etc.), a di-$C_{1-6}$ alkylcarbamoyl (e.g., dimethylcarbamoyl, diethylcarbamoyl, ethylmethylcarbamoyl, etc.), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), and the like.

The substituents for the "$C_{6-14}$ aryloxy-carbonyl," "$C_{7-16}$ aralkyloxy-carbonyl," "$C_{3-8}$ cycloalkyl," "$C_{6-14}$ aryl," "$C_{7-16}$ aralkyl," "$C_{6-14}$ aryloxy," "$C_{7-16}$ aralkyloxy," "$C_{6-14}$ arylthio," "$C_{7-16}$ aralkylthio," "$C_{3-8}$ cycloalkyl-amino," "$C_{6-14}$ aryl-amino," "$C_{3-8}$ cycloalkyl-carbonyl," "$C_{6-14}$ aryl-carbonyl," "$C_{7-16}$ aralkyl-carbonyl," "5- to 7-membered heterocyclic carbonyl containing 1 to 4 hetero atoms of 1 or 2 species selected from nitrogen, sulfur and oxygen atoms in addition to carbon atoms," "$C_{6-14}$ arylsulfonyl," "$C_{6-14}$ arylsulfinyl," "$C_{3-8}$ cycloalkyl-carbonylamino," "$C_{6-14}$ aryl-carbonylamino," "$C_{6-14}$ arylsulfonylamino," "$C_{6-14}$ aryl-carbonyloxy" and "mono- or di-$C_{6-14}$ aryl-carbamoyloxy" in the Substituent Group A include 1 to 5 substituents selected from, for example, a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{1-6}$ alkoxy described above, the optionally substituted $C_{1-6}$ alkylthio described above, the optionally substituted $C_{1-6}$ alkylsulfinyl described above, the optionally substituted $C_{1-6}$ alkylsulfonyl described above, the optionally esterified carboxyl described above, carbamoyl, thiocarbamoyl, a mono-$C_{1-6}$ alkylcarbamoyl, a di-$C_{1-6}$ alkylcarbamoyl, a mono- or di-$C_{6-14}$ arylcarbamoyl, a mono- or di-5- to 7-membered heterocyclic carbamoyl containing 1 to 4 hetero atoms of 1 or 2 species selected from nitrogen, sulfur and oxygen atoms in addition to carbon atoms, and the like.

The "optionally substituted heterocyclic group" in the Substituent Group A includes, for example, a 5- to 14-membered (monocyclic, bicyclic or tricyclic) heterocyclic group containing 1 to 4 hetero atoms of 1 or 2 species selected from nitrogen, sulfur and oxygen atoms in addition to carbon atoms, which may optionally be substituted with a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, the optionally substituted $C_{1-6}$ alkylthio described above, the optionally substituted $C_{6-14}$ arylthio described above, the optionally substituted $C_{7-16}$ aralkylthio described above, the optionally substituted $C_{1-6}$ alkylsulfinyl described above, the optionally substituted $C_{6-14}$ arylsulfinyl described above, the optionally substituted $C_{1-6}$ alkylsulfonyl described above, the optionally substituted $C_{6-14}$ arylsulfonyl described above, the optionally esterified carboxyl described above, carbamoyl, thiocarbamoyl, a mono-$C_{1-6}$ alkylcarbamoyl, a di-lower alkylcarbamoyl, a mono- or di-$C_{6-14}$ arylcarbamoyl, a mono- or di-5- or 7-membered heterocyclic carbamoyl containing 1 to 4 hetero atoms of 1 or 2 species selected from nitrogen, sulfur and oxygen atoms in addition to carbon atoms, or the like; preferably, (i) a 5- to 14-membered (preferably, 5- to 10-membered) aromatic heterocyclic group, (ii) a 5- to 10-membered non-aromatic heterocyclic group or (iii) a monovalent group formed by one optional hydrogen atom from 7- to 10-membered bridged-hetero ring, and among them, a 5-membered aromatic heterocyclic group is preferably used. Specifically used are, for example, an aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl, etc.; a non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The "optionally substituted carbamoyl group" in the Substituent Group A includes a carbamoyl group, which may optionally be substituted with the optionally substituted $C_{1-6}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted heterocyclic group described above, etc., and specific examples include carbamoyl, thiocarbamoyl, a mono-$C_{1-6}$ alkylcarbamoyl (e.g., methylcarbamoyl, ethylcarbamoyl, etc.), di-$C_{1-6}$ alkylcarbamoyl (e.g., dimethylcarbamoyl, diethylcarbamoyl, ethylmethylcarbamoyl, etc.), $C_{1-6}$ alkyl ($C_{1-6}$ alkoxy)carbamoyl (e.g., methyl(methoxy)carbamoyl, ethyl(methoxy)carbamoyl), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 species selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), a 5- to 7-membered cyclic carbamoyl (e.g., 1-pyrrolidinylcarbonyl, 1-piperidinylcarbonyl, hexamethyleneiminocarbonyl), and the like.

The "optionally substituted amino" in the Substituent Group A includes an amino, which may optionally be substituted with 1 or 2 groups selected from the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, formyl, the optionally substituted $C_{1-6}$ alkyl-carbonyl described above, the optionally substituted $C_{3-8}$ cycloalkyl-carbonyl described above, the optionally substituted $C_{6-14}$ aryl-carbonyl described above, the optionally substituted $C_{1-6}$ alkoxy-carbonyl described above, the optionally substituted $C_{1-6}$ alkylsulfonyl described above, an optionally substituted $C_{6-14}$ arylsulfonyl), and the like.

More preferably, these substituents are a halogen atom, hydroxy, a $C_{1-6}$ alkoxy, an optionally halogenated $C_{1-6}$ alkyl, an optionally halogenated $C_{1-6}$ alkoxy, amino, nitro, cyano, etc.

XX10 preferably represents Phe, Trp, 2-naphthylalanine, 2-thienylalanine, tyrosine or 4-fluorophenylalanine, more preferably represents Phe or Trp, and most preferably represents Trp.

In a combination of these groups, there is preferably provided a metastin derivative represented by formula:

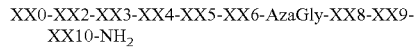

(wherein:
XX0 represents formyl, a $C_{1-6}$ alkanoyl or glycoloyl;
XX2 represents D-Tyr or the chemical bond;
XX3 represents Aze(2), Hyp, Gly, Aib, Leu, Lys, Glu, His (3Me), Tyr(PO$_3$H$_2$), Hyp(Bzl) or Pro(4F);
XX4 represents Asn or 2-amino-3-ureidopropionic acid;
XX5 represents Ser, Thr or Ala;
XX6 represents Phe, Cha, Phe(2F), Phe(3F), Phe(4F) or Phe(4Cl);
AzaGly represents azaglycine;
XX8 represents Leu or Ala(cPr);
XX9 represents Arg or Arg(Me); and,
XX10 represents Phe or Trp); or a salt thereof.

In a combination of these groups, there is more preferably provided a metastin derivative represented by formula:

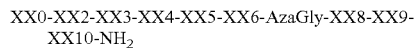

(wherein:
XX0 represents acetyl or glycoloyl (preferably acetyl);
XX2 represents D-Tyr;
XX3 represents Hyp, Glu, Hyp(Bzl) or Pro(4F);
XX4 represents Asn or 2-amino-3-ureidopropionic acid;
XX5 represents Thr;
XX6 represents Phe, Cha, Phe(3F) or Phe(4F);
AzaGly represents azaglycine;
XX8 represents Leu or Ala(cPr);
XX9 represents Arg or Arg(Me); and,
XX10 represents Trp), or a salt thereof.

In the metastin derivatives, all compounds wherein the groups shown by the respective symbols described above are optionally combined are preferably used. The compounds shown by the following compound numbers are also preferably used.

Compound No. 708: des(1)-Ac-[D-Tyr2,D-Trp3,Thr5,AzaGly7,D-Arg9,Trp10]MS10 Ac-D-Tyr-D-Trp-Asn-Thr-Phe-AzaGly-Leu-D-Arg-Trp-NH$_2$ Compound No. 709: des(1-3)-Ac-[Thr5,AzaGly7,Arg(Me)9,Trp10]MS10 Ac-Asn-Thr-Phe-AzaGly-Leu-Arg(Me)-Trp-NH$_2$ (SEQ ID NO: 23)

Compound No. 710: des(1-3)-Decanoyl-[Thr5,AzaGly7,Arg(Me)9,Trp10]MS10 Decanoyl-Asn-Thr-Phe-AzaGly-Leu-Arg(Me)-Trp-NH$_2$ (SEQ ID NO: 24)

Compound No. 712: des(1-2)-[Acp3,Thr5,AzaGly7,Arg(Me)9,Trp10]MS10 Acp-Asn-Thr-Phe-AzaGly-Leu-Arg(Me)-Trp-NH$_2$ (SEQ ID NO: 25)

Compound No. 713: des(1-2)-Ac-[Acp3,Thr5,AzaGly7,Arg(Me)9,Trp10]MS10 Ac-Acp-Asn-Thr-Phe-AzaGly-Leu-Arg(Me)-Trp-NH$_2$ (SEQ ID NO: 26)

Compound No. 714: des(1)-Ac-[D-Tyr2,D-Trp3,Asp(NHPen)4,Thr5,AzaGly7,Arg(Me)9,Trp10]MS10 Ac-D-Tyr-D-Trp-Asp(NHPen)-Thr-Phe-AzaGly-Leu-Arg(Me)-Trp-NH$_2$ Compound No. 715: des(1)-Ac-[D-Tyr2,D-Trp3,Asp(NHcPr)4,Thr5,AzaGly7,Arg(Me)9,Trp10]MS10 Ac-D-Tyr-D-Trp-Asp(NHcPr)-Thr-Phe-AzaGly-Leu-Arg(Me)-Trp-NH$_2$ Compound No. 716: des(1)-Ac-[D-Tyr2,D-Trp3,Asp(NHBzl)4,Thr5,AzaGly7,Arg(Me)9,Trp10]MS10 Ac-D-Tyr-D-Trp-Asp(NHBzl)-Thr-Phe-AzaGly-Leu-Arg(Me)-Trp-NH$_2$ Compound No. 717: des(1)-Ac-[D-Tyr2,D-Trp3,Alb4,Thr5,AzaGly7,Arg(Me)9,Trp10]MS10 Ac-D-Tyr-D-Trp-Alb-Thr-Phe-AzaGly-Leu-Arg(Me)-Trp-NH$_2$ Compound No. 718: des(1)-Ac-[D-Tyr2,D-Pya(4)3,Alb4, Thr5,AzaGly7,Arg(Me)9,Trp10]MS10 Ac-D-Tyr-D-Pya(4)-Alb-Thr-Phe-AzaGly-Leu-Arg(Me)-Trp-NH$_2$ Compound No. 719: des(1)-Ac-[D-Tyr2,D-Trp3,D-Pro5, AzaGly7,Arg(Me)9,Trp10]MS10 Ac-D-Tyr-D-Trp-Asn-D-Pro-Phe-AzaGly-Leu-Arg(Me)-Trp-NH$_2$ Compound No. 720: des(1)-Ac-[D-Tyr2,Aze(2)3,Thr5,AzaGly7,Arg(Me)9,Trp10]MS10 Ac-D-Tyr-Aze(2)-Asn-Thr-Phe-AzaGly-Leu-Arg(Me)-Trp-NH$_2$ Compound No. 721: des(1)-Ac-[D-Tyr2,Pic(2)3,Thr5,AzaGly7,Arg(Me)9,Trp10]MS10 Ac-D-Tyr-Pic(2)-Asn-Thr-Phe-AzaGly-Leu-Arg(Me)-Trp-NH$_2$ Compound No. 722: des(1)-Ac-[D-Tyr2,Pic(3)3,Thr5,AzaGly7,Arg(Me)9,Trp10]MS10 Ac-D-Tyr-Pic(3)-Asn-Thr-Phe-AzaGly-Leu-Arg(Me)-Trp-NH$_2$ Compound No. 723: des(1)-Ac-[D-Tyr2,Hyp3,Thr5,AzaGly7,Arg(Me)9,Trp10]MS10 Ac-D-Tyr-Hyp-Asn-Thr-Phe-AzaGly-Leu-Arg(Me)-Trp-NH$_2$ Compound No. 724: des(1)-Ac-[D-Tyr2,Thz3,Thr5,AzaGly7,Arg(Me)9,Trp10]MS10 Ac-D-Tyr-Thz-Asn-Thr-Phe-AzaGly-Leu-Arg(Me)-Trp-NH$_2$ Compound No. 725: des(1)-Ac-[D-Tyr2,NMeAla3,Thr5,AzaGly7,Arg(Me)9,Trp10]MS10 Ac-D-Tyr-NMeAla-Asn-Thr-Phe-AzaGly-Leu-Arg(Me)-Trp-NH$_2$ Compound No. 726: des(1)-Ac-[D-Tyr2,Gly3,Thr5,AzaGly7,Arg(Me)9,Trp10]MS10 Ac-D-Tyr-Gly-Asn-Thr-Phe-AzaGly-Leu-Arg(Me)-Trp-NH$_2$ Compound No. 727: des(1)-Ac-[D-Tyr2,Aib3,Thr5,AzaGly7,Arg(Me)9,Trp10]MS10 Ac-D-Tyr-Aib-Asn-Thr-Phe-AzaGly-Leu-Arg(Me)-Trp-NH$_2$ Compound No. 728: des(1)-Ac-[D-Tyr2,Abz(2)3,Thr5,AzaGly7,Arg(Me)9,Trp10]MS10 Ac-D-Tyr-Abz(2)-Asn-Thr-Phe-AzaGly-Leu-Arg(Me)-Trp-NH$_2$ Compound No. 730: des(1)-Ac-[D-Tyr2,Aze(3)3,Thr5,AzaGly7,Arg(Me)9,Trp10]MS10 Ac-D-Tyr-Aze(3)-Asn-Thr-Phe-AzaGly-Leu-Arg(Me)-Trp-NH$_2$ Compound No. 731:des(1)-Ac-[D-Tyr2,Sar3,Thr5,AzaGly7, Arg(Me)9,Trp10]MS10 Ac-D-Tyr-Sar-Asn-Thr-Phe-AzaGly-Leu-Arg(Me)-Trp-NH$_2$ Compound No. 732: des(1)-Ac-[D-Tyr2,D-NMeAla3,Thr5, AzaGly7,Arg(Me)9,Trp10]MS10 Ac-D-Tyr-D-NMeAla-Asn-Thr-Phe-AzaGly-Leu-Arg(Me)-Trp-NH$_2$ Compound No. 734: des(1)-Ac-[D-Tyr2,Izc3,Thr5,AzaGly7, Arg(Me)9,Trp10]MS10 Ac-D-Tyr-Izc-Asn-Thr-Phe-AzaGly-Leu-Arg(Me)-Trp-NH$_2$ Compound No. 735: des(1)-Ac-[D-Tyr2,D-Asp3,Thr5,AzaGly7,Arg(Me)9,Trp10]MS10 Ac-D-Tyr-D-Asp-Asn-Thr-Phe-AzaGly-Leu-Arg(Me)-Trp-NH$_2$ Compound No. 736: des(1)-Ac-[D-Tyr2,D-Dap3,Thr5,AzaGly7,Arg(Me)9,Trp10]MS10 Ac-D-Tyr-D-Dap-Asn-Thr-Phe-AzaGly-Leu-Arg(Me)-Trp-NH$_2$ Compound No. 737: des(1)-Ac-[D-Tyr2,D-Ser3,Thr5,AzaGly7,Arg(Me)9,Trp10]MS10 Ac-D-Tyr-D-Ser-Asn-Thr-Phe-AzaGly-Leu-Arg(Me)-Trp-NH$_2$ Compound No. 738: des(1)-Ac-[D-Tyr2,D-Gln3,Thr5,AzaGly7,Arg(Me)9,Trp10]MS10 Ac-D-Tyr-D-Gln-Asn-Thr-Phe-AzaGly-Leu-Arg(Me)-Trp-NH$_2$ Compound No. 739: des(1)-Ac-[D-Tyr2,D-His3,Thr5,AzaGly7,Arg(Me)9,Trp10]MS10 Ac-D-Tyr-D-His-Asn-Thr-Phe-AzaGly-Leu-Arg(Me)-Trp-NH$_2$ Compound No. 740: des(1)-Ac-[D-Tyr2,D-Trp3,Dab4,Thr5, AzaGly7,Arg(Me)9,Trp10]MS10 Ac-D-Tyr-D-Trp-Dab-Thr-Phe-AzaGly-Leu-Arg(Me)-Trp-NH$_2$ Compound No. 742: des(1)-Ac-[D-Tyr2,Ala3,Thr5,AzaGly7,Arg(Me)9,Trp10]MS10 Ac-D-Tyr-Ala-Asn-Thr-Phe-AzaGly-Leu-Arg(Me)-Trp-NH$_2$ Compound No. 743: des(1)-Ac-[D-Tyr2,Leu3,Thr5,AzaGly7,Arg(Me)9,Trp10]MS10 Ac-D-Tyr-Leu-Asn-Thr-Phe-AzaGly-Leu-Arg(Me)-Trp-NH$_2$ Compound No. 744: des(1)-Ac-[D-Tyr2, Ser3,Thr5,AzaGly7,Arg(Me)9,Trp10]MS10 Ac-D-Tyr-Ser-Asn-Thr-Phe-AzaGly-Leu-Arg(Me)-Trp-NH$_2$ Compound No. 745: des(1)-Ac-[D-Tyr2,Lys3,Thr5,AzaGly7,Arg(Me)9,Trp10]MS10 Ac-D-Tyr-Lys-Asn-Thr-Phe-AzaGly-Leu-Arg(Me)-Trp-NH$_2$ Compound No. 746: des(1)-Ac-[D-Tyr2,Glu3,Thr5,AzaGly7,Arg(Me)9,Trp10]MS10 Ac-D-Tyr-Glu-Asn-Thr-Phe-AzaGly-Leu-Arg(Me)-Trp-NH$_2$ Compound No. 747: des(1)-Ac-[D-Tyr2,β-Ala3,Thr5,AzaGly7,Arg(Me)9,Trp10]MS10 Ac-D-Tyr-β-Ala-Asn-Thr-Phe-AzaGly-Leu-Arg(Me)-Trp-NH$_2$ Compound No. 748: des(1)-Ac-[D-Tyr2,D-Trp3,Thr5,Phe(4Cl)6,AzaGly7,Arg(Me)9,Trp10]MS10 Ac-D-Tyr-D-Trp-Asn-Thr-Phe(4Cl)-AzaGly-Leu-Arg(Me)-Trp-NH$_2$ Compound No. 749: des(1)-Ac-[D-Tyr2,D-Trp3,Thr5,Phe(2F)6,AzaGly7,Arg(Me)9,Trp10]MS10 Ac-D-Tyr-D-Trp-Asn-Thr-Phe(2F)-AzaGly-Leu-Arg(Me)-Trp-NH$_2$ Compound No. 750: des(1)-Ac-[D-Tyr2,D-Trp3,Thr5,Phe(3F)6,AzaGly7,Arg(Me)9,Trp10]MS10 Ac-D-Tyr-D-Trp-Asn-Thr-Phe(3F)-AzaGly-Leu-Arg(Me)-Trp-NH$_2$ Compound No. 754: des(1)-Ac-[D-Tyr2,Lys3,Thr5,Phe(2F)6,AzaGly7,Arg(Me)9,Trp10]MS10 Ac-D-Tyr-Lys-Asn-Thr-Phe(2F)-AzaGly-Leu-Arg(Me)-Trp-NH$_2$ Compound No. 755: des(1)-Ac-[D-Tyr2,Glu3,Thr5,Phe(2F)6,AzaGly7,Arg(Me)9,Trp10]MS10 Ac-D-Tyr-Glu-Asn-Thr-Phe(2F)-AzaGly-Leu-Arg(Me)-Trp-NH$_2$ Compound No. 756: des(1)-Ac-[D-Tyr2,Lys3,Thr5,Phe(3F)6,AzaGly7,Arg(Me)9,Trp10]MS10 Ac-D-Tyr-Lys-Asn-Thr-Phe(3F)-AzaGly-Leu-Arg(Me)-Trp-NH$_2$ Compound No. 757: des(1)-Ac-[D-Tyr2,Glu3,Thr5,Phe(3F)6,AzaGly7,Arg(Me)9,Trp10]MS10 Ac-D-Tyr-Glu-Asn-Thr-Phe(3F)-AzaGly-Leu-Arg(Me)-Trp-NH$_2$ Compound No. 758: des(1)-Ac-[D-Tyr2,Lys3,Thr5,Phe(4Cl)6,AzaGly7,Arg(Me)9,Trp10]MS10 Ac-D-Tyr-Lys-Asn-Thr-Phe(4Cl)-AzaGly-Leu-Arg(Me)-Trp-NH$_2$ Compound No. 759: des(1)-Ac-[D-Tyr2,Glu3,Thr5,Phe(4Cl)6,AzaGly7,Arg(Me)9,Trp10]MS10 Ac-D-Tyr-Glu-Asn-Thr-Phe(4Cl)-AzaGly-Leu-Arg(Me)-Trp-NH$_2$ Compound No. 760: des(1)-Ac-[D-Tyr2,Pzc(2)3,Thr5,AzaGly7,Arg(Me)9,Trp10]MS10 Ac-D-Tyr-Pzc(2)-Asn-Thr-Phe-AzaGly-Leu-Arg(Me)-Trp-NH$_2$ Compound No. 763: des(1)-Ac-[D-Tyr2,Hyp3,Thr5,Phe(2F)6,AzaGly7,Arg(Me)9,Trp10]MS10 Ac-D-Tyr-Hyp-Asn-Thr-Phe(2F)-AzaGly-Leu-Arg(Me)-Trp-NH$_2$ Compound No. 764: des(1)-Ac-[D-Tyr2,Trp3,Thr5,Phe(2F)6,AzaGly7,Arg(Me)9,Trp10]MS10 Ac-D-Tyr-Trp-Asn-Thr-Phe(2F)-AzaGly-Leu-Arg(Me)-Trp-NH$_2$ Compound No. 765: des(1)-Ac-[D-Tyr2,Hyp3,Thr5,Phe(3F)6,AzaGly7,Arg(Me)9,Trp10]MS10 Ac-D-Tyr-Hyp-Asn-Thr-Phe(3F)-AzaGly-Leu-Arg(Me)-Trp-NH$_2$ Compound No. 766: des(1)-Ac-[D-Tyr2,Trp3,Thr5,Phe(3F)$_6$,AzaGly7,Arg(Me)9,Trp10]MS10 Ac-D-Tyr-Trp-Asn-Thr-Phe(3F)-AzaGly-Leu-Arg(Me)-Trp-NH$_2$ Compound No. 767: des(1)-Ac-[D-Tyr2,Hyp3,Thr5,Phe(4Cl)6,AzaGly7,Arg(Me)9,Trp10]MS10 Ac-D-Tyr-Hyp-Asn-Thr-Phe(4Cl)-AzaGly-Leu-Arg(Me)-Trp-NH$_2$ Compound No. 768: des(1)-Ac-[D-Tyr2,Trp3,Thr5,Phe(4Cl)6,AzaGly7,Arg(Me)9,Trp10]MS10 Ac-D-Tyr-Trp-Asn-Thr-Phe(4Cl)-AzaGly-Leu-Arg(Me)-Trp-NH$_2$ Compound No. 769: des(1)-Ac-[D-Tyr2,Gly3,Thr5,Phe(4Cl)6,AzaGly7,Arg(Me)9,Trp10]MS10 Ac-D-Tyr-Gly-Asn-Thr-Phe(4Cl)-AzaGly-Leu-Arg(Me)-Trp-NH$_2$ Compound No. 770: des(1)-Ac-[D-Tyr2,Aib3,Thr5,Phe(4Cl)6,AzaGly7,Arg(Me)9,Trp10]MS10 Ac-D-Tyr-Aib-Asn-Thr-Phe(4Cl)-AzaGly-Leu-Arg(Me)-Trp-NH$_2$
Compound No. 771: des(1)-Ac-[D-Tyr2,Orn3,Thr5,AzaGly7,Arg(Me)9,Trp10]MS10 Ac-D-Tyr-Orn-Asn-Thr-Phe-AzaGly-Leu-Arg(Me)-Trp-NH$_2$
Compound No. 772: des(1)-Ac-[D-Tyr2,Thr3,Thr5,AzaGly7,Arg(Me)9,Trp10]MS10 Ac-D-Tyr-Thr-Asn-Thr-Phe-AzaGly-Leu-Arg(Me)-Trp-NH$_2$
Compound No. 773: des(1)-Ac-[D-Tyr2,His(3Me)3,Thr5,AzaGly7,Arg(Me)9,Trp10]MS10 Ac-D-Tyr-His(3Me)-Asn-Thr-Phe-AzaGly-Leu-Arg(Me)-Trp-NH$_2$
Compound No. 774: des(1)-Ac-[D-Tyr2,DL-Ala(Pip)3,Thr5,AzaGly7,Arg(Me)9,Trp10]MS10 Ac-D-Tyr-DL-Ala(Pip)-Asn-Thr-Phe-AzaGly-Leu-Arg(Me)-Trp-NH$_2$
Compound No. 775: des(1)-Ac-[D-Tyr2,Tyr(PO$_3$H$_2$)3,Thr5,AzaGly7,Arg(Me)9,Trp10]MS10 Ac-D-Tyr-Tyr(PO$_3$H$_2$)-Asn-Thr-Phe-AzaGly-Leu-Arg(Me)-Trp-NH$_2$
Compound No. 776: des(1)-Glycoloyl-[D-Tyr2,Hyp3,Thr5,AzaGly7,Arg(Me)9,Trp10]MS10 Glycoloyl-D-Tyr-Hyp-Asn-Thr-Phe-AzaGly-Leu-Arg(Me)-Trp-NH$_2$
Compound No. 777: des(1-2)-Ac-[D-Tyr3,Thr5,AzaGly7,Arg(Me)9,Trp10]MS10 Ac-D-Tyr-Asn-Thr-Phe-AzaGly-Leu-Arg(Me)-Trp-NH$_2$
Compound No. 780: des(1)-Ac-[D-Tyr2,Pro(4NH$_2$)3,Thr5,AzaGly7,Arg(Me)9,Trp10]MS10 Ac-D-Tyr-Pro(4NH$_2$)-Asn-Thr-Phe-AzaGly-Leu-Arg(Me)-Trp-NH$_2$
Compound No. 781: des(1)-Ac-[D-Tyr2,Hyp(Bzl)3,Thr5,AzaGly7,Arg(Me)9,Trp10]MS10 Ac-D-Tyr-Hyp(Bzl)-Asn-Thr-Phe-AzaGly-Leu-Arg(Me)-Trp-NH$_2$
Compound No. 782: des(1)-Ac-[D-Tyr2,D-NMePhe3,Thr5,AzaGly7,Arg(Me)9,Trp10]MS10 Ac-D-Tyr-D-NMePhe-Asn-Thr-Phe-AzaGly-Leu-Arg(Me)-Trp-NH$_2$
Compound No. 783: des(1)-Ac-[D-Tyr2,Gly3,Thr5,Phe(2F)6,AzaGly7,Arg(Me)9,Trp10]MS10 Ac-D-Tyr-Gly-Asn-Thr-Phe(2F)-AzaGly-Leu-Arg(Me)-Trp-NH$_2$
Compound No. 784: des(1)-Ac-[D-Tyr2,Aib3,Thr5,Phe(2F)6,AzaGly7,Arg(Me)9,Trp10]MS10 Ac-D-Tyr-Aib-Asn-Thr-Phe(2F)-AzaGly-Leu-Arg(Me)-Trp-NH$_2$
Compound No. 785: des(1)-Ac-[D-Tyr2,Gly3,Thr5,Phe(3F)6,AzaGly7,Arg(Me)9,Trp10]MS10 Ac-D-Tyr-Gly-Asn-Thr-Phe(3F)-AzaGly-Leu-Arg(Me)-Trp-NH$_2$
Compound No. 786: des(1)-Ac-[D-Tyr2,Aib3,Thr5,Phe(3F)6,AzaGly7,Arg(Me)9,Trp10]MS10 Ac-D-Tyr-Aib-Asn-Thr-Phe(3F)-AzaGly-Leu-Arg(Me)-Trp-NH$_2$
Compound No. 787: des(1)-Ac-[D-Tyr2,Hyp3,Thr5,Phe(4F)6,AzaGly7,Arg(Me)9,Trp10]MS10 Ac-D-Tyr-Hyp-Asn-Thr-Phe(4F)-AzaGly-Leu-Arg(Me)-Trp-NH$_2$
Compound No. 788: des(1)-Ac-[D-Tyr2,Glu3,Thr5,Phe(4F)6,AzaGly7,Arg(Me)9,Trp10]MS10 Ac-D-Tyr-Glu-Asn-Thr-Phe(4F)-AzaGly-Leu-Arg(Me)-Trp-NH$_2$
Compound No. 789: des(1)-Ac-[D-Tyr2,Lys3,Thr5,Phe(4F)6,AzaGly7,Arg(Me)9,Trp10]MS10 Ac-D-Tyr-Lys-Asn-Thr-Phe(4F)-AzaGly-Leu-Arg(Me)-Trp-NH$_2$
Compound No. 790: des(1)-Ac-[D-Tyr2,Gly3,Thr5,Phe(4F)6,AzaGly7,Arg(Me)9,Trp10]MS10 Ac-D-Tyr-Gly-Asn-Thr-Phe(4F)-AzaGly-Leu-Arg(Me)-Trp-NH$_2$
Compound No. 791: des(1)-Ac-[D-Tyr2,Aib3,Thr5,Phe(4F)6,AzaGly7,Arg(Me)9,Trp10]MS10 Ac-D-Tyr-Aib-Asn-Thr-Phe(4F)-AzaGly-Leu-Arg(Me)-Trp-NH$_2$
Compound No. 794: des(1)-Ac-[D-Tyr2,Hyp3,Thr5,D-Phe6,AzaGly7,Arg(Me)9,Trp10]MS10 Ac-D-Tyr-Hyp-Asn-Thr-D-Phe-AzaGly-Leu-Arg(Me)-Trp-NH$_2$
Compound No. 797: des(1)-Ac-[D-Tyr2,Hyp3,Thr5,AzaGly7,Trp10]MS10 Ac-D-Tyr-Hyp-Asn-Thr-Phe-AzaGly-Leu-Arg-Trp-NH$_2$
Compound No. 800: des(1)-Ac-[D-Tyr2,Hyp3,Alb4,Thr5,AzaGly7,Arg(Me)9,Trp10]MS10 Ac-D-Tyr-Hyp-Alb-Thr-Phe-AzaGly-Leu-Arg(Me)-Trp-NH$_2$
Compound No. 801: des(1-5)-4-[Bis-(2-Pyridylmethyl)aminomethyl]benzoyl-[AzaGly7,Arg(Me)9,Trp10]MS10 4-[Bis-(2-Pyridylmethyl)aminomethyl]benzoyl-Phe-AzaGly-Leu-Arg(Me)-Trp-NH$_2$ (SEQ ID NO: 27)
Compound No. 809: des(1)-Ac-[D-Tyr2,Hyp3,NMeSer5,AzaGly7,Arg(Me)9,Trp10]MS10 Ac-D-Tyr-Hyp-Asn-NMeSer-Phe-AzaGly-Leu-Arg(Me)-Trp-NH$_2$
Compound No. 810: des(1)-Ac-[D-Tyr2,Hyp3,Hyp5,AzaGly7,Arg(Me)9,Trp10]MS10 Ac-D-Tyr-Hyp-Asn-Hyp-Phe-AzaGly-Leu-Arg(Me)-Trp-NH$_2$
Compound No. 813: des(1)-Ac-[D-Tyr2,Hyp3,Gly5,AzaGly7,Arg(Me)9,Trp10]MS10 Ac-D-Tyr-Hyp-Asn-Gly-Phe-AzaGly-Leu-Arg(Me)-Trp-NH$_2$
Compound No. 814: des(1)-Ac-[D-Tyr2,Hyp3,Ala5,AzaGly7,Arg(Me)9,Trp10]MS10 Ac-D-Tyr-Hyp-Asn-Ala-Phe-AzaGly-Leu-Arg(Me)-Trp-NH$_2$
Compound No. 815: des(1)-Ac-[D-Tyr2,Hyp3,D-Ala5,AzaGly7,Arg(Me)9,Trp10]MS10 Ac-D-Tyr-Hyp-Asn-D-Ala-Phe-AzaGly-Leu-Arg(Me)-Trp-NH$_2$
Compound No. 816: des(1)-Ac-[D-Tyr2,Hyp3,His4,Thr5,AzaGly7,Arg(Me)9,Trp10]MS10 Ac-D-Tyr-Hyp-His-Thr-Phe-AzaGly-Leu-Arg(Me)-Trp-NH$_2$
Compound No. 843: des(1)-Ac-[D-Tyr2,Hyp3,Gln4,Thr5,AzaGly7,Arg(Me)9,Trp10]MS10 Ac-D-Tyr-Hyp-Gln-Thr-Phe-AzaGly-Leu-Arg(Me)-Trp-NH$_2$
Compound No. 844: des(1)-Ac-[D-Tyr2,Hyp3,D-Asn4,Thr5,AzaGly7,Arg(Me)9,Trp10]MS10 Ac-D-Tyr-Hyp-D-Asn-Thr-Phe-AzaGly-Leu-Arg(Me)-Trp-NH$_2$
Compound No. 845: des(1)-Ac-[D-Tyr2,Hyp3,Cit4,Thr5,AzaGly7,Arg(Me)9,Trp10]MS10 Ac-D-Tyr-Hyp-Cit-Thr-Phe-AzaGly-Leu-Arg(Me)-Trp-NH$_2$
Compound No. 846: des(1)-Ac-[D-Tyr2,Hyp3,D-Thr5,AzaGly7,Arg(Me)9,Trp10]MS10 Ac-D-Tyr-Hyp-Asn-D-Thr-Phe-AzaGly-Leu-Arg(Me)-Trp-NH$_2$
Compound No. 856: des(1)-Ac-[D-Tyr2,Hyp3,Thr5,AzaGly7,Ala(cPr)8,Arg(Me)9,Trp10]MS10 Ac-D-Tyr-Hyp-Asn-Thr-Phe-AzaGly-Ala(cPr)-Arg(Me)-Trp-NH$_2$
Compound No. 860: des(1-5)-4-Ureidobenzoyl-[AzaGly7,Arg(Me)9,Trp10]MS10 4-Ureidobenzoyl-Phe-AzaGly-Leu-Arg(Me)-Trp-NH$_2$ (SEQ ID NO: 28)
Compound No. 861: des(1)-Ac-[D-Tyr2,Hyp3,Arg4,Thr5,AzaGly7,Arg(Me)9,Trp10]MS10 Ac-D-Tyr-Hyp-Arg-Thr-Phe-AzaGly-Leu-Arg(Me)-Trp-NH$_2$
Compound No. 862: des(1)-Ac-[D-Tyr2,Hyp3,Gly4,Thr5,AzaGly7,Arg(Me)9,Trp10]MS10 Ac-D-Tyr-Hyp-Gly-Thr-Phe-AzaGly-Leu-Arg(Me)-Trp-NH$_2$
Compound No. 863: des(1)-Ac-[D-Tyr2,Hyp3,Dap4,Thr5,AzaGly7,Arg(Me)9,Trp10]MS10 Ac-D-Tyr-Hyp-Dap-Thr-Phe-AzaGly-Leu-Arg(Me)-Trp-NH$_2$
Compound No. 864: des(1)-Ac-[D-Tyr2,Hyp3,Dab4,Thr5,AzaGly7,Arg(Me)9,Trp10]MS10 Ac-D-Tyr-Hyp-Dab-Thr-Phe-AzaGly-Leu-Arg(Me)-Trp-NH$_2$
Compound No. 868: des(1)-Ac-[D-Tyr2,Hyp3,Thr5, αMePhe6,AzaGly7,Arg(Me)9, Trp10]MS10 Ac-D-Tyr-Hyp-Asn-Thr-αMePhe-AzaGly-Leu-Arg(Me)-Trp-NH$_2$
Compound No. 870: des(1)-Ac-[D-Tyr2,Hyp3,Thr5,Phe(2Me)6,AzaGly7,Arg(Me)9,Trp10]MS10 Ac-D-Tyr-Hyp-Asn-Thr-Phe(2Me)-AzaGly-Leu-Arg(Me)-Trp-NH$_2$
Compound No. 872: des(1)-Ac-[D-Tyr2,Hyp3,Thr5,Phe(3Me)6,AzaGly7,Arg(Me)9,Trp10]MS10 Ac-D-Tyr-Hyp-Asn-Thr-Phe(3Me)-AzaGly-Leu-Arg(Me)-Trp-NH$_2$
Compound No. 874: des(1)-Ac-[D-Tyr2,Hyp3,Thr5,Phe(4Me)6,AzaGly7,Arg(Me)9,Trp10]MS10 Ac-D-Tyr-Hyp-Asn-Thr-Phe(4Me)-AzaGly-Leu-Arg(Me)-Trp-NH$_2$ Compound No. 877: des(1)-Ac-[D-Tyr2,Hyp3,Thr5,threo-Ser(3Phenyl)6,AzaGly7,Arg(Me)9,Trp10]MS10 Ac-D-Tyr-Hyp-Asn-Thr-threo-Ser(3Phenyl)-AzaGly-Leu-Arg(Me)-Trp-NH$_2$ Compound No. 882: des(1)-Ac-[D-Tyr2,Hyp3,Thr5,erythro-Ser(3Phenyl)6,AzaGly7,Arg(Me)9,Trp 10]MS10 Ac-D-Tyr-Hyp-Asn-Thr-erythro-Ser(3Phenyl)-AzaGly-Leu-Arg(Me)-Trp-NH$_2$ Compound No. 886: des(1)-Ac-[D-Tyr2,Hyp3,Nva4,Thr5,AzaGly7,Arg(Me)9,Trp10]MS10 Ac-D-Tyr-Hyp-Nva-Thr-Phe-AzaGly-Leu-Arg(Me)-Trp-NH$_2$ Compound No. 887: des(1-2)-Ac-[Hyp3,Thr5,AzaGly7,Arg(Me)9,Trp10]MS10 Ac-Hyp-Asn-Thr-Phe-AzaGly-Leu-Arg(Me)-Trp-NH$_2$ (SEQ ID NO: 29)

Compound No. 888: des(1-2)-3-(p-Hydroxyphenyl)propionyl)-[Hyp3,Thr5,AzaGly7,Arg(Me)9,Trp10]MS10 3-(p-Hydroxyphenyl)propionyl-Hyp-Asn-Thr-Phe-AzaGly-Leu-Arg(Me)-Trp-NH$_2$ (SEQ ID NO: 30)

Compound No. 889: des(1-2)-[pGlu3,Thr5,AzaGly7,Arg(Me)9,Trp10]MS10 pGlu-Asn-Thr-Phe-AzaGly-Leu-Arg(Me)-Trp-NH$_2$ (SEQ ID NO: 31)

Compound No. 896: des(1)-Ac-[D-Tyr2,cisHyp3,Thr5,AzaGly7,Arg(Me)9,Trp10]MS10 Ac-D-Tyr-cisHyp-Asn-Thr-Phe-AzaGly-Leu-Arg(Me)-Trp-NH$_2$ Compound No. 897: des(1)-Ac-[D-Tyr2,Pro(4F)3,Thr5,AzaGly7,Arg(Me)9,Trp10]MS10 Ac-D-Tyr-Pro(4F)-Asn-Thr-Phe-AzaGly-Leu-Arg(Me)-Trp-NH$_2$ Compound No. 899: des(1)-Ac-[Tyr2,Hyp3,Thr5,AzaGly7,Arg(Me)9,Trp10]MS10 Ac-Tyr-Hyp-Asn-Thr-Phe-AzaGly-Leu-Arg(Me)-Trp-NH$_2$ (SEQ ID NO: 32)

In particular, the compounds represented by the following compound numbers are preferred as the metastin derivatives.

Ac-D-Tyr-D-Trp-Asp(NHPen)-Thr-Phe-AzaGly-Leu-Arg(Me)-Trp-NH$_2$ (Compound No. 714),
Ac-D-Tyr-D-Trp-Asp(NHcPr)-Thr-Phe-AzaGly-Leu-Arg(Me)-Trp-NH$_2$ (Compound No. 715),
Ac-D-Tyr-D-Trp-Asp(NHBzl)-Thr-Phe-AzaGly-Leu-Arg(Me)-Trp-NH$_2$ (Compound No. 716),
Ac-D-Tyr-D-Trp-Alb-Thr-Phe-AzaGly-Leu-Arg(Me)-Trp-NH$_2$ (Compound No. 717),
Ac-D-Tyr-D-Pya(4)-Alb-Thr-Phe-AzaGly-Leu-Arg(Me)-Trp-NH$_2$ (Compound No. 718),
Ac-D-Tyr-Aze(2)-Asn-Thr-Phe-AzaGly-Leu-Arg(Me)-Trp-NH$_2$ (Compound No. 720),
Ac-D-Tyr-Pic(2)-Asn-Thr-Phe-AzaGly-Leu-Arg(Me)-Trp-NH$_2$ (Compound No. 721),
Ac-D-Tyr-Hyp-Asn-Thr-Phe-AzaGly-Leu-Arg(Me)-Trp-NH$_2$ (Compound No. 723),
Ac-D-Tyr-Thz-Asn-Thr-Phe-AzaGly-Leu-Arg(Me)-Trp-NH$_2$ (Compound No. 724),
Ac-D-Tyr-Gly-Asn-Thr-Phe-AzaGly-Leu-Arg(Me)-Trp-NH$_2$ (Compound No. 726)
Ac-D-Tyr-Alb-Asn-Thr-Phe-AzaGly-Leu-Arg(Me)-Trp-NH$_2$ (Compound No. 727),
Ac-D-Tyr-D-NMeAla-Asn-Thr-Phe-AzaGly-Leu-Arg(Me)-Trp-NH$_2$ (Compound No. 732),
Ac-D-Tyr-D-Gln-Asn-Thr-Phe-AzaGly-Leu-Arg(Me)-Trp-NH$_2$ (Compound No. 738),
Ac-D-Tyr-D-His-Asn-Thr-Phe-AzaGly-Leu-Arg(Me)-Trp-NH$_2$ (Compound No. 739),
Ac-D-Tyr-D-Trp-Dab-Thr-Phe-AzaGly-Leu-Arg(Me)-Trp-NH$_2$ (Compound No. 740),
Ac-D-Tyr-Ala-Asn-Thr-Phe-AzaGly-Leu-Arg(Me)-Trp-NH$_2$ (Compound No. 742),
Ac-D-Tyr-Leu-Asn-Thr-Phe-AzaGly-Leu-Arg(Me)-Trp-NH$_2$ (Compound No. 743),
Ac-D-Tyr-Ser-Asn-Thr-Phe-AzaGly-Leu-Arg(Me)-Trp-NH$_2$ (Compound No. 744),
Ac-D-Tyr-Lys-Asn-Thr-Phe-AzaGly-Leu-Arg(Me)-Trp-NH$_2$ (Compound No. 745),
Ac-D-Tyr-Glu-Asn-Thr-Phe-AzaGly-Leu-Arg(Me)-Trp-NH$_2$ (Compound No. 746),
Ac-D-Tyr-D-Trp-Asn-Thr-Phe(4Cl)-AzaGly-Leu-Arg(Me)-Trp-NH$_2$ (Compound No. 748),
Ac-D-Tyr-D-Trp-Asn-Thr-Phe(2F)-AzaGly-Leu-Arg(Me)-Trp-NH$_2$ (Compound No. 749),
Ac-D-Tyr-D-Trp-Asn-Thr-Phe(3F)-AzaGly-Leu-Arg(Me)-Trp-NH$_2$ (Compound No. 750),
Ac-D-Tyr-Lys-Asn-Thr-Phe(2F)-AzaGly-Leu-Arg(Me)-Trp-NH$_2$ (Compound No. 754),
Ac-D-Tyr-Glu-Asn-Thr-Phe(2F)-AzaGly-Leu-Arg(Me)-Trp-NH$_2$ (Compound No. 755),
Ac-D-Tyr-Lys-Asn-Thr-Phe(3F)-AzaGly-Leu-Arg(Me)-Trp-NH$_2$ (Compound No. 756),
Ac-D-Tyr-Glu-Asn-Thr-Phe(3F)-AzaGly-Leu-Arg(Me)-Trp-NH$_2$ (Compound No. 757),
Ac-D-Tyr-Lys-Asn-Thr-Phe(4Cl)-AzaGly-Leu-Arg(Me)-Trp-NH$_2$ (Compound No. 758),
Ac-D-Tyr-Glu-Asn-Thr-Phe(4Cl)-AzaGly-Leu-Arg(Me)-Trp-NH$_2$ (Compound No. 759),
Ac-D-Tyr-Pzc(2)-Asn-Thr-Phe-AzaGly-Leu-Arg(Me)-Trp-NH$_2$ (Compound No. 760),
Ac-D-Tyr-Hyp-Asn-Thr-Phe(2F)-AzaGly-Leu-Arg(Me)-Trp-NH$_2$ (Compound No. 763),
Ac-D-Tyr-Trp-Asn-Thr-Phe(2F)-AzaGly-Leu-Arg(Me)-Trp-NH$_2$ (Compound No. 764),
Ac-D-Tyr-Hyp-Asn-Thr-Phe(3F)-AzaGly-Leu-Arg(Me)-Trp-NH$_2$ (Compound No. 765),
Ac-D-Tyr-Trp-Asn-Thr-Phe(3F)-AzaGly-Leu-Arg(Me)-Trp-NH$_2$ (Compound No. 766),
Ac-D-Tyr-Hyp-Asn-Thr-Phe(4Cl)-AzaGly-Leu-Arg(Me)-Trp-NH$_2$ (Compound No. 767),
Ac-D-Tyr-Trp-Asn-Thr-Phe(4Cl)-AzaGly-Leu-Arg(Me)-Trp-NH$_2$ (Compound No. 768),
Ac-D-Tyr-Gly-Asn-Thr-Phe(4Cl)-AzaGly-Leu-Arg(Me)-Trp-NH$_2$ (Compound No. 769),
Ac-D-Tyr-Aib-Asn-Thr-Phe(4Cl)-AzaGly-Leu-Arg(Me)-Trp-NH$_2$ (Compound No. 770),
Ac-D-Tyr-Orn-Asn-Thr-Phe-AzaGly-Leu-Arg(Me)-Trp-NH$_2$ (Compound No. 771),
Ac-D-Tyr-Thr-Asn-Thr-Phe-AzaGly-Leu-Arg(Me)-Trp-NH$_2$ (Compound No. 772),
Ac-D-Tyr-His(3Me)-Asn-Thr-Phe-AzaGly-Leu-Arg(Me)-Trp-NH$_2$ (Compound No. 773),
Ac-D-Tyr-Tyr(PO$_3$H$_2$)-Asn-Thr-Phe-AzaGly-Leu-Arg(Me)-Trp-NH$_2$ (Compound No. 775),
Glycoloyl-D-Tyr-Hyp-Asn-Thr-Phe-AzaGly-Leu-Arg(Me)-Trp-NH$_2$ (Compound No. 776),
Ac-D-Tyr-Pro(4NH$_2$)-Asn-Thr-Phe-AzaGly-Leu-Arg(Me)-Trp-NH$_2$ (Compound No. 780),
Ac-D-Tyr-Hyp(Bzl)-Asn-Thr-Phe-AzaGly-Leu-Arg(Me)-Trp-NH$_2$ (Compound No. 781),
Ac-D-Tyr-D-NMePhe-Asn-Thr-Phe-AzaGly-Leu-Arg(Me)-Trp-NH$_2$ (Compound No. 782),
Ac-D-Tyr-Gly-Asn-Thr-Phe(2F)-AzaGly-Leu-Arg(Me)-Trp-NH$_2$ (Compound No. 783),
Ac-D-Tyr-Aib-Asn-Thr-Phe(2F)-AzaGly-Leu-Arg(Me)-Trp-NH$_2$ (Compound No. 784),
Ac-D-Tyr-Gly-Asn-Thr-Phe(3F)-AzaGly-Leu-Arg(Me)-Trp-NH$_2$ (Compound No. 785),
Ac-D-Tyr-Aib-Asn-Thr-Phe(3F)-AzaGly-Leu-Arg(Me)-Trp-NH$_2$ (Compound No. 786), Ac-D-Tyr-Hyp-Asn-Thr-Phe(4F)-AzaGly-Leu-Arg(Me)-Trp-NH$_2$ (Compound No. 787),
Ac-D-Tyr-Glu-Asn-Thr-Phe(4F)-AzaGly-Leu-Arg(Me)-Trp-NH$_2$ (Compound No. 788),
Ac-D-Tyr-Lys-Asn-Thr-Phe(4F)-AzaGly-Leu-Arg(Me)-Trp-NH$_2$ (Compound No. 789),
Ac-D-Tyr-Gly-Asn-Thr-Phe(4F)-AzaGly-Leu-Arg(Me)-Trp-NH$_2$ (Compound No. 790),
Ac-D-Tyr-Alb-Asn-Thr-Phe(4F)-AzaGly-Leu-Arg(Me)-Trp-NH$_2$ (Compound No. 791),
Ac-D-Tyr-Hyp-Asn-Thr-D-Phe-AzaGly-Leu-Arg(Me)-Trp-NH$_2$ (Compound No. 794),
Ac-D-Tyr-Hyp-Asn-Thr-Phe-AzaGly-Leu-Arg-Trp-NH$_2$ (Compound No. 797),
Ac-D-Tyr-Hyp-Alb-Thr-Phe-AzaGly-Leu-Arg(Me)-Trp-NH$_2$ (Compound No. 800),
4-[Bis-(2-Pyridyl methyl)aminomethyl]benzoyl-Phe-AzaGly-Leu-Arg(Me)-Trp-NH$_2$ (SEQ ID NO: 27) (Compound No. 801),
Ac-D-Tyr-Hyp-Asn-NMeSer-Phe-AzaGly-Leu-Arg(Me)-Trp-NH$_2$ (Compound No. 809),
Ac-D-Tyr-Hyp-Asn-Hyp-Phe-AzaGly-Leu-Arg(Me)-Trp-NH$_2$ (Compound No. 810),
Ac-D-Tyr-Hyp-Asn-Gly-Phe-AzaGly-Leu-Arg(Me)-Trp-NH$_2$ (Compound No. 813),
Ac-D-Tyr-Hyp-Asn-Ala-Phe-AzaGly-Leu-Arg(Me)-Trp-NH$_2$ (Compound No. 814),
Ac-D-Tyr-Hyp-Asn-D-Ala-Phe-AzaGly-Leu-Arg(Me)-Trp-NH$_2$ (Compound No. 815),
Ac-D-Tyr-Hyp-His-Thr-Phe-AzaGly-Leu-Arg(Me)-Trp-NH$_2$ (Compound No. 816),
Ac-D-Tyr-Hyp-Gln-Thr-Phe-AzaGly-Leu-Arg(Me)-Trp-NH$_2$ (Compound No. 843),
Ac-D-Tyr-Hyp-D-Asn-Thr-Phe-AzaGly-Leu-Arg(Me)-Trp-NH$_2$ (Compound No. 844),
Ac-D-Tyr-Hyp-Cit-Thr-Phe-AzaGly-Leu-Arg(Me)-Trp-NH$_2$ (Compound No. 845),
Ac-D-Tyr-Hyp-Asn-D-Thr-Phe-AzaGly-Leu-Arg(Me)-Trp-NH$_2$ (Compound No. 846),
Compound No. 856: des(1)-Ac-[D-Tyr2,Hyp3,Thr5,AzaGly7,Ala(cPr)8,Arg(Me)9,Trp10]MS10 Ac-D-Tyr-Hyp-Asn-Thr-Phe-AzaGly-Ala(cPr)-Arg(Me)-Trp-NH$_2$
Compound No. 860: des(1-5)-4-Ureidobenzoyl-[AzaGly7,Arg(Me)9,Trp10]MS10 4-Ureidobenzoyl-Phe-AzaGly-Leu-Arg(Me)-Trp-NH$_2$ (SEQ ID NO: 28)
Compound No. 861: des(1)-Ac-[D-Tyr2,Hyp3,Arg4,Thr5,AzaGly7,Arg(Me)9,Trp10]MS10 Ac-D-Tyr-Hyp-Arg-Thr-Phe-AzaGly-Leu-Arg(Me)-Trp-NH$_2$
Compound No. 862: des(1)-Ac-[D-Tyr2,Hyp3,Gly4,Thr5,AzaGly7,Arg(Me)9,Trp10]MS10 Ac-D-Tyr-Hyp-Gly-Thr-Phe-AzaGly-Leu-Arg(Me)-Trp-NH$_2$.
Compound No. 863: des(1)-Ac-[D-Tyr2,Hyp3,Dap4,Thr5,AzaGly7,Arg(Me)9,Trp10]MS10 Ac-D-Tyr-Hyp-Dap-Thr-Phe-AzaGly-Leu-Arg(Me)-Trp-NH$_2$
Compound No. 864: des(1)-Ac-[D-Tyr2,Hyp3,Dab4,Thr5,AzaGly7,Arg(Me)9,Trp10]MS10 Ac-D-Tyr-Hyp-Dab-Thr-Phe-AzaGly-Leu-Arg(Me)-Trp-NH$_2$
Compound No. 868: des(1)-Ac-[D-Tyr2,Hyp3,Thr5, αMePhe6,AzaGly7,Arg(Me)9, Trp10]MS10 Ac-D-Tyr-Hyp-Asn-Thr-αMePhe-AzaGly-Leu-Arg(Me)-Trp-NH$_2$
Compound No. 870: des(1)-Ac-[D-Tyr2,Hyp3,Thr5,Phe(2Me)6,AzaGly7,Arg(Me)9,Trp10]MS10 Ac-D-Tyr-Hyp-Asn-Thr-Phe(2Me)-AzaGly-Leu-Arg(Me)-Trp-NH$_2$
Compound No. 872: des(1)-Ac-[D-Tyr2,Hyp3,Thr5,Phe(3Me)6,AzaGly7,Arg(Me)9,Trp10]MS10 Ac-D-Tyr-Hyp-Asn-Thr-Phe(3 Me)-AzaGly-Leu-Arg(Me)-Trp-NH$_2$
Compound No. 874: des(1)-Ac-[D-Tyr2,Hyp3,Thr5,Phe(4Me)6,AzaGly7,Arg(Me)9,Trp10]MS10 Ac-D-Tyr-Hyp-Asn-Thr-Phe(4Me)-AzaGly-Leu-Arg(Me)-Trp-NH$_2$
Compound No. 877: des(1)-Ac-[D-Tyr2,Hyp3,Thr5,threo-Ser(3Phenyl)6,AzaGly7,Arg(Me)9,Trp10]MS10 Ac-D-Tyr-Hyp-Asn-Thr-threo-Ser(3Phenyl)-AzaGly-Leu-Arg(Me)-Trp-NH$_2$
Compound No. 882: des(1)-Ac-[D-Tyr2,Hyp3,Thr5,erythro-Ser(3Phenyl)6,AzaGly7,Arg(Me)9,Trp10]MS10 Ac-D-Tyr-Hyp-Asn-Thr-erythro-Ser(3Phenyl)-AzaGly-Leu-Arg(Me)-Trp-NH$_2$
Compound No. 886: des(1)-Ac-[D-Tyr2,Hyp3,Nva4,Thr5,AzaGly7,Arg(Me)9,Trp10]MS10 Ac-D-Tyr-Hyp-Nva-Thr-Phe-AzaGly-Leu-Arg(Me)-Trp-NH$_2$
Compound No. 888: des(1-2)-3-(p-Hydroxyphenyl)propionyl-[Hyp3,Thr5,AzaGly7,Arg(Me)9,Trp10]MS10 3-(p-Hydroxyphenyl)propionyl-Hyp-Asn-Thr-Phe-AzaGly-Leu-Arg(Me)-Trp-NH$_2$ (SEQ ID NO: 30)
Compound No. 896: des(1)-Ac-[D-Tyr2,cisHyp3,Thr5,AzaGly7,Arg(Me)9,Trp10]MS10 Ac-D-Tyr-cisHyp-Asn-Thr-Phe-AzaGly-Leu-Arg(Me)-Trp-NH$_2$
Compound No. 897: des(1)-Ac-[D-Tyr2,Pro(4F)3,Thr5,AzaGly7,Arg(Me)9,Trp10]MS10 Ac-D-Tyr-Pro(4F)-Asn-Thr-Phe-AzaGly-Leu-Arg(Me)-Trp-NH$_2$ or
Compound No. 899: des(1)-Ac-[Tyr2,Hyp3,Thr5,AzaGly7,Arg(Me)9,Trp10]MS10 Ac-Tyr-Hyp-Asn-Thr-Phe-AzaGly-Leu-Arg(Me)-Trp-NH$_2$ (SEQ ID NO: 32).

The metastin derivatives of the present invention or their salts or prodrugs have excellent blood stability, solubility, etc., in addition to the excellent effects of suppressing cancer metastasis and cancer growth, and are useful as agents for preventing or treating cancers (for example, lung cancer, gastric cancer, liver cancer, pancreatic cancer, colorectal cancer, rectal cancer, colonic cancer, prostate cancer, ovarian cancer, cervical cancer, breast cancer, etc.). The metastin derivatives of the present invention or their salts or prodrugs have the effect of controlling pancreatic function and are useful as agents for preventing or treating pancreatic diseases (e.g., acute or chronic pancreatitis, pancreatic cancer, etc.). The metastin derivatives of the present invention or their salts or prodrugs have the effect of controlling placental function and are useful as agents for preventing or treating choriocarcinoma, hydatid mole, invasive mole, miscarriage, fetal hypoplasia, abnormal glucose metabolism, abnormal lipid metabolism or induction of delivery.

Also, the metastin derivatives of the present invention or their salts or prodrugs have the effects of increasing sugar level, promoting pancreatic glucagon secretion and promoting urine formation, and are useful as agents for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes mellitus, fatty atrophy, insulin allergy, insulinoma, arteriosclerosis, thrombotic disorders or lipotoxicity.

In addition, the metastin derivatives of the present invention or their salts or prodrugs have excellent activities of promoting gonadotropic hormone secretion, promoting sex hormone secretion, inducing ovulation or stimulating ovulation, and are useful as low toxic and stable agents, e.g., agents for improving gonadal function, agents for preventing or treating hormone-dependent cancer (e.g., prostate cancer, breast cancer, etc.), infertility, endometriosis, early puberty, myoma of the uterus, etc., agents for inducing or stimulating ovulation, gonadotropic hormone secretagogue agents, contraceptives, sex hormone secretagogue agents, or the like.

Furthermore, the metastin derivatives of the present invention or their salts or prodrugs are useful as agents for preventing or treating Alzheimer's disease, Autism, moderate cognitive impairment, etc.

The metastin derivatives of the present invention or their salts or prodrugs are useful as agents for suppressing gonadotropic hormone secretion or sex hormone secretion; down-regulating agents for gonadotropic hormone or sex hormone; down-regulating agents for human OT7T175 (metastin receptor) protein consisting of the amino acid sequence represented by SEQ ID NO: 9; agents for preventing or treating hormone-dependent cancers (e.g., prostate cancer, breast cancer, etc.; particularly, hormone-sensitive prostate cancer, hormone-sensitive prostate cancer, etc.); agents for preventing or treating endometriosis; agents for inhibiting ovarian follicular maturation; menstrual cycle-suspending agents; agents for treating myoma of the uterus; agents for treating early puberty; contraceptives, etc.

In addition, the metastin derivatives of the present invention or their salts or prodrugs are useful as agents for potentiating immunity (e.g., prophylactic agents for infection after bone-marrow transplant, agents for potentiating immunity intended for cancer, etc); immunostimulator (e.g., regeneration of the thymus, regrowth of the thymus, enhancement of T cell development, etc); agents for preventing or treating bulbospinal muscular atrophy; agents for protecting ovary; agents for preventing or treating benign prostate hypertrophy (BPH); agents for preventing or treating gender identity disorder; or agents for in vitro fertilization (IVF). In addition, they are also useful as agents for preventing or treating infertility, hypogonadism, oligospermia, azoospermia, aspermia, asthenospermia, or necrospermia. Further, they are useful for hormone-dependent diseases (e.g., sex hormone dependent cancer such as prostate cancer, uterine cancer, breast cancer, hypophysial tumor, etc.), prostate gland enlargement, endometriosis, uterine fibroid, early puberty, dysmenorrhea, amenorrhea, menstrual syndrome, multilocular ovary syndrome, postoperative relapse of the above-mentioned cancers, metastasis of the above-mentioned cancers, hypopituitarism, dwarfism (the case where the secretion of growth hormone was compromised with hyposecretion of pituitary hormone, etc.), menopausal disorder, indefinite complaint, sex hormone dependent disorders such as calcium phosphor bone metabolic disorders. It is also applicable for contraception (or infertility when rebound effects after cessation of the drug are utilized), etc.

Furthermore, metastin per se or DNA encoding metastin, etc. are also useful as agents for suppressing gonadotropic hormone secretion or sex hormone secretion; down-regulating agents for gonadotropic hormone or sex hormone; down-regulating agents for human OT7T175 (metastin receptor) protein consisting of the amino acid sequence represented by SEQ ID NO: 9; agents for preventing or treating hormone-dependent cancers (e.g., prostate cancer, breast cancer, etc.; particularly, hormone-sensitive prostate cancer, hormone-sensitive breast cancer, etc.); agents for preventing or treating endometriosis; agents for inhibiting ovarian follicular maturation; menstrual cycle-suspending agents; agents for treating myoma of the uterus; agents for treating early puberty; contraceptives, etc.

The metastin derivatives of the present invention can be prepared by publicly known methods for peptide synthesis. As the methods for peptide synthesis, for example, either solid phase synthesis or liquid phase synthesis may be used. That is, the partial peptide or amino acids that can constitute the peptide of the present invention are repeatedly condensed with the remaining part to give the product having a desired sequence. Where the product has protecting groups, these protecting groups are removed to give the desired peptide. Publicly known methods for condensation and removal of the protecting groups are described in (1) to (5) below.

(1) M. Bodanszky & M. A. Ondetti: Peptide Synthesis, Interscience Publishers, New York (1966)
(2) Schroeder & Luebke: The Peptide, Academic Press, New York (1965)
(3) Nobuo Izumiya, et al.: *Peptide Gosei-no-Kiso to Jikken* (Basics and experiments of peptide synthesis), published by Maruzen Co. (1975)
(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)
(5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the peptide of the present invention. When the peptide obtained by the above methods is in a free form, the peptide can be converted into an appropriate salt by a publicly known method, conversely when the peptide is obtained in a salt form, it can be converted into its free form by publicly known methods.

For condensation of the protected amino acids or peptides, a variety of activation reagents for peptide synthesis may be used, but trisphosphonium salts, tetramethyluronium salts, carbodiimides, etc. are particularly preferred. Examples of trisphosphonium salts include benzotriazol-1-yloxytris(pyrrolidino)phosphonium hexafluorophosphate (PyBOP), bromotris(pyrrolidino) phosphonium hexafluorophosphate (PyBroP) and 7-azabenzotriazol-1-yloxytris(pyrrolidino) phosphonium hexafluorophosphate (PyAOP), examples of tetramethyluronium salts include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluronium tetrafluoroborate (TBTU), 2-(5-norbornene-2,3-dicarboxyimido)-1,1,3,3-tetramethyluronium tetrafluoroborate (TNTU) and O—(N-succimidyl)-1,1,3,3-tetramethyluroniumtetrafluoroborate (TSTU); examples of carbodiimides include DCC, N,N'-diisopropylcarbodiimide (DIPCDI) and N-ethyl-N'-(3-dimethylaminopropyl)carbodimide hydrochloride (EDCI.HCl); etc. For condensation using these reagents, the addition of racemization inhibitors (e.g., HONB, HOBt, HOAt, HOOBt, etc.) is preferred. Solvents used in condensation may be appropriately chosen from solvents that are known to be usable for condensation. For example, acid amides such as anhydrous or hydrous N,N-dimethylformamide, N,N-dimethylacetamide, N-methylpyrrolidone, etc., halogenated hydrocarbons such as methylene chloride, chloroform, etc., alcohols such as trifluoroethanol, phenol, etc., sulfoxides such as dimethyl sulfoxide, etc., tertiary amines such as pyridine, etc., ethers such as dioxane, tetrahydrofuran, etc., nitriles such as acetonitrile, propionitrile, etc., esters such as methyl acetate, ethyl acetate, etc., or suitable mixtures thereof, etc. are used. The reaction temperature is appropriately chosen from the range known to be applicable to peptide binding reactions and is normally suitably chosen from the range of about −20° C. to 50° C. The activated amino acid derivatives are used generally in 1.5 to 6 times excess. In the case of solid phase synthesis, the condensation is examined using the ninhydrin reaction; when the condensation is insufficient, the condensation can be completed by repeating the condensation reaction without removal of the protecting groups. When the condensation is yet insufficient even after repeating the reaction, the unreacted amino acids are acylated with acetic anhydride or acetylimidazole to cancel any adverse effect on the subsequent reaction.

Examples of the protecting groups used to protect amino groups in the starting amino acids include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, trityl, etc. Examples of protecting groups for a carboxyl group include, in addition to the $C_{1-6}$ alkyl group, $C_{3-8}$ cycloalkyl group and $C_{7-14}$ aralkyl group for R described above, allyl, 2-adamantyl, 4-nitrobenzyl, 4-methoxybenzyl, 4-chlorobenzyl, phenacyl group, benzyloxycarbonylhydrazide, tert-butoxycarbonylhydrazide, tritylhydrazide, etc.

The hydroxyl group of serine and threonine can be protected, for example, by esterification or etherification. Examples of groups suitable for this esterification include a group derived from organic acid such as a lower $(C_{2-4})$ alkanoyl group such as acetyl group, an aroyl group such as benzoyl group, etc. Examples of a group suitable for the etherification include benzyl group, tetrahydropyranyl group, tert-butyl group, trytyl group (Trt), etc.

Examples of groups for protecting the phenolic hydroxyl group of tyrosine include Bzl, 2,6-dichlorobenzyl ($Cl_2$-Bzl), 2-nitrobenzyl, Br—Z, tert-butyl, etc.

Examples of groups used to protect the imidazole moiety of histidine include Tos, 4-methoxy-2,3,6-trimethylbenzenesulfonyl (Mtr), DNP, Bom, Bum, Boc, Trt, Fmoc, etc.

Examples of protecting groups for the guanidino group in arginine include Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesitylene-2-sulfonyl (Mts), 2,2,4,6,7-pentamethyldihydrobenzofuran-5-sulfonyl (Pbf), Boc, Z, $NO_2$, etc.

Examples of protecting groups for side chain amino group of lysine include Z, Cl—Z, trifluoroacetyl, Boc, Fmoc, Trt, Mtr, 4,4-dimethyl-2,6-dioxocyclohexylideneyl (Dde); etc.

Examples of protecting groups for the indolyl of tryptophan include formyl (For), Z, Boc, Mts, Mtr, etc.

A protecting group for asparagine and glutamine include Trt, xanthyl (Xan), 4,4'-dimethoxybenzhydryl (Mbh), 2,4,6-trimethoxybenzyl (Tmob), etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, 1-hydroxybenzotriazole (HOBt) or 1-hydroxy-7-azabenzotriazole (HOAt)], etc. As the amino acids in which the amino groups in the starting material are activated, the corresponding phosphorous amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, trimethylsilane bromide (TMSBr), trimethylsilyl trifluoromethanesulfonate, tetrafluoroboric acid, tris(trifluoro)boron, boron tribromide or a mixed solution thereof, a base treatment with diisopropylethylamine, triethylamine, piperidine, piperazine, etc., and reduction with sodium in liquid ammonia. The elimination of protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, etc., dimethylsulfide, 1,4-butanedithiol, 1,2-ethanedithiol, etc. Furthermore, 2,4-dinitrophenyl group used as the protecting group for the imidazole of histidine is removed by a treatment with thiophenol. Formyl group used as the protecting group of the indole of tryptophan is removed by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, removal of the protecting groups and activation of functional groups involved in the reaction may be appropriately chosen from publicly known groups and publicly known means.

Methods for obtaining the amide of the peptide include, for example, solid phase synthesis using resins for the formation of peptide amide. In another method for obtaining the amides of the peptide, for example, the α-carboxyl group of the carboxy terminal amino acid is first protected by amidation; the peptide chain is then extended from the amino group side to a desired length. Thereafter, a peptide in which only the protecting group of the N-terminal α-amino group in the peptide chain has been removed from the peptide and a peptide (or an amino acid) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are removed by the method described above to give the desired crude peptide. This crude peptide is purified by various known purification means. Lyophilization of the major fraction gives the amide of the desired peptide.

When the metastin derivative of the present invention is present in the form of a configurational isomer, a diastereomer, a conformer, or the like, each can be isolated by the separating and purifying means described above, if desired. In addition, when the compound of the present invention is racemic, it can be separated into an S isomer and an R isomer by the conventional optical resolving means.

When steric isomers exist for the metastin derivative of the present invention, the present invention includes both of these isomers alone and the isomers present as a mixture thereof.

In addition, the metastin derivative of the present invention may also be hydrated or non-hydrated.

The metastin derivative of the present invention may also be labeled with an isotope (e.g., $^3H$, $^{14}C$, $^{35}S$), etc.

Throughout the specification, the peptides are represented in accordance with the conventional way of describing peptides, that is, the N-terminus (amino terminus) at the left hand and the C-terminus (carboxyl terminus) at the right hand. In the peptides, the C-terminus is usually in the form of an amide (—$CONH_2$), a carboxyl group (—COOH), a carboxylate (—COO$^-$), an alkylamide (—CONHR) or an ester (—COOR) and the amide (—$CONH_2$) is particularly preferred. Examples of R in the ester or alkylamide include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc., pivaloyloxymethyl group, which are widely used as an ester for oral use, and the like.

Examples of a salt of the metastin derivative of the present invention include a metal salt, an ammonium salt, a salt with an organic base, a salt with inorganic acid, a salt with organic acid, a salt with basic or acidic amino acid, and the like. Preferred examples of the metal salt include alkali metal salts such as sodium salts, potassium salts, etc.; alkaline earth metal salts such as calcium salts, magnesium salts, barium salts, etc.; aluminum salts; and the like. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of salts with basic amino acids include salts with arginine, lysine, ornithine, etc., and preferred examples of salts with acidic amino acids include salts with aspartic acid, glutamic acid, etc.

Among them, pharmaceutically acceptable salts are preferable. For example, when the compound has an acidic functional group, inorganic salts such as alkali metal salts (e.g., sodium salt, potassium salt, etc.), alkaline earth metal salts (e.g., calcium salt, magnesium salt, barium salt, etc.), ammonium salts, etc. are preferable. When the compound has a basic functional group, salts with inorganic acids with hydrochloric acid, hydrobromic acid, nitric acid, sulfuric acid, phosphoric acid, etc., and salts with organic acids such as acetic acid, phthalic acid, fumaric acid, oxalic acid, tartaric acid, maleic acid, citric acid, succinic acid, methanesulfonic acid, p-toluenesulfonic acid, etc. are preferable.

The prodrug of the metastin derivative or a salt thereof (hereinafter sometimes simply referred to as the metastin derivative of the present invention) refers to such a metastin derivative that is converted into the metastin derivative of the present invention under physiological conditions or with a reaction due to an enzyme, a gastric acid, etc., in the living body. In other words, the prodrug of the present invention is the metastin derivative that undergoes enzymatic oxidation, reduction, hydrolysis, etc. to be converted into the metastin derivative of the present invention, or the metastin derivative that undergoes hydrolysis, etc. by gastric acid, etc. to be converted into the metastin derivative of the present invention.

Examples of the prodrug of the metastin derivative of the present invention include a metastin derivative wherein an amino group of the metastin derivative of the present invention is substituted with an acyl, an alkyl, phosphoric acid, etc. (e.g., metastin derivatives wherein an amino group of the metastin derivative of the present invention is substituted with eicosanoyl, alanyl, pentylaminocarbonyl (5-methyl-2-oxo-1, 3-dioxolen-4-yl)methoxycarbonyl, tetrahydrofuranyl, pyrrolidylmethyl, pivaloyloxymethyl, tert-butyl, etc); metastin derivatives wherein a hydroxy group of the metastin derivative of the present invention is substituted with an acyl, an alkyl, phosphoric acid, boric acid, etc. (e.g., metastin derivatives wherein an hydroxy group of the metastin derivative of the present invention is substituted with acetyl, palmitoyl, propanoyl, pivaloyl, succinyl, fumaryl, alanyl, dimethylaminomethylcarbonyl, etc.); and metastin derivatives wherein a carboxy group of the metastin derivative of the present invention is substituted with ester, amide, etc. (e.g., metastin derivatives wherein the carboxy group of the metastin derivative of the present invention is converted into the ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, methylamide, etc); and the like. These metastin derivatives can be produced from the metastin derivatives of the present invention by per se known methods.

The prodrugs of the metastins derivative of the present invention may be those that are converted into the metastin derivatives of the present invention under the physiological conditions as described in "Pharmaceutical Research and Development", Vol. 7 (Drug Design), pages 163-198, published 1990 by Hirokawa Publishing Co.

The metastin derivatives of the present invention or their salts or prodrugs (hereinafter sometimes simply referred to as the compound of the present invention) possess the cancer metastasis suppressing activity or the cancer growth suppressing activity. Thus, the metastin derivatives are useful for medicaments such as agents for preventing or treating all cancers (e.g., lung cancer, gastric cancer, liver cancer, pancreas cancer, colorectal cancer, rectal cancer, colonic cancer, prostate cancer, ovarian cancer, cervical cancer, breast cancer, etc.), and the like.

The compound of the present invention also possesses the effect of controlling pancreatic function and is thus useful as a medicament such as an agent for preventing or treating various pancreatic diseases (e.g., acute or chronic pancreatitis, pancreatic cancer, etc.).

Furthermore, the compound of the present invention possesses the effect of controlling placental function and is thus useful as a medicament such as an agent for preventing or treating choriocarcinoma, hydatid mole, invasive mole, miscarriage, fetal hypoplasia, abnormal glucose metabolism, abnormal lipid metabolism or induction of delivery, etc.

Moreover, the compound of the present invention possesses the effects of increasing sugar level, promoting pancreatic glucagon secretion and promoting urine formation and is thus useful as a medicament such as hyperglycemic agents, pancreatic glucagon secretagogue agents or agents for promoting urine formation, which are useful for agents for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes mellitus, fatty atrophy, insulin allergy, insulinoma, arteriosclerosis, thrombotic disorders or lipotoxicity; and the like.

In addition, the compound of the present invention also possesses the effects of promoting gonadotropic hormone (e.g., FSH, LH, etc.) secretion, promoting sex hormone [e.g., androgens (e.g., testosterone, androstenedione, etc.), estrogens (e.g., estradiol, estrone, etc.), progesterones, etc.] secretion, improving gonadal function and inducing or stimulating ovulation, as well as a sexual maturation effect, etc., and hence, can be used as an agent for improving gonadal function, an agent for inducing or stimulating ovulation, a gonadotropic hormone secretagogue agent or a sex hormone secretagogue agent, or an agent for preventing or treating hormone-dependent cancers [e.g., prostate cancer, breast cancer, etc.], infertility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular function disorder, azoospermia, hypoandrogenemia, etc.], endometriosis, early puberty, myoma of the uterus, etc.

Furthermore, the prodrug of the metastin derivative of the present invention or its salt is useful as an agent for preventing or treating Alzheimer's disease, Autism, moderate cognitive impairment, etc.

Moreover, the compound of the present invention has excellent blood stability, solubility and solution stability, as compared to native metastin such as metastin 54 (1-54) or metastin 10 (45-54).

The metastin derivative of the present invention or its salt or prodrug, metastin per se, or DNA encoding metastin, etc. is useful as an agent for suppressing gonadotropic hormone (e.g., FSH, LH) secretion or sex hormone [e.g., androgen (e.g., testosterone, androstenedione), estrogen (e.g., estradiol, estrone), progesterone] secretion; a down-regulating agent for gonadotropic hormone or sex hormone; in particular, it is useful for suppressing gonadotropic hormone secretion or sex hormone secretion via down-regulation of gonadotropic hormone or sex hormone (wherein, the down-regulation of gonadotropic hormone or sex hormone may be pulse loss of LHRH or depletion of LHRH) or down-regulation of human OT7T175 (metastin receptor) protein consisting of the amino acid sequence represented by SEQ ID NO: 9; particularly useful as an agent for preventing or treating hormone-dependent cancers (e.g., prostate cancer, breast cancer, etc.; especially a prostate cancer, hormone-sensitive prostate cancer, etc.); an agent for preventing or treating endometriosis; an agent for inhibiting ovarian follicular maturation; a menstrual cycle-suspending agent; an agent for treating myoma of the uterus; an agent for treating early puberty; or as a contraceptive, etc. Where the metastin derivative of the present invention or its salt or prodrug, metastin per se, or DNA encoding metastin, etc. has normal agonist activity, an effective dose of the metastin derivative sufficient to suppress the secretion of gonadotropic hormone or sex hormone is administered at the site or tissue where the therapeutic effects are to be exerted, so that the metastin derivative is present in a dose more than required (i.e., the metastin derivative is administered in an excess over the normal effective dose, at which the metastin derivative exerts the effects of suppressing cancer metastasis, suppressing cancer growth, etc.; or the effect of promoting gonadotropic hormone secretion, the effect of promoting sex hormone secretion, etc.) to exhibit the effects of suppressing gonadotropic hormone secretion or sex hormone secretion. Specific examples include sustained or continuous administration of the normal effective dose (including an administration technique to gradually release the pharmaceutical ingredients by bolus administration); and the like. Further when the metastin derivative of the present invention or its salt or the prodrug thereof, etc. has a sufficient agonist activity more than required (a super-agonist activity), it becomes possible to sustain the activities more than exhibited by the necessary dose at the site or tissue where the therapeutic effect are to be exhibited. It is therefore sufficient even by normal effective dose administration to suppress the secretion of gonadotropic hormone or sex hormone, whereby the effect of suppressing gonadotropic hormone secretion or sex hormone secretion is exhibited.

In other words, an effective dose of the metastin derivative of the present invention or its salt or prodrug, metastin per se, or DNA encoding metastin, etc. sufficient to suppress the secretion of gonadotropic hormone or sex hormone is administered so that the metastin derivative is present in a dose more than required at the site or tissue where the therapeutic effects are to be exerted, or its activities can be sustained more than required, which enables to exhibit the effects of suppressing gonadotropic hormone secretion or sex hormone secretion.

The pharmaceutical comprising the compound of the present invention is low toxic. Therefore, the compound of the present invention can be safely administered either directly as it is or as a mixture with pharmacologically acceptable carriers, orally or parenterally (e.g., topically, rectally, intravenously, etc.), in the form of pharmaceutical preparations such as tablets (including dragees and film-coated tablets), powdery dosage forms, granules, capsules (including soft capsules), liquid dosage forms, injections, suppositories, sustained release dosage forms, etc., in accordance with publicly known means generally used in process for producing pharmaceutical preparations.

The compound of the present invention is contained in the pharmaceutical preparation of the present invention in about 0.01 to about 100 wt %, based on the total weight of the preparation.

A dose of the compound of the present invention may vary depending upon subject to be administered, target organ, conditions, route of administration, etc., and in oral administration, the compound is generally administered to the patient with cancer (as 60 kg body weight) in a daily dose of about 0.01 to about 100 mg, preferably about 0.1 to about 50 mg and more preferably about 0.1 to about 20 mg. In parenteral administration, a single dose of the compound may vary depending upon subject to be administered, target organ, conditions, route of administration, etc., and in the form of an injectable dosage form, it is advantageous to administer the compound to the patient with cancer (as 60 kg body weight) generally in a daily dose of about 0.001 to about 30 mg, preferably about 0.01 to about 20 mg, and more preferably about 0.01 to about 10 mg. For other animal species, the corresponding dose as converted per 60 kg weight can be administered.

Pharmacologically acceptable carriers, which may be used in manufacturing the pharmaceutical preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include lactose, saccharose, D-mannitol, starch, cornstarch, crystalline cellulose, light anhydrous silicic acid, etc.

Examples of lubricants include magnesium stearate, calcium stearate, talc, colloidal silica, etc.

Examples of binders include crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include starch, carboxymethylcellulose, carboxymethylcellulose calcium, sodium carboxymethyl starch, L-hydroxypropylcellulose, etc.

Examples of solvents include water for injection, alcohol, propylene glycol, Macrogol, sesame oil, corn oil, olive oil, etc.

Examples of dissolution aids include polyethylene glycol, propylene glycol, D-mannitol, benzyl benzoate, ethanol, trisaminomethane, cholesterol, triethanolamine, sodium carbonate, sodium citrate, etc.

Examples of suspending agents include surfactants such as stearyl triethanolamine, sodium laurylsulfate, lauryl aminopropionate, lecithin, benzalkonium chloride, benzethonium chloride, glycerine monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.

Examples of isotonizing agents include glucose, D-sorbitol, sodium chloride, glycerine, D-mannitol, etc.

Examples of buffers include buffering solutions of a phosphate, acetate, carbonate, citrate, etc.

Examples of soothing agents include benzyl alcohol, etc.

Examples of preservatives include p-hydroxybenzoates, chlorobutanol, benzyl alcohol, phenethyl alcohol, dehydroacetic acid, sorbic acid, etc.

Examples of antioxidants include a sulfite, ascorbic acid, α-tocopherol, etc.

Furthermore, the compound of the present invention can be used in combination with drugs other than the compound of the present invention.

Examples of the drugs, which can be used in combination with the compound of the present invention (hereinafter sometimes simply referred to as concomitant drugs), include chemotherapeutic agents for treating cancer, hormonal therapeutic agents, immunotherapeutic agents, etc. (hereinafter simply referred to as concomitant agents).

Examples of "chemotherapeutic agents" include alkylating agents, antimetabolites, anticancer antibiotics, anticancer agents derived from plants, etc.

Examples of "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, rnelphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, etc.

Examples of "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, etc.), aminopterin, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, etc.

Examples of "anticancer antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride; pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, etc.

Examples of "anticancer agents derived from plants" include etoposide, etoposide phosphate, vinblastine sulfate, vincristine sulfate, vindesine sulfate, teniposide, paclitaxel, docetaxel, vinorelbine, etc.

Examples of "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, etc.), pill dosage forms, mepitiostane, testrolactone, aminoglutethimide, LH-RH agonists (e.g., goserelin acetate, buserelin, Leuprorelin, etc.), droloxifene, epitiostanol, ethinylestradiol sulfonate, aromatase inhibitors (e.g., fadrozole hydrochloride, anastrozole, retrozole, exemestane, vorozole, formestane, etc.), anti-androgens (e.g., flutamide, bicartamide, nilutamide, etc.), 5α-reductase inhibitors (e.g., finasteride, epristeride, etc.), adrenocorticohormone drugs (e.g., dexamethasone, prednisolone, betamethasone, triamcinolone, etc.), androgen synthesis inhibitors (e.g., abiraterone, etc.), retinoid and drugs that retard retinoid metabolism (e.g., liarozole, etc.), and among them, LH-RH agonists (e.g., goserelin acetate, buserelin, Leuprorelin, etc.) are preferable.

Examples of "immunotherapeutic agents (BRM)" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, etc.

The combined use of the compound of the present invention and a concomitant drug exhibits the following excellent effects.

(1) The dose can be reduced as compared to the dose when the compound of the present invention or a concomitant drug is administered alone.

(2) A drug concomitantly administered with the compound of the present invention can be chosen depending on the condition (mild, severe, etc.) of a patient.

(3) A concomitant drug, whose functional mechanism is different from that of the compound of the present invention, can be chosen so that a treatment period can be set longer.

(4) A concomitant drug, whose functional mechanism is different from that of the compound of the present invention, can be chosen so that sustained therapeutic effects can be achieved.

(5) A synergistic effect can be obtained by the concomitant use of the compound of the present invention and a concomitant drug.

In addition, the compound of the present invention can reduce values of testosterone to emasculate level immediately after medication. Thus when the concomitant drug such as LH-RH agonist (e.g., goserelin acetate, buserelin, Leuprorelin etc.; preferably Leuprorelin) is used in combination with the compound of the present invention, the values of testosterone can be reduced to emasculate level immediately after medication of the compound of the present invention. Further, since the combined use of the concomitant drug such as LH-RH agonist (e.g., goserelin acetate, buserelin, Leuprorelin, etc.; preferably Leuprorelin) and the compound of the present invention results in prolonged preservation of hormone-dependent period, it can advantageously be used.

Hereinafter, the combined use of the compound of the present invention and the concomitant drug is referred to as "the combined preparation of the present invention."

When the combined preparation of the present invention is used, a dosing period of the compound of the present invention and the concomitant drug is not restricted; the compound of the present invention or its pharmaceutical composition and the concomitant drug or its pharmaceutical composition may be administered to the subject to be administered either simultaneously or at certain time intervals. The dose of the concomitant drug may be modified according to the dose used clinically and may be appropriately chosen depending upon subject to be administered, route for administration, disease, combination, etc.

A mode for administration of the combined preparation of the present invention is not particularly limited, but it is sufficient that the compound of the present invention is used in combination with the concomitant drug at the time of administration. For such mode of administration, there are, for example, (1) administration of a single dosage form obtained by mixing the compound of the present invention and the concomitant drug together at the same time, (2) simultaneous administration of two dosage forms prepared separately from the compound of the present invention and the concomitant drug through the same route for administration, (3) administration of two dosage forms prepared separately from the compound of the present invention and the concomitant drug at certain time intervals through the same route for administration, (4) simultaneous administration of two dosage forms prepared separately from the compound of the present invention and the concomitant drug through different routes for administration, (5) administration of two dosage forms prepared separately from the compound of the present invention and the concomitant drug at certain time intervals (e.g., administration of the compound of the present invention and the concomitant drug in this order, or administration in a reversed order) through different routes for administration, etc.

The combined preparation of the present invention is low toxic and thus can be safely administered orally or parenterally (e.g., topically, rectally, intravenously, etc.) either directly as they are or in the form of pharmaceutical preparations such as tablets (including dragees and film-coated tablets), powdery dosage forms, granules, capsules (including soft capsules), liquid dosage forms, injections, suppositories, sustained release dosage forms, etc., which are obtained by mixing the compound of the present invention or (and) the concomitant drug described above with pharmacologically acceptable carriers by publicly known methods. Injectable dosage forms can be administered intravenously, intramuscularly or subcutaneously, into the organ, or directly at the focus.

Pharmacologically acceptable carriers, which may be used to manufacture the combined preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include lactose, saccharose, D-mannitol, starch, cornstarch, crystalline cellulose, light anhydrous silicic acid, etc.

Examples of lubricants include magnesium stearate, calcium stearate, talc, colloidal silica, etc.

Examples of binders include crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include starch, carboxymethylcellulose, carboxymethylcellulose calcium, sodium carboxymethyl starch, L-hydroxypropylcellulose, etc.

Examples of solvents include water for injection, alcohol, propylene glycol, Macrogol, sesame oil, corn oil, olive oil, etc.

Examples of dissolution aids include polyethylene glycol, propylene glycol, D-mannitol, benzyl benzoate, ethanol, trisaminomethane, cholesterol, triethanolamine, sodium carbonate, sodium citrate, etc.

Examples of suspending agents include surfactants such as stearyltriethanolamine, sodium laurylsulfate, lauryl aminopropionate, lecithin, benzalkonium chloride, benzethonium chloride, glycerine monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc.

Examples of isotonizing agents include glucose, D-sorbitol, sodium chloride, glycerine, D-mannitol, etc.

Examples of buffers include buffering solutions of a phosphate, acetate, carbonate, citrate, etc.

Examples of soothing agents include benzyl alcohol, etc.

Examples of preservatives include p-hydroxybenzoates, chlorobutanol, benzyl alcohol, phenethyl alcohol, dehydroacetic acid, sorbic acid, etc.

Examples of antioxidants include a sulfite, ascorbic acid, α-tocopherol, etc.

In the combined preparation of the present invention, a ratio of the compound of the present invention to the concomitant drug can be appropriately chosen depending upon subject to be administered, route for administration, disease, etc.

For example, the amount of the compound of the present invention contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of the concomitant drug contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of additives such as a carrier, etc. contained in the combined preparation of the present invention varies depending on the dosage form of the preparation, and is usually about 1 to 99.99% by weight, preferably about 10 to 90% by weight, based on the total weight of the preparation.

These amounts may be the same, also when the compound of the present invention and the concomitant drug are separately prepared, respectively.

These preparations can be manufactured by per se publicly known methods conventionally used in general.

For example, the compound of the present invention or the concomitant drug can be prepared into an injectable dosage form by formulating with a dispersing agent (e.g., Tween 80 (manufactured by Atlas Powder Company, USA), HCO 60 (manufactured by Nikko Chemicals Co., Ltd.), polyethylene glycol, carboxymethyl cellulose, sodium alginate, hydroxypropylmethyl cellulose, dextrin, etc.), a stabilizer (e.g., ascorbic acid, sodium pyrosulfite), a surfactant (e.g., polysorbate 80, macrogol, etc.), a solubilizing agent (e.g., glycerin, ethanol, etc.), a buffering agent (e.g., phosphoric acid or its alkali metal salt, citric acid or its alkali metal salt, etc.), an isotonizing agent (e.g., sodium chloride, potassium chloride, mannitol, sorbitol, glucose, etc.), a pH adjusting agent (e.g., hydrochloric acid, sodium hydroxide, etc.), a preservative (e.g., ethyl p-oxybenzoate, benzoic acid, methylparabene, propylparabene, benzyl alcohol, etc.), a solubilizer (e.g., concentrated glycerin, meglumine, etc.), a dissolution aid (e.g., propylene glycol, saccharose, etc.), a soothing agent (e.g., glucose, benzyl alcohol, etc.), to prepare into aqueous injection; or by dissolving, suspending, or emulsifying with a vegetable oil such as olive oil, sesame oil, cottonseed oil, corn oil, etc., a dissolution aid such as propylene glycol or the like to prepare into an oily injection.

An oral dosage form can be produced in a conventional manner by adding to the compound of the present invention or the concomitant drug, for example, an excipient (e.g., lactose, saccharose, starch, etc.), a disintegrating agent (e.g., starch, calcium carbonate, etc.), a binder (e.g., starch, gum arabic, carboxymethyl cellulose, polyvinylpyrrolidone, hydroxypropyl cellulose, etc.), a lubricant (e.g., talc, magnesium stearate, polyethylene glycol 6000, etc.) and other additives, compressing the resulting mixture and, if necessary, coating the compressed product for the purpose of taste masking, enteric degradation or sustained release by techniques per se publicly known. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (manufactured by Rohm Company, Germany, methacrylic acid/acrylic acid copolymer) and dyes (e.g., iron oxide, titanium dioxide). The oral dosage form may be either an immediate release dosage form or a sustained release dosage form.

For example, in a suppository, the compound of the present invention or the concomitant drug is prepared into an oily or aqueous solid, semi-solid or liquid composition by techniques per se publicly known. Oily bases used for the composition described above include glycerides of higher fatty acids [e.g., cacao butter, uitepsols (manufactured by Dynamite Nobel Company, Germany), etc.], moderate fatty acids [e.g., miglyols (manufactured by Dynamite Nobel Company, Germany), etc.], vegetable oils (e.g., sesame oil, soybean oil, cottonseed oil, etc.), and the like. Aqueous bases include, for example, polyethylene glycols and propylene glycol. Bases for aqueous gels include, for example, natural rubbers, cellulose derivatives, vinyl polymers, acrylic polymers, etc.

Examples of the sustained release dosage form above include sustained release microcapsules, and the like.

Sustained release microcapsules can be obtained by per se publicly known methods, and are preferably prepared in the form of, e.g., a sustained release dosage form by the method [2] shown below and administered.

Preferably, the compound of the present invention is prepared into a dosage form for oral administration such as a solid dosage form (e.g., powdery dosage form, granules, tablets, capsules) or into a dosage form for rectal administration such as a suppository, etc. A dosage form for oral administration is particularly preferred.

The concomitant drug can be prepared into the dosage form described above, depending on the kind of drug.

Hereinafter, [1] an injectable preparation of the compound of the present invention or the concomitant drug and its production, [2] a sustained release or immediate release preparation of the compound of the present invention or the concomitant drug and its production and [3] a sublingual, buccal or rapid oral disintegrating preparations of the compound of the present invention or the concomitant drug and its production will be specifically described.

[1] Injectable Preparation and its Production

An injectable preparation obtained by dissolving the compound of the present invention or the concomitant drug in water is preferred. The injectable preparation may contain a benzoate and/or a salicylate.

The injectable preparation is obtained by dissolving the compound of the present invention or the concomitant drug and optionally a benzoate and/or a salicylate in water.

Examples of the benzoate and/or salicylate described above include an alkali metal salt such as sodium and potassium salts, etc., an alkaline earth metal salt such as calcium and magnesium salts, etc., an ammonium salt, a meglumine salt, a salt of an organic acid such as trometamol, and the like.

The concentration of the compound of the present invention or the concomitant drug in the injectable preparation is about 0.05 to 50 w/v %, preferably about 0.3 to 20 w/v %. The concentration of the benzoate and/or salicylate is 0.5 to 50 w/v %, preferably 3 to 20 w/v %.

Furthermore, additives generally used in an injectable preparation such as a stabilizer (ascorbic acid, sodium pyrosulfite, etc.), a surfactant (polysorbate 80, macrogol, etc.), a solubilizing agent (glycerin, ethanol, etc.), a buffering agent (phosphoric acid and its alkali metal salt, citric acid and its alkali metal salt, etc.), an isotonizing agent (sodium chloride, potassium chloride, etc.), a dispersing agent (hydroxypropylmethyl cellulose, dextrin), a pH adjusting agent (hydrochloric acid, sodium hydroxide, etc.), a preservative (ethyl p-oxybenzoate, benzoic acid, etc.), a solubilizer (concentrated glycerin, meglumine, etc.), a dissolution aid (propylene glycol, saccharose, etc.), a soothing agent (glucose, benzyl alcohol, etc.) are appropriately added to the preparation. Any of these additives is added in an amount generally used in an injectable preparation.

The injectable preparation is adjusted to pH of 2 to 12, preferably 2.5 to 8.0 by adding a pH adjusting-agent.

The injectable preparation is obtained by dissolving both the compound of the present invention or the concomitant drug and optionally a benzoate and/or salicylate, and, if necessary, the above additives in water. These components may be dissolved in any order according to the same manner as in a conventional injectable preparation.

An aqueous solution for injection is preferably warmed, and used as an injectable preparation after sterilization by filtration or autoclaved as in a conventional injectable preparation to provide for an injectable preparation.

An aqueous injectable preparation is preferably autoclaved, e.g., at 100 to 121° C. for 5 to 30 minutes.

Moreover, the preparation may be in a solution form to which antibacterial activity is imparted to be usable as a multiple dosage form in divided dosing.

[2] Sustained Release or Immediate Release Preparation and its Production

A preferred sustained release preparation comprises a core comprising the compound of the present invention or the concomitant drug, which is optionally coated with a water-insoluble material or a swelling polymer. For example, a sustained release preparation for oral administration of a once-daily dosage form is preferred.

Examples of the water-insoluble material used for the coating agent include cellulose ethers such as ethyl cellulose, butyl cellulose, etc., cellulose esters such as cellulose acetate, cellulose propionate, etc., polyvinyl esters such as polyvinyl acetate, polyvinyl butyrate, etc., acrylic acid polymers such as an acrylic acid/methacrylic acid copolymer, a methyl methacrylate copolymer, an ethoxyethyl methacrylate/cinnamoethyl methacrylate/aminoalkyl methacrylate copolymer, a polyacrylic acid, a polymethacrylic acid, a methacrylic acid alkylamide copolymer, a poly(methyl methacrylate), a polymethacrylate, an aminoalkyl methacrylate copolymer, a poly (methacrylic anhydride), a glycidyl methacrylate copolymer, in particular, a series of Eudragits (Rohm & Pharma) such as Eudragit RS-100, RL-100, RS-30D, RL-30D, RL-PO and RS-PO (ethyl acrylate/methyl methacrylate/chlorotrimethyl methacrylate/ethyl ammonium copolymer) and Eudragit NE-30D (methyl methacrylate/ethyl acrylate copolymer), etc., hydrogenated oils such as hydrogenated castor oil (e.g., LUBRI WAX (Freund Industrial Co., Ltd.), etc.), waxes such as carnauba wax, a fatty acid glycerin ester, paraffin, etc., polyglycerin fatty acid esters, etc.

The swelling polymer is preferably a polymer having an acidic removable group and exhibiting pH-dependent swelling, and a polymer having an acidic removable group, which undergoes a less swelling at an acidic pH such as in the stomach but is swollen extensively at a neutral pH such as in the small and large intestines, is preferred.

Examples of such a polymer having an acidic removable group and exhibiting pH-dependent swelling include a crosslinked polyacrylic acid polymer such as Carbomers 934P, 940, 941, 974P, 980, 1342, etc., polycarbophil and calcium polycarbophil (all manufactured by BF Goodrich Chemicals), Hivis Wakos 103, 104, 105 and 304 (all manufactured by Wako Pure Chemical Industries, Ltd.), etc.

The coating agent used in the sustained release preparation may further contain a hydrophilic material.

Examples of the hydrophilic material include a polysaccharide which may have a sulfate group, such as pullulan, dextrin, alkali metal alginates, etc., a polysaccharide having a hydroxyalkyl group or a carboxyalkyl group such as hydroxypropyl cellulose, hydroxypropylmethyl cellulose, sodium carboxymethylcellulose, etc., methyl cellulose, polyvinyl pyrrolidone, polyvinyl alcohol, polyethylene glycol, etc.

The amount of the water-insoluble material contained in the coating agent of the sustained release preparation is about 30 to about 90% (w/w), preferably about 35 to about 80% (w/w), more preferably about 40 to about 75% (w/w), and the swelling polymer content is about 3 to about 30% (w/w), preferably about 3 to about 15% (w/w). The coating agent may further contain a hydrophilic material, and the amount of the hydrophilic material contained in the coating agent is about 50% (w/w) or less, preferably about 5 to about 40% (w/w), more preferably about 5 to about 35% (w/w). As used herein, the % (w/w) above is used to mean a % by weight based on the coating agent composition, which is the remainder of the coating agent solution after removing any solvent (e.g., water, a lower alcohol such as methanol, ethanol, etc.).

The sustained release preparation is manufactured by preparing a core containing a drug as illustrated below, followed by coating the resulting core with a coating agent solution obtained by heat-melting a water-insoluble material or a swelling polymer or by dissolving or dispersing such a material in a solvent.

I. Production of Drug-Containing Core

The shape of a core containing a drug to be coated with a coating agent (hereinafter sometimes simply referred to as a core) is not specifically limited but preferably prepared into a particulate shape such as granules, fine granules, or the like.

When the core is granules or fine granules, they have a mean particle size of preferably about 150 to about 2,000 µm, more preferably about 500 to about 1,400 µm.

The core can be prepared in a conventional manner. For example, a drug is mixed with a suitable excipient, binder, disintegrating agent, lubricant, stabilizer, etc., and then subjected to wet extrusion granulation, fluidized bed granulation, or the like.

The drug content in the core is about 0.5 to about 95% (w/w), preferably about 5.0 to about 80% (w/w), more preferably about 30 to about 70% (w/w).

Examples of the excipient contained in the core include a saccharide such as saccharose, lactose, mannitol, glucose, etc., starch, crystalline cellulose, calcium phosphate, cornstarch, etc. Among them, crystalline cellulose and cornstarch are preferred.

Examples of the binder used include polyvinyl alcohol, hydroxypropyl cellulose, polyethylene glycol, polyvinyl pyrrolidone, Pluronic F68, gum arabic, gelatin, starch, etc. Examples of the disintegrating agent include calcium carboxymethyl cellulose (ECG505), sodium croscarmellose (Ac-Di-Sol), crosslinked polyvinyl pyrrolidone (crospovidone), low substituted hydroxypropyl cellulose (L-HPC), etc. Among them, hydroxypropyl cellulose, polyvinyl pyrrolidone and low substituted hydroxypropyl cellulose are preferred. Examples of the lubricant and the anticoagulant include talc, magnesium stearate and its inorganic salts, and examples of the lubricant include polyethylene glycol, etc. Examples of the stabilizer include an acid such as tartaric acid, citric acid, succinic acid, fumaric acid, maleic acid, etc.

In addition to the technique described above, the core can be prepared by using other techniques such as an tumbling granulation technique, a pan coating technique, a fluidized bed coating technique and a melt granulation technique, wherein a drug or a mixture of the drug with an excipient, a lubricant, etc. is portionwise added to inert carrier particles as seeds for the core with spraying a binder dissolved in a suitable solvent such as water, a lower alcohol (e.g., methanol, ethanol, etc.) or the like. Examples of the inert carrier particles include those prepared from saccharose, lactose, starch, crystalline cellulose and waxes, and, preferably, these carriers have a mean particle size of about 100 µm to about 1,500 µm.

In order to separate the drug contained in the core from a coating agent, the surface of the core may be covered with a protective material. Examples of the protective material include the hydrophilic material described above and water-insoluble material. The preferred protective material is polyethylene glycol or a polysaccharide having a hydroxyalkyl group or a carboxyalkyl group, more preferably, hydroxypropylmethyl cellulose and hydroxypropyl cellulose. The protective material may contain, as a stabilizer, an acid such as tartaric acid, citric acid, succinic acid, fumaric acid, maleic acid, etc., and a lubricant such as talc. When the protective material is used, the amount thereof to be coated is about 1 to about 15% (w/w), preferably about 1 to about 11% (w/w), more preferably about 2 to about 8% (w/w) based on the core.

The protective material can be coated by a conventional coating method and specifically, the core is spray-coated with the protective material by a fluidized bed coating technique, a pan coating technique, etc.

II. Coating of Core with Coating Agent

The core obtained in I above is coated with a coating agent solution prepared by melt-heating the water-insoluble material and pH-dependent swelling polymer described above and a hydrophilic material or by dissolving or dispersing them in a solvent to obtain a sustained release preparation.

As a coating method of the core with the coating agent solution, there are, for example, spray-coating, etc.

The composition ratio of the water-insoluble material, swelling polymer and hydrophilic material in the coating agent solution can be appropriately chosen to be within the amounts of the respective components contained in the coating.

The amount of the coating agent is about 1 to about 90% (w/w), preferably about 5 to about 50% (w/w), more preferably about 5 to about 35% (w/w) based on the core (excluding the protective material coating).

As the solvent for the coating agent solution, water and an organic solvent can be used singly or as a mixture thereof. When a mixture is used, the ratio of water and the organic solvent (water/organic solvent: a weight ratio) may vary with the range of 1 to 100%, and is preferably 1 to about 30%. The organic solvent is not particularly limited so far as it can dissolve the water-insoluble material, and examples of the solvent include a lower alcohol such as methyl alcohol, ethyl alcohol, isopropyl alcohol, n-butyl alcohol, etc., a lower alkanone such as acetone, acetonitrile, chloroform, methylene chloride, etc. Among them, a lower alcohol is preferred, with ethyl alcohol and isopropyl alcohol being more preferred. Water and a mixture of water and an organic solvent are used preferably as solvents for the coating agent solution. In this case, an acid such as tartaric acid, citric acid, succinic acid, fumaric acid, maleic acid, etc. may be added to the coating agent solution, if necessary, for the purpose of stabilizing the coating agent solution.

To carry out the coating through spray coating, the coating can be made using a conventional coating method. Specifically, the core is sprayed with a coating agent solution by a fluidized bed coating technique, a pan coating technique, or the like. At this time, a lubricant such as talc, titanium oxide, magnesium stearate, calcium stearate, light silicic anhydride, etc., and a plasticizer such as glycerin fatty ester, hardened castor oil, triethyl citrate, cetyl alcohol, stearyl alcohol, etc. may also be added.

After coating with a coating agent, an antistatic agent such as talc may also be admixed, if necessary.

The immediate release preparation may be a liquid (solution, suspension, emulsion, etc.) or a solid (particles, pills, tablets, etc.). An oral preparation and a parenteral preparation such as an injectable preparation may be used, and an oral preparation is preferred.

The immediate release preparation may usually contain a carrier, additives and an excipient (hereinafter sometimes abbreviated as excipients) which are conventionally used in the pharmaceutical field, in addition to a drug which is an active ingredient. The pharmaceutical excipients are not specifically limited so long as they are excipients conventionally used in the pharmaceutical field. Examples of the excipient for an oral solid preparation include lactose, starch, corn starch, crystalline cellulose (Avicel PH101, manufactured by Asahi Kasei Corporation, etc.), powdered sugar, granulated sugar, mannitol, light silicic anhydride, magnesium carbonate, calcium carbonate, L-cysteine, etc., with corn starch and mannitol being preferred. Any of these excipients may be employed alone or in combination with each other. The amounts of the excipients are, for example, about 4.5 to about 99.4 w/w %, preferably about 20 to about 98.5 w/w %, more preferably about 30 to about 97 w/w %, based on the total weight of the immediate release preparation.

The content of drug in the immediate release preparation may appropriately be selected from the range of about 0.5% to about 95%, preferably about 1% to about 60% to the whole amount of the immediate release preparation.

When the immediate release preparation is an oral solid preparation, the preparation contains a disintegrating agent in addition to the components described above. Examples of the disintegrating agent include calcium carboxymethylcellulose (ECG505 manufactured by GOTOKU CHEMICAL Co., Ltd.), sodium croscarmellose (for example, Ac-Di-Sol manufactured by Asahi Kasei Corporation), crospovidone (for example, COLIDON CL manufactured by BASF), low-substituted hydroxypropyl cellulose (Shin-Etsu chemical Co., Ltd.), carboxymethyl starch (MATSUTANI CHEMICAL INDUSTRY Co., Ltd.), sodium carboxymethyl starch (EX-ORITAB manufactured by KIMURA SANGYO), partial a starch (PCS manufactured by Asahi Kasei Corporation), etc. For example, the disintegrating agent that disintegrates granules by water absorption or swelling upon contact with water, or forming a channel between the active component comprising the core and an excipient can be used. Any of these disintegrating agents can be used alone or in combination with each other. The amount of the disintegrating agent used may be appropriately chosen depending upon the type and the amount of the drug used or a particular preparation design for the intended release performance. For example, the amount is about 0.05 to about 30 w/w %, preferably about 0.5 to about 15 w/w % based on the total weight of the immediate release preparation.

When the immediate release preparation is an oral solid preparation, the oral solid preparation may optionally contain additives conventionally used in a solid preparation, in addition to the components described above. Examples of the additives include binders (for example, sucrose, gelatin, powdery gum arabic, methyl cellulose, hydroxypropyl cellulose, hydroxypropylmethyl cellulose, carboxymethylcellulose, polyvinyl pyrrolidone, pullran, dextrin, etc.), lubricants (polyethylene glycol, magnesium stearate, talc, light silicic anhydride (for example, aerosil (NIPPON AEROSIL)), surfactants (for example, anionic surfactants such as sodium alkylsulfate, nonionic surfactants such as polyoxyethylene fatty ester, polyoxyethylene sorbitan fatty ester, polyoxyethylene castor oil derivatives, etc.), colorants (for example, tar colorants, caramel, colcothar, titanium oxide, riboflavins), if necessary, corrigents (for example, sweeteners, flavors, etc.), adsorbents, preservatives, wetting agents, antistatic agents, etc. Furthermore, an organic acid such as tartaric acid, citric acid, succinic acid, fumaric acid or the like can also be added as a stabilizer.

As the binder above, hydroxypropyl cellulose, polyethylene glycol and polyvinyl pyrrolidone, etc. are preferably used.

The immediate release preparation can be prepared by mixing the components described above and kneading the mixture, if necessary, and then molding according to a conventional technique for making pharmaceutical preparations. The mixing above can be carried out in a conventional manner, e.g., by mixing, kneading, etc. Specifically, where the immediate release preparation is in the form of particles, the preparation can be prepared by mixing components with a vertical granulator, a multi-purpose kneader (HATA IRON WORKS CO., LTD), a fluidized bed granulator FD-5S (POWREX CORPORATION) or the like, and then granulating the resulting by wet extrusion granulation or fluidized bed granulation by a technique similar to that for preparing the core of the sustained release preparation described above.

The immediate release preparation and the sustained release preparation thus obtained can be compounded, as they are, or, together with appropriate pharmaceutical excipients, in pharmaceutical preparations separately in a conventional manner to prepare respective preparations for administering in combination with each other simultaneously or at certain time intervals. Alternatively, both preparations may be compounded in a single dosage form for oral administration (e.g., granules, fine granules, tablets, capsules) as they are, or, together with appropriate pharmaceutical excipients. Both preparations in the form of granules or fine granules may also be filled in a single capsule for oral administration.

[3] Sublingual, Buccal or Rapid Oral Disintegrating Preparation and its Production A sublingual, buccal or rapid oral disintegrating preparation may be in the form of a solid preparation such as a tablet, or may be in the form of an oral mucosal patch (film) or oral disintegrating film.

The sublingual, buccal or rapid oral disintegrating preparation is preferably a preparation containing the compound of the present invention or the concomitant drug and an excipient. The preparation may also contain auxiliary agents such as a lubricant, an isotonizing agent, a hydrophilic carrier, a water-dispersible polymer, a stabilizer, etc. Further for the purpose of promoting the absorption and enhancing the bioavailability, the preparation may also contain β-cyclodextrin or β-cyclodextrin derivatives (e.g., hydroxypropyl-β-cyclodextrin, etc.), and the like.

Examples of the above excipient include lactose, saccharose, D-mannitol, starch, crystalline cellulose, light silicic anhydride, etc. Examples of the lubricant include magnesium stearate, calcium stearate, talc, colloidal silica, etc., with magnesium stearate and colloidal silica being preferred. Examples of the isotonizing agent include sodium chloride, glucose, fructose, mannitol, sorbitol, lactose, saccharose, glycerin and urea, with mannitol being particularly preferred. As the hydrophilic carrier, there are, for example, a swelling hydrophilic carrier such as crystalline cellulose, ethyl cellulose, crosslinked polyvinyl pyrrolidone, light silicic anhydride, silicic acid, dicalcium phosphate, calcium carbonate, etc., with crystalline cellulose (e.g., microcrystalline cellulose, etc.) being preferred. As the water-dispersible polymer, there are, for example, a gum (e.g., tragacanth gum, acacia gum, guar gum), alginate (e.g., sodium alginate), cellulose derivatives (e.g., methyl cellulose, carboxymethylcellulose, hydroxymethyl cellulose, hydroxypropyl cellulose, hydroxypropylmethyl cellulose), gelatin, water-soluble starch, polyacrylic acid (e.g., carbomer), polymethacrylic acid, polyvinyl alcohol, polyethylene glycol, polyvinyl pyrrolidone, polycarbophil, ascorbate palmitate salt, etc., with hydroxypropylmethyl cellulose, polyacrylic acid, alginate, gelatin, carboxymethylcellulose, polyvinyl pyrrolidone and polyethylene glycol being preferred. Hydroxypropylmethyl cellulose is particularly preferred. As the stabilizer, there are, for example, cysteine, thiosorbitol, tartatic acid, citric acid, sodium carbonate, ascorbic acid, glycine, sodium sulfite, etc., with citric acid and ascorbic acid being particularly preferred.

The sublingual, buccal or rapid oral disintegrating preparation can be prepared by mixing the compound of the present invention or the concomitant drug and an excipient by a method per se known. Furthermore, if desired, the auxiliary agents described above, such as the lubricant, isotonizing agent, hydrophilic carrier, water-dispersible polymer, stabilizer, colorant, sweetener, preservative, etc. may also be admixed. After mixing the components described above simultaneously or at certain time intervals, the mixture is compressed into tablets to obtain the sublingual, buccal or rapid oral disintegration tablet. In order to obtain a suitable hardness, a solvent such as water, an alcohol, etc. can be used to moisturize or wet the components before or after tabletting, followed by drying.

In preparing the oral mucosal patch (film), the compound of the present invention or the concomitant drug and the water-dispersible polymer (preferably, hydroxypropyl cellulose, hydroxypropylmethyl cellulose), excipient, etc. described above are dissolved in a solvent such as water, etc. and then the resulting solution is cast into a film. In addition, additives such as a plasticizer, a stabilizer, an antioxidant, a preservative, a colorant, a buffering agent, a sweeteners, etc. may be added to the preparation. A glycol such as polyethylene glycol, propylene glycol, etc. may be added to impart an appropriate elasticity to a film, and a bioadhesive polymer (e.g., polycarbophile, carbopol) may also be added to enhance the adhesion of the film to the oral mucosal lining. The casting can be carried out by pouring a solution onto a non-adhesive surface, spreading the solution using a coater such as a doctor blade in a uniform thickness (preferably, approximately 10 to 1000 microns), and then drying the solution to form a film. The film thus formed is dried at room temperature or while warming, and then cut into pieces each having a desired surface area.

A preferred rapid oral disintegrating preparation is, for example, a rapid diffusion preparation in a solid network form, which comprises the compound of the present invention or the concomitant drug and a water-soluble or water-diffusible carrier inert to the compound of the present invention or the concomitant drug. The network is formed by sublimating a solvent from the solid composition comprising a solution of the compound of the present invention or the concomitant drug in a suitable solvent.

In addition to the compound of the present invention or the concomitant drug, the composition of the rapid oral disintegrating preparation may preferably contain a matrix-forming agent and secondary components.

Examples of the matrix-forming agent include gelatins, dextrins and animal or vegetable proteins from soybean, wheat, psyllium seed, etc.; gummy materials such as gum arabic, guar gum, agar, xanthan gum, etc.; polysaccharides; alginates; carboxymethylcelluloses; carrageenans; dextrans; pectins; synthetic polymers such as polyvinyl pyrrolidones; materials derived from gelatin-gum arabic complexes, etc. The matrix-forming agent further includes saccharides such as mannitol, dextrose, lactose, galactose, trehalose, etc.; cyclic saccharides such as cyclodextrins, etc.; inorganic salts such as sodium phosphate, sodium chloride, aluminum silicate, etc.; amino acids having 2 to 12 carbon atoms such as glycine, L-alanine, L-aspartic acid, L-glutamic acid, L-hydroxyproline, L-isoleucine, L-leucine, L-phenylalanine, etc.

One or more matrix-forming agents can be incorporated into a solution or suspension before solidification. The matrix-forming agents may be present in addition to a surfactant, or may be present in the absence of a surfactant. The matrix-forming agents serve not only to form a matrix itself, but also assist to maintain diffusion of the compound of the present invention or the concomitant drug in the solution or suspension.

The composition may contain a secondary component such as a preservative, an antioxidant, a surfactant, a thickening agent, a colorant, pH adjusting agent, a flavor, a sweetener, a taste masking agent, etc. As the suitable colorant, there are, for example, iron oxide red, black and yellow, FD & C dyes available from ERIS & EVERALD such as FD & C Blue No. 2 and FD & C Red No. 40, etc. Examples of the suitable flavor include mint, raspberry, licorice, orange, lemon, grape fruit, caramel, vanilla, cherry, grape flavor and a combination thereof. Examples of the suitable pH adjusting agent include citric acid, tartaric acid, phosphoric acid, hydrochloric acid and maleic acid. Examples of the suitable sweetener include aspartame, acesulfame K and thaumatine. Examples of the suitable taste masking agent include sodium bicarbonate, ion exchange resins, cyclodextrin inclusion compounds, adsorbents and microencapsulated apomorphine.

The preparation generally contains the compound of the present invention or the concomitant drug in an amount of about 0.1 to about 50% by weight, preferably about 0.1 to about 30% by weight and, preferably, the preparation (the sublingual tablet, buccal, etc. described above) allows 90% or more of the compound of the present invention or the concomitant drug to be dissolved (in water) within a time period of about 1 to about 60 minutes, preferably about 1 minute to about 15 minutes, more preferably about 2 minutes to about 5 minutes, or is a rapid oral disintegrating preparation which disintegrates within about 1 to about 60 seconds, preferably about 1 to about 30 seconds, more preferably about 1 to about 10 seconds, after being placed in the oral cavity.

The amount of the above excipient is about 10 to about 99% by weight, preferably about 30 to about 90% by weight based on the total weight of the preparation. The amount of β-cyclodextrin or β-cyclodextrin derivative is about 0 to about 30% by weight based on the total weight of the preparation. The amount of the lubricant is about 0.01 to about 10% by weight, preferably about 1 to about 5% by weight based on the total weight of the preparation. The amount of the isotonizing agent is about 0.1 to about 90% by weight, preferably about 10 to about 70% by weight based on the total weight of the preparation. The amount of the hydrophilic carrier is about 0.1 to about 50% by weight, preferably about 10 to about 30% by weight based on the total weight of the preparation. The amount of the water-dispersible polymer is about 0.1 to about 30% by weight, preferably about 10 to about 25% by weight based on the total weight of the preparation. The amount of the stabilizer is about 0.1 to about 10% by weight, preferably about 1 to about 5% by weight based on the total weight of the preparation. If necessary, the preparation described above may further contain additives such as a colorant, a sweetener, a preservative, etc.

A dose of the combined preparations of the present invention varies depending upon kind of the compound of the present invention, age, body weight, conditions, dosage form, route for administration, dosing period, etc.

A dose of the compound of the present invention may vary depending upon subject to be administered, target organ, conditions, route of administration, etc., and in oral administration, the compound is generally administered to the patient with cancer (as 60 kg body weight) in a daily dose of about 0.01 to about 100 mg, preferably about 0.1 to about 50 mg and more preferably about 0.1 to about 20 mg. In parenteral administration, a single dose of the compound may vary depending upon subject to be administered, target organ, conditions, route of administration, etc., and in the form of an injectable dosage form, it is advantageous to intravenously administer the compound to the patient with cancer (as 60 kg body weight) generally in a daily dose of about 0.001 to about 30 mg, preferably about 0.01 to about 20 mg, and more preferably about 0.01 to about 10 mg. For other animal species, the corresponding dose as converted per 60 kg weight can be administered. Of course, the dose may vary depending on individual conditions as described above; in such a case, a dose less than the dose given above may be sufficient, or a dose higher than the range above may be used.

It is possible to set any range of a dose for the concomitant drug, so long as it causes no adverse side effects. A daily dose of the concomitant drug may vary depending on the severity of disease, the age, sex, body weight and susceptibility of the subject, dosing period and intervals, characteristics, formulation, type and active components of the pharmaceutical preparation, etc. and is not particularly limited. For example, in oral administration, the dose is about 0.001 to 2000 mg, preferably about 0.01 to 500 mg, and more preferably about 0.1 to 100 mg per kg body weight of mammals in terms of a drug; usually, this dose is administered by dividing 1 to 4 times per day.

When the pharmaceutical preparations of the present invention are administered, they may be administered concomitantly. Alternatively, the concomitant drug is first administered and then the compound of the present invention is administered, or the compound of the present invention is first administered and then the concomitant drug is administered. When they are administered at certain time intervals, the intervals vary depending on the active component to be administered, dosage form and route of administration; for example, when the concomitant drug is first administered, the compound of the present invention may be administered within 1 minute to 3 days, preferably 10 minutes to 1 day, more preferably 15 minutes to 1 hour after the administration of the concomitant drug. When the compound of the present invention is first administered, the concomitant drug may be administered within 1 minute to 1 day, preferably 10 minutes to 6 hours, more preferably 15 minutes to 1 hour after the administration of the compound of the present invention.

As a preferred method of administration, for example, about 0.001 to 200 mg/kg of the concomitant drug in the form of an oral dosage preparation is administered orally and, after about 15 minutes, about 0.005 to 0.5 mg/kg of the compound of the present invention in the form of a parenteral preparation is administered parenterally as a daily dose.

As the metastins, there are used, for example, human metastin described in WO 00/24890, mouse or rat metastin described in WO 01/75104, etc.

Specific examples of human metastin include a peptide comprising the N-terminal 47th-54th amino acid sequence in the amino acid sequence represented by SEQ ID NO: 1 and consisting of 8 to 54 amino acid residues, and the like.

The "peptide comprising the N-terminal 47th-54th amino acid sequence in the amino acid sequence represented by SEQ ID NO: 1 and consisting of 8 to 54 amino acid residues" may be any peptide, as far as it is a peptide comprising the N-terminal 47th-54th amino acid sequence in the amino acid sequence represented by SEQ ID NO: 1 and consisting of 8 to 54 amino acid residues, but means that these peptides have substantially the same physiological activity (e.g., a receptor binding activity, a signal transduction action, a sugar level elevating action, a pancreatic glucagon secretion promoting action, a urine formation promoting action, etc.). Specifically, there are used (i) a peptide having the amino acid sequence represented by SEQ ID NO: 1, (ii) a peptide comprising the N-terminal 47th-54th amino acid sequence at the C terminus in the amino acid sequence represented by SEQ ID NO: 1 and consisting of 8 to 15 amino acid residues, etc.

More specifically; human metastin used includes (i) a peptide consisting of the amino acid sequence represented by SEQ ID NO: 1 (human metastin 54 (1-54)), (ii) a peptide consisting of the N-terminal 40th-54th amino acid sequence in the amino acid sequence represented by SEQ ID NO: 1 (human metastin 15 (40-54); SEQ ID NO: 15), (iii) a peptide consisting of the N-terminal 45th-54th amino acid sequence in the amino acid sequence represented by SEQ ID NO: 1 (human metastin 10 (45-54); SEQ ID NO: 16), (iv) a peptide consisting of the N-terminal 46th-54th amino acid sequence in the amino acid sequence represented by SEQ ID NO: 1 (human metastin 9 (46-54); SEQ ID NO: 17), (v) a peptide consisting of the N-terminal 47th-54th amino acid sequence in the amino acid sequence represented by SEQ ID NO: 1 (human metastin 8 (47-54); SEQ ID NO: 18), etc.

As mouse metastin (A), there are used, for example, (i) a peptide comprising the N-terminal 134th-141st amino acid sequence in the amino acid sequence represented by SEQ ID NO: 3 and consisting of 8 to 52 amino acid residues. Specific examples of mouse metastin (A) used include (i) a peptide consisting of the N-terminal 90th-141st amino acid sequence in the amino acid sequence represented by SEQ ID NO: 3, (ii) a peptide consisting of the N-terminal 132nd-141st amino acid sequence in the amino acid sequence represented by SEQ ID NO: 3, (iii) a peptide consisting of the N-terminal 127th-141st amino acid sequence in the amino acid sequence represented by SEQ ID NO: 3, and the like.

As mouse metastin (B), there are used, for example, (i) a peptide comprising the N-terminal 138th-145th amino acid sequence in the amino acid sequence represented by SEQ ID NO: 5 and consisting of 8 to 52 amino acid residues. Specific examples of mouse metastin (B) used include a peptide consisting of the N-terminal 94th-145th amino acid sequence in the amino acid sequence represented by SEQ ID NO: 5, and the like.

As rat metastin, there are used, for example, (i) a peptide comprising the N-terminal 112th-119th amino acid sequence in the amino acid sequence represented by SEQ ID NO: 7 and consisting of 8 to 52 amino acid residues. Specific examples of rat metastin used include (i) a peptide consisting of the N-terminal 68th-119th amino acid sequence in the amino acid sequence represented by SEQ ID NO: 7, (ii) a peptide consisting of the N-terminal 110th-119th amino acid sequence in the amino acid sequence represented by SEQ ID NO: 7, (iii) a peptide consisting of the N-terminal 105th-119th amino acid sequence in the amino acid sequence represented by SEQ ID NO: 7, and the like.

Throughout the specification, the metastins are represented in accordance with the conventional way of describing peptides, that is, the N-terminus (amino terminus) at the left hand and the C-terminus (carboxyl terminus) at the right hand. In the peptide represented by SEQ ID NO: 1, the C-terminus may be in any form of a carboxyl group (—COOH), a carboxylate (—COO$^-$), an amide (—CONH$_2$) and an ester (—COOR). Herein, examples of R of the ester group or alkyl amide include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, benzhydryl, etc., or an α-naphthyl-$C_{1-2}$ alkyl group such as α-naphthylmethyl, etc.; pivaloyloxymethyl group, which are widely used as an ester for oral use, and the like.

Furthermore, the metastins include peptides, wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated peptides such as glycopeptides bound to sugar chains.

For salts of the metastin of the present invention, preferred are salts with physiologically acceptable bases (e.g., alkali metal salts) or acids (e.g., organic acids or inorganic acids), etc., especially preferred are physiologically acceptable acid addition salts. Examples of such salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNAs encoding metastins, there are used, for example, DNAs encoding human metastin described in WO 00/24890, DNAs encoding mouse or rat metastin described in WO 01/75104, etc.

The DNAs encoding the metastins may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

The DNA encoding human metastin, mouse metastin precursor (A), mouse metastin precursor (B) or rat metastin precursor may be any DNA, so long as each is a DNA containing a base sequence represented by SEQ ID NO: 2, SEQ ID NO: 4, SEQ ID NO: 6 or SEQ ID NO: 8, or a DNA having a base sequence hybridizable to the base sequence represented by any base sequence represented by SEQ ID NO: 2, SEQ ID NO: 4, SEQ ID NO: 6 or SEQ ID NO: 8 under highly stringent conditions and encoding the human metastin, mouse metastin (A), mouse metastin (B) or rat metastin described above.

Specific examples of the DNA hybridizable to the base sequence represented by any of SEQ ID NO: 2, SEQ ID NO: 4, SEQ ID NO: 6 or SEQ ID NO: 8 include DNAs containing a base sequence having at least about 70% homology, preferably at least about 80% homology, more preferably at least about 90% homology and the most preferably at least about 95% homology, to the base sequence represented by any of SEQ ID NO: 2, SEQ ID NO: 4, SEQ ID NO: 6 or SEQ ID NO: 8.

Homology in the base sequence can be measured under the following conditions (an expectation value=10; gaps are allowed; filtering=ON; match score=1; mismatch score=−3) using the homology scoring algorithm NCBI BLAST (National Center for Biotechnology Information Basic Local Alignment Search Tool).

The hybridization can be carried out by per se publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

Specifically, as the DNA encoding the human metastin consisting of the amino acid sequence represented by SEQ ID NO: 1, the DNA consisting of the base sequence represented by SEQ ID NO: 2 is used. Accordingly, for the base sequence encoding the human metastin consisting of the various amino acid sequences described above, a base sequence corresponding to each of the partial amino acid sequences in the amino acid sequence represented by SEQ ID NO: 1 may be chosen from the base sequence represented by SEQ ID NO: 2.

As the DNA encoding the mouse metastin precursor (A) comprising the amino acid sequence represented by SEQ ID NO: 3, there are employed a DNA consisting of the base sequence represented by SEQ ID NO: 4, and the like. Accordingly, for the base sequence encoding the mouse metastin precursor (A) consisting of the various amino acid sequences described above, a base sequence corresponding to each of the partial amino acid sequences in the amino acid sequence represented by SEQ ID NO: 3 may be chosen from the base sequence represented by SEQ ID NO: 4.

As the DNA encoding the mouse metastin precursor (B) comprising the amino acid sequence represented by SEQ ID NO: 5, there are employed a DNA consisting of the base sequence represented by SEQ ID NO: 6, and the like. Accordingly, for the base sequence encoding the mouse metastin precursor (B) comprising of the various amino acid sequences described above, a base sequence corresponding to each of the partial amino acid sequences in the amino acid sequence represented by SEQ ID NO: 5 may be chosen from the base sequence represented by SEQ ID NO: 6.

As the DNA encoding the rat metastin comprising the amino acid sequence represented by SEQ ID NO: 7, there are employed a DNA consisting of the base sequence represented by SEQ ID NO: 8, and the like. Accordingly, for the base sequence encoding the rat metastin consisting of the various amino acid sequences described above, a base sequence corresponding to each of the partial amino acid sequences in the amino acid sequence represented by SEQ ID NO: 7 may be chosen from the base sequence represented by SEQ ID NO: 8.

More specifically, for the peptide consisting of the amino acid sequence represented by SEQ ID NO: 1 (human metastin 54 (1-54)), a DNA containing the base sequence represented by SEQ ID NO: 2, etc. is used.

For the peptide consisting of the N-terminal 40th-54th amino acid sequence in the amino acid sequence represented by SEQ ID NO: 1 (human metastin 15 (40-54); SEQ ID NO: 15), a DNA containing the base sequence represented by SEQ ID NO: 19, etc. is used.

For the peptide consisting of the N-terminal 45th-54th amino acid sequence in the amino acid sequence represented by SEQ ID NO: 1 (human metastin 10 (45-54); represented by SEQ ID NO: 16), a DNA containing the base sequence represented by SEQ ID NO: 20, etc. is used.

For the peptide consisting of the N-terminal 46th-54th amino acid sequence in the amino acid sequence represented by SEQ ID NO: 1 (human metastin 9 (46-54); represented by SEQ ID NO: 17), a DNA containing the base sequence represented by SEQ ID NO: 21, etc. is used.

For the peptide consisting of the N-terminal 47th-54th amino acid sequence in the amino acid sequence represented by SEQ ID NO: 1 (human metastin 8 (47-54); represented by SEQ ID NO: 18), a DNA containing the base sequence represented by SEQ ID NO: 22, etc. is used.

As the metastin receptor, its partial peptides or salts thereof, there are used, for example, a human metastin receptor, its partial peptides or salts thereof described in WO 00/24890, a mouse or rat human metastin receptor, its partial peptides or salts thereof described in WO 01/75104, etc.

Specifically, a protein comprising the same or substantially the same amino acid sequence as the amino acid sequence represented by SEQ ID NO: 9, SEQ ID NO: 11 or SEQ ID NO: 13, etc. is used as the metastin receptor.

The amino acid sequence which is substantially the same amino acid sequence as the amino acid sequence represented by SEQ ID NO: 9, SEQ ID NO: 11 or SEQ ID NO: 13 includes, for example, an amino acid sequence having at least about 70% homology, preferably at least about 80% homology, more preferably at least about 90% homology, and most preferably at least about 95% homology, to the amino acid sequence represented by SEQ ID NO: 9, SEQ ID NO: 11 or SEQ ID NO: 13.

Homology of the amino acid sequences can be determined under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

As the protein comprising substantially the same amino acid sequence as the amino acid sequence represented by SEQ ID NO: 9, SEQ ID NO: 11 or SEQ ID NO: 13, preferred is a protein having substantially the same amino acid sequence as the amino acid sequence represented by SEQ ID NO: 9, SEQ ID NO: 11 or SEQ ID NO: 13 and having the activity of the same nature as that of a protein having the amino acid sequence represented by SEQ ID NO: 9, SEQ ID NO: 11 or SEQ ID NO: 13, etc.

As the activity of substantially the same nature, there are, for example, a ligand binding activity, a signal transduction activity, and the like. The "substantially the same nature" is used to mean that the nature of these activities is equivalent in terms of quality. Thus, the activities such as a ligand binding activity, a signal transduction activity, etc. are preferably equivalent (e.g., about 0.01 to 100 times, preferably about 0.5 to 10 times, more preferably 0.5 to 2 times), but differences in quantitative factors such as a level of these activities, or such as a molecular weight of the protein may be present and allowable.

The activities such as a ligand binding activity, a signal transduction activity, etc. can be assayed by per se publicly known method with modifications and may be determined according to methods of determining a ligand or screening methods described in, e.g., WO 00/24890 or WO 01/75104.

Examples of the metastin receptor used include proteins comprising (i) the amino acid sequence represented by SEQ ID NO: 9, SEQ ID NO: 11 or SEQ ID NO: 13, of which at least 1 or 2 (preferably about 1 to about 30, more preferably about 1 to about 10 and most preferably several (1 or 2)) amino acids are deleted; (ii) the amino acid sequence represented by SEQ ID NO: 9, SEQ ID NO: 11 or SEQ ID NO: 13, to which at least 1 or 2 (preferably about 1 to about 30, more preferably about 1 to about 10 and most preferably several (1 or 2)) amino acids are added; (iii) the amino acid sequence represented by SEQ ID NO: 9, SEQ ID NO: 11 or SEQ ID NO: 13, in which at least 1 or 2 (preferably about 1 to about 30, more preferably about 1 to about 10 and most preferably several (1 or 2)) amino acids are substituted by other amino acids; or (iv) a combination of these amino acid sequences; and the like.

Throughout the specification, the metastin receptors are represented in accordance with the conventional way of describing peptides, that is, the N-terminus (amino terminus) at the left hand and the C-terminus (carboxyl terminus) at the right hand. In the metastin receptors including the metastin receptor represented by SEQ ID NO: 9, SEQ ID NO: 11 or SEQ ID NO: 13, the C-terminus may be in any form of a carboxyl group (—COOH), a carboxylate (—COO—), an amide (—CONH$_2$) and an ester (—COOR). Herein, examples of R of the ester group include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc., or an α-naphthyl-$C_{1-2}$ alkyl group such as α-naphthylmethyl, etc.; and pivaloyloxymethyl group, which are widely used as an ester for oral use, and the like.

Where the metastin receptors contain a carboxyl group (or a carboxylate) at a position other than the C-terminus, the carboxyl group may be amidated or esterified and such amides or esters are also included within the receptor protein of the present invention. In this case, the ester group used may be the same group as the C-terminal esters described above.

Furthermore, the metastin receptors include those wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the metastin receptors include human metastin receptor consisting of the amino acid sequence represented by SEQ ID NO: 9, rat metastin receptor consisting of the amino acid sequence represented by SEQ ID NO: 11, mouse metastin receptor consisting of the amino acid sequence represented by SEQ ID NO: 13, etc.

The partial peptides of the metastin receptor (hereinafter sometimes simply referred to as the partial peptide) may be any peptide, so long as they are partial peptides of the metastin receptor described above; there are used those such as protein molecules of the metastin receptor, which are the sites exposed outside the cell membrane, and having a ligand binding activity.

Specifically, the partial peptide of the metastin receptor consisting of the amino acid sequence represented by SEQ ID NO: 9, SEQ ID NO: 11 or SEQ ID NO: 13 is a peptide containing the parts analyzed to be extracellular domains (hydrophilic domains) in the hydrophobic plotting analysis. A peptide containing a hydrophobic domain in part can be used as well. In addition, the peptide may contain each domain separately or a plurality of domains together.

In the metastin receptor, preferred partial peptides are those having the number of amino acids of at least 20, preferably at least 50, and more preferably at least 100, in the amino acid sequence described above, which constitutes the metastin receptor.

The partial peptide may be a peptide having the amino acid sequence described above, of which at least 1 or 2 (preferably about 1 to about 10 and more preferably several (1 or 2)) amino acids are deleted; to which at least 1 or 2 (preferably about 1 to about 10 and more preferably several (1 or 2)) amino acids are added; or, in which at least 1 or 2 (preferably about 1 to about 10 and more preferably several (1 or 2)) amino acids are substituted by other amino acids.

In the partial peptide, the C terminus may be any form of a carboxyl group (—COOH), a carboxylate (—COO$^-$), an amide (—CONH$_2$) and an ester (—COOR), as in the metastin receptor described above.

Furthermore, the partial peptides include peptides, wherein the amino group at the N-terminal methionine residue is protected with a protecting group; those wherein the N-terminal region is cleaved in vivo and the glutamyl group thus formed is pyroglutaminated; those wherein a substituent on the side chain of an amino acid in the molecule is protected with a suitable protecting group, or conjugated peptides such as glycopeptides bound to sugar chains, as in the metastin receptors described above.

For salts of the metastin receptor or the partial peptide, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNA encoding the metastin receptor or its partial peptides, there are used, for example, a DNA encoding the human metastin receptor or its partial peptides described in WO 00/24890, a DNA encoding the mouse or rat metastin receptor or its partial peptides described in WO 01/75104, etc.

The DNAs encoding the metastin receptor or its partial peptides may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding human metastin receptor, mouse metastin receptor or rat metastin receptor may be any DNA, so long as it is a DNA comprising each base sequence represented by SEQ ID NO: 10, SEQ ID NO: 12 or SEQ ID NO: 14, or a DNA comprising a base sequence hybridizable to the base sequence represented by SEQ ID NO: 10, SEQ ID NO: 12 or SEQ ID NO: 14 under highly stringent conditions and encoding a receptor having the activity of substantially the same nature (e.g., a ligand binding activity, a signal transduction activity, etc.) as that of the human metastin receptor, mouse metastin receptor or rat metastin receptor consisting of the amino acid sequence represented by SEQ ID NO: 10, SEQ ID NO: 12 or SEQ ID NO: 14.

Examples of the DNA hybridizable to the base sequence represented by any of SEQ ID NO: 10, SEQ ID NO: 12 or SEQ ID NO: 14 include DNAs comprising a base sequence having at least about 70% homology, preferably at least about 80% homology, more preferably at least about 90% homology and the most preferably at least about 95% homology, to the base sequence represented by any of SEQ ID NO: 10, SEQ ID NO: 12 or SEQ ID NO: 14.

Homology in the base sequence can be measured under the following conditions (an expectation value=10; gaps are allowed; filtering=ON; match score=1; mismatch score=−3) using the homology scoring algorithm NCBI BLAST (National Center for Biotechnology Information Basic Local Alignment Search Tool).

The hybridization can be carried out by per se publicly known methods or by modifications of these methods, for example, according to the method described in Molecular Cloning, 2nd (J. Sambrook et al., Cold Spring Harbor Lab. Press, 1989), etc. A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as the DNA encoding the human metastin receptor consisting of the amino acid sequence represented by SEQ ID NO: 9, the DNA consisting of the base sequence represented by SEQ ID NO: 10 is used.

As the DNA encoding the rat metastin receptor consisting of the amino acid sequence represented by SEQ ID NO: 11, the DNA consisting of the base sequence represented by SEQ ID NO: 12 is used.

As the DNA encoding the mouse metastin receptor consisting of the amino acid sequence represented by SEQ ID NO: 13, the DNA consisting of the base sequence represented by SEQ ID NO: 14 is used.

The metastin receptors, their partial peptides or salts thereof and the DNAs encoding the metastin receptors or their partial peptides can be obtained or produced by the methods described in WO 00/24890 or WO 01/75104.

The present invention will be described in detail by referring to EXAMPLES, FORMULATION EXAMPLES AND TEST EXAMPLES, but is not deemed to be limited thereto, and any modification may be made without departing from the scope of the present invention.

In the following EXAMPLES, the term "room temperature" normally means a temperature of about 10° C. to about 35° C. In percentages, the yield is shown by mol/mol % and the solvent used in chromatography by vol %, and the remaining by wt %. In proton NMR spectra, data on OH, NH protons, etc. that are broad and unidentified are not shown.

The other abbreviations used in the specification mean as follows.

| Abbreviation | Description |
| --- | --- |
| 10Ψ,CSNH | C-terminal-$CONH_2$ at the 10-position is substituted with —$CSNH_2$. |
| 1Ψ2,$CH_2$NH | The —CONH— bond between the 1- and 2-positions is substituted with the —$CH_2$NH— bond. |
| 2Ψ3,$CH_2$NH | The —CONH— bond between the 2- and 3-positions is substituted with the —$CH_2$NH— bond. |
| 3Ψ4,$CH_2$NH | The —CONH— bond between the 3- and 4-positions is substituted with the —$CH_2$NH— bond. |
| 4Ψ5,$CH_2$NH | The —CONH— bond between the 4- and 5-positions is substituted with the —$CH_2$NH— bond. |
| 6Ψ7,CSNH | The —CONH— bond between the 6- and 7-positions is substituted with the —CSNH— bond. |
| 6Ψ7,NHCO | The —CONH— bond between the 6- and 7-positions is substituted with the —NHCO— bond. |
| 6Ψ7,$CH_2$NH | The —CONH— bond between the 6- and 7-positions is substituted with the —$CH_2$NH— bond. |
| 6Ψ7,$CH_2$O | The —CONH— bond between the 6- and 7-positions is substituted with the —$CH_2$O— bond. |
| 7Ψ8,$CH_2$NH | The —CONH— bond between the 7- and 8-positions is substituted with the —$CH_2$NH— bond. |
| 8Ψ9,$CH_2$NH | The —CONH— bond between the 8- and 9-positions is substituted with the —$CH_2$NH— bond. |
| 9Ψ10,$CH_2$NH | The —CONH— bond between the 9- and 10-positions is substituted with the —$CH_2$NH— bond. |
| Abu | 2-aminobutanoic acid |
| Abz(2) | 2-aminobenzoic acid |
| Abz(3) | 3-aminobenzoic acid |
| Ac | acetyl |
| AcONB | N-acetoxy-5-norbornene-2,3-dicarboximide |
| Acp | 6-aminocaproic acid |
| AcOEt | ethyl acetate |
| AcOH | acetic acid |
| Aib | α-aminoisobutanoic acid |
| Ala(2-Qui) | 2-quinolylalanine |
| Ala(3-Bzt) | 3-benzothienylalanine |
| Ala(cPr) | cyclopropylalanine |
| Ala(Pip) | (4-piperidin-1-yl)alanine |
| Alb | Albizziin 2-amino-3-ureidopropionic acid |
| Ambz(4) | 4-aminomethylbenzoyl |
| Arg(Ac) | $N^{\omega}$-acetylarginine |
| Arg($Boc_2$, Me) | $N^{\omega,\omega'}$-bis-tert-butoxycarbonyl-$N^{\omega}$-methylarginine |
| Arg(Et) | $N^{\omega}$-ethylarginine |
| Arg(Me) | $N^{\omega}$-methylarginine |
| Arg(asy$Me_2$) or Arg($Me_2$)asym | asymmetric-$N^{\omega,\omega}$-dimethylarginine |
| Arg(sym$Me_2$) or Arg($Me_2$)sym | symmetric-$N^{\omega,\omega'}$-dimethylarginine |
| Arg($NO_2$) | $N^{\omega}$-nitroarginine |
| Arg(Pbf) | $N^{\omega}$-2,2,4,6,7-pentamethyldihydrobenzofuransulfonylarginine |
| Arg(n-Pr) | $N^{\omega}$-propylarginine |
| Arg(Tos) | $N^{\omega}$-tosylarginine |
| Asp(NHMe) | $N^{\omega}$-methylasparagine |
| Asp($NMe_2$) | $N^{\omega,\omega}$-dimethylasparagine |
| Asp(NHPen) | $N^{\omega}$-pentylasparagine |
| Asp(NHcPr) | $N^{\omega}$-cyclopropylasparagine |
| Asp(NHBzl) | $N^{\omega}$-benzylasparagine |
| AzaGly | azaglycine |
| AzaPhe | azaphenylalanine |
| Aze(2) | azetidine-2-carboxylic acid |
| Aze(3) | azetidine-3-carboxylic acid |
| β-Ala | β-alanine |
| Boc | tert-butoxycarbonyl |
| $Boc_2O$ | di-tert-butyl dicarbonate |
| Br-Z | 2-bromobenzyloxycarbonyl |

| Abbreviation | Description |
| --- | --- |
| Bu$^t$ | tert-butyl |
| Bzl | benzyl |
| CDI | 1,1'-carbonyldiimidazole |
| Cha | cyclohexylalanine |
| CIP | 2-chloro-1,3-dimethylimidazolium tetrafluoroborate |
| Cit | citrulline |
| Clt resin | 2-chlorotrytyl resin |
| Cl-Z | 2-chlorobenzyloxycarbonyl |
| cPr | cyclopropyl |
| Dab | 2,4-diaminobutanoic acid |
| Dap | 2,3-diaminopropionic acid |
| Dap(Ac) | $N^\beta$-acetyl-β-diaminopropionic acid |
| Dap(For) | $N^\beta$-formyl-β-diaminopropionic acid |
| Dap(Gly) | $N^\beta$-glycyl-β-diaminopropionic acid |
| Dap(GnGly) | $N^\beta$-(N-guanidinoglycyl)-β-diaminopropionic acid |
| DCM | dichloromethane |
| DEA | diethylamine |
| DIEA | N,N-diisopropylethylamine |
| DIPCDI | 1,3-diisopropylcarbodiimide |
| DMAP | 4-dimethylaminopyridine |
| DMF | N,N-dimethylformamide |
| EDT | 1,2-ethanedithiol |
| Fmoc | 9-fluorenylmethoxycarbonyl |
| For | formyl |
| γ-Abu | 4-aminobutanoic acid |
| γ-MeLeu | γ-methylleucine |
| Gn | guanidino |
| GuAmb | 4-guanidinomethylbenzoyl |
| Har | homoarginine |
| Har(Me) | $N^\omega$-methylhomoarginine |
| His(3Me) | 3-methylhistidine II-methylhistidine |
| HOAt | 1-hydroxy-7-azabenzotriazole |
| HOBt | 1-hydroxybenzotriazole |
| HONB | N-hydroxy-5-norbornene-2,3-dicarboximide |
| Hph | homophenylalanine |
| cisHyp | cis-4-hydroxyproline |
| Hyp | trans-4-hydroxyproline |
| Hyp(Bzl) | O-benzyl-trans-4-hydroxyproline |
| IndPr | 3-(indole-3-yl)propionyl |
| Izc | imidazolidine-2-carboxylic acid |
| Lys(Me$_2$) | $N^{\epsilon,\epsilon}$-dimethyllysine |
| MBHA | p-methylbenzhydrylamine |
| MeOH | methanol |
| Mtt | 4-methyltrytyl |
| N((CH$_2$)$_3$Gn)Gly | N-(3-guanidinopropyl)glycine |
| Nal(1) | 1-naphthylalanine |
| Nal(2) | 2-naphthylalanine |
| Nar | norarginine |
| Nar(Me) | $N^\omega$-methylnorarginine |
| Nle | norleucine |
| NMeAla | $N^\alpha$-methylalanine |
| NMeArg | $N^\alpha$-methylarginine |
| NMeAsn | $N^\alpha$-methylasparagine |
| NMeLeu | $N^\alpha$-methylleucine |
| NMePhe | $N^\alpha$-methylphenylalanine |
| NMeSer | $N^\alpha$-methylserine |
| NMeTrp | $N^\alpha$-methyltryptophan |
| NMeTyr | $N^\alpha$-methyltyrosine |
| Nva | Norvaline |
| OBu$^t$ | tert-butoxy |
| Orn | ornithine |
| Orn(Mtt) | $N^\delta$-(4-methyltrytyl)ornithine |
| PAL | 5-(4-(9-fluorenylmethoxycarbonyl)aminomethyl-3,5-dimethoxyphenoxy)valeric acid |
| Pbf | 2,2,4,6,7-pentamethyldihydrobenzofuran-5-sulfonyl |
| pGlu | pyroglutamic acid |
| Phe(2Cl) | 2-chlorophenylalanine |
| Phe(2F) | 2-fluorophenylalanine |
| Phe(2Me) | 2-methylphenylalanine |
| Phe(3,4Cl$_2$) | 3,4-dichlorophenylalanine |
| Phe(3,4F$_2$) | 3,4-difluorophenylalanine |
| Phe(3CF$_3$) | 3-trifluoromethylphenylalanine |
| Phe(3Cl) | 3-chlorophenylalanine |
| Phe(3F) | 3-fluorophenylalanine |
| Phe(3Me) | 3-methylphenylalanine |
| Phe(4Cl) | 4-chlorophenylalanine |
| Phe(4CN) | 4-cyanophenylalanine |
| Phe(4F) | 4-fluorophenylalanine |
| Phe(4Gn) | 4-guanidinophenylalanine |

| Abbreviation | Description |
| --- | --- |
| Phe(4NH$_2$) | 4-aminophenylalanine |
| Phe(4NO$_2$) | 4-nitrophenylalanine |
| Phe(4CN) | 4-cyanophenylalanine |
| Phe(4Me) | 4-methylphenylalanine |
| Phe(F$_5$) | pentafluorophenylalanine |
| αMePhe | α-methylphenylalanine |
| PheΨ(CH$_2$O)Gly | The —CONH— bond between Phe and Gly is substituted with the —CH$_2$O— bond. |
| PheΨ(CSNH)—NH$_2$ | The C-terminal phenylalanylamide is substituted with the phenylalanylthioamide. |
| Phg | phenylglycine |
| PhOH | phenol |
| PhSMe | thioanisole |
| Pic(2) | pipecolinic acid |
| Pic(3) | 3-piperidinecarboxylic acid |
| Pip(2) | 2-aminopipecolinic acid |
| Pro | proline |
| Pro(4F) | trans-4-fluoroproline |
| Pro(4NH$_2$) | cis-4-aminoproline |
| Pya(2) | 2-pyridylalanine |
| Pya(3) | 3-pyridylalanine |
| Pya(4) | 4-pyridylalanine |
| PyAOP | (7-azabenzotriazole-1-yloxy)-tris(pyrrolidino)phosphonium hexafluorophosphate |
| PyBOP | (benzotriazol-1-yloxy)-tris(pyrrolidino)phosphonium hexafluorophosphate |
| PyBrop | bromo-tris(pyrrolidino)phosphonium hexafluorophosphate |
| Pzc(2) | piperazine-2-carboxylic acid |
| Sar | N-methylglycine |
| Ser(Ac) | O-acetylserine |
| Ser(Me) | O-methylserine |
| Ser(3Phenyl) | 3-phenylserine |
| Thi | 2-thienylalanine |
| Thz | thioproline |
| Tic | 1,2,3,4-tetrahydroisoquinoline-2-carboxylic acid |
| TIS | triisopropylsilane |
| Tle | tert-leucine |
| Tos | tosyl |
| Trp(For) | N$^{in}$-formyltryptophan |
| Trt | trytyl |
| Tyr(Me) | O-methyltyrosine |
| Tyr(PO$_3$H$_2$) | O-phosphotyrosine |
| TyrΨ(CH$_2$NH)Asn | The —CONH— bond between Tyr and Asn is substituted with the —CH$_2$NH— bond. |
| TFA | trifluoroacetic acid |
| TFE | trifluoroethanol |
| Z | benzyloxycarbonyl |

In the specification, where the codes of bases and amino acids are denoted by abbreviations, they are based on the abbreviations in accordance with the IUPAC-IUB-Commission on Biochemical Nomenclature or the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
Y: thymine or cytosine
N: thymine, cytosine, adenine or guanine
R: adenine or guanine
M: cytosine or adenine
W: thymine or adenine
S: cytosine or guanine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
TFA: trifluoroacetic acid
EIA: enzyme immunoassay
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine Trp or W: tryptophan
Pro or P: proline
Asn or N: asparagine
Gln or Q: glutamine
pGlu: pyroglutamic acid The sequence identification numbers in the sequence listing of the specification indicates the following sequence, respectively.

[SEQ ID NO: 1]
This shows the amino acid sequence of human-derived metastin (Metastin).

[SEQ ID NO: 2]
This shows the base sequence of DNA encoding human metastin.

[SEQ ID NO: 3]
This shows the amino acid sequence of mouse metastin precursor (A).

[SEQ ID NO: 4]
This shows the base sequence of DNA encoding mouse metastin precursor (A), which is the base sequence in plasmid pCMV-mKiSS-1 harbored on transformant Escherichia coli DH10B/pCMV-mKiSS-1.

[SEQ ID NO: 5]
This shows the amino acid sequence of mouse metastin precursor (B).

[SEQ ID NO: 6]
This shows the base sequence of DNA encoding mouse metastin precursor (B), which is the base sequence in plasmid pCR2.1-mKiSS-1.4A harbored on transformant Escherichia coli DH5α/pCPR2.1-mKiSS-1.4A.

[SEQ ID NO: 7]
This shows the amino acid sequence of rat-derived metastin precursor

[SEQ ID NO: 8]
This shows the base sequence of DNA encoding rat metastin precursor.

[SEQ ID NO: 9]
This shows the amino acid sequence of human OT7T175 (metastin receptor).

[SEQ ID NO: 10]
This shows the base sequence of DNA encoding human OT7T175 (metastin receptor).

[SEQ ID NO: 11]
This shows the amino acid sequence of rat OT7T175 (metastin receptor).

[SEQ ID NO: 12]
This shows the base sequence of DNA encoding rat OT7T175 (metastin receptor).

[SEQ ID NO: 13]
This shows the amino acid sequence of mouse OT7T175 (metastin receptor).

[SEQ ID NO: 14]
This shows the base sequence of DNA encoding mouse OT7T175 (metastin receptor).

[SEQ ID NO: 15]
This shows the amino acid sequence of human metastin 15 (40-54).

[SEQ ID NO: 16]
This shows the amino acid sequence of human metastin 10 (45-54) (MS10).

[SEQ ID NO: 17]
This shows the amino acid sequence of human metastin 9 (46-54).

[SEQ ID NO: 18]
This shows the amino acid sequence of human metastin 8 (47-54).

[SEQ ID NO: 19]
This shows the base sequence of DNA encoding human metastin 15 (40-54).

[SEQ ID NO: 20]
This shows the base sequence of DNA encoding human metastin 10 (45-54).

[SEQ ID NO: 21]
This shows the base sequence of DNA encoding human metastin 9 (46-54).

[SEQ ID NO: 22]
This shows the base sequence of DNA encoding human metastin 8 (47-54).

The transformant Escherichia coli DH10B/pCMV-mKiSS-1 has been on deposit since Jan. 24, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan, as the Accession Number FERM BP-7003 and since Dec. 16, 1999 with Institute for Fermentation (IFO), located at 2-17-85, Juso-Honmachi, Yodogawa-ku, Osaka-shi, Osaka, Japan, as the Accession Number IFO 16348.

The transformant Escherichia coli DH5α/pCR2.1-mKiSS-1.4A has been on deposit since Mar. 6, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan, as the Accession Number FERM BP-7073 and since Feb. 16, 2000 with Institute for Fermentation (IFO), located at 2-17-85 Juso-Honmachi, Yodogawa-ku, Osaka-shi, Osaka, Japan, as the Accession Number IFO 16360.

EXAMPLES

Reference Example 1

Production of N-methyl-N,N'-Bis-Boc-1-guanylpyrazole

Under a nitrogen flow, 720 mg of 60% NaH in oil was dissolved in 20 μL of dry DMF and 20 mL of dry DMF solution of 5.59 g of N,N'-Bis-Boc-1-guanylpyrazole commercially available was added to the solution at 0° C., followed by stirring for 10 minutes. After 1.68 mL of methyl iodide was added thereto, the mixture was stirred at room temperature for 24 hours. After the solvent was removed by distillation, the residue was dissolved in AcOEt and the solution washed with 1N HCl aq. solution, satd. NaHCO$_3$ aq. solution and then satd NaCl aq. solution. After drying over Na$_2$SO$_4$, the solvent was concentrated and the concentrate was purified by flush column chromatography (ethyl acetate/n-hexane=1/4) using silica gel 60 (200 mL) to give 5.35 g (yield 91.6%) of N-methyl-N,N'-bis-Boc-1-guanylpyrazole as a colorless oil.

$^1$H NMR (300 MHz, CDCl$_3$): δ 8.00 (br s, 1H), 7.69 (br s, 1H), 6.42 (dd, 1H, J=2.7, 1.5 Hz), 3.25 (s, 3H), 1.53 (s, 9H), 1.30 (s, 9H)

Elemental analysis as C$_{15}$H$_{24}$N$_4$O$_4$
Calcd.: C, 55.54; H, 7.46; N, 17.27
Found: C, 55.36; H, 7.48; N, 17.06
Rf1: 0.64, Rf2: 0.79

Developing Solvent for TLC:
Rf1 (ethyl acetate/n-hexane=1/2), Rf2 (methanol/chloroform=2/98)
Elution time on HPLC: 26.7 mins.
Elution Conditions:
Column: Wakosil-II 5C18 HG (4.6×100 mm)
Linear density gradient elution with eluants A/B=100/0-20/80, using 0.1% TFA in water as eluant A and acetonitrile containing 0.1% TFA as eluant B (40 mins.)
Flow rate: 1.0 ml/min.

Reference Example 2

Production of
N-methyl-N,N'-Bis-Z-1-guanylpyrazole

In an argon atmosphere, 40 mg of 60% NaH in oil was dissolved in 5 mL of dry DMF and 5 mL of dry DMF solution of 380 mg of N,N'-Bis-Z-1-guanylpyrazole commercially available was added to the solution at 0° C., followed by stirring for 10 minutes. After 125 μL of methyl iodide was added thereto, the mixture was stirred at room temperature for 15 hours. After the solvent was distilled off, the residue was dissolved in AcOEt and the solution washed with 1N HCl aq. solution, satd. NaHCO$_3$ aq. solution and then satd. NaCl aq. solution. After drying over Na$_2$SO$_4$, the solvent was concentrated to give 393 mg of the crude product. From the crude product, 170 mg was purified by flush column chromatography (ethyl acetate/n-hexane=1/4) using silica gel 60 (75 mL) to give 353 mg (yield 89.5%) of N-methyl-N,N'-bis-Z-1-guanylpyrazole as a colorless oil.
$^1$H NMR (300 MHz, CDCl$_3$): δ 7.97 (br s, 1H), 7.61 (d, 1H, J=1.0 Hz), 7.37-7.32 (m, 4H), 7.29-7.26 (m, 4H), 7.16-7.13 (m, 2H), 6.36 (dd, 1H, J=2.8, 1.6 Hz), 5.18 (s, 2H), 5.04 (s, 2H), 3.22 (s, 3H)
Elemental analysis as C$_{21}$H$_{20}$N$_4$O$_4$
Calcd.: C, 64.28; H, 5.14; N, 14.28
Found: C, 64.09; H, 5.24; N, 14.43
Rf1: 0.50, Rf2: 0.86
Developing Solvent for TLC:
Rf1 (ethyl acetate/n-hexane=1/2)
Rf2 (methanol/chloroform=2/98)
Elution time on HPLC: 28.9 mins.
Elution Conditions:
Column: Wakosil-II 5C18 HG (4.6×100 mm)
Linear density gradient elution with eluants A/B=100/0-20/80, using 0.1% TFA in water as eluant A and acetonitrile containing 0.1% TFA as eluant B (40 mins.)
Flow rate: 1.0 ml/min.

Example 1

(Synthesis A): Production of des(1)-Ac-[D-Tyr2,D-Trp3,Thr5,AzaGly7,D-Arg9,Trp10]MS10 (Compound No. 708)

Trp(Boc), D-Arg(Pbf) and Leu were introduced in this order into 178 mg of Rink Amide MBHA Resin (0.56 mmol/g) on an ABI 433A peptide synthesizer to produce H-Leu-D-Arg(Pbf)-Trp(Boc)-Rink Amide MBHA resin. Separately, 116.3 mg (0.4 mmol) of Fmoc-NHNH$_2$.HCl was suspended in 1 mL of DMF, and under ice cooling a suspension of 61.6 mg (0.38 mmol) of CDI in 10 ml of THF was added thereto. Subsequently, 139.4 μl (0.8 mmol) of DIEA was added to the mixture, followed by stirring at room temperature for an hour. The resulting reaction solution was added to the H-Leu-D-Arg(Pbf)-Trp(Boc)-Rink Amide MBHA resin described above, followed by stirring at room temperature for 15 hours. After completion of the reaction, the resin was washed and, Phe, Thr(Bu$^t$) and Asn(Trt) were introduced in this order into the resulting Fmoc-AzaGly-Leu-D-Arg(Pbf)-Trp(Boc)-Rink Amide MBHA resin on ABI 433A. The resin was divided into halves, one of which was taken out and the remaining half was applied again on ABI 433A, whereby D-Trp(Boc) and D-Tyr (Bu$^t$) were introduced in this order to give the H-D-Tyr(Bu$^t$)-D-Trp(Boc)-Asn(Trt)-Thr(Bu$^t$)-Phe-AzaGly-Leu-D-Arg(Pbf)-Trp(Boc)-Rink Amide MBHA resin. Subsequently, the product was treated for 20 minutes in 3 ml of DMF with 9.4 μl (0.1 mmol) of Ac$_2$O and 17.4 μl (0.1 mmol) of DIEA for N-terminal acetylation. The resin was washed and dried to give 202.2 mg of the Ac-D-Tyr(Bu$^t$)-D-Trp(Boc)-Asn(Trt)-Thr(Bu$^t$)-Phe-AzaGly-Leu-D-Arg(Pbf)-Trp(Boc)-Rink Amide MBHA resin. To the resin obtained, 1.5 mL of TFA/PhSMe/m-cresol/H$_2$O/TIS/EDT (80/5/5/5/2.5/2.5) was added and the mixture was stirred for 90 minutes. Diethyl ether was added to the reaction solution, the resulting precipitate was centrifuged, and the supernatant was removed. This procedure was repeated twice for washing. The residue was extracted with an aqueous acetic acid solution and the extract was filtered to remove the resin. Then, linear density gradient elution (60 minutes) was performed at a flow rate of 15 ml/min with eluants A/B: 70/30-60/40 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized to give 16.2 mg of white powders.
Mass spectrum (M+H)$^+$ 1284.9 (calcd. 1284.6)
Elution time on HPLC: 13.3 mins.
Elution Conditions:
Column: YMC-AM301 (4.6×100 mm)
Linear density gradient elution with eluants A/B=80/20-30/70, using 0.1% TFA in water as eluant A and acetonitrile containing 0.1% TFA as eluant B (25 mins.)
Flow rate: 1.0 ml/min.

Example 2

Production of Fmoc-AzaGly-Leu-Arg(Boc$_2$, Me)-Trp(Boc)-Rink Amide MBHA Resin (SEQ ID NO:33)

After 5 g (0.4 mmol/g) of commercially available Rink Amide MBHA resin was swollen in DMF, the resin was treated with 50 ml of 20% piperidine/DMF solution for 20 minutes to remove the Fmoc group. The resin obtained was washed with DMF and treated with 4.213 g (8 mmol) of Fmoc-Trp(Boc)-OH, 1.272 mL (8 mmol) of DIPCDI and 16 mL (8 mmol) of 0.5M HOAt/DMF solution at room temperature for 90 minutes, whereby Trp(Boc) was introduced to give the Fmoc-Trp(Boc)-Rink Amide MBHA resin. In a similar manner, Orn(Mtt) was introduced to give 2 mmol of the Fmoc-Orn(Mtt)-Trp(Boc)-Rink Amide MBHA resin. After the resin obtained was washed and swollen with DCM, 50 mL of TFA/TIS/DCM (Jan. 5, 1994) was added thereto, followed by shaking for 10 minutes and removing the solution through filtration. This procedure was repeated until yellow color caused by free Mtt group in a TFA/TIS/DCM (Jan. 5, 1994) solution disappeared when the solution was added; thus the Mtt group was removed.

The resulting Fmoc-Orn-Trp(Boc)-Rink Amide MBHA resin was neutralized with 5%-DIEA/DCM solution. After washing with DCM, 25 mL of DCM-TFE (4:1) and 1.946 g (6 mmol) of N-methyl-N,N'-bis-Boc-1-guanylpyrazole obtained in REFERENCE EXAMPLE 1 were added to the resin. DIEA was added to the mixture to adjust pH of the resulting solution to 10. The solution was shaken for 15 hours to give 6.195-g of Fmoc-Arg(Boc$_2$,Me)-Trp(Boc)-Rink Amide MBHA resin. Fmoc-Leu was introduced into the obtained resin as in the same manner described above. The resin was divided in halves and the Fmoc group was removed from the thus obtained Fmoc-Leu-Arg(Boc$_2$,Me)-Trp(Boc)-Rink Amide MBHA resin (1 mmol) to give H-Leu-Arg(Boc$_2$, Me)-Trp(Boc)-Rink Amide MBHA resin (1 mmol).

Separately, 1.745 g (6 mmol) of Fmoc-NHNH$_2$HCl was suspended in 20 mL of DMF-THF (4:1). Under ice cooling, 973 mg (6 mmol) of CDI and 2.09 mL (12 mmol) of DIEA were added to the suspension, followed by stirring at room temperature for an hour. The resulting reaction solution was added to the H-Leu-Arg(Boc$_2$,Me)-Trp(Boc)-Rink Amide MBHA resin described above, and the mixture was stirred at room temperature for 15 hours. After completion of the reaction, the resin was washed and dried to give 3.314 g of the Fmoc-AzaGly-Leu-Arg(Boc$_2$,Me)-Trp(Boc)-Rink Amide MBHA resin (SEQ ID NO: 33).

Example 3

(Synthesis B): Production of des(1-3)-Ac-[Thr5, AzaGly7,Arg(Me)9,Trp10]MS10 (Compound No. 709)

After 5.455 g (0.55 mmol/g) of commercially available Rink Amide MBHA resin was swollen in DMF, the resin was treated with 50 ml of 20% piperidine/DMF solution for 20 minutes to remove the Fmoc group. The resin obtained was washed with DMF and then treated with 6.319 g (12 mmol) of Fmoc-Trp(Boc)-OH, 1.908 mL (12 mmol) of DIPCDI and 24 mL (12 mmol) of 0.5M HOAt/DMF solution at room temperature for 90 minutes, whereby Trp(Boc) was introduced to give the Fmoc-Trp(Boc)-Rink Amide MBHA resin. In a similar manner, Orn(Mtt) was introduced to give 3 mmol of the Fmoc-Orn(Mtt)-Trp(Boc)-Rink Amide MBHA resin. The resin obtained was washed with DCM and swollen, and then 50 mL of TFA/TIS/TFE/DCM (1/5/19/75) was added to the resin, followed by shaking for 10 minutes and removing the solution through filtration. This procedure was repeated until yellow color caused by free Mtt group in a TFA/TIS/TFE/DCM (1/5/19/75) solution disappeared when the solution was added thereto; thus, the Mtt group was removed.

The resulting Fmoc-Orn-Trp(Boc)-Rink Amide MBHA resin was neutralized with 5%-DIEA/DCM solution. After washing with DCM, 20 mL of DCM-TFE (4:1) and 2.919 g (9 mmol) of N-methyl-N,N'-bis-Boc-1-guanylpyrazole obtained in REFERENCE EXAMPLE 1 were added to the resin. DIEA was added to the mixture to adjust pH of the solution to 10. The mixture was shaken for 15 hours to give the Fmoc-Arg(Boc$_2$,Me)-Trp(Boc)-Rink Amide MBHA resin. Fmoc-Leu was introduced into the obtained resin as in the same manner described above. The Fmoc group was then removed from the thus obtained Fmoc-Leu-Arg(Boc$_2$,Me)-Trp(Boc)-Rink Amide MBHA resin (3 mmol) to give the H-Leu-Arg(Boc$_2$,Me)-Trp(Boc)-Rink Amide MBHA resin (3 mmol).

Separately, 3.489 g (12 mmol) of Fmoc-NHNH$_2$.HCl was suspended in 20 mL of DMF. Under ice cooling, a suspension of 1.849 g (11.4 mmol) of CDI in 20 mL of THF was added and then 4.181 mL (24 mmol) of DIEA was added to the mixture, followed by stirring at room temperature for an hour. The resulting reaction solution was added to the H-Leu-Arg (Boc$_2$,Me)-Trp(Boc)-Rink Amide MBHA resin described above, followed by stirring at room temperature for 15 hours. After completion of the reaction, the resin was washed and dried to give the Fmoc-AzaGly-Leu-Arg(Boc$_2$,Me)-Trp (Boc)-Rink Amide MBHA resin (SEQ ID NO: 33).

The resin obtained was swollen in DMF and then treated with 30 ml of 20% piperidine/DMF solution for 20 minutes to remove the Fmoc group. After the resin obtained was washed with DMF, the resin was treated with 5.419 g (12 mmol) of Trt-Phe-OH 0.5AcOEt, 6.257 g (12 mmol) of PyAOP, 24 mL (12 mmol) of 0.5M HOAt/DMF and 7.316 mL (42 mmol) of DIEA at room temperature for 90 minutes to give the Trt-Phe-AzaGly-Leu-Arg(Boc$_2$,Me)-Trp(Boc)-Rink Amide MBHA resin (SEQ ID NO: 34). After the resin obtained was washed with DCM and swollen, 50 mL of TFA/TIS/TFE/DCM (1/5/19/75) was added to the resin, followed by shaking for 10 minutes and removing the solution through filtration. This procedure was repeated until yellow brown color caused by the free Trt group in a TFA/TIS/TFE/DCM (1/5/19/75) solution disappeared when the solution was added; thus the Trt group was removed. The H-Phe-AzaGly-Leu-Arg(Boc$_2$, Me)-Trp(Boc)-Rink Amide MBHA resin (SEQ ID NO: 35) obtained was neutralized with 5%-DIEA/DMF solution and washed in DMF. Thereafter, the resin was treated with 4.780 g (12 mmol) of Fmoc-Thr(Bu$^t$)-OH, 1.908 mL (12 mmol) of DIPCDI and 24 mL (12 mmol) of 0.5M HOAt/DMF at room temperature for 90 minutes to introduce Thr(Bu$^t$). Subsequently, the Fmoc deprotection through treatment with 50 ml of 20% piperidine/DMF solution for 20 minutes and condensation by the DIPCDI/HOAt method as in the introduction of Thr(Bu$^t$) were performed to introduce Asn(Trt). The resin was then washed and dried to give 10.624 g of the Fmoc-Asn (Trt)-Thr(Bu$^t$)-Phe-AzaGly-Leu-Arg(Boc$_2$,Me)-Trp(Boc)-Rink Amide MBHA resin (SEQ ID NO: 36). After 100 mg (0.03 mmol) of the resulting resin was swollen in DMF, the resin was treated with 3 ml of 20% piperidine/DMF solution for 20 minutes to remove the Fmoc group. The resin obtained was washed with DMF and treated in 1 ml of DMF with 9.4 µL (0.1 mmol) of Ac$_2$O and 17.4 µL (0.1 mmol) of DIEA at room temperature for 30 minutes for N-terminal acetylation. The resin was washed and dried to give 94.2 mg of the Ac-Asn(Trt)-Thr(Bu$^t$)-Phe-AzaGly-Leu-Arg(Boc$_2$,Me)-Trp (Boc)-Rink Amide MBHA resin.

To the resin obtained, 0.75 mL of TFA/PhSMe/m-cresol/ H$_2$O/TIS/EDT (80/5/5/5/2.5/2.5) was added and the mixture was stirred for 90 minutes. Diethyl ether was added to the reaction solution, the resulting precipitate was centrifuged, and the supernatant was removed. This procedure was repeated twice for washing. The residue was extracted with an aqueous acetic acid solution and the extract was filtered to remove the resin. Thereafter, linear density gradient elution (60 minutes) was performed at a flow rate of 15 ml/min with eluants A/B: 76/24-66/34 using: 0.1% TFA in water and eluant B: eluant A: 0.1% TFA-containing acetonitrile on preparative HPLC using YMC Pack R&D-ODS-5-B S-5, 120A column (30×250 mm). The fractions containing the product were collected and lyophilized to give 2.8 mg of white powders.

Mass spectrum (M+H)$^+$ 949.8 (Calcd. 949.5)
Elution time on HPLC: 10.2 mins.
Elution Conditions:
  Column YMC-AM301 (4.6×100 mm)
  Linear density gradient elution with eluants A/B=80/20-30/70, using 0.1% TFA in water as eluant A and acetonitrile containing 0.1% TFA as eluant B (25 mins.)
  Flow rate: 1.0 ml/min.

Example 4

(Synthesis C): Production of des(1-2)-Ac-[Acp3, Thr5,AzaGly7,Arg(Me)9,Trp10]MS10 (Compound No. 713)

After 100 mg (0.03 mmol) of the Fmoc-Asn(Trt)-Thr(Bu$^t$)-Phe-AzaGly-Leu-Arg(Boc$_2$,Me)-Trp(Boc)-Rink Amide MBHA resin (SEQ ID NO: 36) was swollen in DMF, the resin was treated with 3 ml of 20% piperidine/DMF solution for 20 minutes to remove the Fmoc group. The resin was washed with DMF and then treated in 1 mL of DMF with 70.6 mg (0.2 mmol) of Fmoc-Acp-OH, 104.2 mg (0.2 mmol) of PyAOP and 52.4 µL (0.2 mmol) of DIEA at room temperature for 90 minutes to introduce Acp; thus, the Fmoc-Acp-Asn(Trt)-Thr (Bu$^t$)-Phe-AzaGly-Leu-Arg(Boc$_2$,Me)-Trp(Boc)-Rink Amide MBHA resin (SEQ ID NO: 38) was obtained. The obtained resin was treated with 3 ml of 20% piperidine/DMF solution and then washed with DMF to remove the Fmoc group. Subsequently, the resin was treated in 1 mL of DMF with 9.4 µL (0.1 mmol) of Ac$_2$O and 17.4 µL (0.1 mmol) of DIEA at room temperature for 30 minutes to acetylate the N terminus. The treated resin was then washed and dried to give 101.2 mg of the Ac-Acp-Asn(Trt)-Thr(Bu$^t$)-Phe-AzaGly-Leu-Arg(Boc$_2$,Me)-Trp(Boc)-Rink Amide MBHA resin (SEQ ID NO: 39). To the resin obtained, 0.75 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the extract was filtered to remove the resin. Then, linear density gradient elution (60 minutes) was performed at a flow rate of 15 ml/min with eluants A/B: 77/23-67/33 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized to give 7.3 mg of white powders.

Mass spectrum (M+H)$^+$ 1062.7 (Calcd. 1062.6)
Elution time on HPLC: 10.7 mins.
Elution Conditions:
Column YMC-AM301 (4.6×100 mm)
Linear density gradient elution with eluants A/B=80/20-30/70, using 0.1% TFA in water as eluant A and acetonitrile containing 0.1% TFA as eluant B (25 mins.)
Flow rate: 1.0 mL/min.

Example 5

(Synthesis D): Production of Ac-D-Tyr-D-Trp-Asp(NHPen)-Thr-Phe-AzaGly-Leu-Arg(Me)-Trp-NH$_2$ (Compound No. 714)

Using 661 mg (0.25 mmol) of the Fmoc-AzaGly-Leu-Arg(Boc$_2$,Me)-Trp(Boc)-Rink amide MBHA resin (SEQ ID NO: 33), the peptide chain was extended on a peptide synthesizer ABI 433A (Fmoc/DCC/HOBt) to give the H-D-Tyr(Bu$^t$)-D-Trp(Boc)-Asp(Bu$^t$)-Thr(Bu$^t$)-Phe-AzaGly-Leu-Arg(Boc$_2$, Me)-Trp(Boc)-Rink amide MBHA resin. To the resin, 5 mL of DMF, 111 mg of AcONB and 87 µL of DIEA were added, followed by shaking for 3 hours. The resin was washed and then dried to give the Ac-D-Tyr(Bu$^t$)-D-Trp(Boc)-Asp(Bu$^t$)-Thr(Bu$^t$)-Phe-AzaGly-Leu-Arg(Boc$_2$,Me)-Trp(Boc)-Rink amide MBHA resin. To the 9/10 amount of the resin, 5 mL of TFA/PhSMe/m-cresol/H$_2$O/TIS/EDT (80/5/5/5/2.5/2.5) was added and the mixture was shaken for 2 hours and ether was added for precipitation. The washing procedure with ether was repeated and then dried to give 218.4 mg of Ac-D-Tyr-D-Trp-Asp-Thr-Phe-AzaGly-Leu-Arg(Me)-Trp-NH$_2$. To 32.5 mg of the product, 1 mL of DMF, 5.7 µL of aminopentane, 13.5 mg of HOBt, 26.0 mg of PyBOP and 26.1 µL of DIEA, and the mixture was stirred for 24 hours. After the solvent was removed by distillation, ether was added for precipitation. The washing procedure with ether was repeated and the dried. The residue was dissolved in an aqueous acetic acid solution. After insoluble matters were removed by filtration, linear-density gradient elution (60 minutes) was performed with eluants A/B: 65/35-55/45 using: eluant A: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 11.0 mg of white powders.

Mass spectrum (M+H)$^+$ 1368.9 (Calcd. 1368.7)
Elution time on HPLC: 20.9 mins.
Elution Conditions:
Column: Wakosil-II 5C18 (4.6×100 mm)
Linear density gradient elution with eluants A/B=0.100/0-50/50, using 0.1% TFA in water as eluant A and acetonitrile containing 0.1% TFA as eluant B (25 mins.)
Flow rate: 1.0 ml/min.

Example 6

(Synthesis E): Production of des(1)-Ac-[D-Tyr2,D-Trp3,Alb4,Thr5,AzaGly7,Arg(Me)9,Trp10]MS10 (Compound No. 717)

Using 132 mg (0.05 mmol) of the Fmoc-AzaGly-Leu-Arg(Boc$_2$,Me)-Trp(Boc)-Rink amide MBHA resin (SEQ ID NO: 33), the peptide chain was extended on a peptide synthesizer ABI 433A (Fmoc/DCC/HOBt) to give the H-D-Tyr(Bu$^t$)-D-Trp(Boc)-Alb-Thr(Bu$^t$)-Phe-AzaGly-Leu-Arg(Boc$_2$,Me)-Trp(Boc)-Rink amide MBHA resin. To the resin, 2 mL of DMF, 23 mg of AcONB and 17 µL of DIEA were added, followed by shaking for 3 hours. The resin was washed and then dried to give the Ac-D-Tyr(Bu$^t$)-D-Trp(Boc). Alb-Thr (Bu$^t$)-Phe-AzaGly-Leu-Arg(Boc$_2$,Me)-Trp(Boc)-Rink amide MBHA resin. To the resin, 1 mL of TFA/PhSMe/m-cresol/H$_2$O/TIS/EDT (80/5/5/5/2.5/2.5) was added, followed by stirring for 2 hours. Ether was added to the reaction solution, the resulting precipitate was centrifuged and the supernatant was removed. This procedure was repeated for washing. The residue was extracted with an aqueous acetic acid solution and insoluble matters were removed by filtration. Then, linear density gradient elution (60 minutes) was performed with eluants A/B: 69/31-59/41 using: eluant A: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 4.8 mg of white powders.

Mass spectrum (M+H)$^+$ 1313.9 (Calcd. 1313.7)
Elution time on HPLC: 18.3 mins.
Elution Conditions:
Column: Wakosil-II 5C18 (4.6×100 mm)
Linear density gradient elution with eluants A/B=100/0-50/50, using 0.1% TFA in water as eluant A and acetonitrile containing 0.1% TFA as eluant B (25 mins.)
Flow rate: 1.0 m/min.

Example 7

Production of des(1)-Ac-[D-Tyr2,Hyp3,Thr5,Aza-Gly7,Arg(Me)9,Trp10]MS10 (Compound No. 723)

The Fmoc-AzaGly-Leu-Arg(Boc$_2$,Me)-Trp(Boc)-Rink amide MBHA resin (SEQ ID NO: 33), 800 mg (0.3 mmol), was used as a starting material, and the starting material was reacted on peptide synthesizer ABI 433A (according to the Fmoc/DCC/HOBt 0.25 mmol protocol) to introduce Phe, Thr(Bu$^t$), Asn(Trt), Hyp(Bu$^t$) and D-Tyr(Bu$^t$) in this order thereby to give the H-D-Tyr(Bu$^t$)-Hyp(Bu$^t$)-Asn(Trt)-Thr(Bu$^t$)-Phe-AzaGly-Leu-Arg(Boc$_2$,Me)-Trp(Boc)-Rink amide MBHA resin. Subsequently, the resin was treated for 20 minutes in DMF with 94.4 µl (1 mmol) of Ac$_2$O and 174.2 µl (1 mmol) of DIEA for N-terminal acetylation to give 1.049 g of the Ac-D-Tyr(Bu$^t$)-Hyp(Bu$^t$)-Asn(Trt)-Thr(Bu$^t$)-Phe-AzaGly-Leu-Arg(Boc$_2$,Me)-Trp(Boc)-Rink amide MBHA resin. The same procedure was carried out again to give 1.035 g of the resin. To each resin, 8 mL of TFA/PhSMe/m-cresol/H$_2$O/TIS/EDT (8015/515/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Thereafter, linear density gradient elution (60 minutes) was performed at a flow rate of 15 ml/min with eluants A/B: 76/24-66/34 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 159.5 mg, were dissolved in 200 mL of water and 550 µL of ion exchange resin BioRAD AG1×8 AcO$^-$ form was added to the solution. While manually stirring the reaction solution sometimes, the solution was allowed to stand for an hour. The solution was filtered through a membrane filter to remove the resin and give 134.5 mg of white powders as the acetate. To the purified sample (the acetate) obtained, 6.725 ml of glacial acetic acid was added and the mixture was sonicated for 5 minutes. Subsequently, 20.175 ml of pure water was added to prepare 5 mg/ml/25% aqueous acetic acid solution. The resulting 5 mg/ml solution was dispensed by 4 ml each in six vials, and the rest of the solution was transferred to a vial. These vials were frozen at −80° C. for 2 hours and then lyophilized, in which the lyophilization was performed while cooling at −40° C. for an hour, −20° C. for 2 hours, 0° C. for 12 hours, 5° C. for 8 hours and 20° C. for 5 hours. As a result, six vials of 20 mg each and one vial of 12.34 mg were obtained.

Mass spectrum (M+H) 1225.9 (Calcd. 1225.6)

Anal. for amino acids (20% HCl containing 4% thioglycolic acid, 110° C., hydrolysis for 24 hours; figures in parentheses show theoretical values.): Asp 0.99 (1); Thr 0.96 (1); Leu 0.98 (1); Tyr 0.98 (1); Phe 1.00 (1)

Elution time on HPLC: 11.4 mins.

Elution Conditions:

Column: YMC ODS AM-301 (4.6×100 mm) (4.6×100 mm)

Linear density gradient elution with eluants A/B=80/20-30/70, using 0.1% TFA in water as eluant A and acetonitrile containing 0.1% TFA as eluant B (25 mins.)

Flow rate: 1.0 ml/min.

Example 8

Production of des(1)-Ac-[D-Tyr2,Gly3,Thr5,Aza-Gly7,Arg(Me)9,Trp10]MS10 (Compound No. 726)

The Fmoc-AzaGly-Leu-Arg(Boc$_2$,Me)-Trp(Boc)-Rink amide MBHA resin (SEQ ID NO: 33), 661 mg (0.25 mmol), was used as a starting material, and the starting material was reacted on peptide synthesizer ABI 433A (according to the Fmoc/DCC/HOBt 0.25 mmol protocol) to introduce Phe, Thr(Bu$^t$), Asn(Trt), Gly and D-Tyr(Bu$^t$) in this order thereby to give the H-D-Tyr(Bu$^t$)-Gly-Asn(Trt)-Thr(Bu$^t$)-Phe-AzaGly-Leu-Arg(Boc$_2$,Me)-Trp(Boc)-Rink amide MBHA resin. Subsequently, the resin was treated for 20 minutes in DMF with 94.4 µl (1 mmol) of Ac$_2$O and 174.2 µl (1 mmol) of DIEA for N-terminal acetylation to give 866.6 mg of the Ac-D-Tyr(Bu$^t$)-Gly-Asn(Trt)-Thr(Bu$^t$)-Phe-AzaGly-Leu-Arg(Boc$_2$,Me)-Trp(Boc)-Rink amide MBHA resin. To the resin obtained, 8 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 76/24-66/34 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 42.9 mg, were dissolved in 50 mL of water and 153 µL of ion exchange resin BioRAD AG1×8 AcO$^-$ form was added to the solution. While manually stirring the reaction solution sometimes, the solution was allowed to stand for an hour. The solution was then filtered through a membrane filter to remove the resin and give 39.9 mg of white powders as the acetate. To the purified sample (the acetate) obtained, 1.995 ml of glacial acetic acid was added and the mixture was sonicated for 5 minutes. Subsequently, 5.985 ml of pure water was added to prepare 5 mg/ml/25% aqueous acetic acid solution. The resulting 5 mg/ml solution was dispensed in one vial of 4 ml, and the rest of the solution was transferred to a vial. These vials were frozen at −80° C. for 2 hours and then lyophilized, in which the lyophilization was performed while cooling at −40° C. for an hour, −20° C. for 2 hours, 0° C. for 12 hours, 5° C. for 8 hours and 20° C. for 5 hours. As a result, one vial of 20 mg and one vial of 19.08 mg prepared from the remaining solution were obtained.

Mass spectrum (M+H)$^+$ 1169.7 (Calcd. 1169.6)

Anal. for amino acids (20% HCl containing 4% thioglycolic acid, 110° C., hydrolysis for 24 hours; figures in parentheses show theoretical values.): Asp 0.98 (1); Thr 0.93 (1); Gly 0.97 (1); Leu 0.94 (1); Tyr 0.97 (1); Phe 1.00 (1)

Elution time on HPLC: 11.3 mins.

Elution Conditions:

Column: YMC ODS AM-301 (4.6×100 mm)

Linear density gradient elution with eluants A/B=80/20-30/70, using 0.1% TFA in water as eluant A and acetonitrile containing 0.1% TFA as eluant B (25 mins.)

Flow rate: 1.0 ml/min.

Example 9

Production of des(1)-Ac-[D-Tyr2,Aib3,Thr5,AzaGly7, Arg(Me)9,Trp10]MS10 (Compound No. 727)

The Fmoc-Asn(Trt)-Thr(Bu$^t$)-Phe-AzaGly-Leu-Arg(Boc$_2$,Me)-Trp(Boc)-Rink amide MBHA resin (SEQ ID NO: 36), 1325 mg (0.4 mmol), was used as a starting material, and the starting material was reacted by the manual solid phase synthesis (Fmoc/DIPCDI/HOAt) to introduce Aib and D-Tyr(Bu$^t$) in this order. Thus, the H-D-Tyr(Bu$^t$)-Aib-Asn(Trt)-Thr(Bu$^t$)-Phe-AzaGly-Leu-Arg(Boc$_2$,Me)-Trp(Boc)-Rink amide MBHA resin was obtained. Subsequently, 5 mL of DMF, 265 mg of AcONB and 209 μL of DIEA were added and the mixture was shaken for 3 hours for N-terminal acetylation to give the Ac-D-Tyr(Bu$^t$)-Aib-Asn(Trt)-Thr(Bu$^t$)-Phe-AzaGly-Leu-Arg(Boc$_2$,Me)-Trp(Boc)-Rink amide MBHA resin. To the resin obtained, 8 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 72/28-62/38 using: eluant A: 0.1% TFA in water and eluant B: 0.1%. TFA-containing acetonitrile on preparative HPLC using YMC Pack R&D-ODS-5-B S-5, 120A column (30×250 mm). The fractions containing the product were collected and lyophilized. The obtained white powders were dissolved in 50 mL of water and 150 μL of ion exchange resin BioRAD AG1×8 AcO$^-$ form was added to the solution. While manually stirring the reaction solution sometimes, the solution was allowed to stand for an hour. The solution was then filtered through a membrane filter to remove the resin and give 41.9 mg of white powders as the acetate. To the purified sample (the acetate) obtained, 2.095 ml of glacial acetic acid was added and the mixture was sonicated for 5 minutes. Subsequently, 6.285 ml of pure water was added to prepare 5 mg/ml/25% aqueous acetic acid solution. The resulting 5 mg/ml solution was dispensed in one vial of 4 ml and one vial of 3 ml, and the rest of the solution was transferred to a vial. These vials were frozen at −80° C. for 2 hours and then lyophilized, in which the lyophilization was performed while cooling at −40° C. for an hour, −20° C. for 2 hours, 0° C. for 12 hours, 5° C. for 8 hours and 20° C. for 5 hours. As a result, one vial of 20 mg, one vial of 15 mg and one vial of 4.8 mg prepared from the remaining solution were obtained.

Mass spectrum (M+H)$^+$ 1197.7 (Calcd. 1197.6)

Anal. for amino acids (20% HCl containing 4% thioglycolic acid, 110° C., hydrolysis for 24 hours; figures in parentheses show theoretical values.): Asp 0.98 (1); Thr 0.94 (1); Leu 0.95 (1); Tyr 0.97 (1); Phe 1.00 (1)

Elution time on HPLC: 13.0 mins.
Elution Conditions:
Column YMC-AM301 (4.6×100 mm)
Linear density gradient elution with eluants A/B 80/20-30/70, using 0.1% TFA in water as eluant A and acetonitrile containing 0.1% TFA as eluant B (25 mins.)
Flow rate: 1.0 ml/min.

Example 10

Production of des(1)-Ac-[D-Tyr2,Glu3,Thr5,AzaGly7,Arg(Me)9,Trp10]MS10 (Compound No. 746)

The Fmoc-AzaGly-Leu-Arg(Boc$_2$,Me)-Trp(Boc)-Rink Amide MBHA resin (SEQ ID NO: 33), 661 mg (0.25 mmol), was used as a starting material, and the starting material was reacted on a peptide synthesizer ABI 433A (according to the Fmoc/DCC/HOBt 0.25 mmol protocol), whereby Phe, Thr(Bu$^t$), Asn(Trt), Glu(OBu$^t$) and D-Tyr(Bu$^t$) were introduced in this order to give the H-D-Tyr(Bu$^t$)-Glu(OBu$^t$)-Asn(Trt)-Thr(Bu$^t$)-Phe-AzaGly-Leu-Arg(Boc$_2$,Me)-Trp(Boc)-Rink Amide MBHA resin. Subsequently, the resin was treated for 20 minutes in DMF with 94.4 μl (1 mmol) of Ac$_2$O and 174.2 μl (1 mmol) of DIEA for N-terminal acetylation to give 940.0 mg of the Ac-D-Tyr(Bu$^t$)-Glu(OBu$^t$)-Asn(Trt)-Thr(Bu$^t$)-Phe-AzaGly-Leu-Arg(Boc$_2$,Me)-Trp(Boc)-Rink Amide MBHA resin. To the resin obtained, 6 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 76/24-66/34 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 57.3 mg, were dissolved in 100 mL of water and 192 μL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the solution was allowed to stand for an hour. The solution was then filtered through a membrane filter to remove the resin and the resin was lyophilized to give 42.7 mg of white powders. To the purified sample (the acetate) obtained, 2.135 ml of glacial acetic acid was added and the mixture was sonicated for 5 minutes. Subsequently, 6.405 ml of pure water was added to prepare 5 mg/ml/25% aqueous acetic acid solution. The resulting solution was dispensed by 4 ml each in two vials, and the rest of the solution was transferred to a vial. These vials were frozen at −80° C. for 2 hours and then lyophilized, in which the lyophilization was performed while cooling at −40° C. for 4 hours, −20° C. for 2 hours, 0° C. for 12 hours, 5° C. for 8 hours and 20° C. for 5 hours. As a result, two vials of 20 mg each and one vial of 0.52 mg prepared from the remaining solution were obtained.

Mass spectrum (M+H)$^+$ 1241.8 (Calcd. 1241.4)

Anal. for amino acids (20% HCl containing 4% thioglycolic acid, 110° C., hydrolysis for 24 hours; figures in parentheses show theoretical values.): Asp 0.99 (1); Thr 0.95 (1); Glu 0.96 (1); Leu 0.98 (1); Tyr 0.98 (1); Phe 1.00 (1)

Elution time on HPLC: 11.4 mins.
Elution Conditions:
Column: YMC ODS AM-301 (4.6×100 mm)
Linear density gradient elution with eluants A/B=80/20-30/70, using 0.1% TFA in water as eluant A and acetonitrile containing 0.1% TFA as eluant B (25 mins.)
Flow rate: 1.0 ml/min.

Example 11

Production of des(1)-Ac-[D-Tyr2,Lys3,Thr5,Phe(3F)6,AzaGly7,Arg(Me)9,Trp10]MS10 (Compound No. 756)

The Fmoc-AzaGly-Leu-Arg(Boc$_2$,Me)-Trp(Boc)-Rink amide MBHA resin (SEQ ID NO: 33), 661 mg (0.25 mmol), was used as a starting material, and the starting material was reacted on ABI 433A peptide synthesizer (according to the Fmoc/DCC/HOBt 0.25 mmol protocol), whereby Phe(3F), Thr(Bu$^t$), Asn(Trt), Lys(Boc) and D-Tyr(Bu$^t$) were introduced in this order to give the H-D-Tyr(Bu$^t$)-Lys(Boc)-Asn(Trt)-Thr(Bu$^t$)-Phe(3F)-AzaGly-Leu-Arg(Boc$_2$,Me)-Trp(Boc)-Rink amide MBHA resin. Subsequently, the resin was treated for 20 minutes in DMF with 94.4 µl (1 mmol) of Ac$_2$O and 174.2 µl (1 mmol) of DIEA for N-terminal acetylation to give 881.7 mg of the Ac-D-Tyr(Bu$^t$)-Lys(Boc)-Asn(Trt)-Thr(Bu$^t$)-Phe(3F)-AzaGly-Leu-Arg(Boc$_2$,Me)-Trp(Boc)-Rink amide MBHA resin. To the resin obtained, 6 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 77/23-67/33 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 47.7 mg, were dissolved in 50 mL of water and 316 µL of ion exchange resin BioRAD AG1×8 AcO$^-$ form was added to the solution. While manually stirring the reaction solution sometimes, the solution was allowed to stand for an hour. The solution was then filtered through a membrane filter to remove the resin and give 42.2 mg of white powders as the acetate. To the purified sample (the acetate) obtained, 2.11 ml of glacial acetic acid was added and the mixture was sonicated for 5 minutes. Subsequently, 6.33 ml of pure water was added to prepare 5 mg/ml/25% aqueous acetic acid solution. The resulting 5 mg/ml solution was dispensed in two vials of 4 ml each, and the rest of the solution was transferred to a vial. These vials were frozen at −80° C. for 2 hours and then lyophilized, in which the lyophilization was performed while cooling at −40° C. for an hour, −20° C. for 2 hours, 0° C. for 12 hours, 5° C. for 8 hours and 20° C. for 5 hours. As a result, two vials of 20 mg and one vial of 0.20 mg prepared from the remaining solution were obtained.

Mass spectrum (M+H)$^+$ 1258.8 (Calcd. 1258.6)

Anal. for amino acids (20% HCl containing 4% thioglycolic acid, 110° C., hydrolysis for 24 hours; figures in parentheses show theoretical values.): Asp 0.99 (1); Thr 0.95 (1), Leu 0.95 (1); Tyr 0.99 (1); Phe(3F) 1.00 (1); Lys 0.97 (1)

Elution time on HPLC: 10.8 mins.

Elution Conditions:

Column: YMC ODS AM-301 (4.6×100 mm)

Linear density gradient elution with eluants A/B=80/20-30/70, using 0.1% TFA in water as eluant A and acetonitrile containing 0.1% TFA as eluant B (25 mins.)

Flow rate: 1.0 ml/min.

Example 12

Production of des(1)-Ac-[D-Tyr2,Glu3,Thr5,Phe(3F)$_6$,AzaGly7,Arg(Me)9,Trp10]MS10 (Compound No. 757)

The Fmoc-AzaGly-Leu-Arg(Boc$_2$,Me)-Trp(Boc)-Rink Amide MBHA resin (SEQ ID NO: 33), 661 mg (0.25 mmol), was used as a starting material, and the starting material was reacted on ABI 433A peptide synthesizer (according to the Fmoc/DCC/HOBt 0.25 mmol protocol), whereby Phe(3F), Thr(Bu$^t$), Asn(Trt), Glu(OBu$^t$) and D-Tyr(Bu$^t$) were introduced in this order to give the H-D-Tyr(Bu$^t$)-Glu(OBu$^t$)-Asn(Trt)-Thr(Bu$^t$)-Phe(3F)-AzaGly-Leu-Arg(Boc$_2$,Me)-Trp(Boc)-Rink Amide MBHA resin. Subsequently, the resin was treated for 20 minutes in DMF with 94.4 µl (1 mmol) of Ac$_2$O and 174.2 µl (1 mmol) of DIEA for N-terminal acetylation to give 872.5 mg of the Ac-D-Tyr(Bu$^t$)-Glu(OBu$^t$)-Asn(Trt)-Thr(Bu$^t$)-Phe(3F)-AzaGly-Leu-Arg(Boc$_2$,Me)-Trp(Boc)-Rink Amide MBHA resin. To the resin obtained, 8 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 74.5/25.5-64.5/35.5 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 60.0 mg, were dissolved in 100 mL of water and 198 µL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the solution was allowed to stand for an hour. The solution was then filtered through a membrane filter to remove the resin and give 45.2 mg of white powders as the acetate. To the purified sample (the acetate) obtained, 2.26 ml of glacial acetic acid was added and the mixture was sonicated for 5 minutes. Subsequently, 6.78 ml of pure water was added to prepare 5 mg/ml/25% aqueous acetic acid solution. The resulting 5 mg/ml solution was dispensed by 4 ml each in two vials, and the rest of the solution was transferred to a vial. These vials were frozen at −80° C. for 2 hours and then lyophilized, in which the lyophilization was performed while cooling at −40° C. for an hour, −20° C. for 2 hours, 0° C. for 12 hours, 5° C. for 8 hours and 20° C. for 5 hours. As a result, two vials of 20 mg and one vial of 3.81 mg prepared from the remaining solution were obtained.

Mass spectrum (M+H)$^+$ 1259.9 (Calcd. 1259.6)

Anal. for amino acids (20% HCl containing 4% thioglycolic acid, 110° C., hydrolysis for 24 hours; figures in parentheses show theoretical values.): Asp 0.99 (1); Thr 0.94 (1); Glu 0.99 (1); Leu 0.94 (1); Tyr 0.97 (1); Phe(3F) 1.00 (1)

Elution time on HPLC: 11.9 mins.

Elution Conditions:

Column: YMC ODS AM-301 (4.6×100 mm)

Linear density gradient elution with eluants A/B=80/20-30/70, using 0.1% TFA in water as eluant A and acetonitrile containing 0.1% TFA as eluant B (25 mins.)

Flow rate: 1.0 ml/min.

Example 13

Production of des(1)-Ac-[D-Tyr2,Hyp3,Thr5,Phe(4F)$_6$,AzaGly7,Arg(Me)9,Trp10]MS10 (Compound No. 787)

The Fmoc-AzaGly-Leu-Arg(Boc$_2$,Me)-Trp(Boc)-Rink Amide MBHA resin (SEQ ID NO: 33), 661 mg (0.25 mmol), was used as a starting material, and the starting material was reacted on peptide synthesizer ABI 433A (according to the Fmoc/DCC/HOBt 0.25 mmol protocol), whereby Phe(4F), Thr(Bu$^t$), Asn(Trt), Hyp(Bu$^t$) and D-Tyr(Bu$^t$) were introduced in this order to give the H-D-Tyr(Bu$^t$)-Hyp(Bu$^t$)-Asn (Trt)-Thr(Bu$^t$)-Phe(4F)-AzaGly-Leu-Arg(Boc$_2$,Me)-Trp(Boc)-Rink Amide MBHA resin. Subsequently, the resin was treated for 20 minutes in DMF with 94.4 µl (1 mmol) of Ac$_2$O and 174.2 µl (1 mmol) of DIEA for N-terminal acetylation to give 832.8 mg of the Ac-D-Tyr(Bu$^t$)-Hyp(Bu$^t$)-Asn(Trt)-Thr(Bu$^t$)-Phe(4F)-AzaGly-Leu-Arg(Boc$_2$,Me)-Trp(Boc)-Rink Amide MBHA resin. The same procedure was carried out again to give 823.9 mg of the resin. To each resin, 6 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 74/26-64/36 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 117.7 mg, were dissolved in 200 mL of water and 394 µL of ion exchange resin AG1×8 AcO$^-$ form, which was obtained by converting commercially available BioRAD AG1×8 Cl$^-$ form into the acetate type in a conventional manner, was added to the solution. While manually stirring the reaction solution sometimes, the solution was allowed to stand for an hour. The solution was then filtered through a membrane filter to remove the resin and give 115.5 mg of white powders as the acetate. To the purified sample (the acetate) obtained, 5.775 ml of glacial acetic acid was added and the mixture was sonicated for 5 minutes. Subsequently, 17.325 ml of pure water was added to prepare 5 mg/ml/25% aqueous acetic acid solution. The resulting 5 mg/ml solution was dispensed by 4 ml each in five vials, and the rest of the solution was transferred to a vial. These vials were frozen at −80° C. for 2 hours and then lyophilized, in which the lyophilization was performed while cooling at −40° C. for 4 hours, −20° C. for 2 hours, 0° C. for 12 hours, 5° C. for 8 hours and 20° C. for 5 hours. As a result, five vials of 20 mg and one vial of 11.95 mg prepared from the remaining solution were obtained.

Mass spectrum (M+H)$^+$ 1243.6 (Calcd. 1243.6)

Anal. for amino acids (20% HCl containing 4% thioglycolic acid, 110° C., hydrolysis for 24 hours; figures in parentheses show theoretical values.): Asp 1.01 (1); Thr 0.96 (1); Leu 0.97 (1); Tyr 1.02 (1); Phe(4F) 1.00 (1)

Elution time on HPLC: 12.0 mins.
Elution Conditions:
  Column: YMC ODS AM-301 (4.6×100 mm)
  Linear density gradient elution with eluants A/B=80/20-30/70, using 0.1% TFA in water as eluant A and acetonitrile containing 0.1% TFA as eluant B (25 mins.)
  Flow rate: 1.0 ml/min.

Example 14

Production of des(1)-Ac-[D-Tyr2,Hyp3,Thr5,AzaGly7,Trp10]MS10 (Compound No. 797)

The Rink amide MBHA resin, 357 mg (0.25 mmol), was used as a starting material, and the starting material were reacted on peptide synthesizer ABI 433A (according to the Fmoc/DCC/HOBt 0.25 mmol protocol), whereby Trp(Boc), Arg(Pbf) and Leu were introduced to give the H-Leu-Arg(Pbf)-Trp(Boc)-Rink amide MBHA resin. In a separate reactor, 290.75 mg (1 mmol) of the Fmoc-NHNH$_2$.HCl was weighed and dissolved in DMF. Under ice cooling, a suspension of 156.9 mg (0.95 mmol) of CDI in THF and 339.7 µl of DIEA were added and the mixture was stirred at room temperature for an hour. The mixture was added to the H-Leu-Arg(Pbf)-Trp(Boc)-Rink amide MBHA resin, followed by stirring at room temperature overnight. After the resin was washed, Phe, Thr(Bu$^t$), Asn(Trt), Hyp(Bu$^t$) and D-Tyr(Bu$^t$) were introduced in this order again on peptide synthesizer ABI 433A (according to the Fmoc/DCC/HOBt 0.25 mmol protocol) to give the H-D-Tyr(Bu$^t$)-Hyp(Bu$^t$)-Asn(Trt)-Thr(Bu$^t$)-Phe-AzaGly-Leu-Arg(Pbf)-Trp(Boc)-Rink amide MBHA resin. Subsequently, the resin was treated for 20 minutes in DMF with 94.4 µl (1 mmol) of Ac$_2$O and 174.2 µl (1 mmol) of DIEA for N-terminal acetylation to give 596.6 mg of the Ac-D-Tyr(Bu$^t$)-Hyp(Bu$^t$)-Asn(Trt)-Thr(Bu$^t$)-Phe-AzaGly-Leu-Arg(Pbf)-Trp(Boc)-Rink amide MBHA resin. To the resin obtained, 4 mL of TFA/PhSMe/m-cresol/H$_2$O/TIS/EDT (8015/5/5/2.5/2.5) was added, followed by stirring for 90 minutes. Diethyl ether was added to the reaction solution; the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 74/26-64/36 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 146.3 mg, were dissolved in 100 mL of water and 530 µL of ion exchange resin BioRAD AG1×8 AcO$^-$ was added to the solution, followed by stirring for an hour. After the resin was removed by cotton plug filtration through silica wool, the same amount of the resin was again added and the mixture was stirred for an hour. The solution was filtered through a membrane filter to remove the resin and lyophilized to give 127.3 mg of white powders as the acetate.

Mass spectrum (M+H)$^+$ 1211.1 (Calcd. 1211.6)

Anal. for amino acids (20% HCl containing 4% thioglycolic acid, 110° C., hydrolysis for 24 hours; figures in parentheses show theoretical values.): Asp 0.99 (1); Thr 0.96 (1); Leu 0.93 (1); Tyr 0.98 (1); Phe 1.00 (1); Arg 0.99 (1)

Elution time on HPLC: 11.4 mins.
Elution Conditions:
  Column YMC ODS AM-301 (4.6×100 mm)
  Linear density gradient elution with eluants A/B=80/20-30/70, using 0.1% TFA in water as eluant A and acetonitrile containing 0.1% TFA as eluant B (25 mins.)
  Flow rate: 1.0 ml/min.

Example 15

Production of des(1)-Ac-[D-Tyr2,Hyp3,Alb4,Thr5,AzaGly7,Arg(Me)9,Trp10]MS10 (Compound No. 800)

The Fmoc-AzaGly-Leu-Arg(Boc$_2$,Me)-Trp(Boc)-Rink amide MBHA resin (SEQ ID NO: 33) (0.378 mmol/g), 661 mg (0.25 mmol), was used as a starting material, and the starting material were reacted on peptide synthesizer ABI 433A (according to the Fmoc/DCC/HOBt 0.25 mmol protocol), whereby Phe, Thr(Bu$^t$), Alb, Hyp(Bu$^t$) and D-Tyr(Bu$^t$) were introduced in this order thereby to give the H-D-Tyr(Bu$^t$)-Hyp(Bu$^t$)-Alb-Thr(Bu$^t$)-Phe-Gly-Leu-Arg(Boc$_2$,Me)-Trp(Boc)-Rink amide MBHA resin. Subsequently, the resin was treated for 20 minutes in DMF with 94.4 µl (1 mmol) of Ac$_2$O and 174.2 µl (1 mmol) of DIEA for N-terminal acetylation to give 1.173 g of the Ac-D-Tyr(Bu$^t$)-Hyp(Bu$^t$)-Asn (Trt)-Thr(Bu$^t$)-Phe-AzaGly-Leu-Arg(Boc$_2$,Me)-Trp(Boc)-Rink amide MBHA resin. To the resin obtained, 7 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Thereafter, linear density gradient elution (60 minutes) was performed at a flow rate of 8 ml/min with eluants A/B: 74/26-64/36 using: eluant A: 0.1% TFA in water and eluant B: 0.1% TFA-containing acetonitrile on preparative HPLC using Daisopak-SP100-5-ODS-P (20×250 mm). The fractions containing the product were collected and lyophilized. The obtained white powders, 94.8 mg, were dissolved in 20 mL of water and 320 µL of ion exchange resin BioRAD AG1×8 AcO$^-$ form was added to the solution. The solution was filtered through a membrane filter to remove the resin and lyophilized to give 79.4 mg of white powders as the acetate.

Mass spectrum (M+H)$^+$ 1240.4 (Calcd. 1240.6)

Anal. for amino acids (20% HCl containing 4% thioglycolic acid, 110° C., hydrolysis for 24 hours; figures in parentheses show theoretical values.): Thr 1.02 (1); Leu 0.99 (1); Tyr 1.00 (1); Phe 1.00 (1)

Elution time on HPLC: 12.3 mins.
Elution Conditions:
Column: YMC ODS AM-301 (4.6×100 mm)
Linear density gradient elution with eluants A/B=80/20-30/70, using 0.1% TFA in water as eluant A and acetonitrile containing 0.1% TFA as eluant B (25 mins.)
Flow rate: 1.0 ml/min.

Example 16

(Synthesis F): Production of des(1-5)-4-[bis-(2-pyridylmethyl)aminomethyl]benzoyl-[AzaGly7, Arg(Me)9,Trp10]MS10 (Compound No. 801)

In a reactor, 265 mg (0.1 mmol) of the Fmoc-AzaGly-Leu-Arg(Boc$_2$,Me)-Trp(Boc)-Rink amide MBHA resin (SEQ ID NO: 33) (0.378 mmol/g) was weighed, and washed and swollen in DMF. The resin was then treated in 5 ml of 20% piperidine/DMF solution for 20 minutes for Fmoc deprotection. The resin was treated with 155.0 mg (0.4 mmol) of Fmoc-Phe-OH, 63.6 µL (0.4 mmol) of DIPCDI and 0.8 mL (0.4 mmol) of 0.5M HOAt/DMF at room temperature for 90 minutes to introduce Phe. Subsequently, Fmoc deprotection through treatment in 5 ml of 20% piperidine/DMF solution for 20 minutes and condensation by the DIPCDI/HOAt method as in the Phe introduction, whereby Ambz(4) was introduced to give the Fmoc-Ambz(4)-Phe-AzaGly-Leu-Arg (Boc$_2$,Me)-Trp(Boc)-Rink Amide MBHA resin (SEQ ID NO: 40). After Fmoc deprotection, the resulting resin was treated for 10 minutes in DMF with 11.4 µl (0.12 mmol) of 2-pyridinecarboxyaldehyde in the presence of 50 µl of AcOH, 41.1 mg (0.4 mmol) of NaBH$_3$CN was added to thereto and the mixture was stirred for an hour. After washing in DMF, the same procedure was repeated again. The resin obtained was washed in DMF and MeOH and dried to give 281.4 mg of the 4-[Bis-(2-Pyridylmethyl)aminomethyl]benzoyl-Phe-Aza-Gly-Leu-Arg(Boc$_2$,Me)-Trp(Boc)-Rink Amide MBHA resin (SEQ ID NO: 41).

To the resin obtained, 2 mL of TFA/PhSMe/m-cresol/H$_2$O/TIS/EDT (80/5/5/5/2.5/2.5) was added, followed by stirring for 90 minutes. Diethyl ether was added to the reaction solution, the resulting precipitate was centrifuged, and the supernatant was removed. This procedure was repeated twice for washing. The residue was extracted with an aqueous acetic acid solution and the resin was removed by filtration. Then, linear density gradient elution (60 minutes) was performed at a flow rate of 15 ml/min with eluants A/B: 76/24-66/34 using: eluant A: 0.1% TFA in water and eluant B: 0.1% TFA-containing acetonitrile on preparative HPLC using YMC Pack R&D-ODS-5-B S-5, 120A column (30×250 mm). The fractions containing the product were collected and lyophilized. The obtained white powders, 17.3 mg, were dissolved in 20 mL of AcCN-water (9:1) and 210 µL of ion exchange resin BioRAD AG1×8 AcO$^-$ was added to the solution. While manually stirring the reaction solution sometimes, the solution was filtered through a membrane filter to remove the resin and lyophilized to give 10.8 mg of white powders as the acetate.

Mass spectrum (M+H)$^+$ 1007.3 (Calcd. 1007.5)
Elution time on HPLC: 10.7 mins.
Elution Conditions:
Column: YMC ODS AM-301 (4.6×100 mm)
Linear density gradient elution with eluants A/B=80/20-30/70, using 0.1% TFA in water as eluant A and acetonitrile containing 0.1% TFA as eluant B (25 mins.)
Flow rate: 1.0 ml/min.

The structures of compounds synthesized as in EXAMPLES 1 to 16 or compounds synthesized by synthesis methods similar to EXAMPLES 1 to 6 and physicochemical properties of these compounds are shown in TABLE 1A below.

The description of the column "Synthesis method" in the Table represents that the compound may be synthesized or was synthesized by or according to the synthesis method described therein.

More specifically, "A" in the column "Synthesis method" of Compound number 708 represents that the compound was synthesized by the synthesis method A as described in EXAMPLE 1.

"B" in the column "Synthesis method" of Compound number 709 represents that the compound was synthesized by the synthesis method B as described in EXAMPLE 3.

"C" in the column "Synthesis method" of Compound number 713 represents that the compound was synthesized by the synthesis method C as described in EXAMPLE 4.

"D" in the column "Synthesis method" of Compound number 714 represents that the compound was synthesized by the synthesis method D as described in EXAMPLE 5.

"E" in the column "Synthesis method" of Compound number 717 represents that the compound was synthesized by the synthesis method Eas described in EXAMPLE 6.

Each description in the column "Synthesis method" of each compound described in EXAMPLES 7 to 16 represents that the compound may be synthesized according to each synthesis method described therein.

Each description in the column "Synthesis method" of each compound which are not described in EXAMPLES 1 to 16 represents that the compound was synthesized according to each synthesis method described therein.

The description of the column "HPLC condition" in the Table represents that each compound was eluted by each HPLC condition of "a", "b" or "c" described therein.

TABLE 1A

| Compound number | Structure | M + H+ (obs.) | M + H+ (cal.) | HPLC (min.) | HPLC condition | Synthesis method |
|---|---|---|---|---|---|---|
| 708 | des(1)-Ac-[D-Tyr2,D-Trp3,Thr5,AzaGly7,D-Arg9,Trp10]MS10 | 1284.9 | 1284.6 | 13.3 | a | A |
| 709 | des(1-3)-Ac-[Thr5,AzaGly7,Arg(Me)9,Trp10]MS10 | 949.8 | 949.5 | 10.2 | a | B |
| 710 | des(1-3)-Decanoyl-[Thr5,AzaGly7,Arg(Me)9,Trp10]MS10 | 1061.9 | 1061.6 | 19.4 | a | B |
| 712 | des(1-2)-[Acp3,Thr5,AzaGly7,Arg(Me)9,Trp10]MS10 | 1020.7 | 1020.6 | 9.2 | a | C |
| 713 | des(1-2)-Ac-[Acp3,Thr5,AzaGly7,Arg(Me)9,Trp10]MS10 | 1062.7 | 1062.6 | 10.7 | a | C |
| 714 | des(1)-Ac-[D-Tyr2,D-Trp3,Asp(NHPen)4,Thr5,AzaGly7,Arg(Me)9,Trp10]MS10 | 1368.9 | 1368.7 | 20.9 | b | D |
| 715 | des(1)-Ac-[D-Tyr2,D-Trp3,Asp(NHcPr)4,Thr5,AzaGly7,Arg(Me)9,Trp10]MS10 | 1339.1 | 1338.7 | 18.4 | b | D |
| 716 | des(1)-Ac-[D-Tyr2,D-Trp3,Asp(NHBzl)4,Thr5,AzaGly7,Arg(Me)9,Trp10]MS10 | 1389.0 | 1388.7 | 20.2 | b | D |
| 717 | des(1)-Ac-[D-Tyr2,D-Trp3,Alb4,Thr5,AzaGly7,Arg(Me)9,Trp10]MS10 | 1313.9 | 1313.7 | 18.3 | b | E |
| 718 | des(1)-Ac-[D-Tyr2,D-Pya(4)3,Alb4,Thr5,AzaGly7,Arg(Me)9,Trp10]MS10 | 1275.9 | 1275.6 | 14.5 | b | E |
| 719 | des(1)-Ac-[D-Tyr2,D-Trp3,D-Pro5,AzaGly7,Arg(Me)9,Trp10]MS10 | 1294.8 | 1294.6 | 18.4 | b | E |
| 720 | des(1)-Ac-[D-Tyr2,Aze(2)3,Thr5,AzaGly7,Arg(Me)9,Trp10]MS10 | 1195.8 | 1195.6 | 11.7 | a | E |
| 721 | des(1)-Ac-[D-Tyr2,Pic(2)3,Thr5,AzaGly7,Arg(Me)9,Trp10]MS10 | 1223.8 | 1223.6 | 12.5 | a | E |
| 722 | des(1)-Ac-[D-Tyr2,Pic(3)3,Thr5,AzaGly7,Arg(Me)9,Trp10]MS10 | 1223.8 | 1223.6 | 11.7 | a | E |
| 723 | des(1)-Ac-[D-Tyr2,Hyp3,Thr5,AzaGly7,Arg(Me)9,Trp10]MS10 | 1225.9 | 1225.6 | 11.4 | a | E |
| 724 | des(1)-Ac-[D-Tyr2,Thz3,Thr5,AzaGly7,Arg(Me)9,Trp10]MS10 | 1227.8 | 1227.6 | 12.6 | a | E |
| 725 | des(1)-Ac-[D-Tyr2,NMeAla3,Thr5,AzaGly7,Arg(Me)9,Trp10]MS10 | 1197.8 | 1197.6 | 12.0 | a | E |
| 726 | des(1)-Ac-[D-Tyr2,Gly3,Thr5,AzaGly7,Arg(Me)9,Trp10]MS10 | 1169.7 | 1169.6 | 11.3 | a | E |
| 727 | des(1)-Ac-[D-Tyr2,Aib3,Thr5,AzaGly7,Arg(Me)9,Trp10]MS10 | 1197.7 | 1197.6 | 13.0 | a | E |
| 728 | des(1)-Ac-[D-Tyr2,Abz(2)3,Thr5,AzaGly7,Arg(Me)9,Trp10]MS10 | 1231.6 | 1231.7 | 13.1 | a | E |
| 730 | des(1)-Ac-[D-Tyr2,Aze(3)3,Thr5,AzaGly7,Arg(Me)9,Trp10]MS10 | 1195.8 | 1195.6 | 11.0 | a | E |
| 731 | des(1)-Ac-[D-Tyr2,Sar3,Thr5,AzaGly7,Arg(Me)9,Trp10]MS10 | 1183.8 | 1183.6 | 11.5 | a | E |
| 732 | des(1)-Ac-[D-Tyr2,D-NMeAla3,Thr5,AzaGly7,Arg(Me)9,Trp10]MS10 | 1197.8 | 1197.6 | 12.9 | a | E |
| 734 | des(1)-Ac-[D-Tyr2,Izc3,Thr5,AzaGly7,Arg(Me)9,Trp10]MS10 | 1210.7 | 1210.6 | 10.5 | a | E |
| 735 | des(1)-Ac-[D-Tyr2,D-Asp3,Thr5,AzaGly7,Arg(Me)9,Trp10]MS10 | 1227.9 | 1227.6 | 11.4 | a | E |
| 736 | des(1)-Ac-[D-Tyr2,D-Dap3,Thr5,AzaGly7,Arg(Me)9,Trp10]MS10 | 1198.9 | 1198.6 | 10.1 | a | E |
| 737 | des(1)-Ac-[D-Tyr2,D-Ser3,Thr5,AzaGly7,Arg(Me)9,Trp10]MS10 | 1199.8 | 1199.6 | 11.0 | a | E |
| 738 | des(1)-Ac-[D-Tyr2,D-Gln3,Thr5,AzaGly7,Arg(Me)9,Trp10]MS10 | 1240.9 | 1240.9 | 10.9 | a | E |
| 739 | des(1)-Ac-[D-Tyr2,D-His3,Thr5,AzaGly7,Arg(Me)9,Trp10]MS10 | 1249.4 | 1249.4 | 10.2 | a | E |
| 740 | des(1)-Ac-[D-Tyr2,D-Trp3,Dab4,Thr5,AzaGly7,Arg(Me)9,Trp10]MS10 | 1284.5 | 1284.7 | 16.2 | b | E |
| 742 | des(1)-Ac-[D-Tyr2,Ala3,Thr5,AzaGly7,Arg(Me)9,Trp10]MS10 | 1183.8 | 1183.6 | 11.8 | a | E |
| 743 | des(1)-Ac-[D-Tyr2,Leu3,Thr5,AzaGly7,Arg(Me)9,Trp10]MS10 | 1226.0 | 1225.6 | 13.6 | a | E |
| 744 | des(1)-Ac-[D-Tyr2,Ser3,Thr5,AzaGly7,Arg(Me)9,Trp10]MS10 | 1199.8 | 1199.3 | 11.3 | a | E |
| 745 | des(1)-Ac-[D-Tyr2,Lys3,Thr5,AzaGly7,Arg(Me)9,Trp10]MS10 | 1241.0 | 1240.7 | 10.3 | a | E |
| 746 | des(1)-Ac-[D-Tyr2,Glu3,Thr5,AzaGly7,Arg(Me)9,Trp10]MS10 | 1241.8 | 1241.4 | 11.4 | a | E |
| 747 | des(1)-Ac-[D-Tyr2,β-Ala3,Thr5,AzaGly7,Arg(Me)9,Trp10]MS10 | 1183.8 | 1183.3 | 11.0 | a | E |
| 748 | des(1)-Ac-[D-Tyr2,D-Trp3,Thr5,Phe(4Cl)6,AzaGly7,Arg(Me)9,Trp10]MS10 | 1333.0 | 1332.6 | 15.2 | a | E |
| 749 | des(1)-Ac-[D-Tyr2,D-Trp3,Thr5,Phe(2F)6,AzaGly7,Arg(Me)9,Trp10]MS10 | 1316.9 | 1316.6 | 14.2 | a | E |
| 750 | des(1)-Ac-[D-Tyr2,D-Trp3,Thr5,Phe(3F)6,AzaGly7,Arg(Me)9,Trp10]MS10 | 1316.9 | 1316.6 | 14.4 | a | E |
| 754 | des(1)-Ac-[D-Tyr2,Lys3,Thr5,Phe(2F)6,AzaGly7,Arg(Me)9,Trp10]MS10 | 1258.8 | 1258.6 | 10.6 | a | E |
| 755 | des(1)-Ac-[D-Tyr2,Glu3,Thr5,Phe(2F)6,AzaGly7,Arg(Me)9,Trp10]MS10 | 1259.8 | 1259.6 | 11.7 | a | E |
| 756 | des(1)-Ac-[D-Tyr2,Lys3,Thr5,Phe(3F)6,AzaGly7,Arg(Me)9,Trp10]MS10 | 1258.8 | 1258.6 | 10.8 | a | E |
| 757 | des(1)-Ac-[D-Tyr2,Glu3,Thr5,Phe(3F)6,AzaGly7,Arg(Me)9,Trp10]MS10 | 1259.9 | 1259.6 | 11.9 | a | E |
| 758 | des(1)-Ac-[D-Tyr2,Lys3,Thr5,Phe(4Cl)6,AzaGly7,Arg(Me)9,Trp10]MS10 | 1274.8 | 1274.6 | 11.6 | a | E |
| 759 | des(1)-Ac-[D-Tyr2,Glu3,Thr5,Phe(4Cl)6,AzaGly7,Arg(Me)9,Trp10]MS10 | 1275.8 | 1275.6 | 12.8 | a | E |
| 760 | des(1)-Ac-[D-Tyr2,Pzc(2)3,Thr5,AzaGly7,Arg(Me)9,Trp10]MS10 | 1224.8 | 1224.6 | 10.2 | a | E |
| 763 | des(1)-Ac-[D-Tyr2,Hyp3,Thr5,Phe(2F)6,AzaGly7,Arg(Me)9,Trp10]MS10 | 1243.8 | 1243.6 | 11.5 | a | E |
| 764 | des(1)-Ac-[D-Tyr2,Trp3,Thr5,Phe(2F)6,AzaGly7,Arg(Me)9,Trp10]MS10 | 1316.9 | 1316.6 | 14.6 | a | E |
| 765 | des(1)-Ac-[D-Tyr2,Hyp3,Thr5,Phe(3F)6,AzaGly7,Arg(Me)9,Trp10]MS10 | 1243.6 | 1243.6 | 12.0 | a | E |
| 766 | des(1)-Ac-[D-Tyr2,Trp3,Thr5,Phe(3F)6,AzaGly7,Arg(Me)9,Trp10]MS10 | 1316.4 | 1316.6 | 14.8 | a | E |
| 767 | des(1)-Ac-[D-Tyr2,Hyp3,Thr5,Phe(4Cl)6,AzaGly7,Arg(Me)9,Trp10]MS10 | 1259.7 | 1259.6 | 12.9 | a | E |
| 768 | des(1)-Ac-[D-Tyr2,Trp3,Thr5,Phe(4Cl)6,AzaGly7,Arg(Me)9,Trp10]MS10 | 1332.4 | 1332.6 | 15.6 | a | E |
| 769 | des(1)-Ac-[D-Tyr2,Gly3,Thr5,Phe(4Cl)6,AzaGly7,Arg(Me)9,Trp10]MS10 | 1203.5 | 1203.5 | 13.0 | a | E |
| 770 | des(1)-Ac-[D-Tyr2,Aib3,Thr5,Phe(4Cl)6,AzaGly7,Arg(Me)9,Trp10]MS10 | 1261.4 | 1231.6 | 14.7 | a | E |
| 771 | des(1)-Ac-[D-Tyr2,Orn3,Thr5,AzaGly7,Arg(Me)9,Trp10]MS10 | 1226.3 | 1226.4 | 14.2 | b | E |
| 772 | des(1)-Ac-[D-Tyr2,Thr3,Thr5,AzaGly7,Arg(Me)9,Trp10]MS10 | 1213.4 | 1213.6 | 15.6 | b | E |
| 773 | des(1)-Ac-[D-Tyr2,His(3Me)3,Thr5,AzaGly7,Arg(Me)9,Trp10]MS10 | 1263.3 | 1263.6 | 14.4 | b | E |
| 774 | des(1)-Ac-[D-Tyr2,DL-Ala(Pip)3,Thr5,AzaGly7,Arg(Me)9,Trp10]MS10 | 1266.3 | 1266.7 | 14.5 | b | E |
| 775 | des(1)-Ac-[D-Tyr2,Tyr(PO3H2)3,Thr5,AzaGly7,Arg(Me)9,Trp10]MS10 | 1254.8 | 1254.6 | 15.7 | b | E |
| 776 | des(1)-Glycoloyl-[D-Tyr2,Hyp3,Thr5,AzaGly7,Arg(Me)9,Trp10]MS10 | 1241.3 | 1241.6 | 15.3 | b | E |
| 777 | des(1-2)-[D-Tyr3,Thr5,AzaGly7,Arg(Me)9,Trp10]MS10 | 1112.6 | 1112.3 | 15.4 | b | E |
| 780 | des(1)-Ac-[D-Tyr2,Pro(4NH2)3,Thr5,AzaGly7,Arg(Me)9,Trp10]MS10 | 1224.7 | 1224.6 | 10.3 | a | E |
| 781 | des(1)-Ac-[D-Tyr2,Hyp(Bzl)3,Thr5,AzaGly7,Arg(Me)9,Trp10]MS10 | 1315.8 | 1315.7 | 15.7 | a | E |
| 782 | des(1)-Ac-[D-Tyr2,D-NMePhe3,Thr5,AzaGly7,Arg(Me)9,Trp10]MS10 | 1273.8 | 1273.6 | 15.4 | a | E |
| 783 | des(1)-Ac-[D-Tyr2,Gly3,Thr5,Phe(2F)6,AzaGly7,Arg(Me)9,Trp10]MS10 | 1187.8 | 1187.6 | 11.7 | a | E |
| 784 | des(1)-Ac-[D-Tyr2,Aib3,Thr5,Phe(2F)6,AzaGly7,Arg(Me)9,Trp10]MS10 | 1215.8 | 1215.6 | 13.4 | a | E |
| 785 | des(1)-Ac-[D-Tyr2,Gly3,Thr5,Phe(3F)6,AzaGly7,Arg(Me)9,Trp10]MS10 | 1187.7 | 1187.6 | 11.9 | a | E |
| 786 | des(1)-Ac-[D-Tyr2,Aib3,Thr5,Phe(3F)6,AzaGly7,Arg(Me)9,Trp10]MS10 | 1215.8 | 1215.6 | 13.5 | a | E |
| 787 | des(1)-Ac-[D-Tyr2,Hyp3,Thr5,Phe(4F)6,AzaGly7,Arg(Me)9,Trp10]MS10 | 1243.6 | 1243.6 | 12.0 | a | E |
| 788 | des(1)-Ac-[D-Tyr2,Glu3,Thr5,Phe(4F)6,AzaGly7,Arg(Me)9,Trp10]MS10 | 1259.5 | 1259.6 | 11.9 | a | E |
| 789 | des(1)-Ac-[D-Tyr2,Lys3,Thr5,Phe(4F)6,AzaGly7,Arg(Me)9,Trp10]MS10 | 1258.6 | 1258.6 | 10.8 | a | E |

TABLE 1A-continued

| Compound number | Structure | M + H+ (obs.) | M + H+ (cal.) | HPLC (min.) | HPLC condition | Synthesis method |
|---|---|---|---|---|---|---|
| 790 | des(1)-Ac-[D-Tyr2,Gly3,Thr5,Phe(4F)6,AzaGly7,Arg(Me)9,Trp10]MS10 | 1187.4 | 1187.6 | 11.9 | a | E |
| 791 | des(1)-Ac-[D-Tyr2,Aib3,Thr5,Phe(4F)6,AzaGly7,Arg(Me)9,Trp10]MS10 | 1215.2 | 1215.6 | 13.6 | a | E |
| 794 | des(1)-Ac-[D-Tyr2,Hyp3,Thr5,D-Phe6,AzaGly7,Arg(Me)9,Trp10]MS10 | 1225.5 | 1225.6 | 11.8 | a | E |
| 797 | des(1)-Ac-[D-Tyr2,Hyp3,Thr5,AzaGly7,Trp10]MS10 | 1211.1 | 1211.6 | 11.4 | a | A |
| 800 | des(1)-Ac-[D-Tyr2,Hyp3,Alb4,Thr5,AzaGly7,Arg(Me)9,Trp10]MS10 | 1240.4 | 1240.6 | 12.3 | a | E |
| 801 | des(1-5)-4-[Bis-(2-Pyridylmethyl)aminomethyl]benzoyl-[AzaGly7,Arg(Me)9,Trp10]MS10 | 1007.3 | 1007.5 | 10.7 | a | F |
| 809 | des(1)-Ac-[D-Tyr2,Hyp3,NMeSer5,AzaGly7,Arg(Me)9,Trp10]MS10 | 1225.6 | 1225.6 | 10.3 | c | E |
| 810 | des(1)-Ac-[D-Tyr2,Hyp3,Hyp5,AzaGly7,Arg(Me)9,Trp10]MS10 | 1237.6 | 1237.6 | 10.5 | c | E |
| 813 | des(1)-Ac-[D-Tyr2,Hyp3,Gly5,AzaGly7,Arg(Me)9,Trp10]MS10 | 1181.5 | 1181.6 | 10.1 | c | E |
| 814 | des(1)-Ac-[D-Tyr2,Hyp3,Ala5,AzaGly7,Arg(Me)9,Trp10]MS10 | 1195.4 | 1195.6 | 11.0 | c | E |
| 815 | des(1)-Ac-[D-Tyr2,Hyp3,D-Ala5,AzaGly7,Arg(Me)9,Trp10]MS10 | 1195.6 | 1195.6 | 10.8 | c | E |
| 816 | des(1)-Ac-[D-Tyr2,Hyp3,His4,Thr5,AzaGly7,Arg(Me)9,Trp10]MS10 | 1248.6 | 1248.6 | 9.7 | c | E |
| 843 | des(1)-Ac-[D-Tyr2,Hyp3,Gln4,Thr5,AzaGly7,Arg(Me)9,Trp10]MS10 | 1239.8 | 1239.6 | 10.4 | c | E |
| 844 | des(1)-Ac-[D-Tyr2,Hyp3,D-Asn4,Thr5,AzaGly7,Arg(Me)9,Trp10]MS10 | 1225.6 | 1225.6 | 10.2 | c | E |
| 845 | des(1)-Ac-[D-Tyr2,Hyp3,Cit4,Thr5,AzaGly7,Arg(Me)9,Trp10]MS10 | 1269.0 | 1268.7 | 10.3 | c | E |
| 846 | des(1)-Ac-[D-Tyr2,Hyp3,D-Thr5,AzaGly7,Arg(Me)9,Trp10]MS10 | 1226.1 | 1225.6 | 10.3 | c | E |
| 856 | des(1)-Ac-[D-Tyr2,Hyp3,Thr5,AzaGly7,Ala(cPr)8,Arg(Me)9,Trp10]MS10 | 1223.9 | 1223.6 | 10.9 | a | E |
| 860 | des(1-5)-4-Ureidobenzoyl-[AzaGly7,Arg(Me)9,Trp10]MS10 | 854.7 | 854.4 | 17.7 | b | F |
| 861 | des(1)-Ac-[D-Tyr2,Hyp3,Arg4,Thr5,AzaGly7,Arg(Me)9,Trp10]MS10 | 1268.1 | 1267.7 | 10.5 | c | E |
| 862 | des(1)-Ac-[D-Tyr2,Hyp3,Gly4,Thr5,AzaGly7,Arg(Me)9,Trp10]MS10 | 1168.9 | 1168.6 | 11.2 | c | E |
| 863 | des(1)-Ac-[D-Tyr2,Hyp3,Dap4,Thr5,AzaGly7,Arg(Me)9,Trp10]MS10 | 1198.2 | 1197.6 | 9.9 | c | E |
| 864 | des(1)-Ac-[D-Tyr2,Hyp3,Dab4,Thr5,AzaGly7,Arg(Me)9,Trp10]MS10 | 1212.3 | 1211.6 | 9.9 | c | E |
| 868 | des(1)-Ac-[D-Tyr2,Hyp3,Thr5,αMePhe6,AzaGly7,Arg(Me)9,Trp10]MS10 | 1240.0 | 1239.6 | 13.4 | a | E |
| 870 | des(1)-Ac-[D-Tyr2,Hyp3,Thr5,Phe(2Me)6,AzaGly7,Arg(Me)9,Trp10]MS10 | 1239.7 | 1239.6 | 12.5 | a | E |
| 872 | des(1)-Ac-[D-Tyr2,Hyp3,Thr5,Phe(3Me)6,AzaGly7,Arg(Me)9,Trp10]MS10 | 1239.6 | 1239.6 | 12.7 | a | E |
| 874 | des(1)-Ac-[D-Tyr2,Hyp3,Thr5,Phe(4Me)6,AzaGly7,Arg(Me)9,Trp10]MS10 | 1239.6 | 1239.6 | 12.5 | a | E |
| 877 | des(1)-Ac-[D-Tyr2,Hyp3,Thr5,threo-Ser(3Phenyl)6,AzaGly7,Arg(Me)9,Trp10]MS10 | 1241.1 | 1241.6 | 10.5 | a | E |
| 882 | des(1)-Ac-[D-Tyr2,Hyp3,Thr5,erythro-Ser(3Phenyl)6,AzaGly7,Arg(Me)9,Trp10]MS10 | 1241.6 | 1241.6 | 10.9 | a | E |
| 886 | des(1)-Ac-[D-Tyr2,Hyp3,Nva4,Thr5,AzaGly7,Arg(Me)9,Trp10]MS10 | 1210.8 | 1210.6 | 14.0 | a | E |
| 887 | des(1-2)-Ac-[Hyp3,Thr5,AzaGly7,Arg(Me)9,Trp10]MS10 | 1062.7 | 1062.5 | 10.2 | a | B |
| 888 | des(1-2)-3-(p-Hydroxyphenyl)propionyl-[Hyp3,Thr5,AzaGly7,Arg(Me)9,Trp10]MS10 | 1168.7 | 1168.6 | 12.2 | a | B |
| 889 | des(1-2)-[pGlu3,Thr5,AzaGly7,Arg(Me)9,Trp10]MS10 | 1018.5 | 1018.5 | 10.3 | a | B |
| 896 | des(1)-Ac-[D-Tyr2,cisHyp3,Thr5,AzaGly7,Arg(Me)9,Trp10]MS10 | 1225.6 | 1225.4 | 12.4 | a | E |
| 897 | des(1)-Ac-[D-Tyr2,Pro(4F)3,Thr5,AzaGly7,Arg(Me)9,Trp10]MS10 | 1227.4 | 1227.6 | 12.9 | a | E |
| 899 | des(1)-Ac-[Tyr2,Hyp3,Thr5,AzaGly7,Arg(Me)9,Trp10]MS10 | 1225.7 | 1225.4 | 17.0 | b | E | a: 20-70% AcCN/25 min, flow1 ml/min, YMC ODS AM-301 (4.6 × 100 mm)
b: 0-50% AcCN/25 min, flow1 ml/min, Wakosil-II 5C18 HG (4.6 × 100 mm)
c: 20-70% AcCN/25 min flow1 ml/min SHISEIDO CAPCELL PAK C18 MGII (4.6 × 100 mm)

The structures of compounds in TABLE 1A above are shown in TABLE 1B.

TABLE 1B

| Compound No. | Structure |
|---|---|
| 708 | 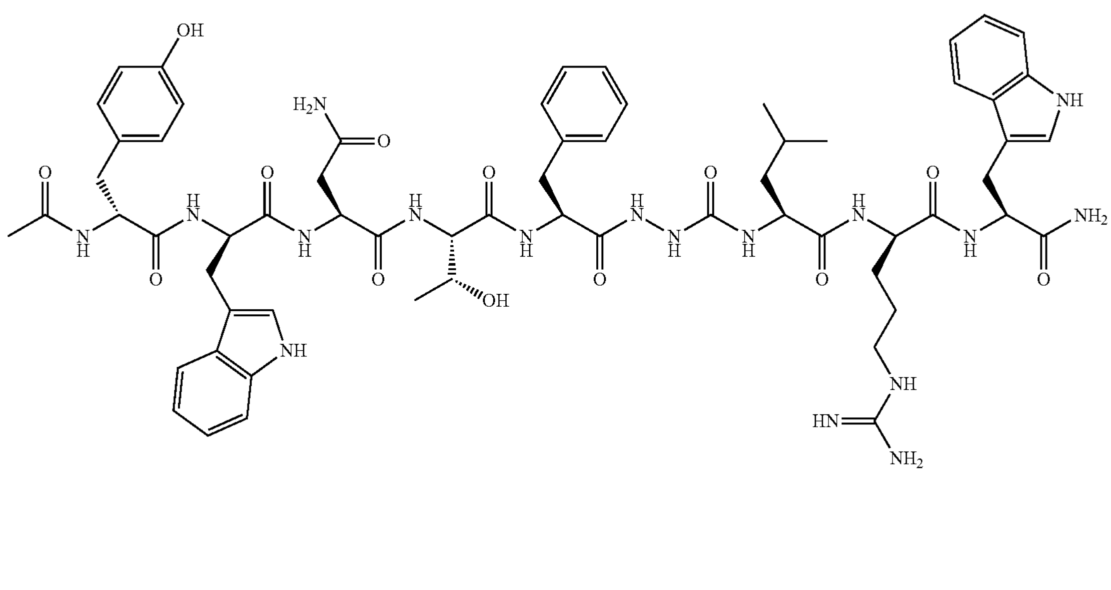 |

US 7,960,348 B2
TABLE 1B-continued
| Compound No. | Structure |
|---|---|
| 709 | 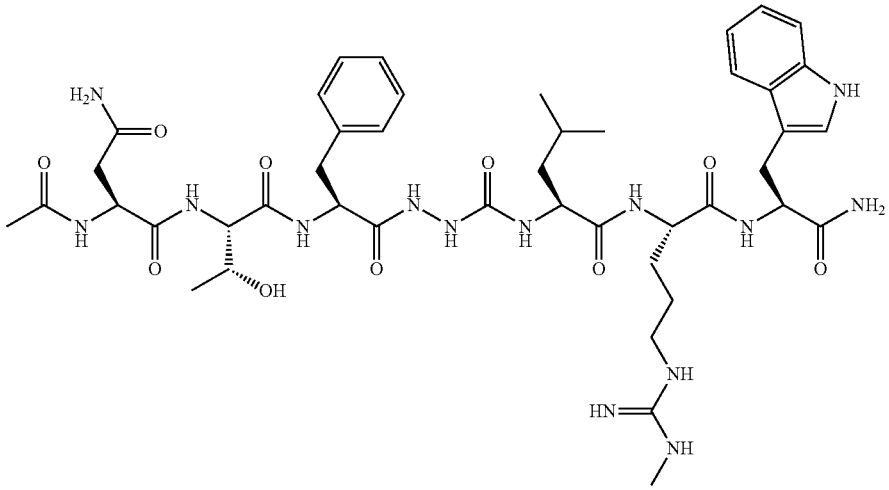 |
| 710 | 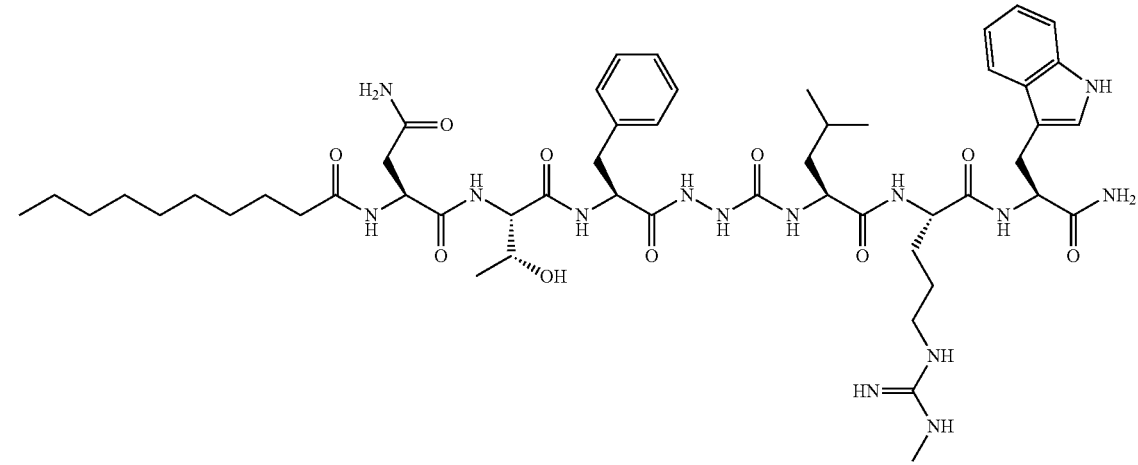 |
| 712 | 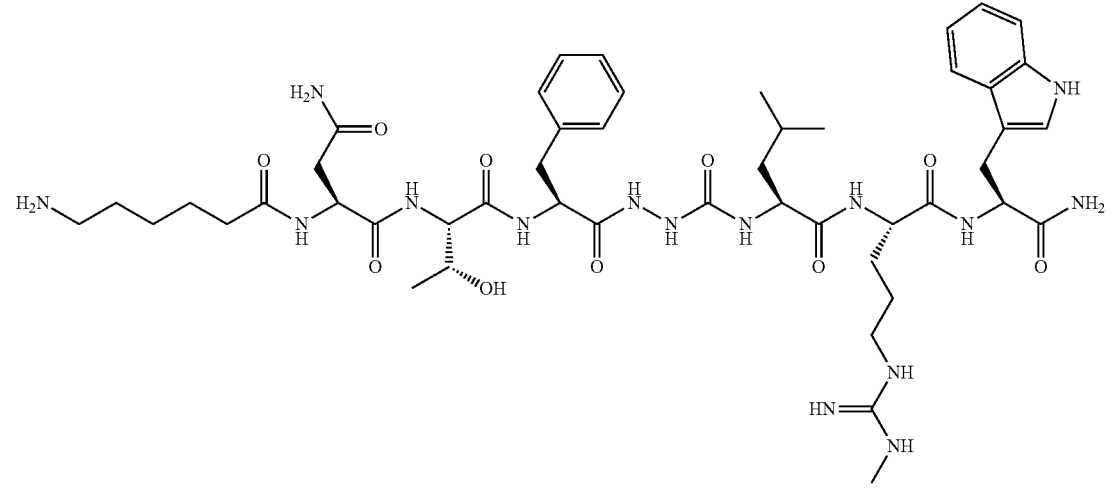 |

TABLE 1B-continued
| Compound No. | Structure |
|---|---|
| 713 | 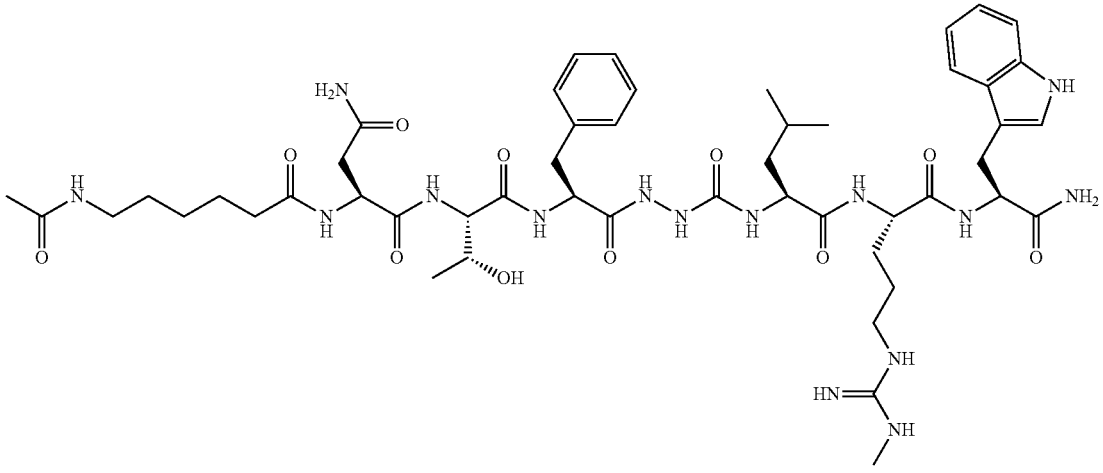 |
| 714 | 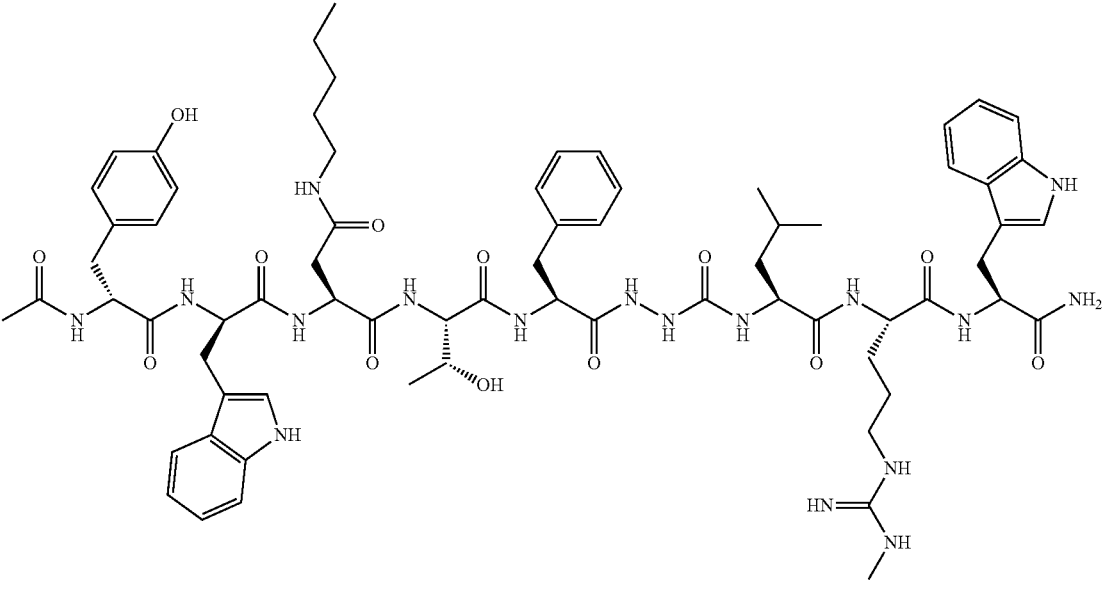 |
| 715 | 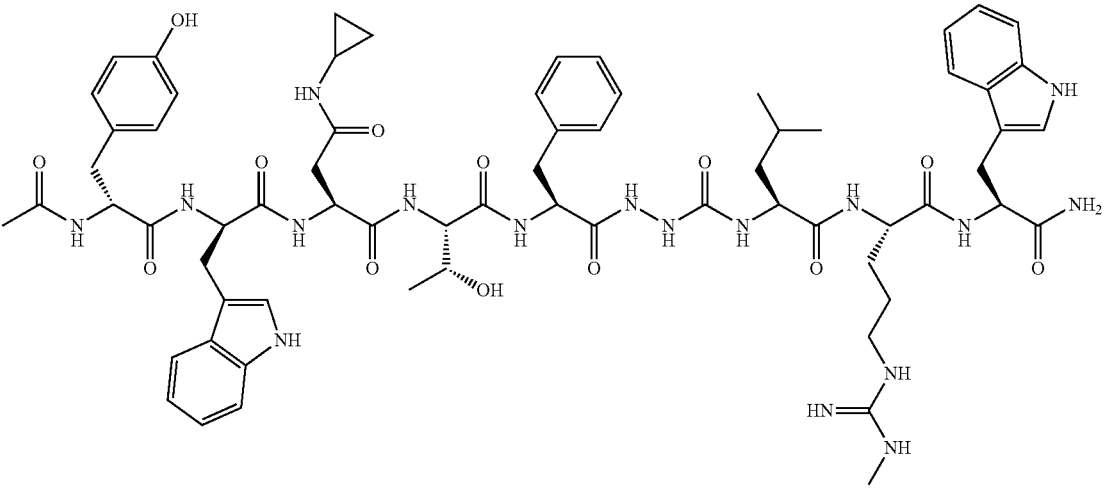 |

US 7,960,348 B2
93                                                                94
TABLE 1B-continued
| Compound No. | Structure |
|---|---|
| 716 | 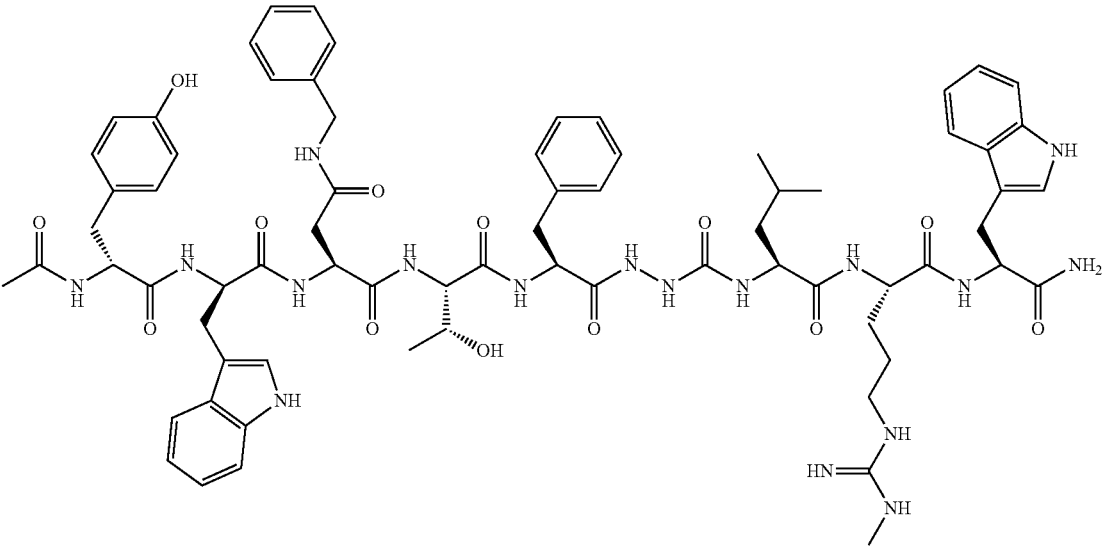 |
| 717 | 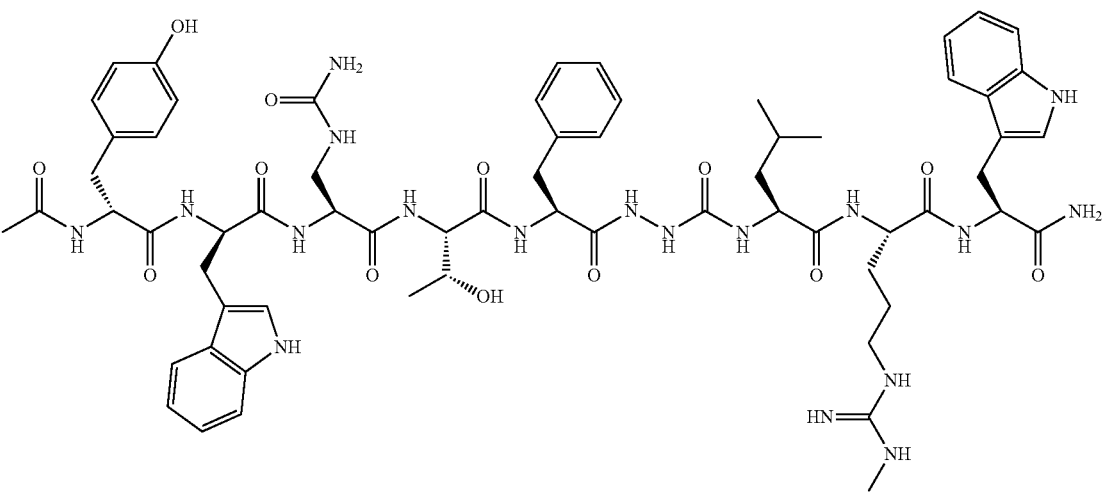 |
| 718 | 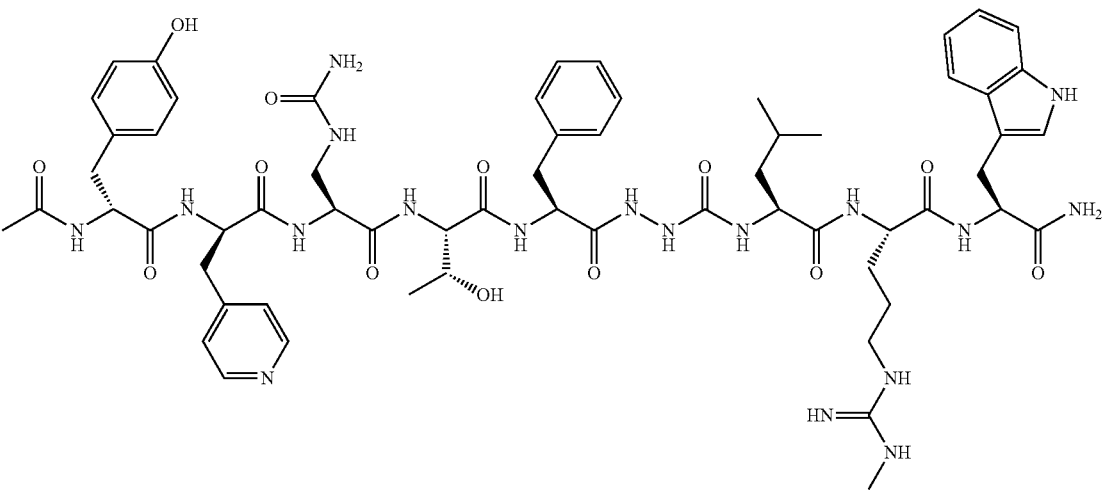 |

TABLE 1B-continued

| Compound No. | Structure |
|---|---|
| 719 | 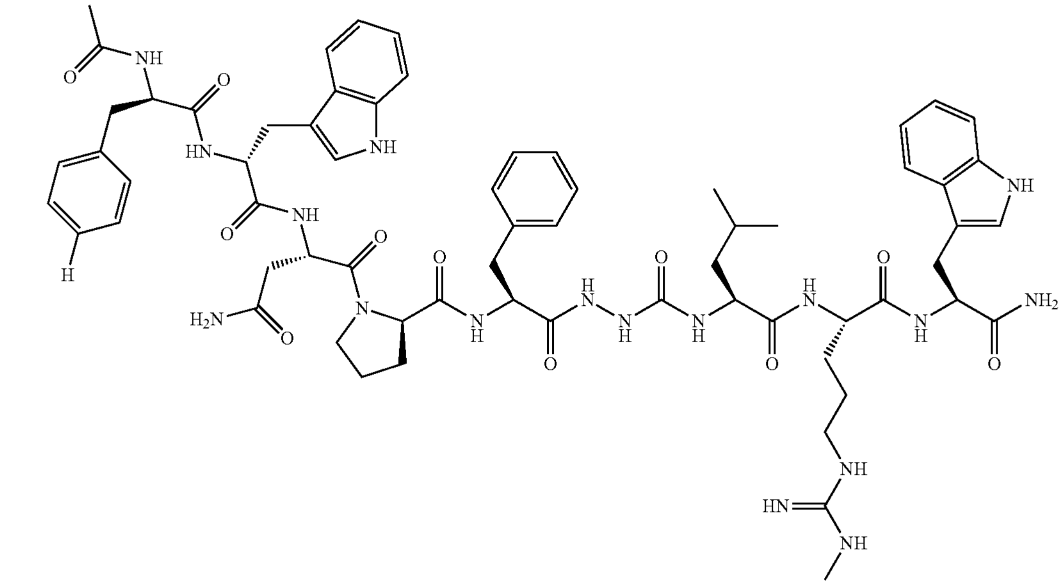 |
| 720 | 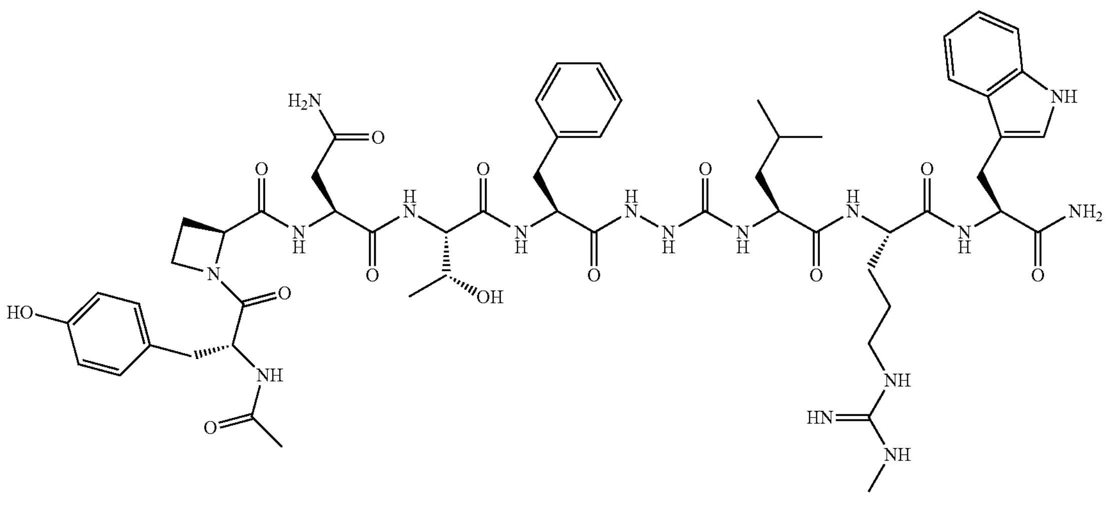 |
| 721 | 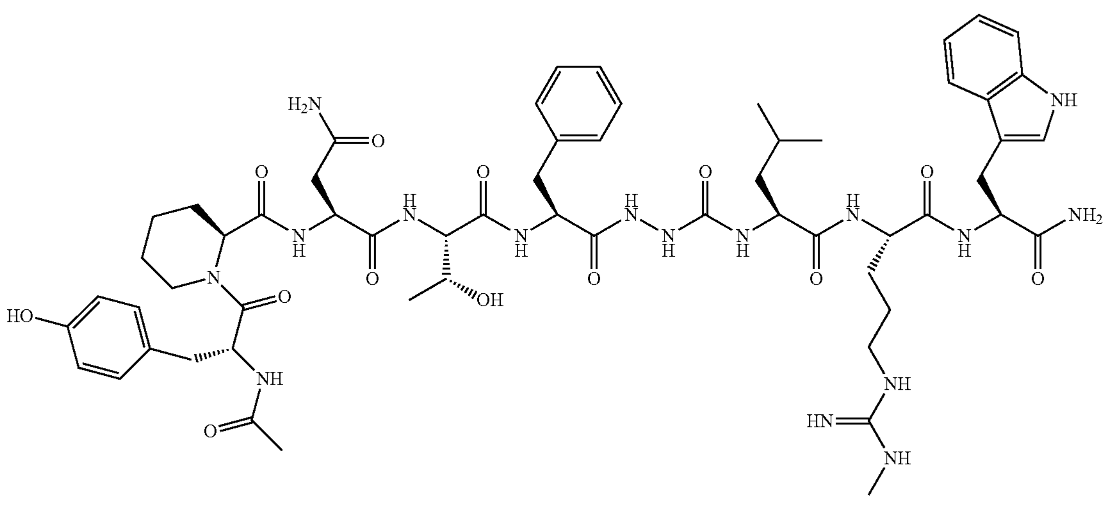 |

TABLE 1B-continued

| Compound No. | Structure |
|---|---|
| 722 | 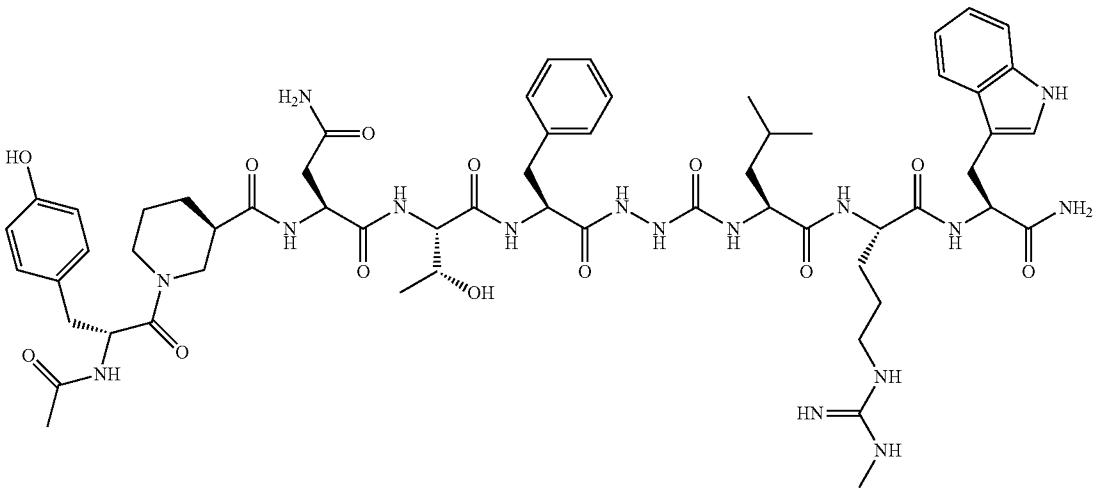 |
| 723 | 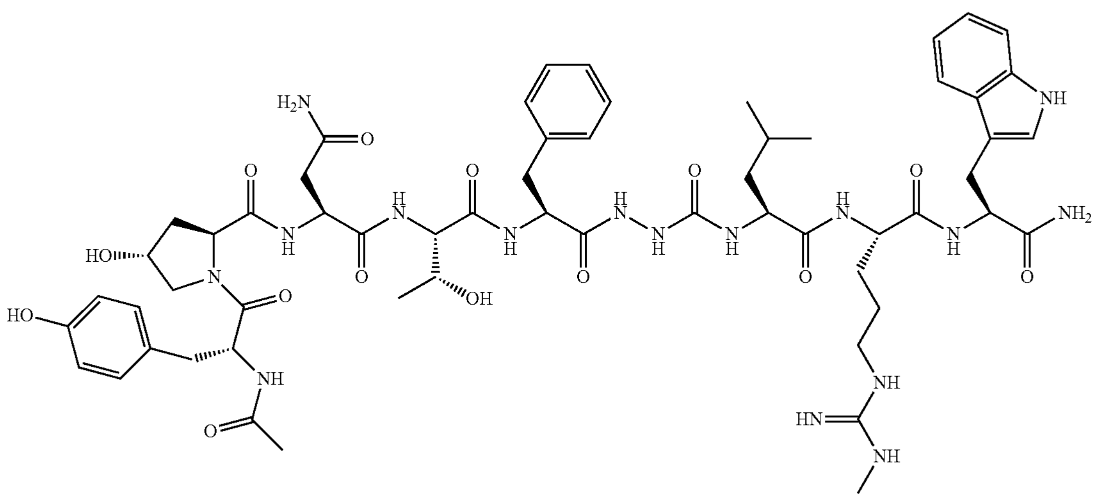 |
| 724 | 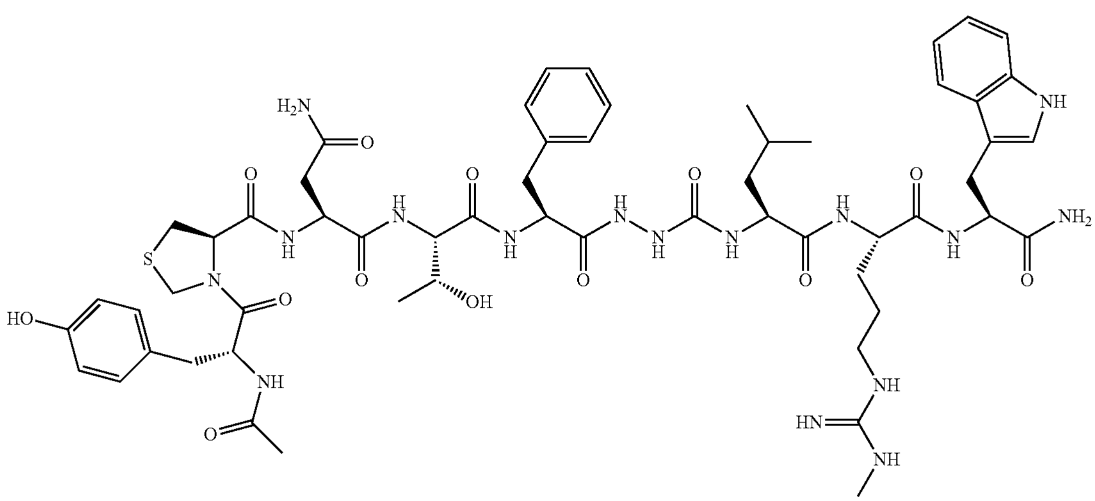 |

TABLE 1B-continued

| Compound No. | Structure |
|---|---|
| 725 | 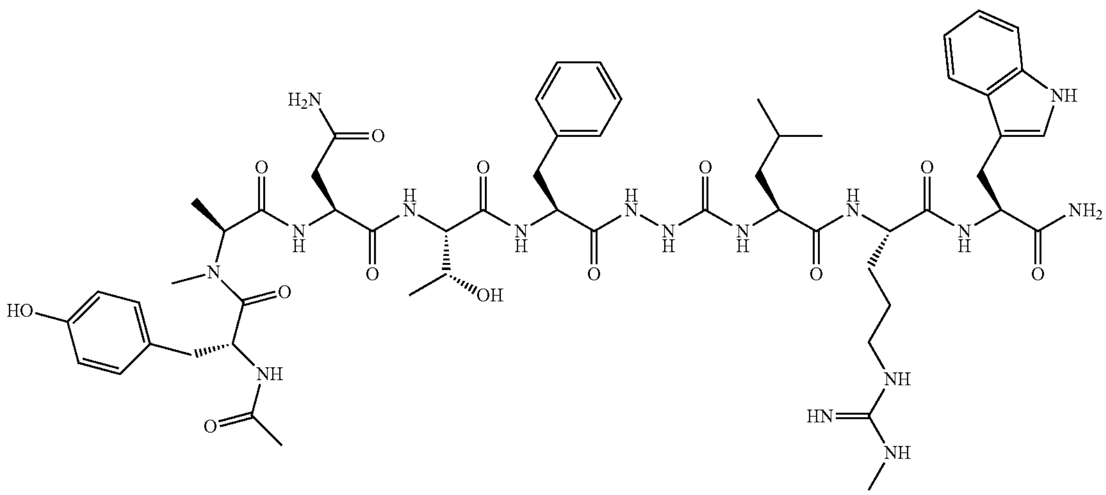 |
| 726 | 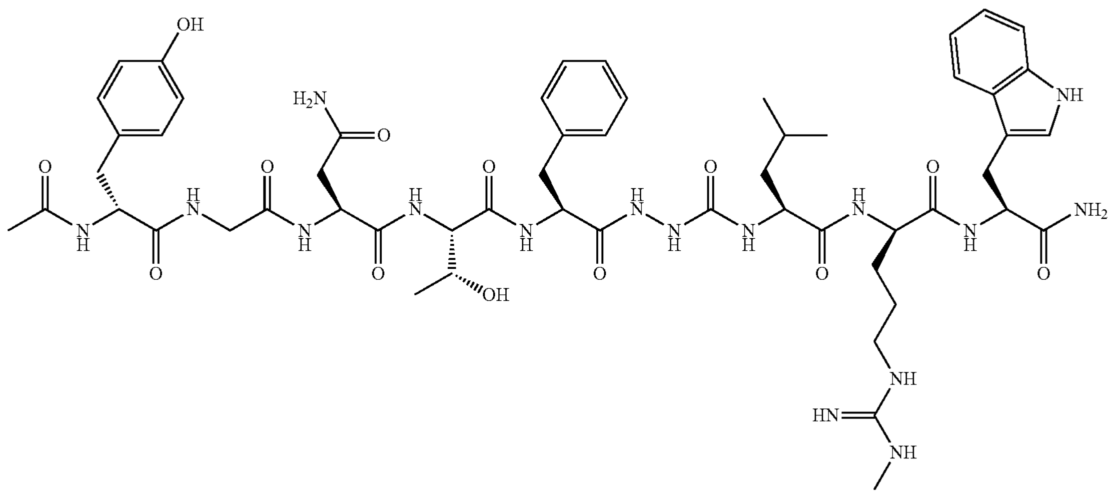 |
| 727 | 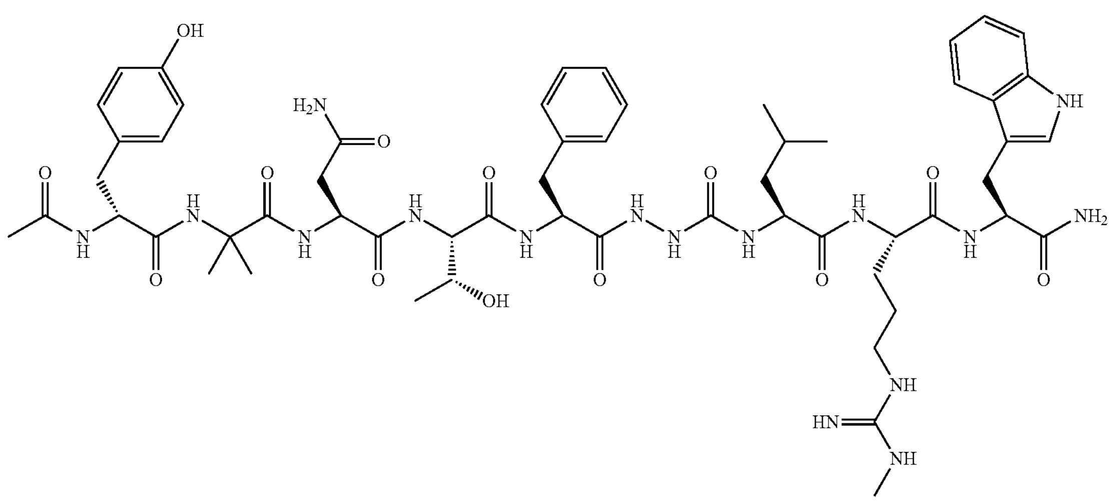 |

TABLE 1B-continued
| Compound No. | Structure |
|---|---|
| 728 | 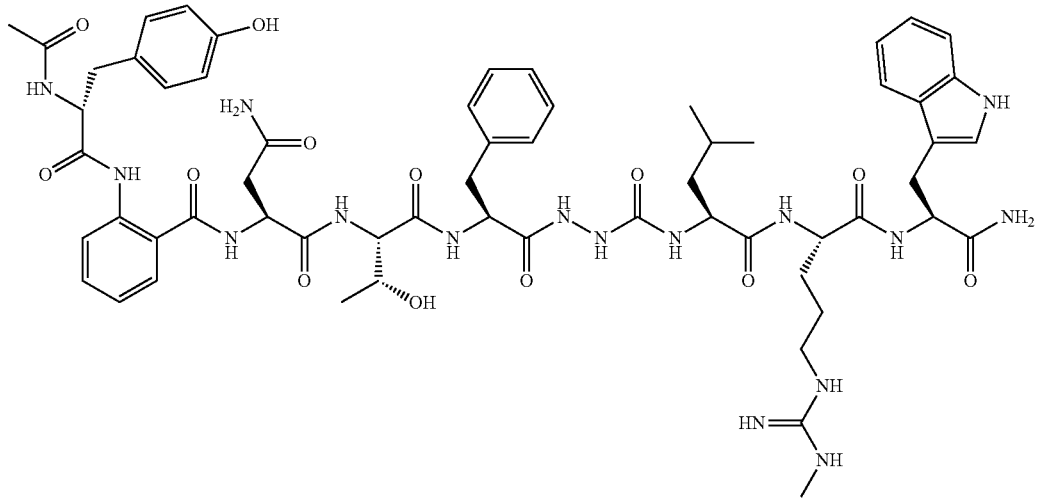 |
| 730 | 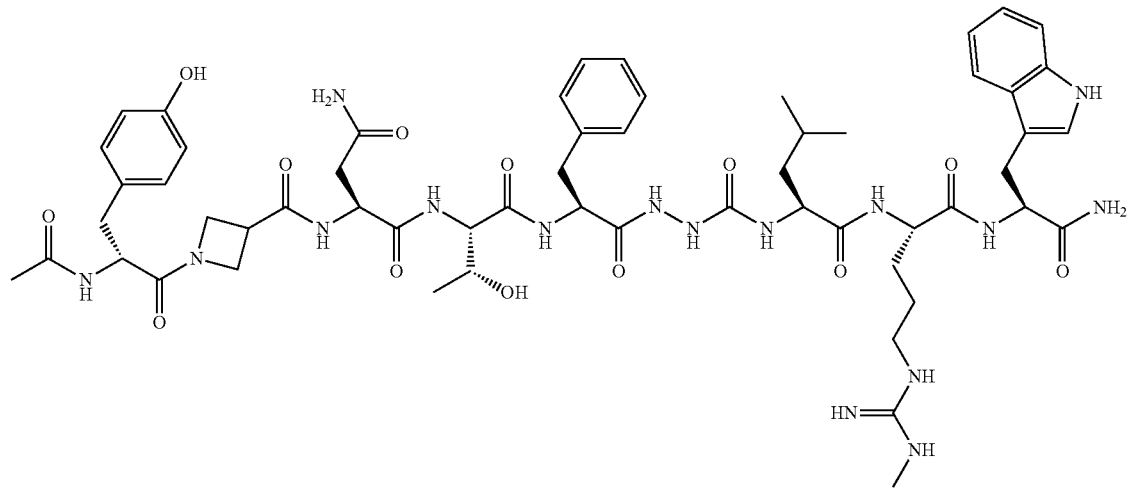 |
| 731 | 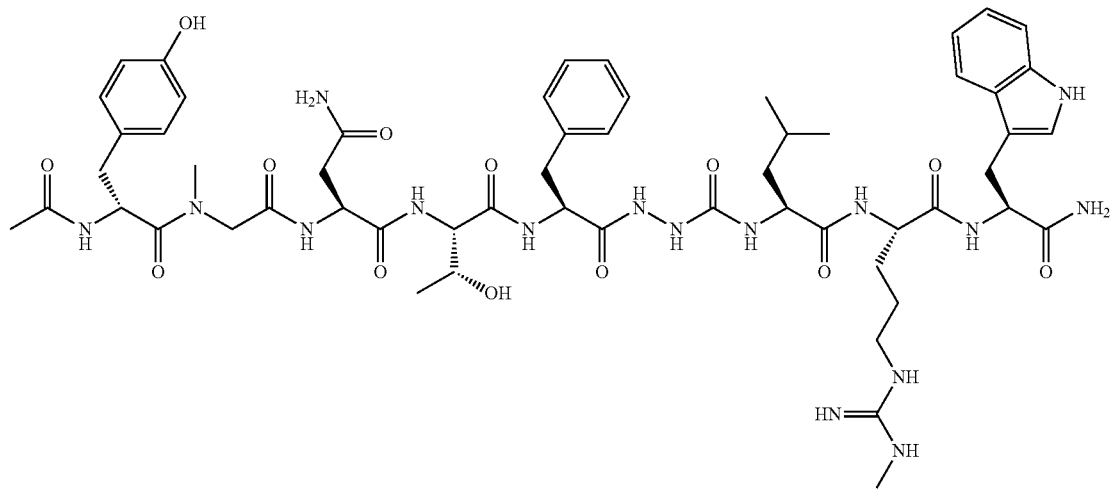 |

TABLE 1B-continued
| Compound No. | Structure |
|---|---|
| 732 | 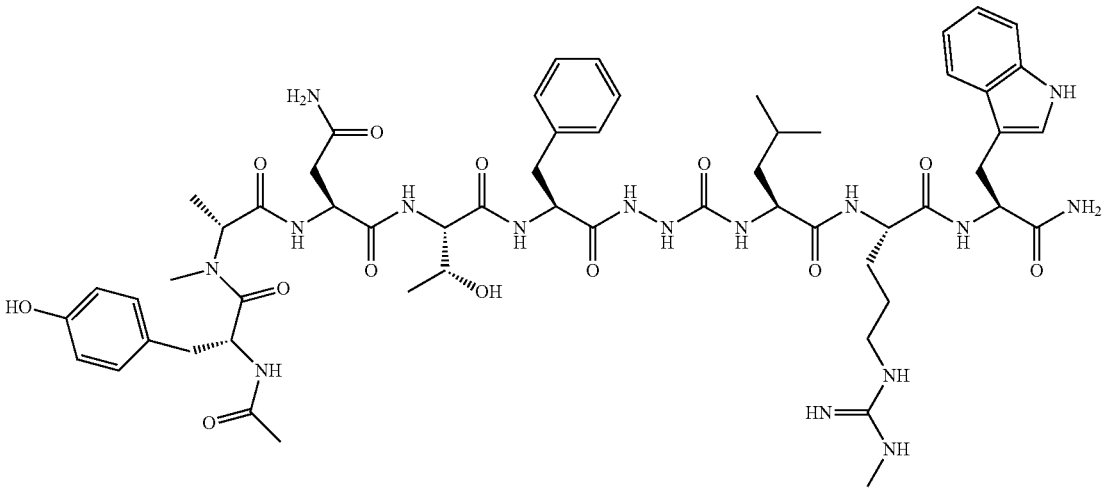 |
| 734 | 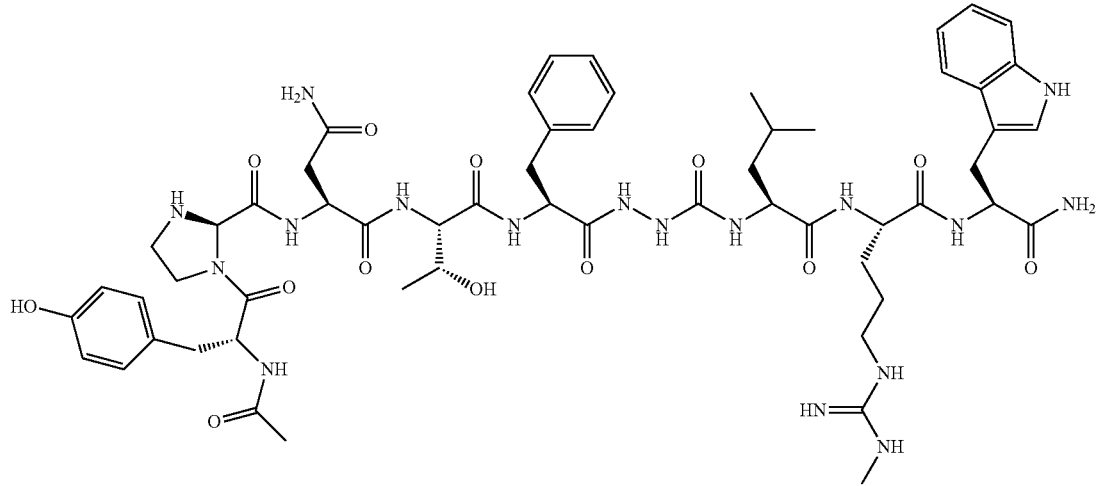 |
| 735 | 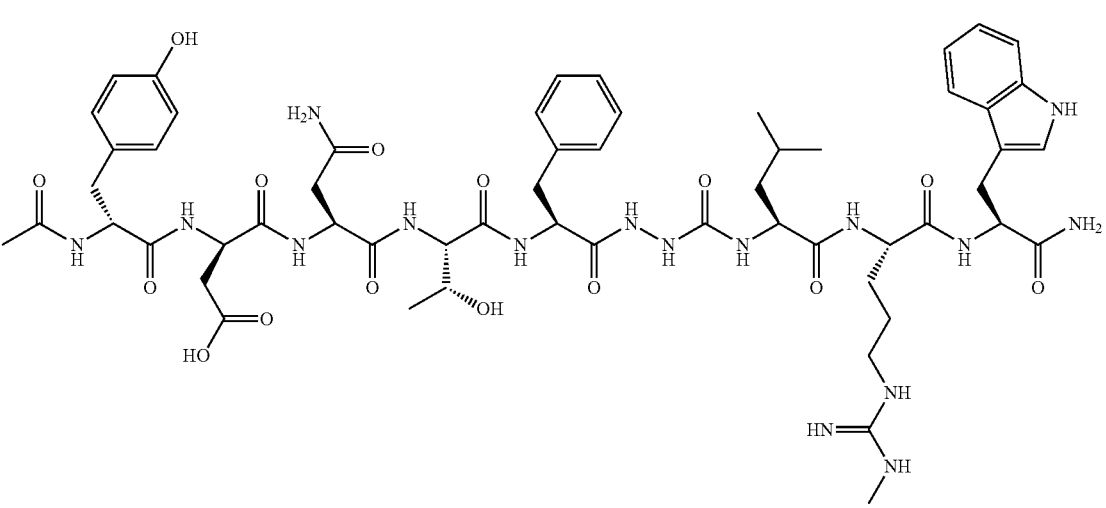 |

TABLE 1B-continued

| Compound No. | Structure |
|---|---|
| 736 | 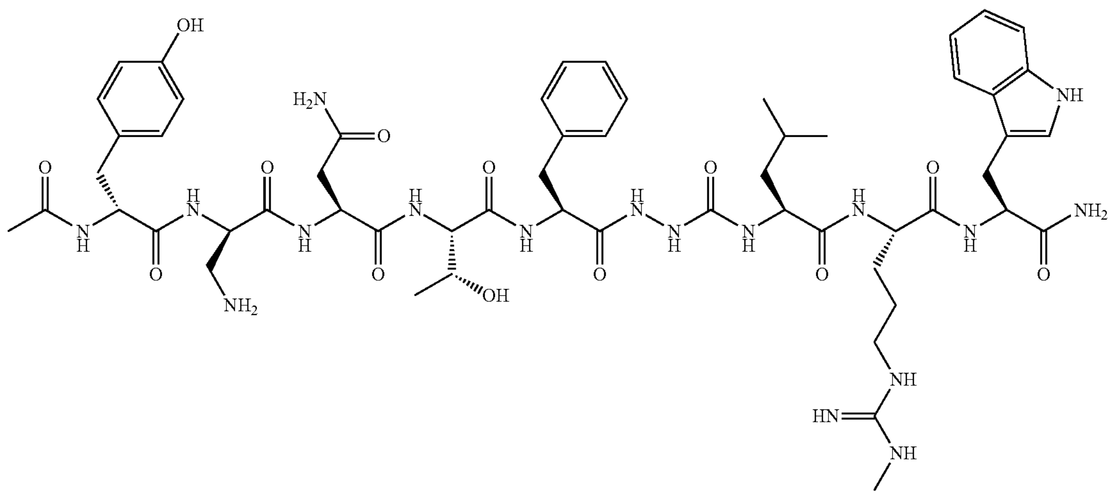 |
| 737 | 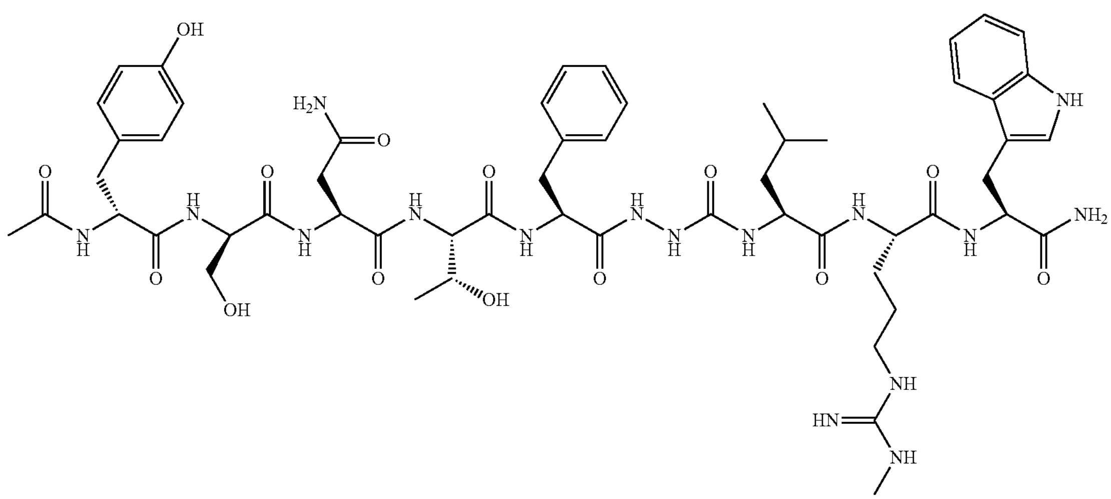 |
| 738 | 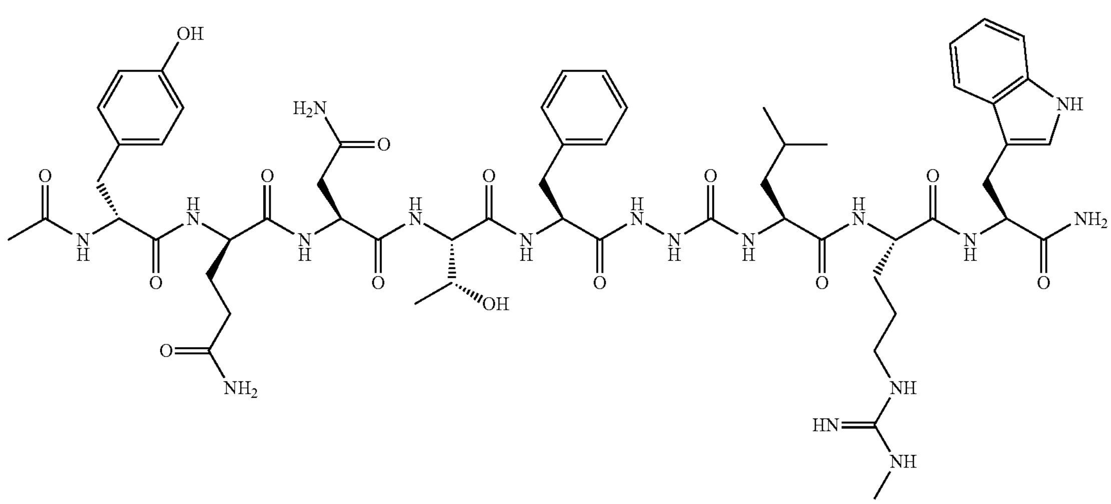 |

TABLE 1B-continued
| Compound No. | Structure |
|---|---|
| 739 | 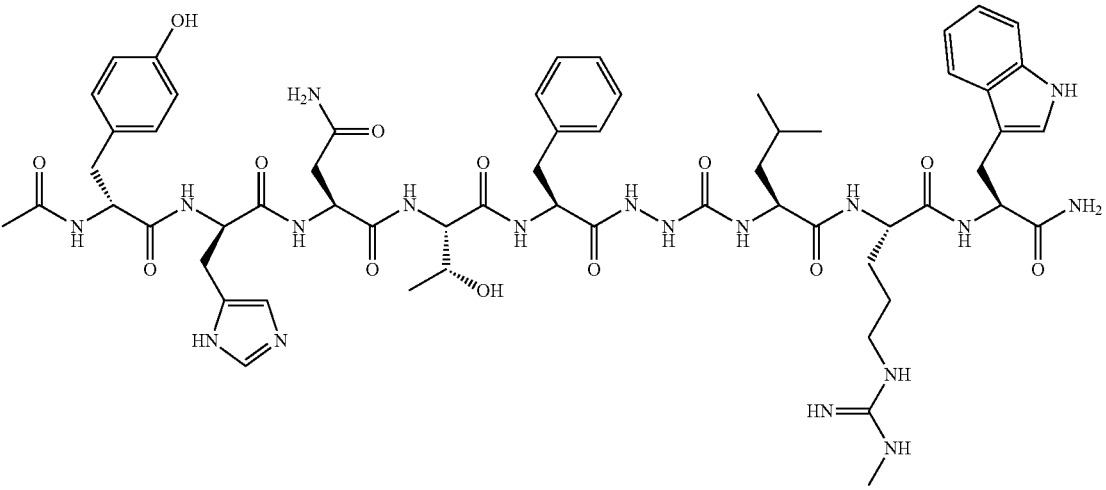 |
| 740 | 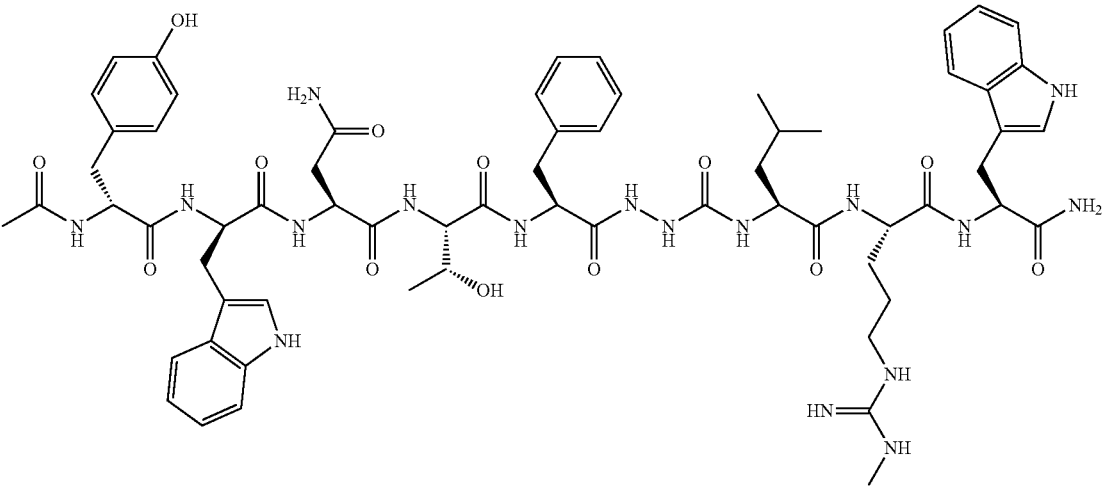 |
| 742 | 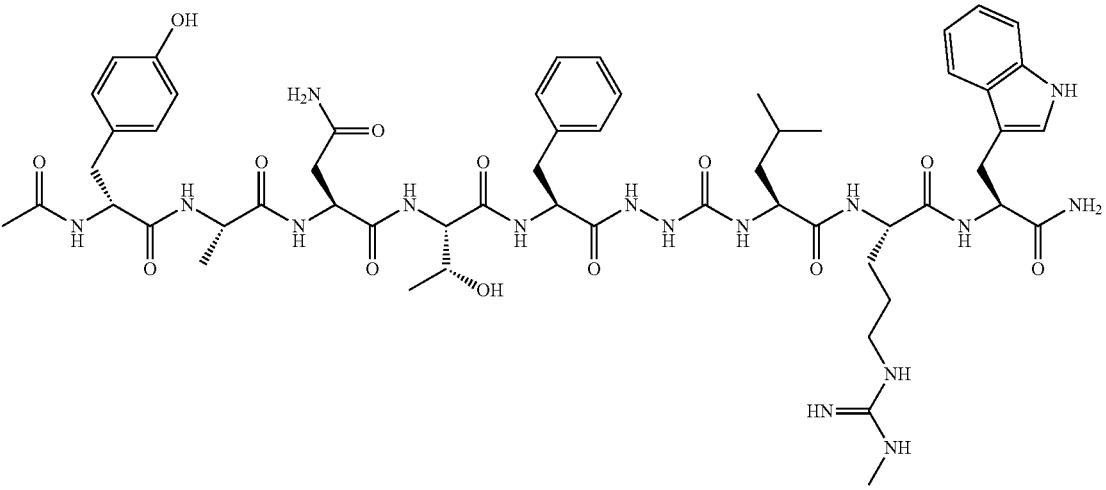 |

TABLE 1B-continued
| Compound No. | Structure |
|---|---|
| 743 | 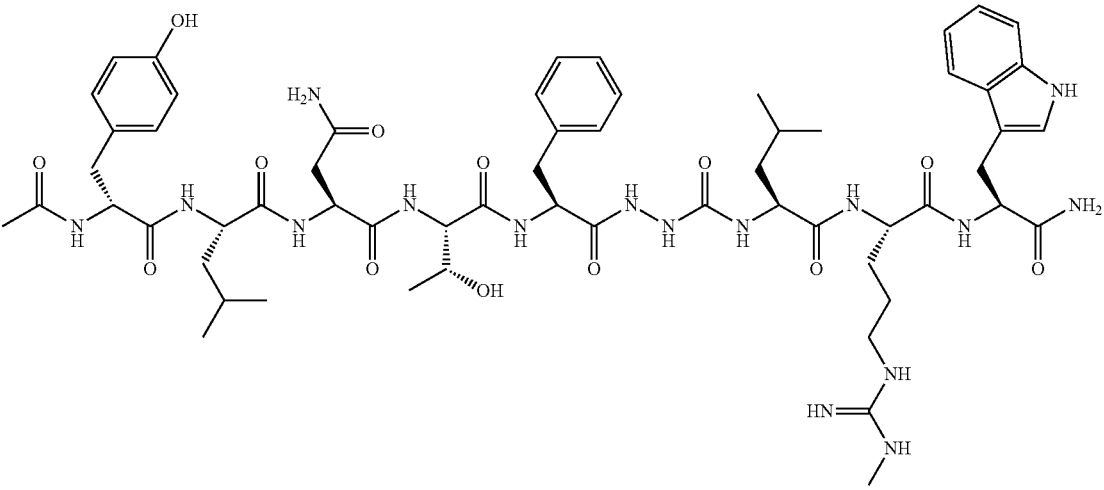 |
| 744 | 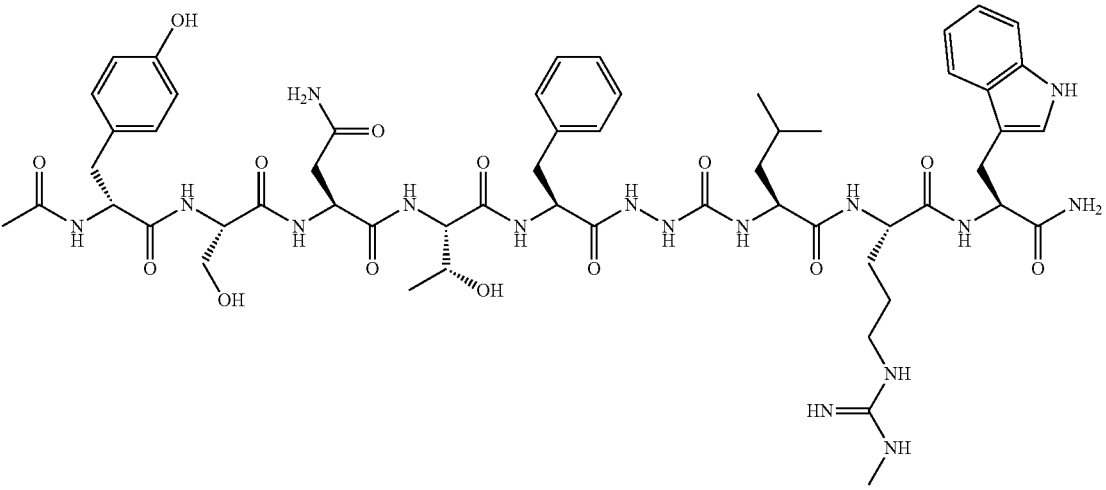 |
| 745 | 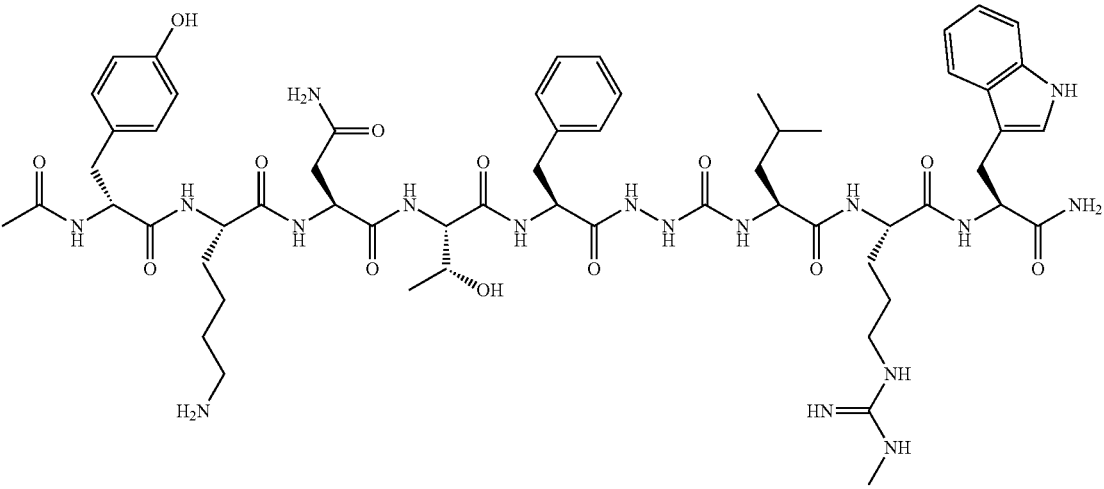 |

TABLE 1B-continued
| Compound No. | Structure |
|---|---|
| 746 | 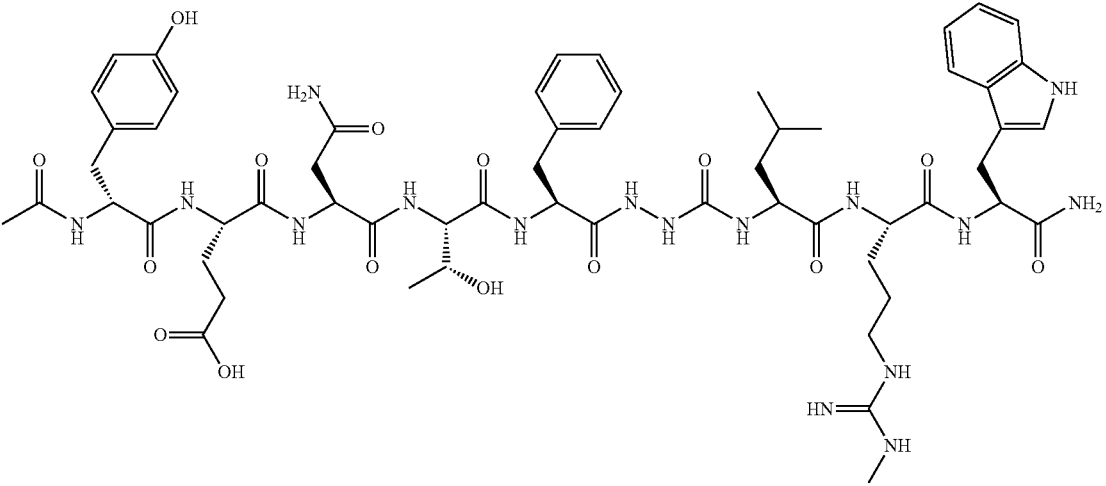 |
| 747 | 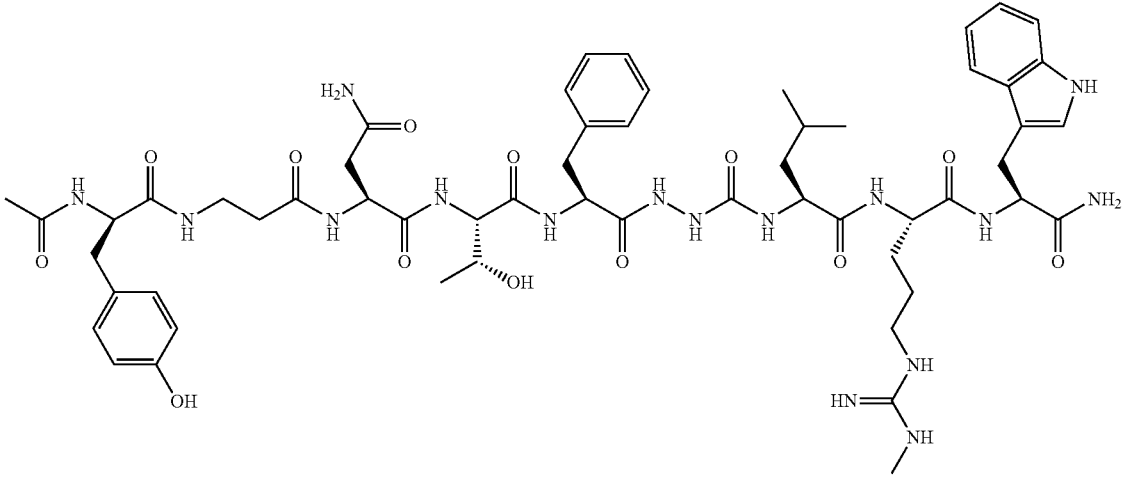 |
| 748 | 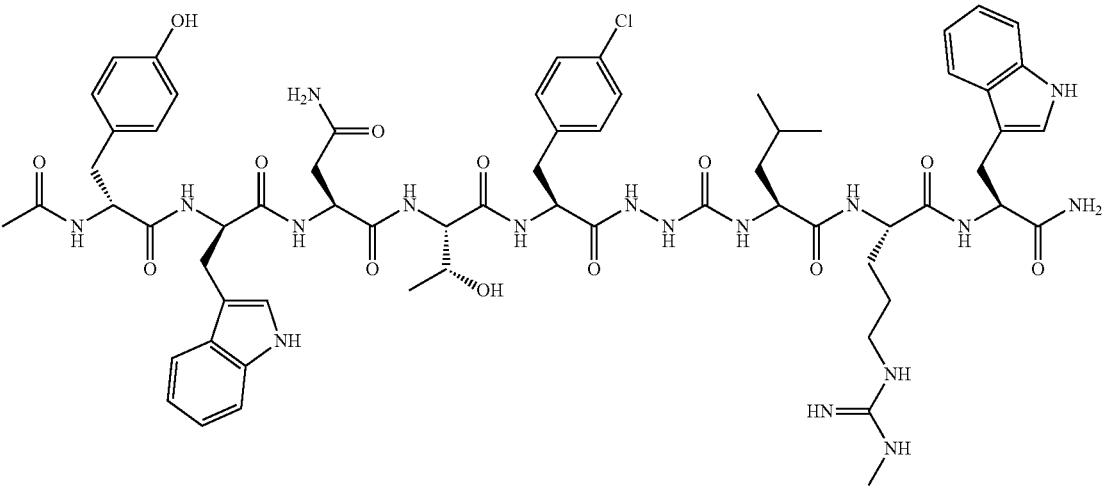 |

TABLE 1B-continued
| Compound No. | Structure |
|---|---|
| 749 | 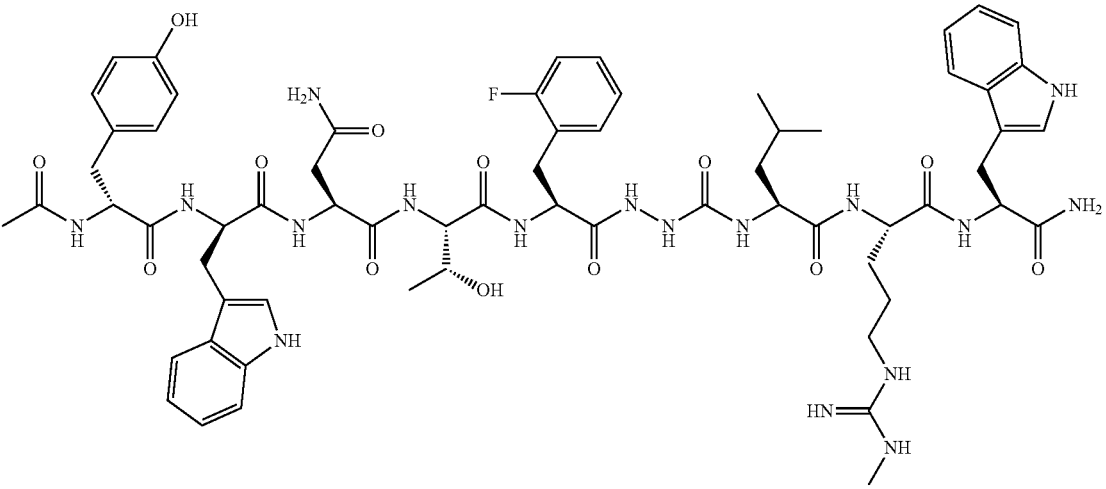 |
| 750 | 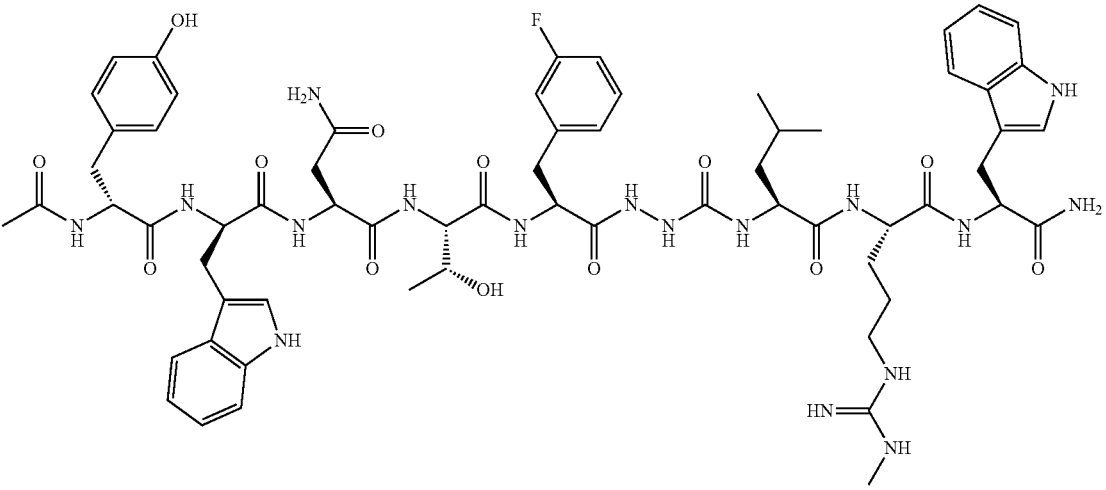 |
| 754 | 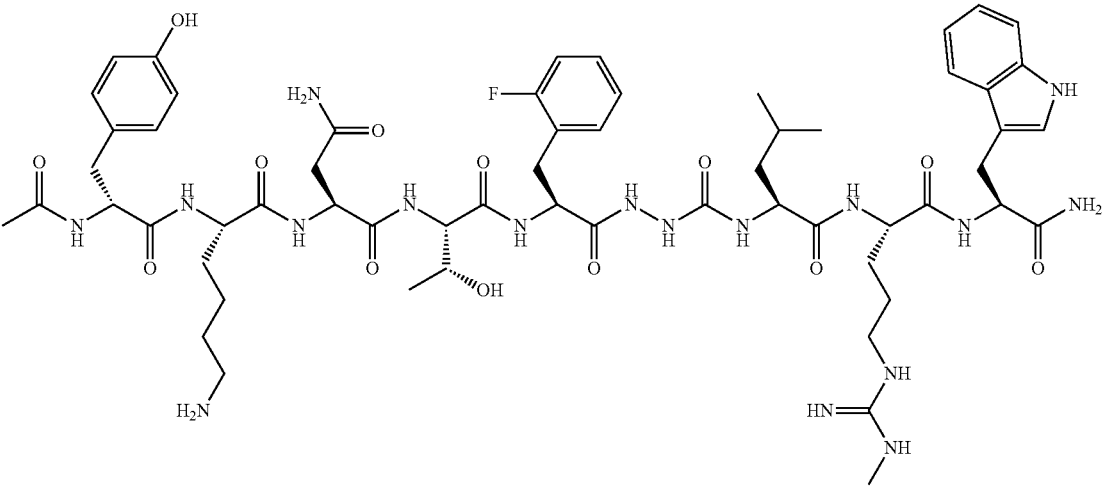 |

TABLE 1B-continued

| Compound No. | Structure |
|---|---|
| 755 | 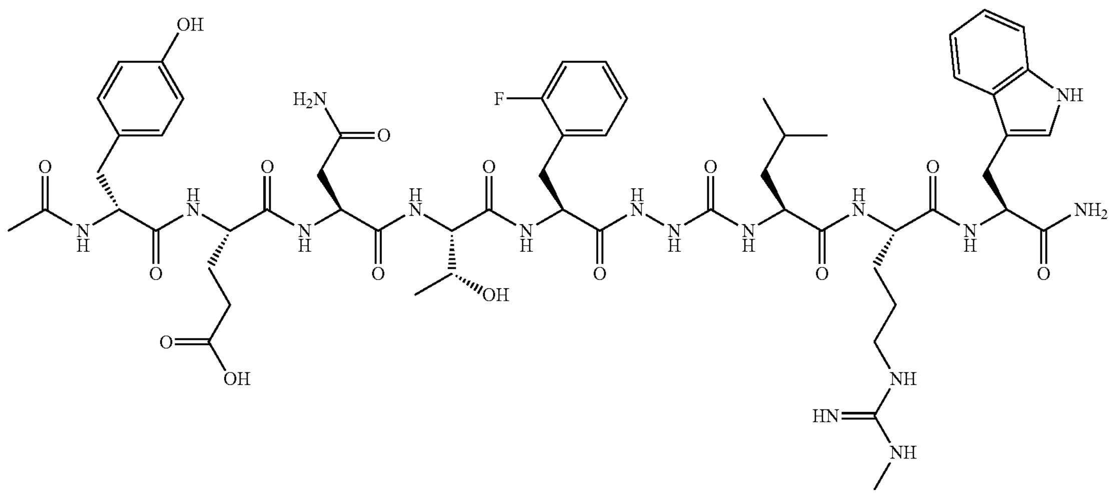 |
| 756 | 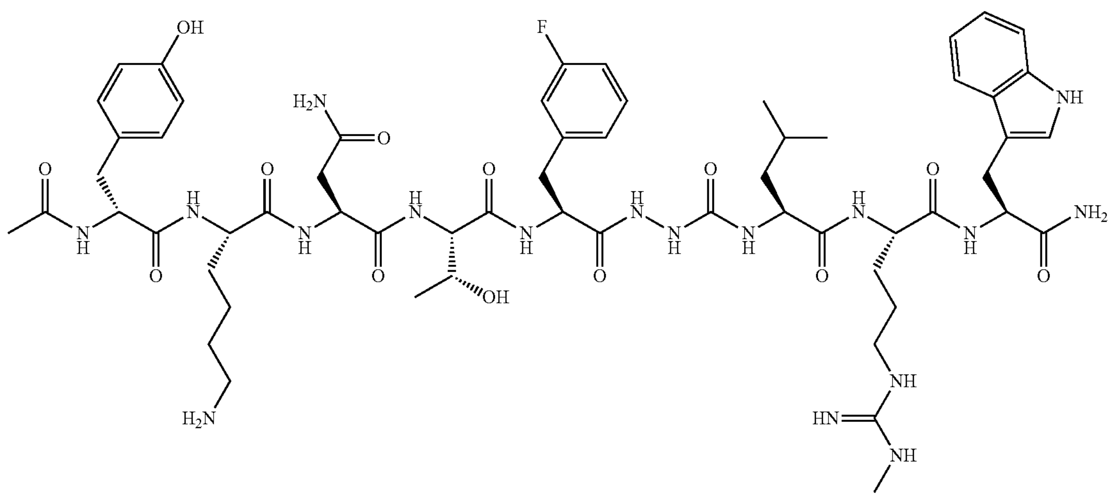 |
| 757 | 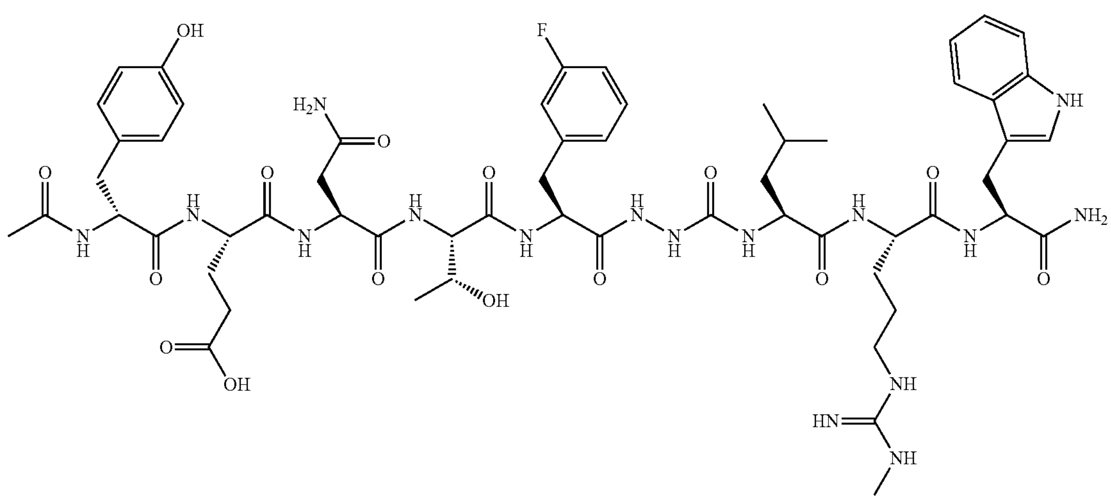 |

TABLE 1B-continued

| Compound No. | Structure |
|---|---|
| 758 | 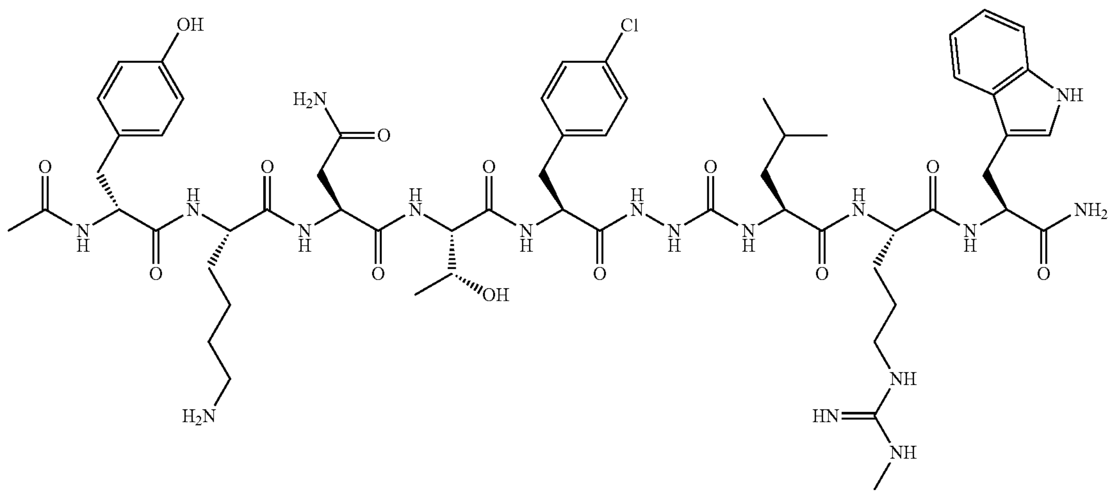 |
| 759 | 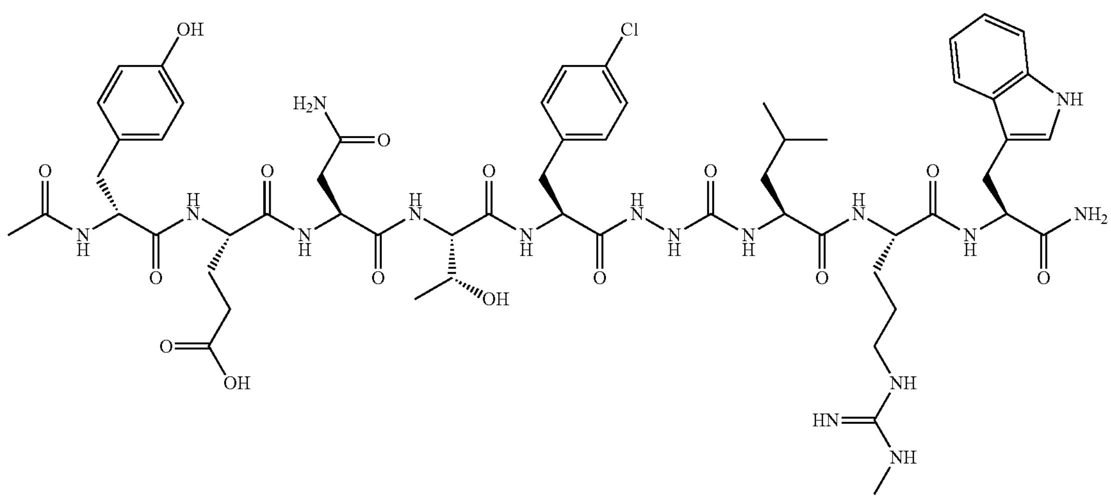 |
| 760 | 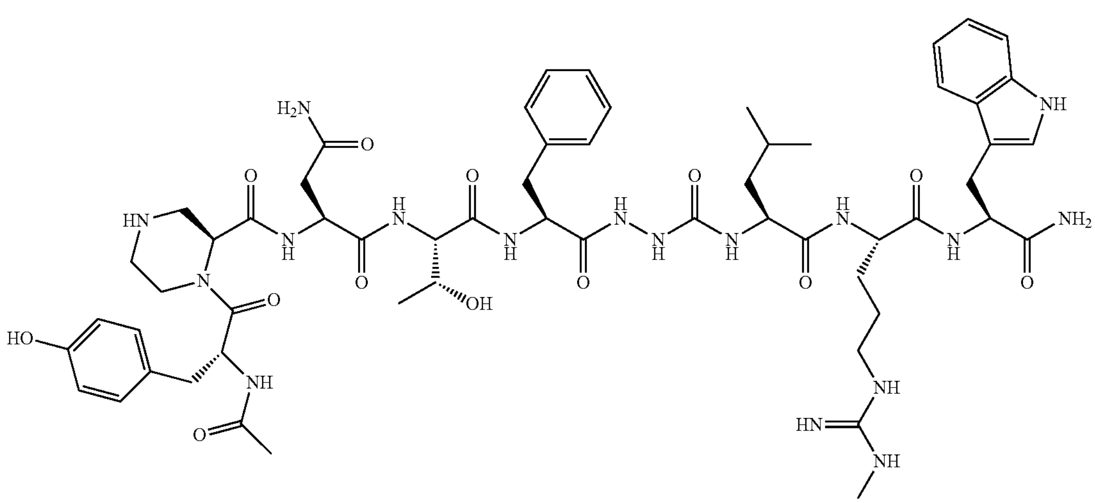 |

TABLE 1B-continued
| Compound No. | Structure |
|---|---|
| 763 | 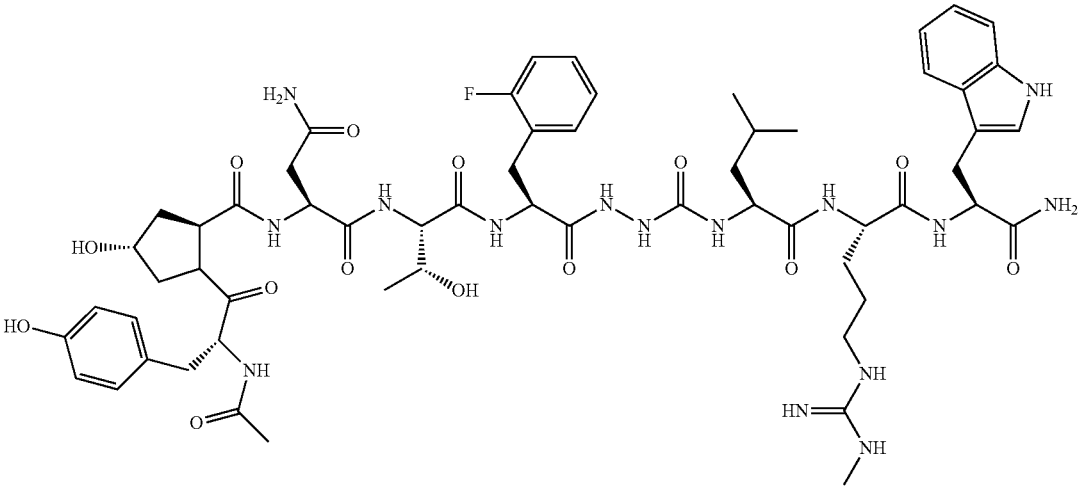 |
| 764 | 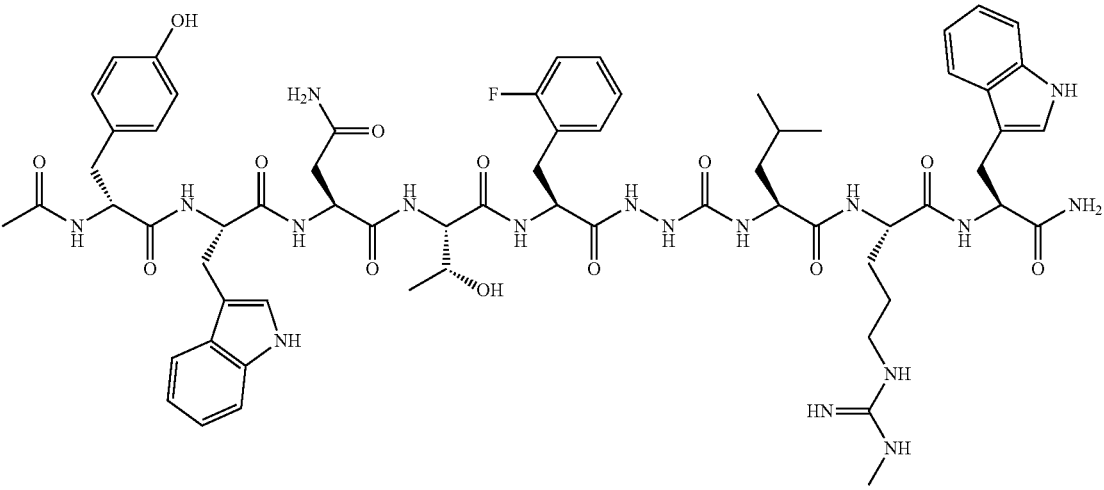 |
| 765 | 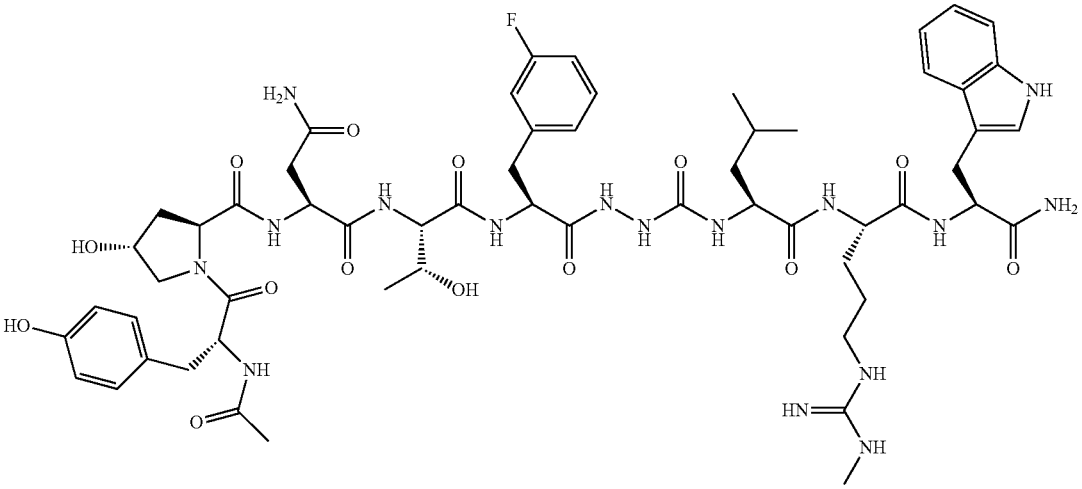 |

TABLE 1B-continued
| Compound No. | Structure |
|---|---|
| 766 | 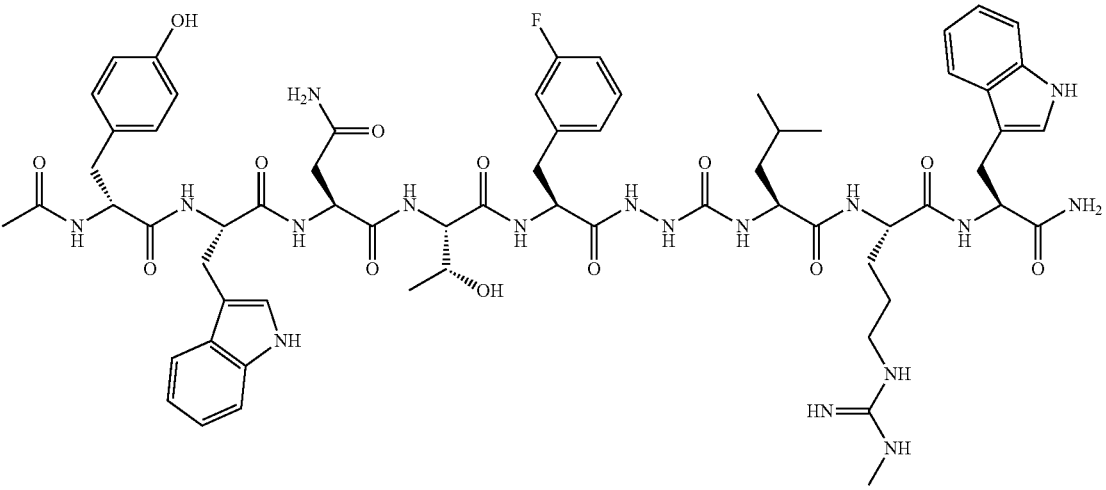 |
| 767 | 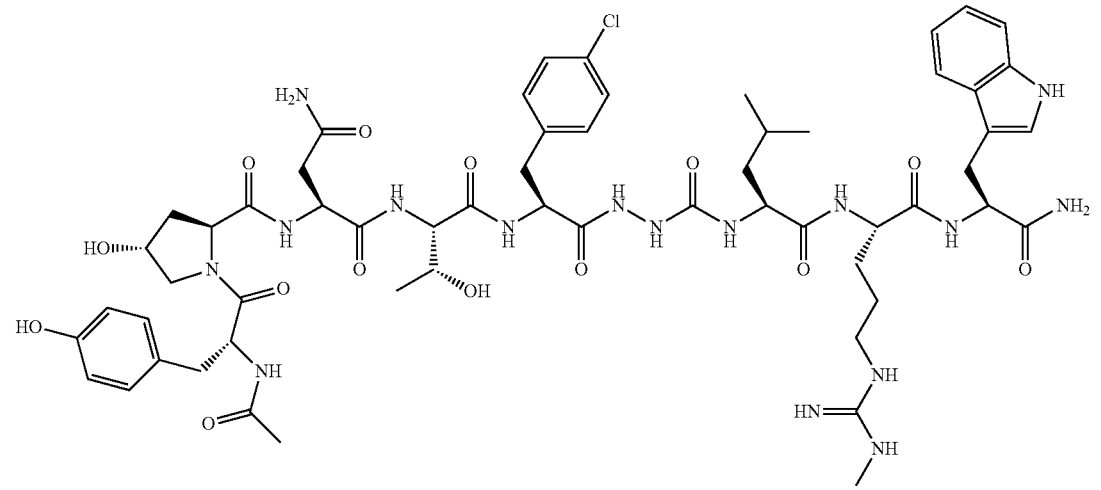 |
| 768 | 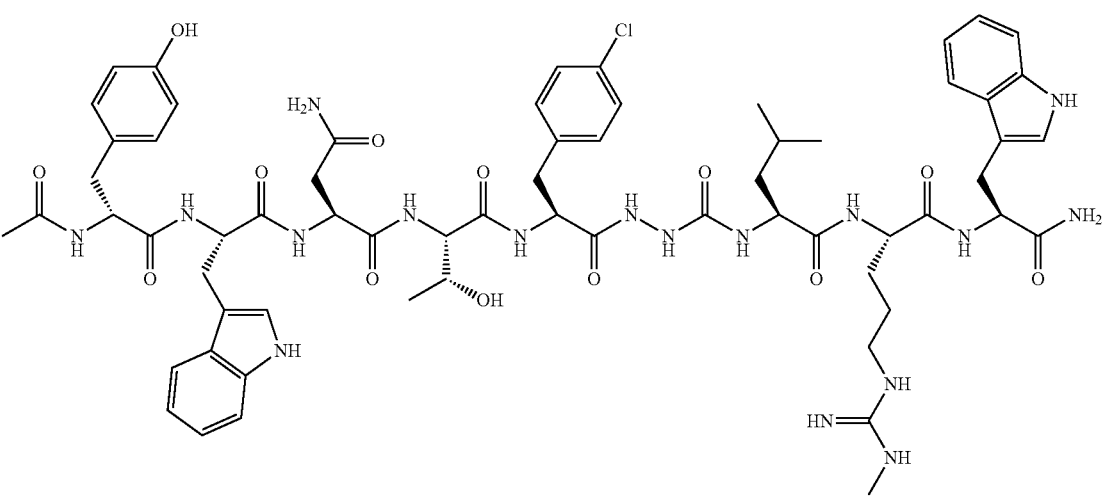 |

US 7,960,348 B2
123 124
TABLE 1B-continued
| Compound No. | Structure |
|---|---|
| 769 | 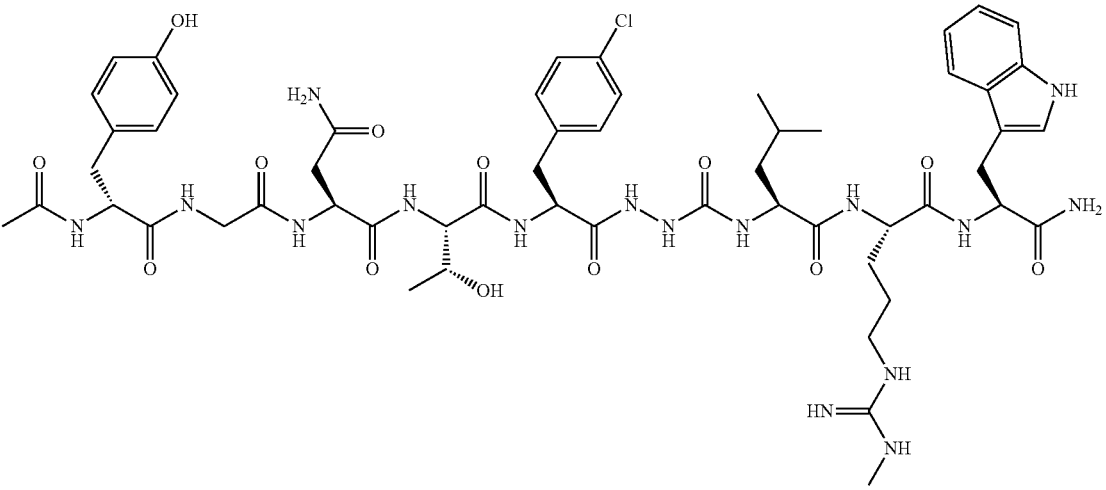 |
| 770 | 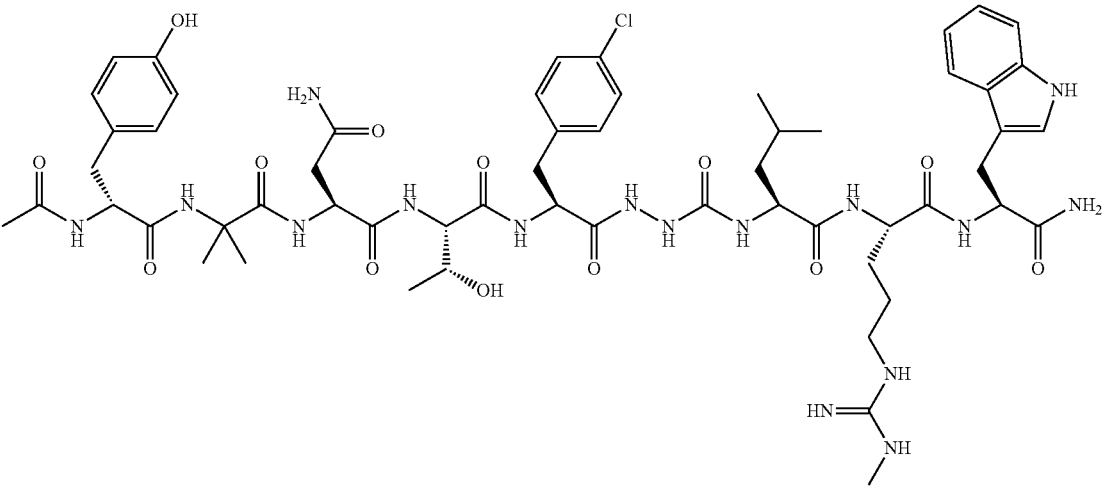 |
| 771 | 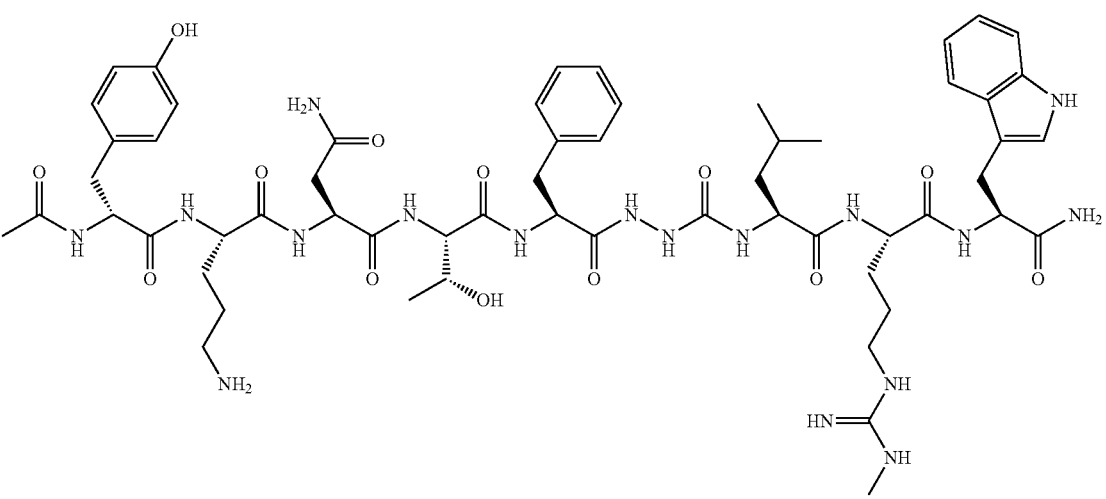 |

TABLE 1B-continued
| Compound No. | Structure |
|---|---|
| 772 | 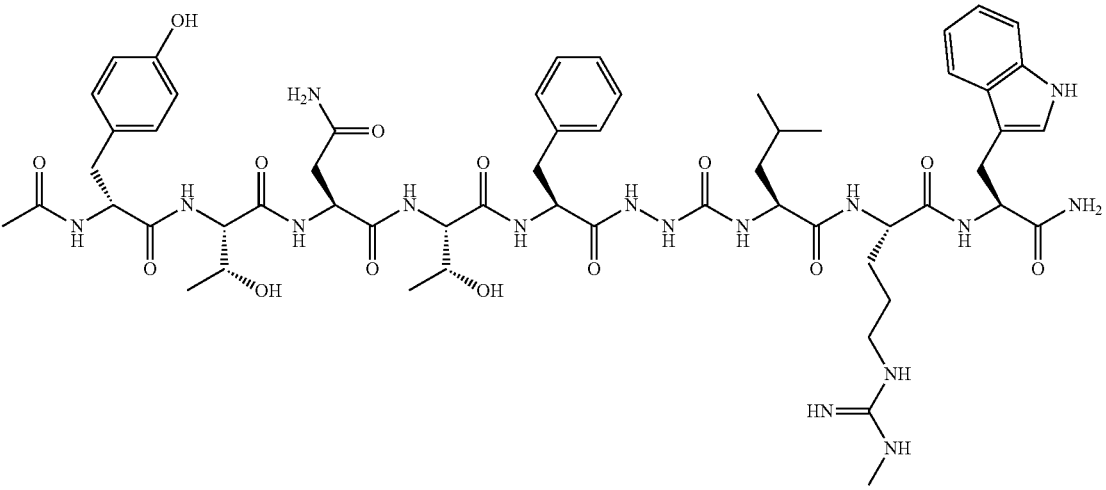 |
| 773 | 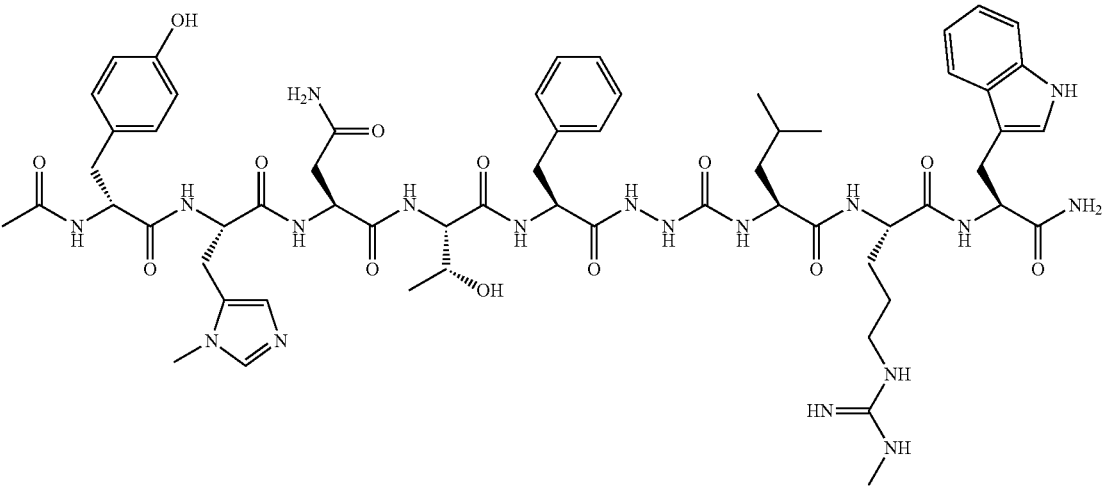 |
| 774 | 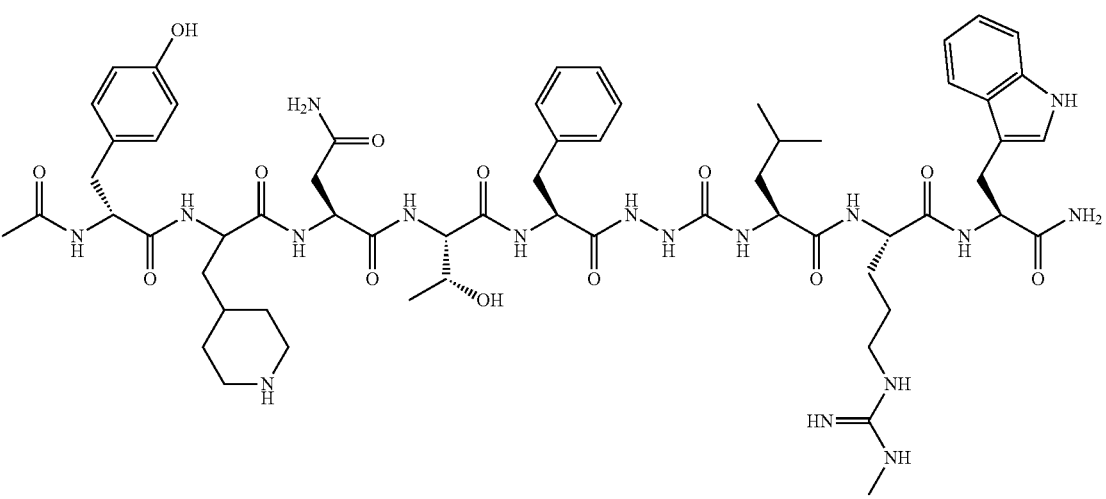 |

TABLE 1B-continued
| Compound No. | Structure |
|---|---|
| 775 | 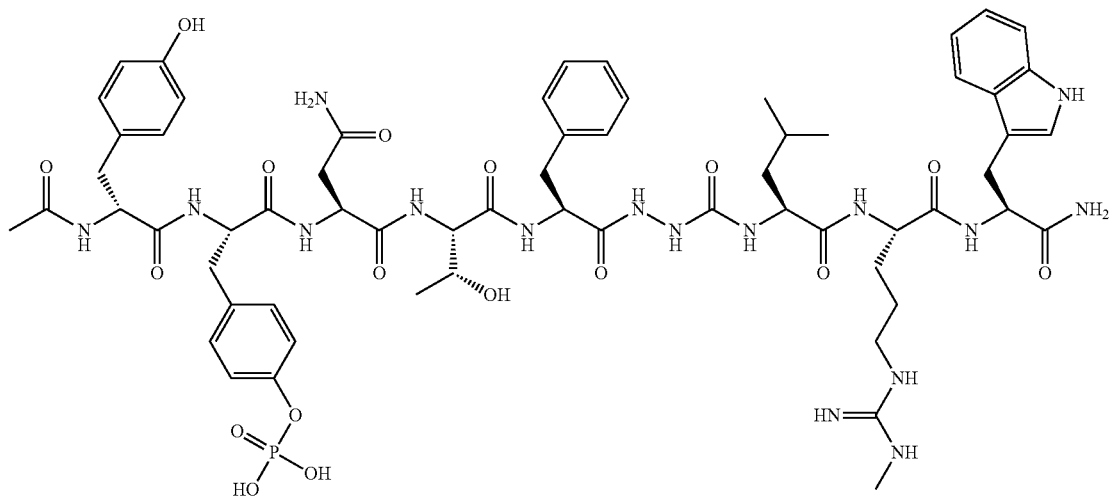 |
| 776 | 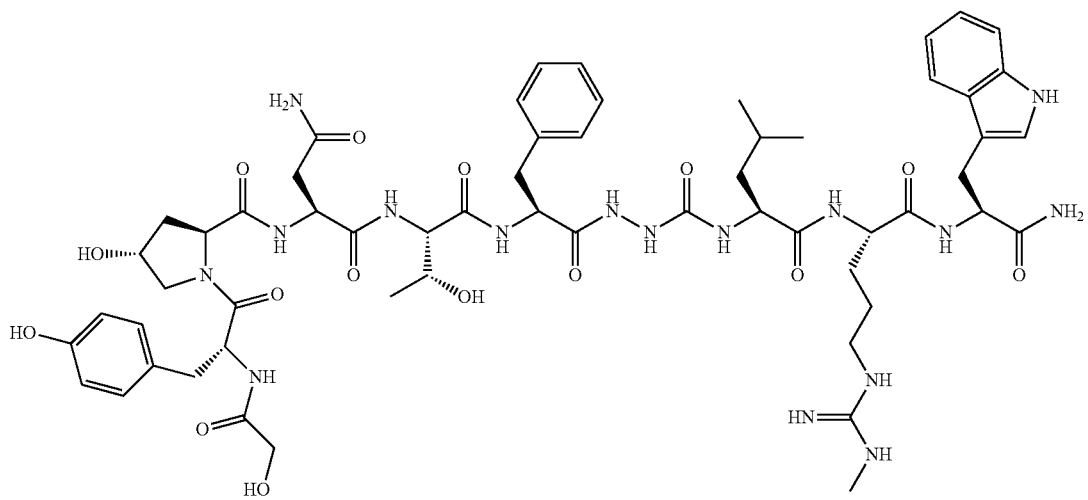 |
| 777 | 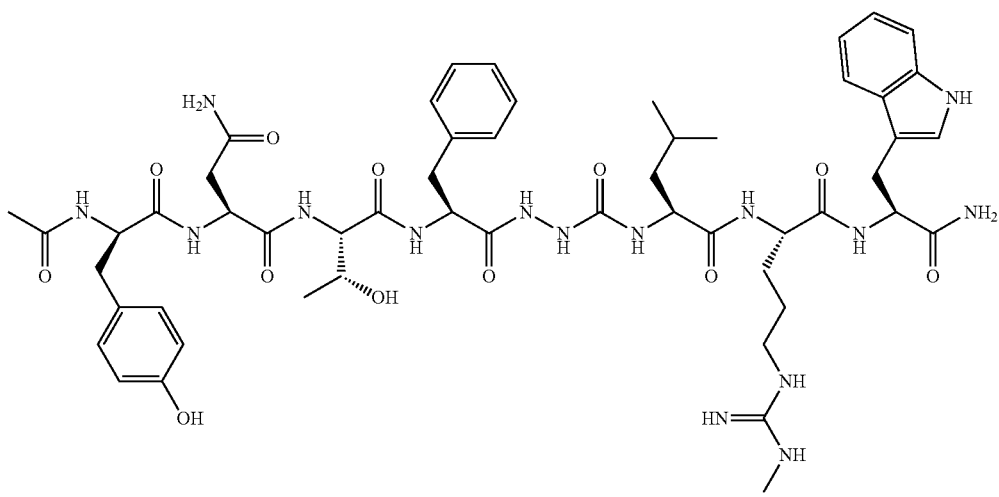 |

TABLE 1B-continued
| Compound No. | Structure |
|---|---|
| 780 | 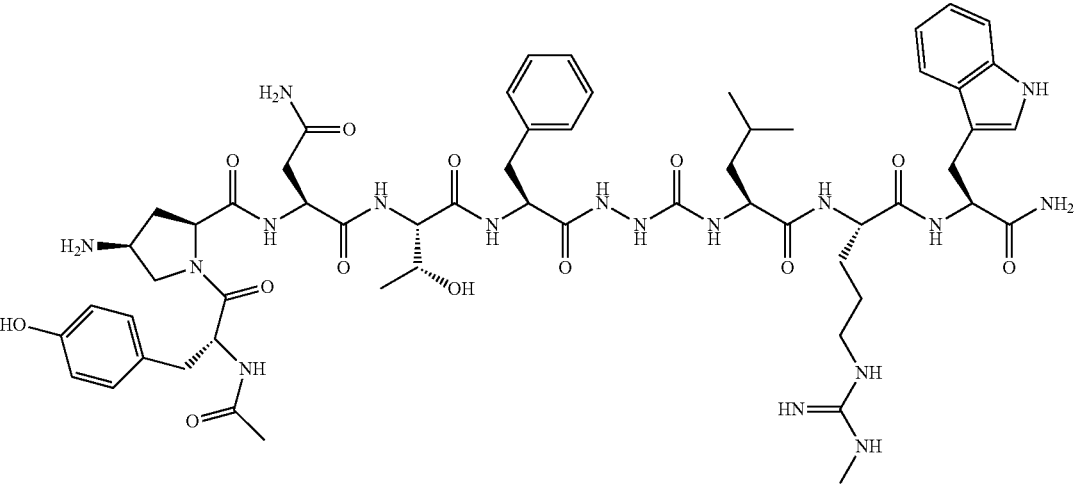 |
| 781 | 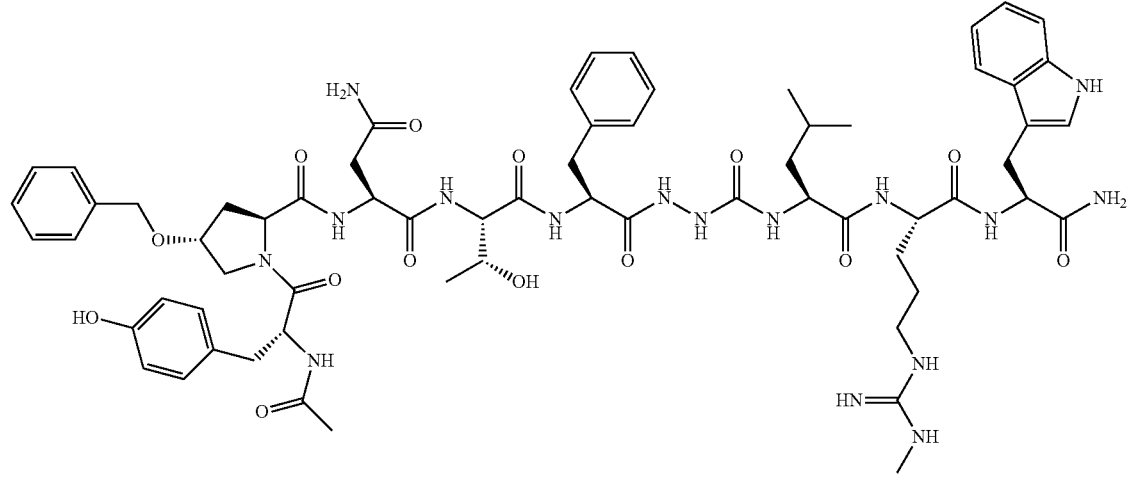 |
| 782 | 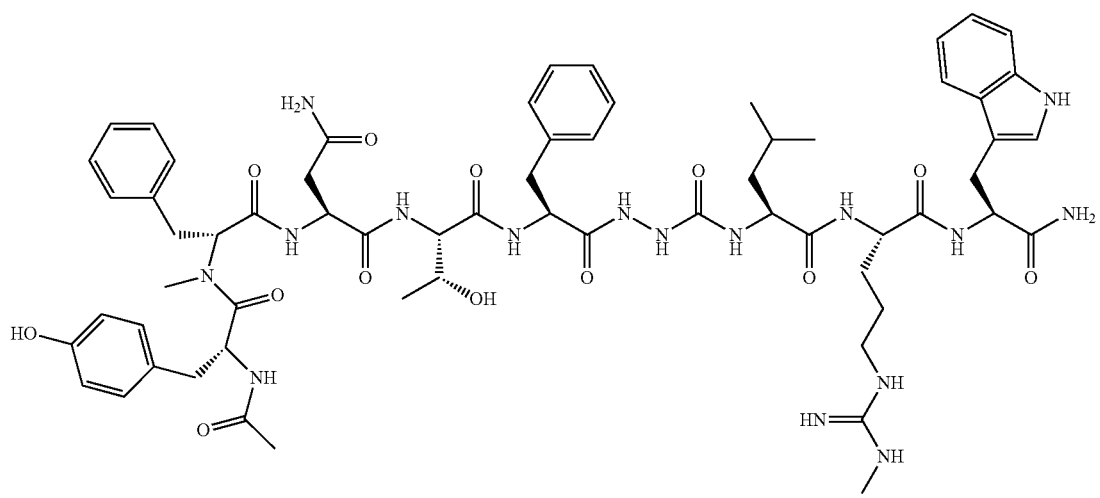 |

TABLE 1B-continued
| Compound No. | Structure |
|---|---|
| 783 | 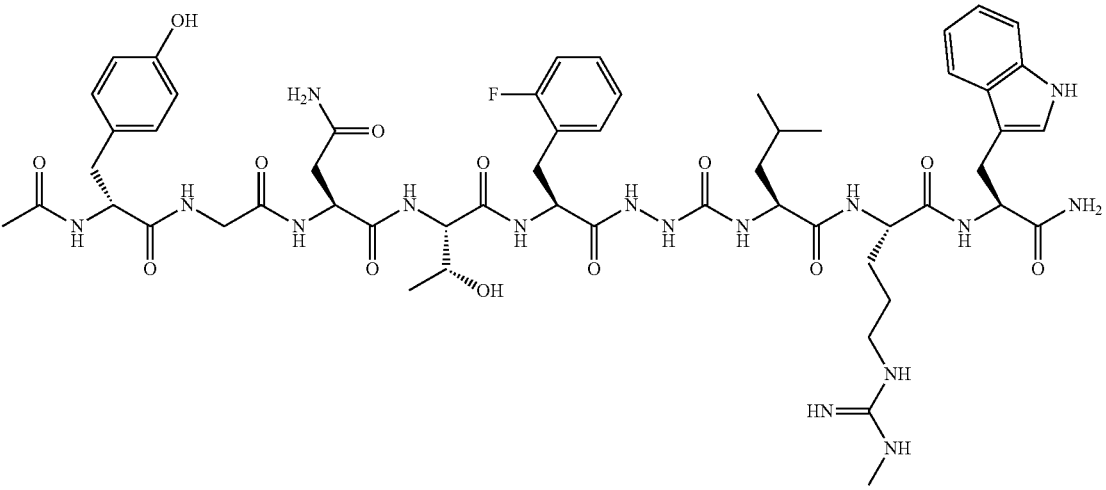 |
| 784 | 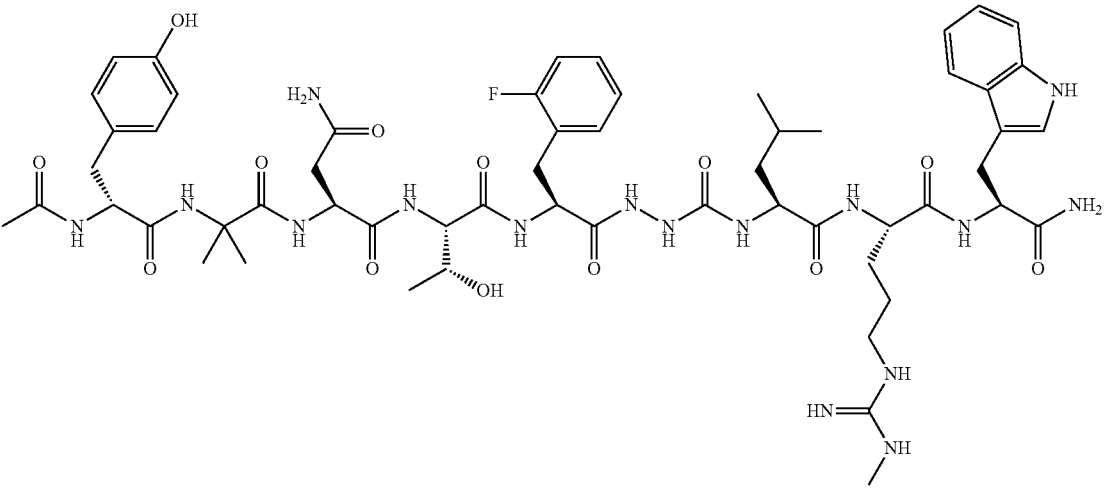 |
| 785 | 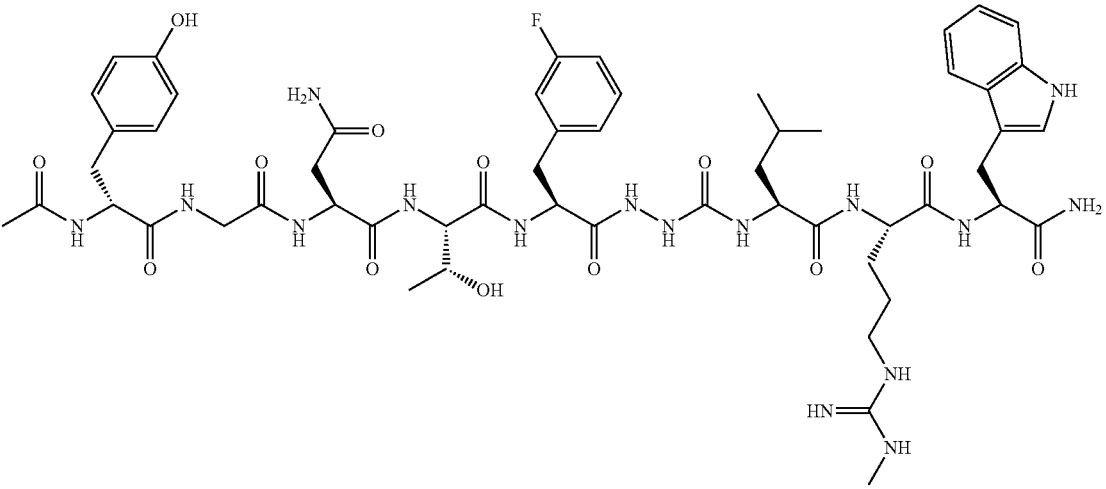 |

TABLE 1B-continued

| Compound No. | Structure |
|---|---|
| 786 | 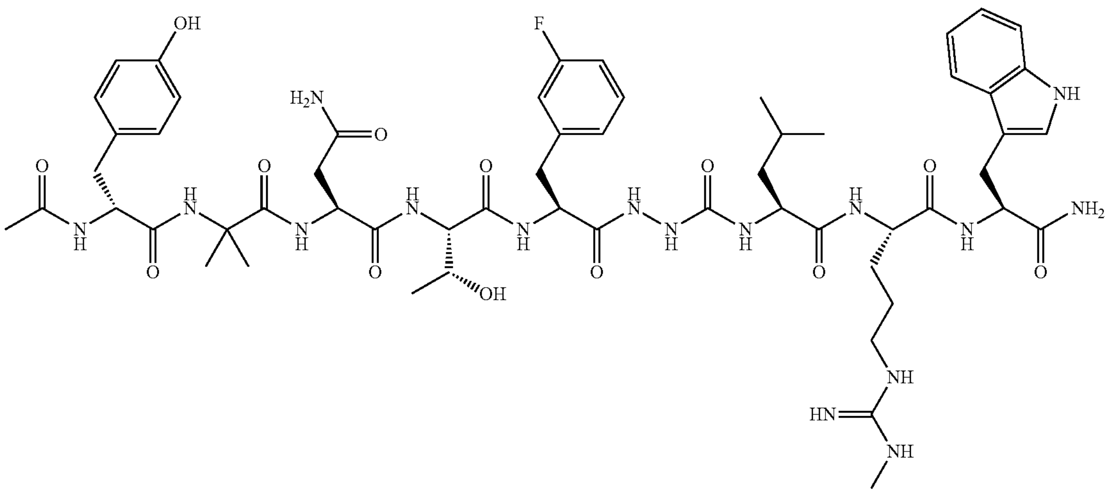 |
| 787 | 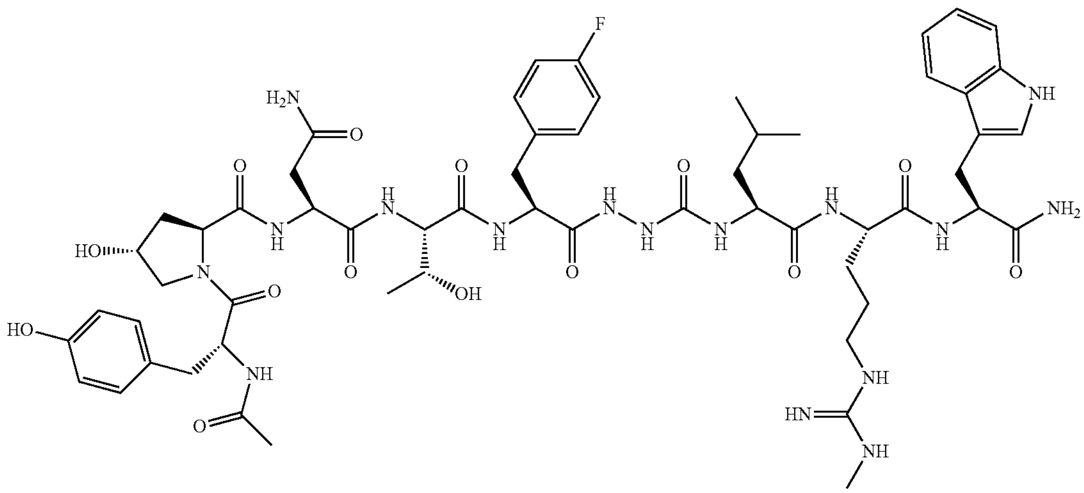 |
| 788 | 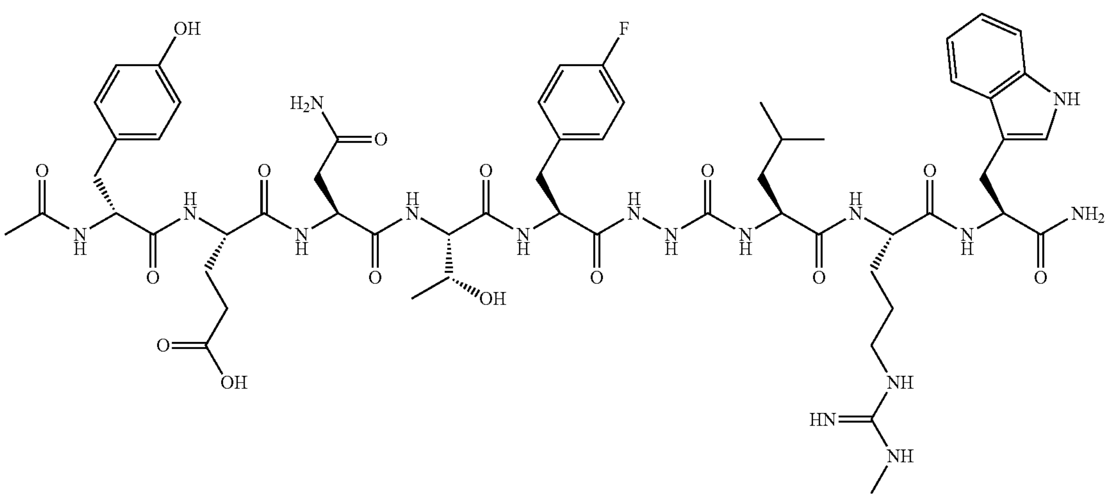 |

TABLE 1B-continued
| Compound No. | Structure |
|---|---|
| 789 | 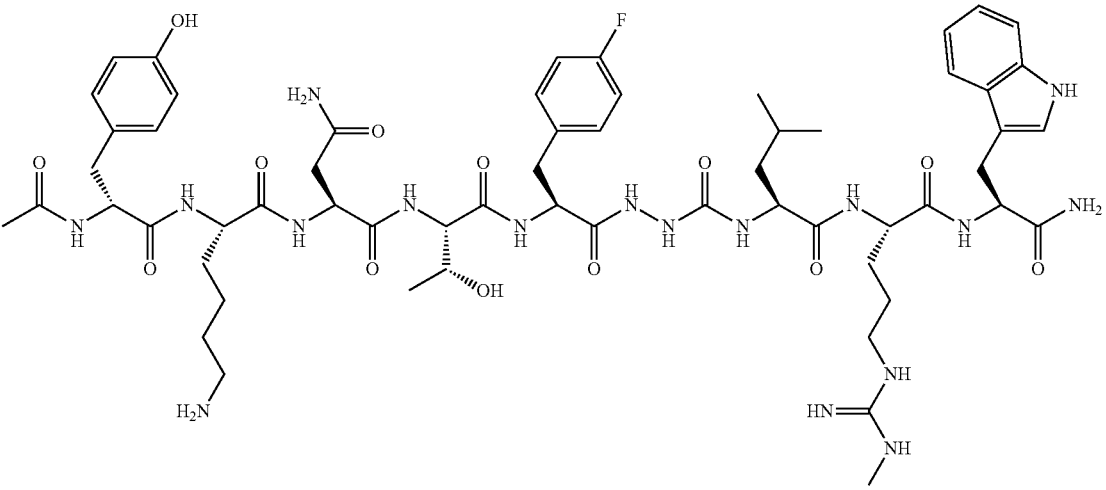 |
| 790 | 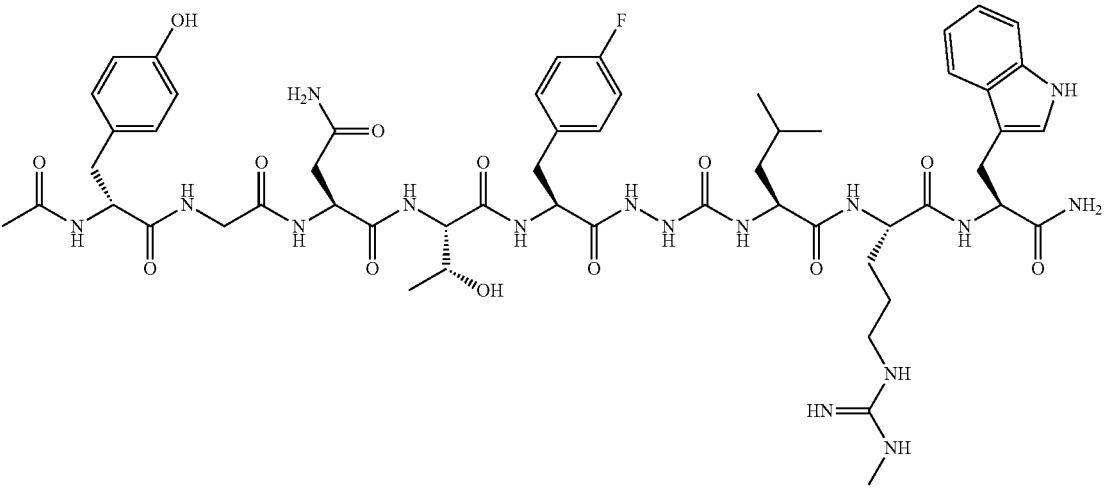 |
| 791 | 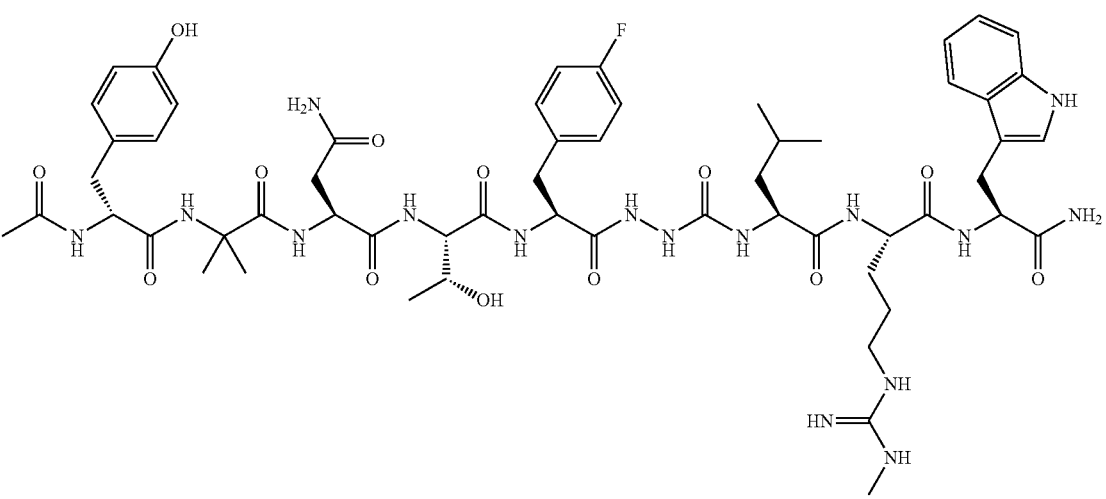 |

TABLE 1B-continued
| Compound No. | Structure |
|---|---|
| 794 | 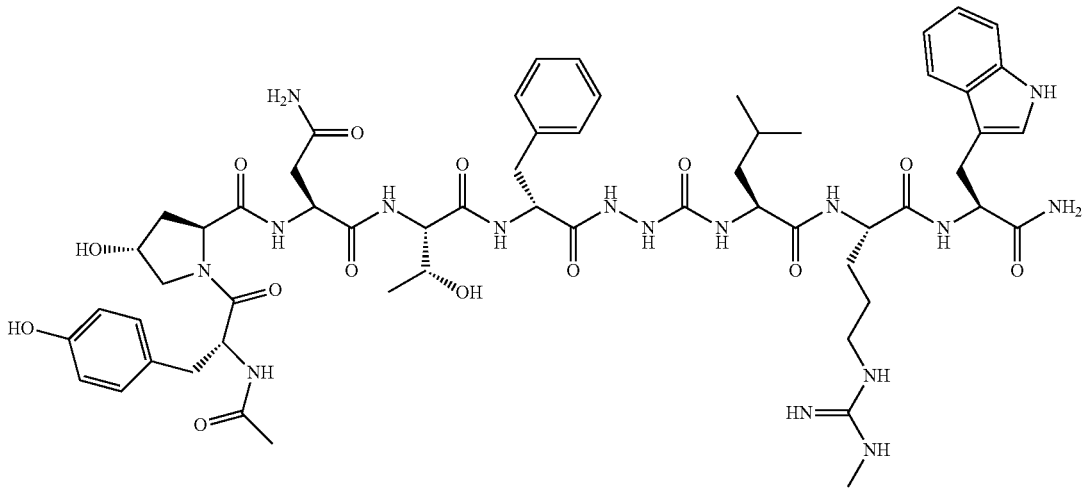 |
| 797 | 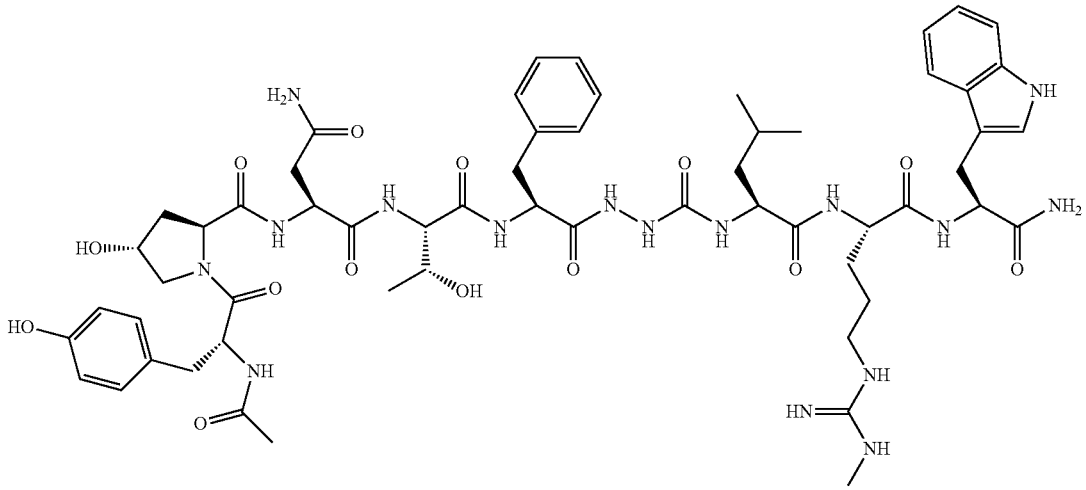 |
| 800 | 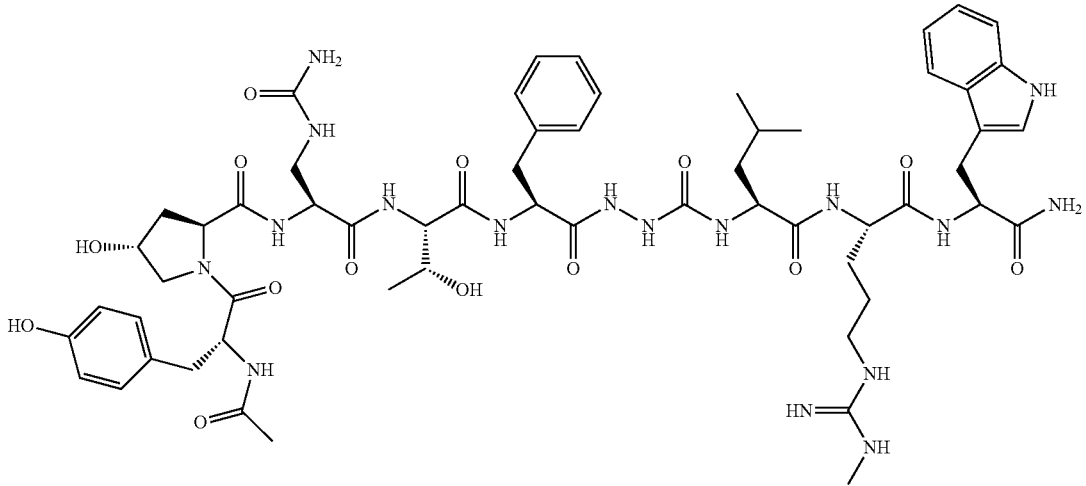 |

TABLE 1B-continued
| Compound No. | Structure |
|---|---|
| 801 | 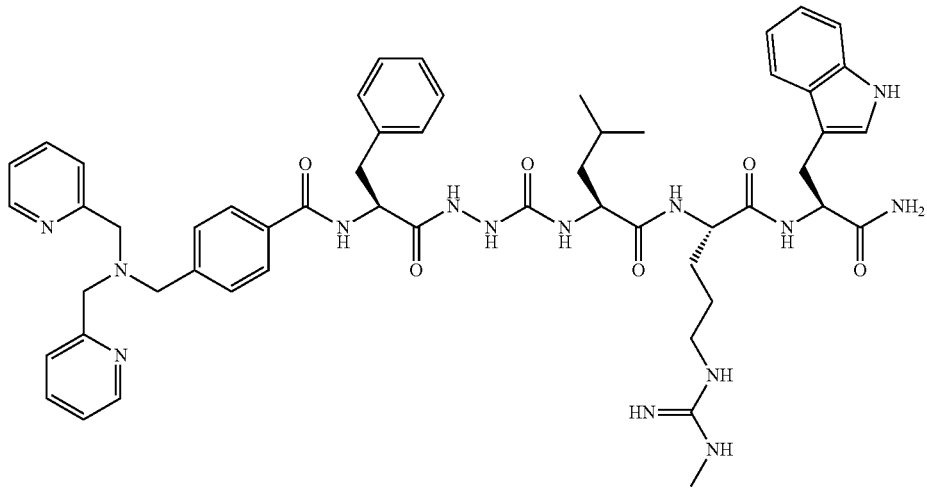 |
| 809 | 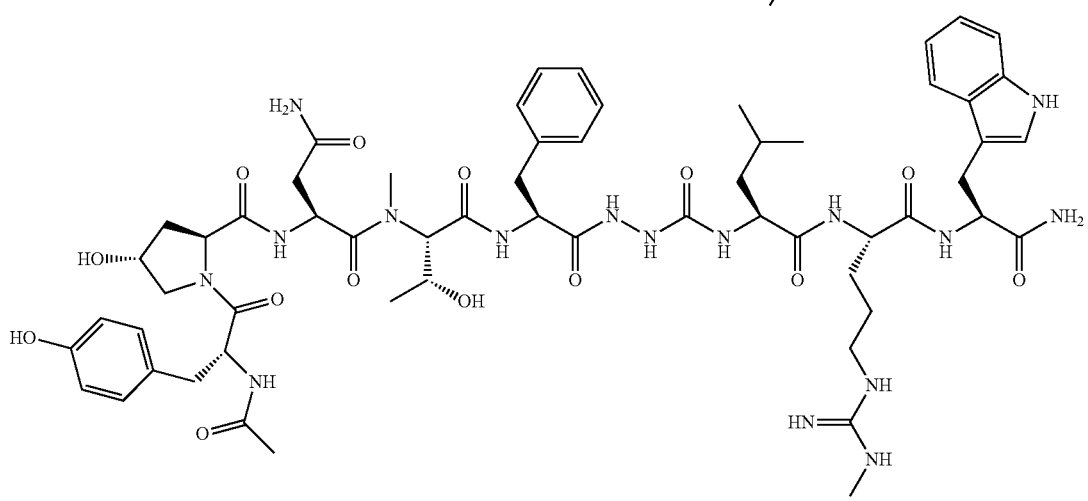 |
| 810 | 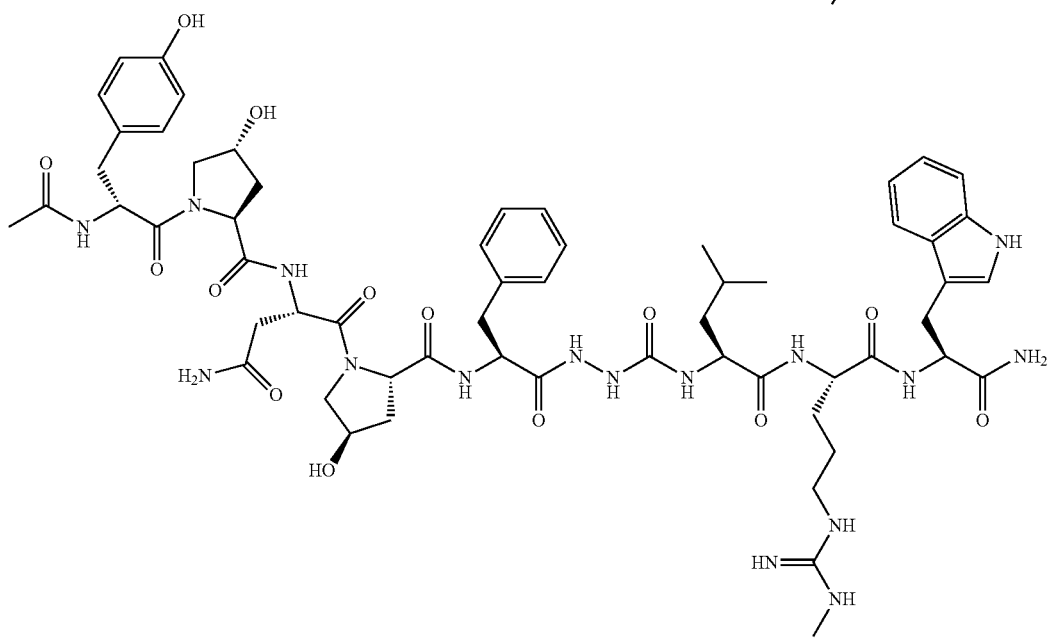 |

TABLE 1B-continued
| Compound No. | Structure |
| --- | --- |
| 813 | 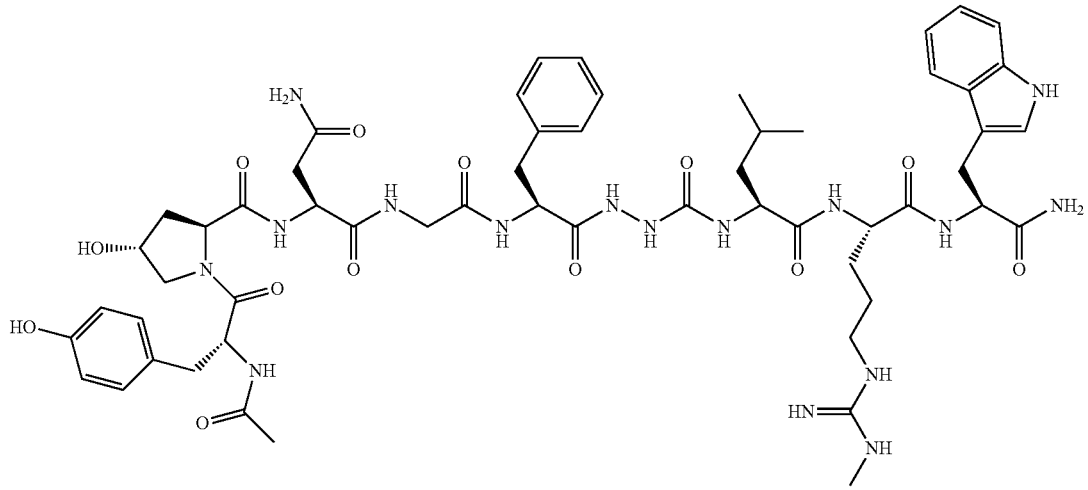 |
| 814 | 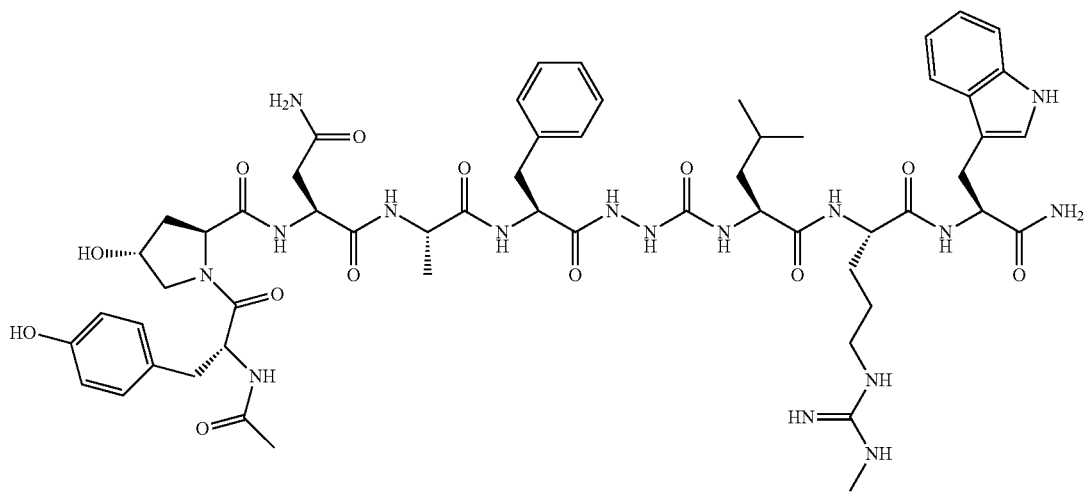 |
| 815 | 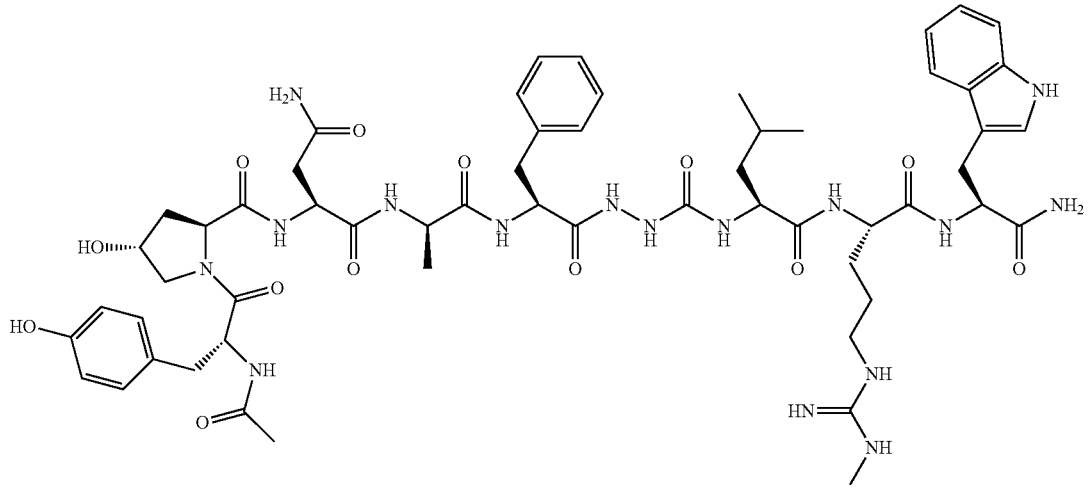 |

TABLE 1B-continued
| Compound No. | Structure |
|---|---|
| 816 | 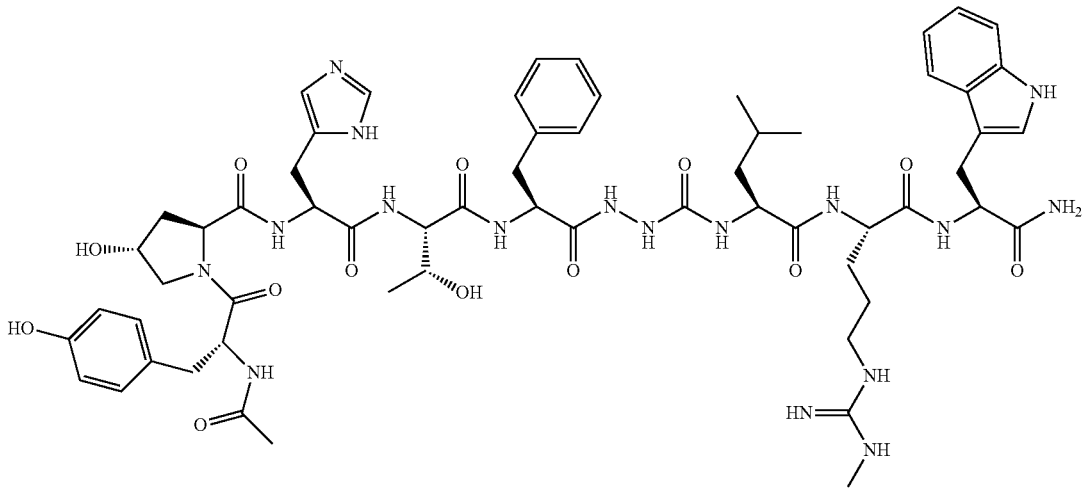 |
| 843 | 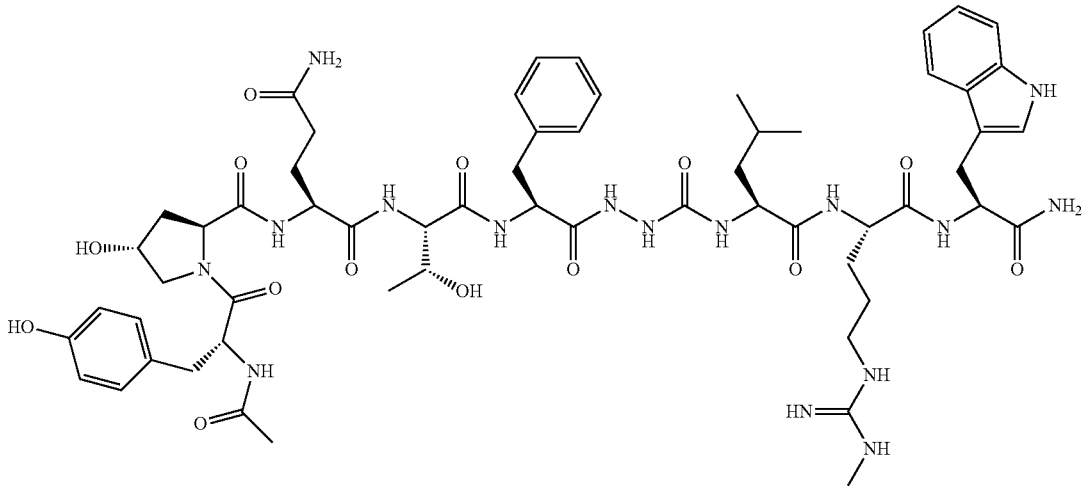 |
| 844 | 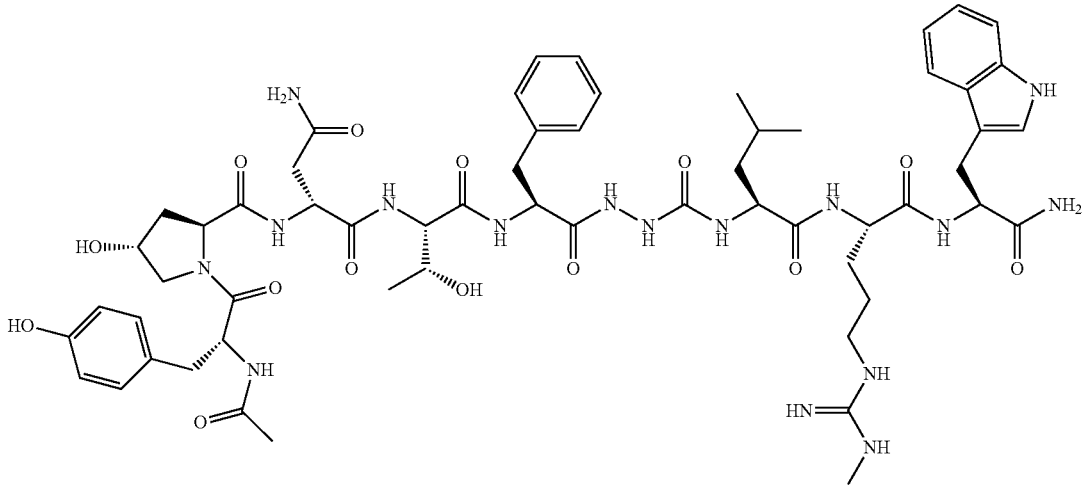 |

| Compound No. | Structure |
|---|---|
| 845 | 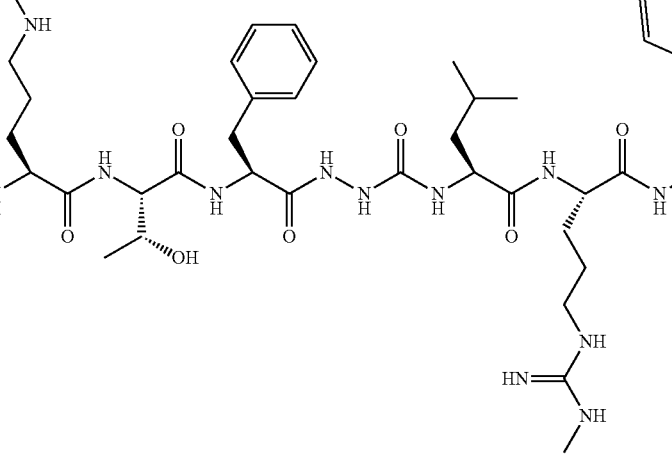 |
| 846 | 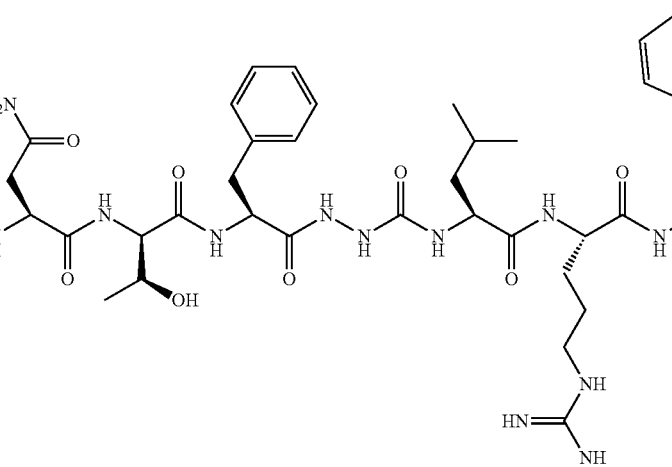 |
| 856 | 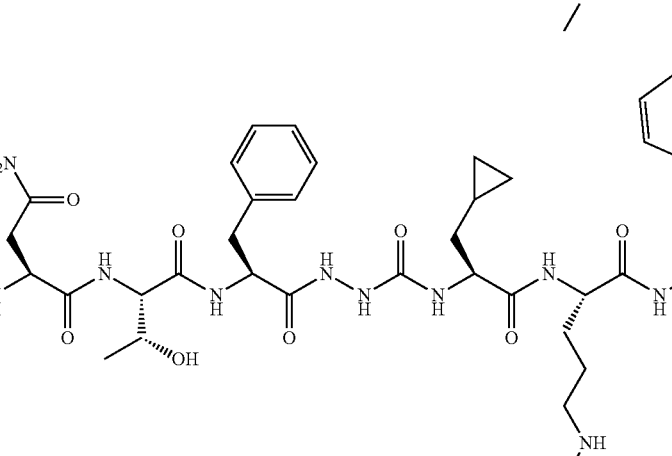 |

TABLE 1B-continued

| Compound No. | Structure |
|---|---|
| 860 | 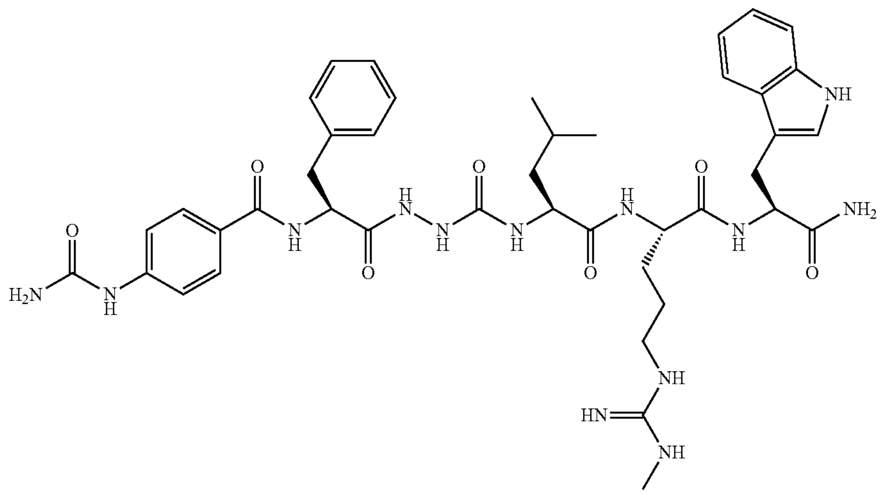 |
| 861 | 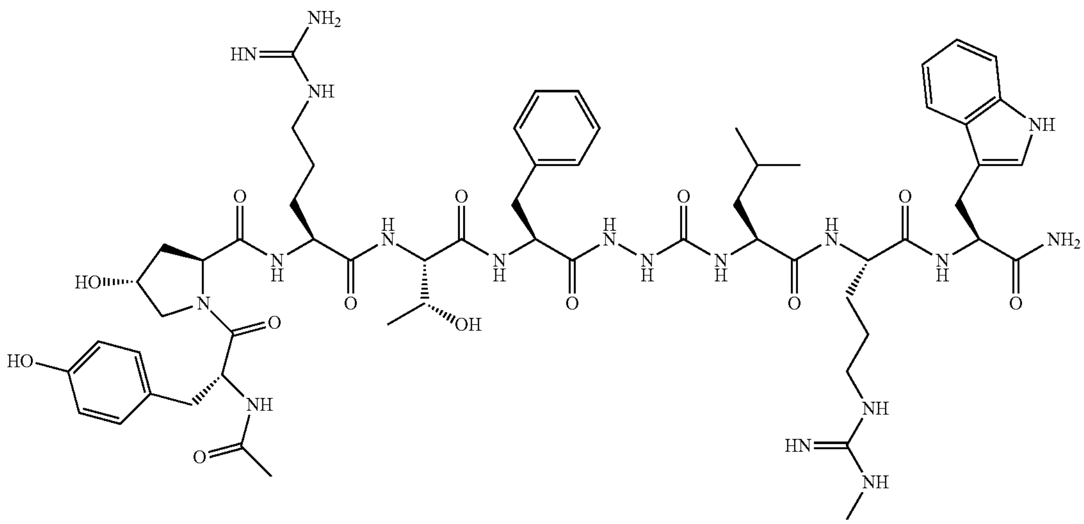 |
| 862 | 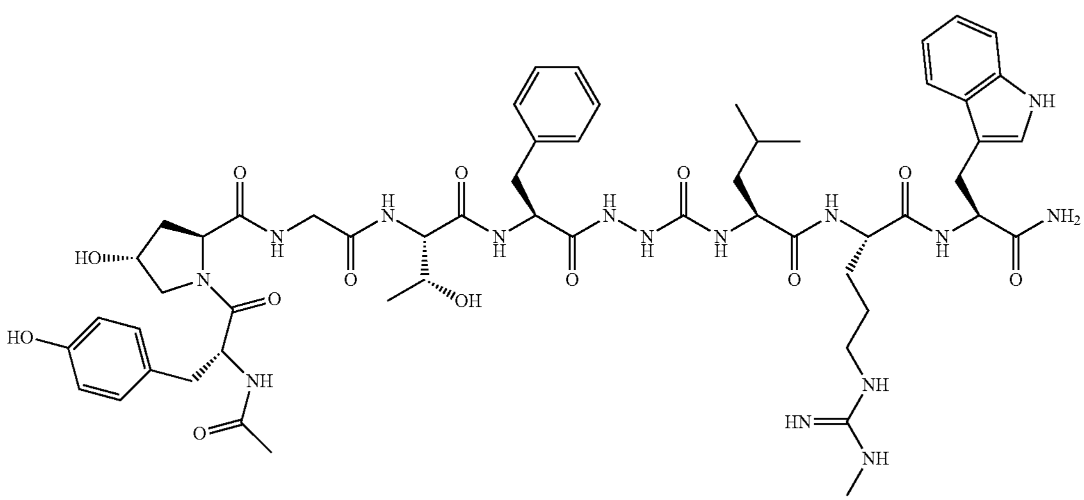 |

US 7,960,348 B2
149 150
TABLE 1B-continued
| Compound No. | Structure |
|---|---|
| 863 | 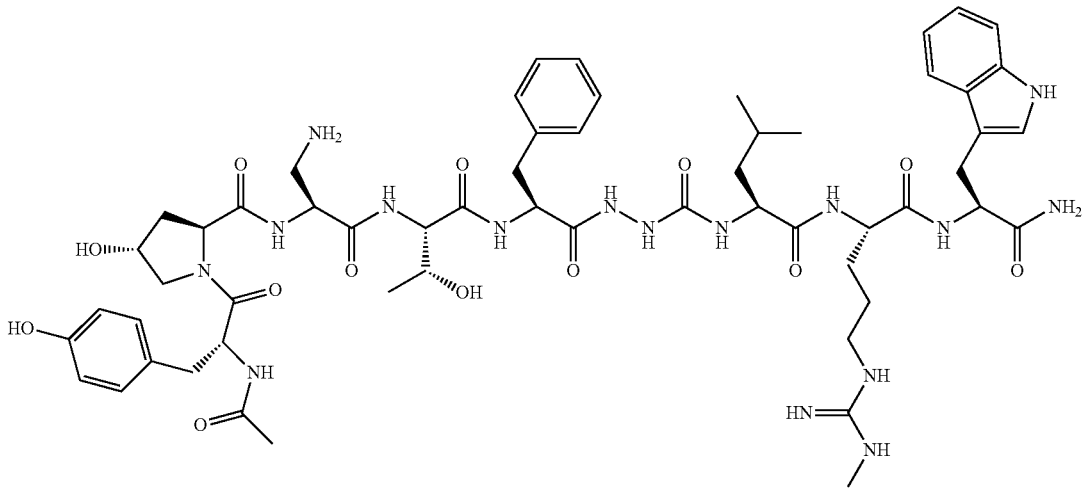 |
| 864 | 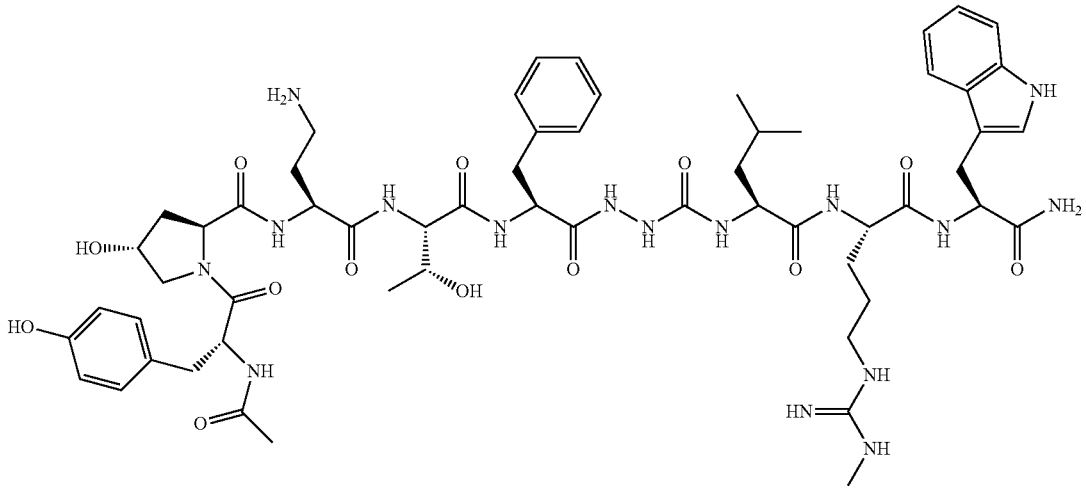 |
| 868 | 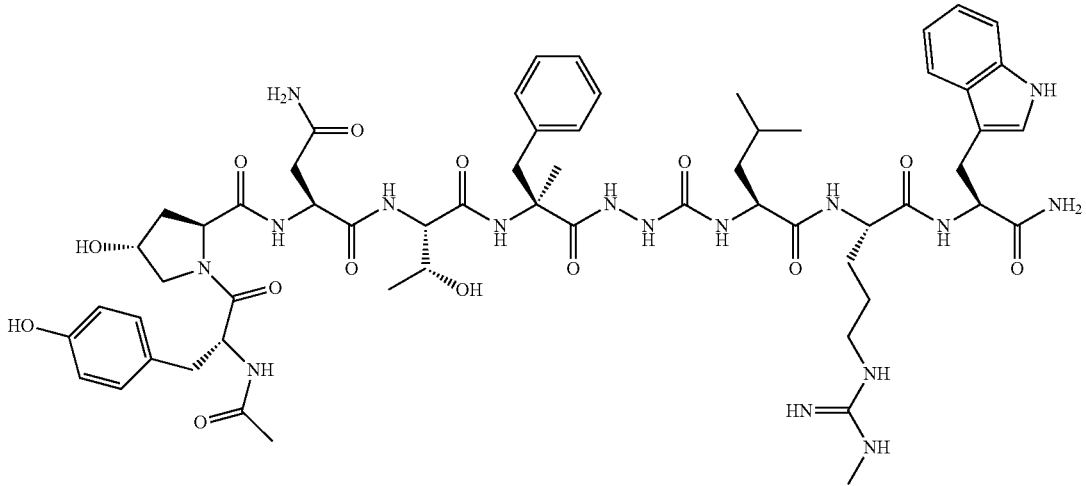 |

TABLE 1B-continued
| Compound No. | Structure |
|---|---|
| 870 | 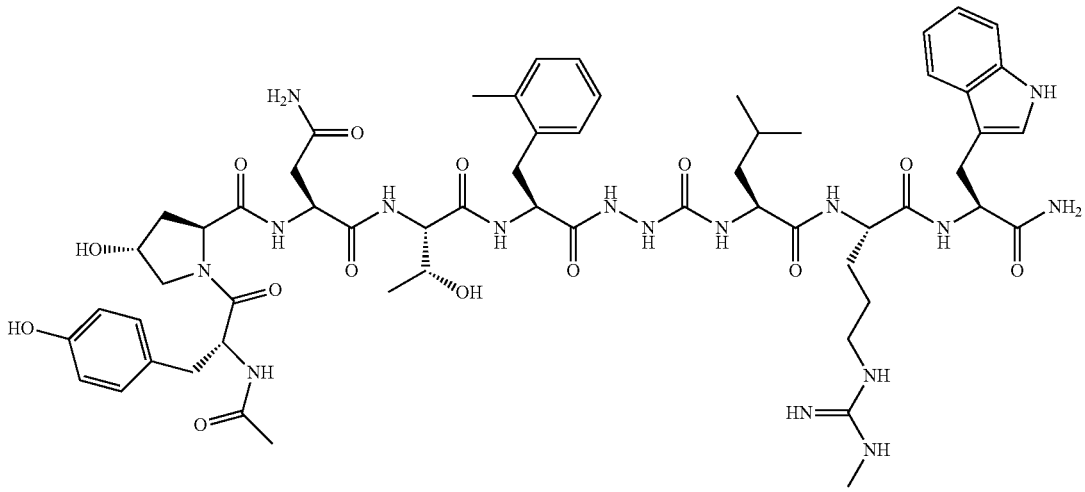 |
| 872 | 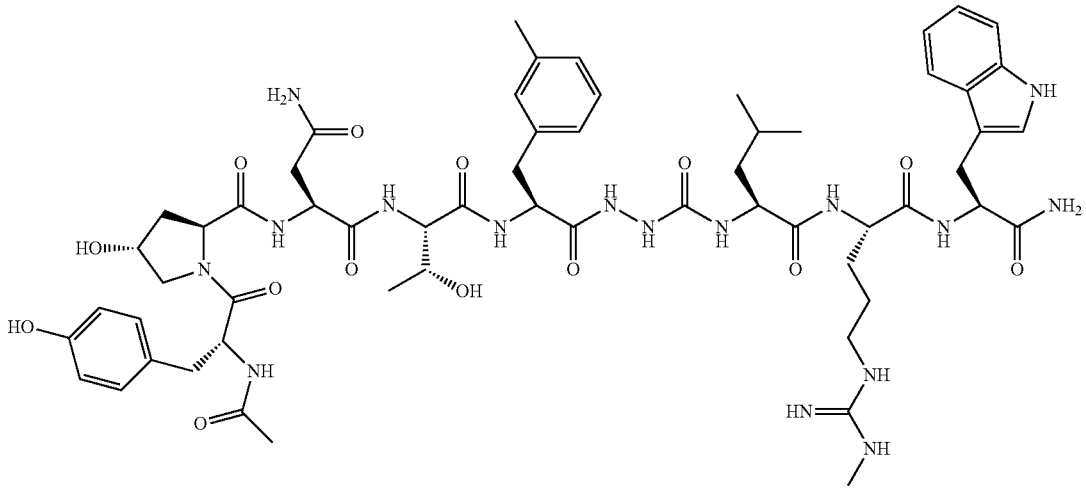 |
| 874 | 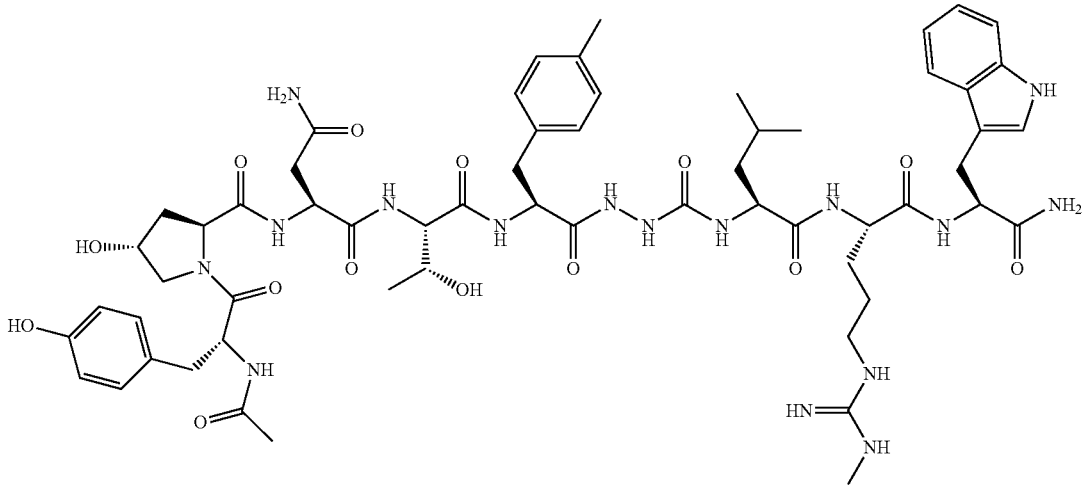 |

TABLE 1B-continued
| Compound No. | Structure |
|---|---|
| 877 | 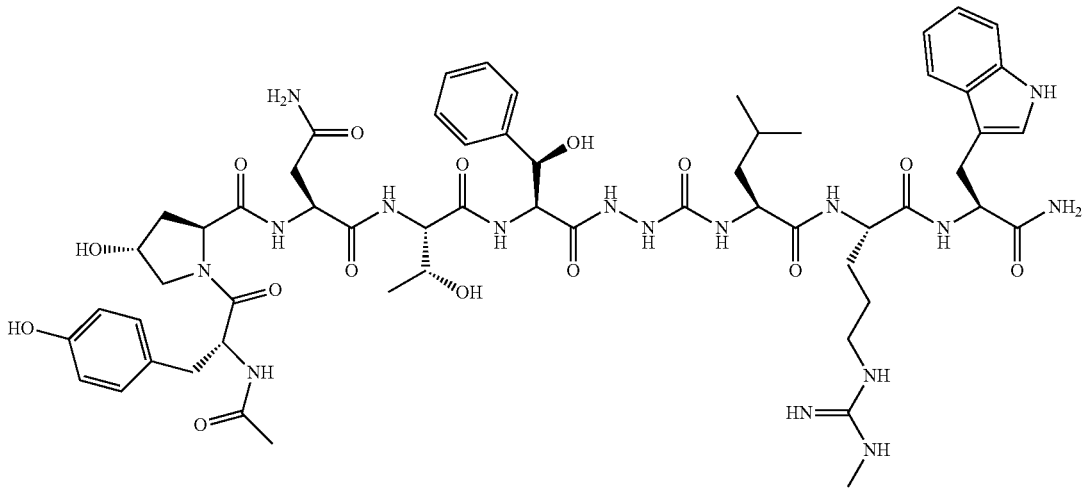 |
| 882 | 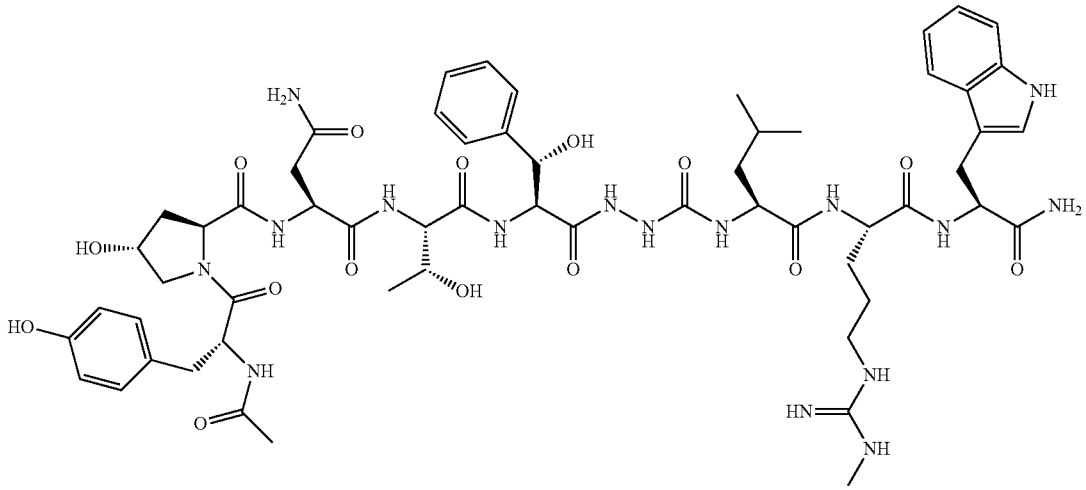 |
| 886 | 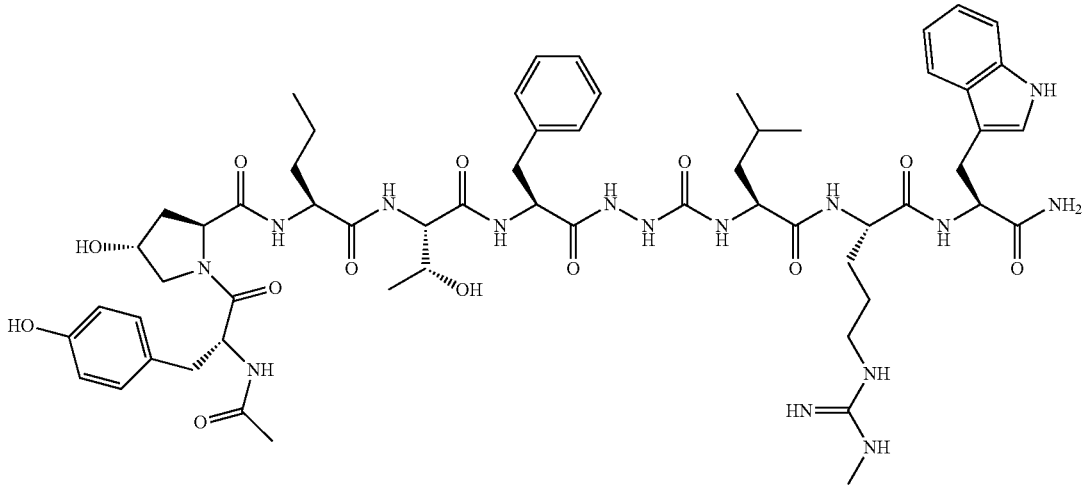 |

TABLE 1B-continued

| Compound No. | Structure |
|---|---|
| 887 | 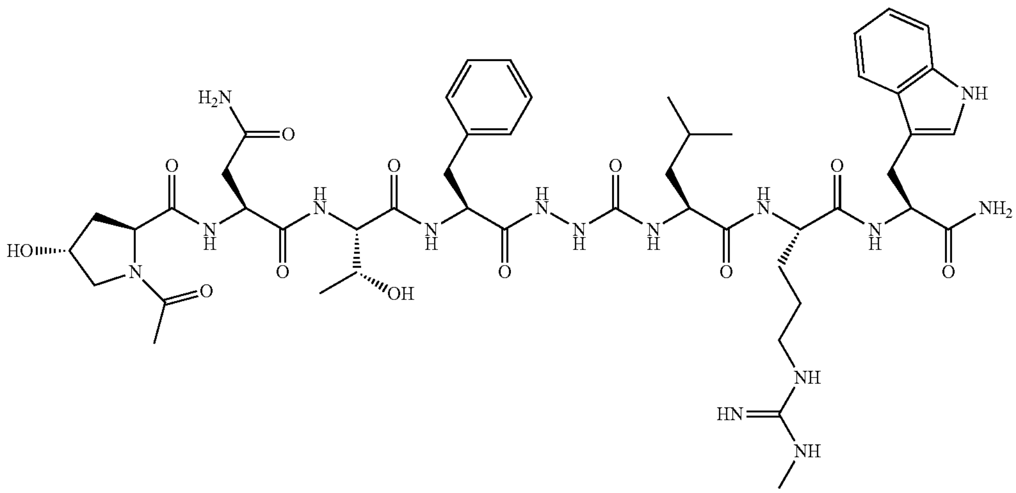 |
| 888 | 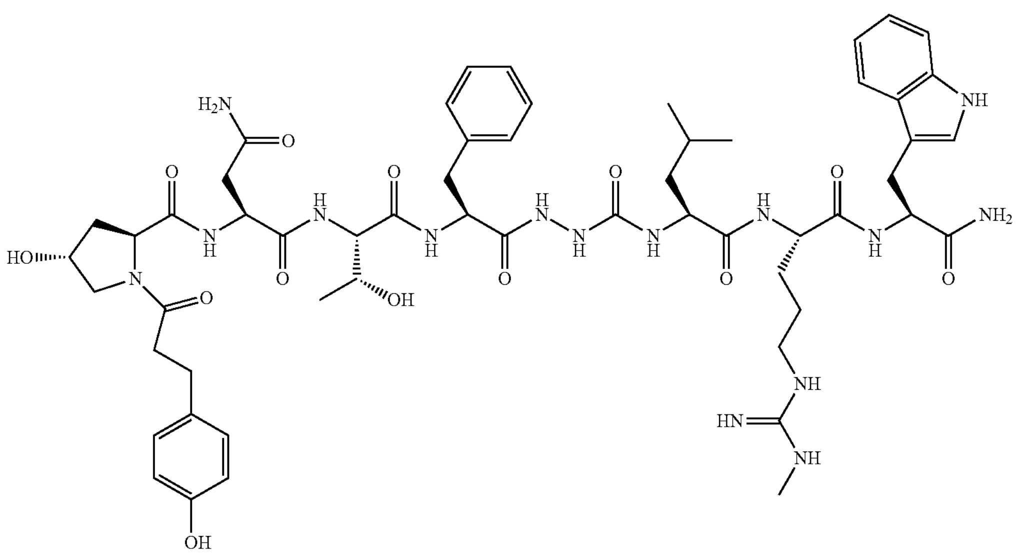 |
| 889 | 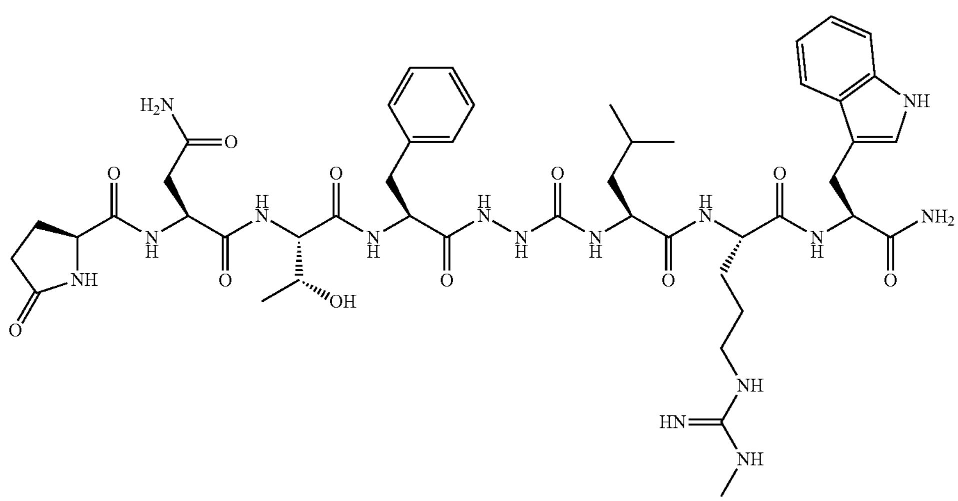 |

TABLE 1B-continued
| Compound No. | Structure |
|---|---|
| 896 | 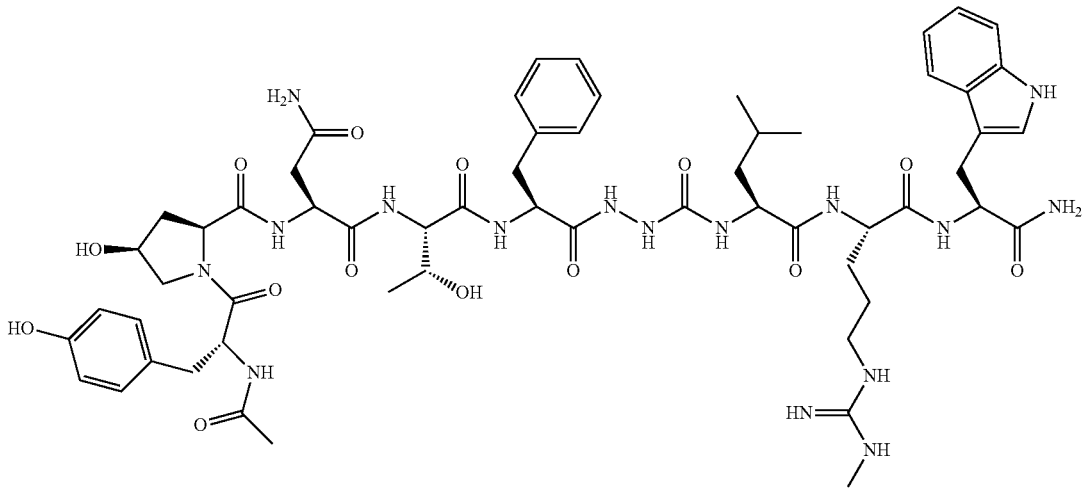 |
| 897 | 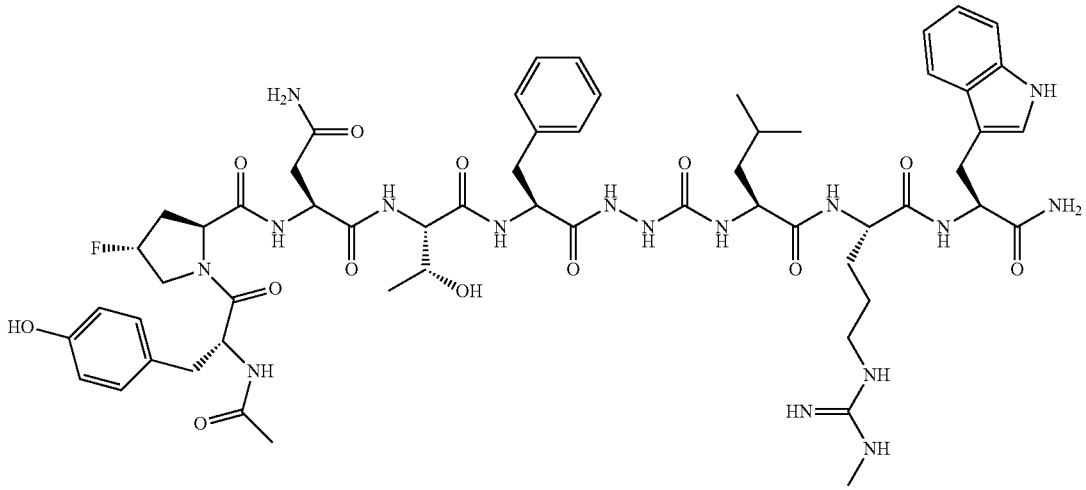 |
| 899 | 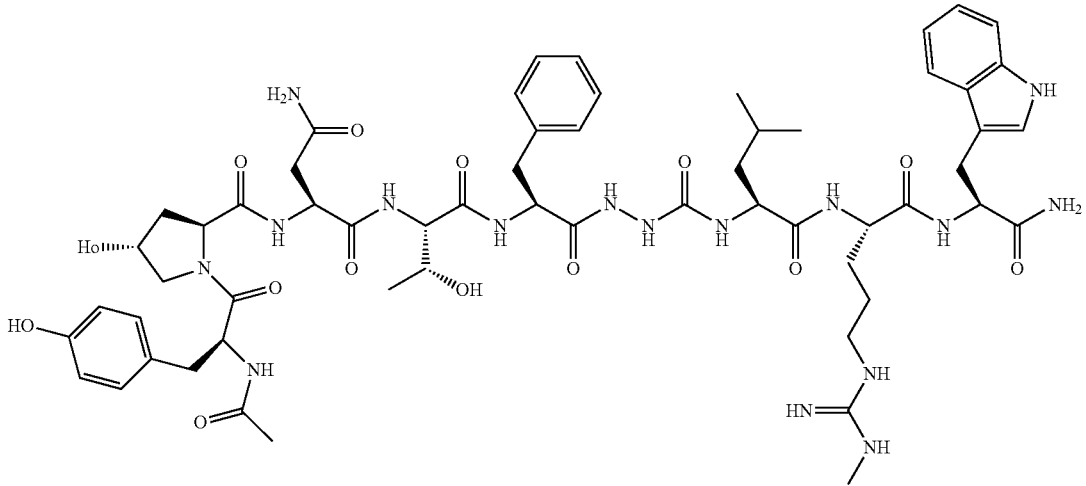 |

Test Example 1

Assay for Intracellular Ca Ion Level-Increasing Activity Using FLIPR

In accordance with the method described in JPA 2000-312590, the intracellular Ca ion level-increasing activity was measured using FLIPR.

The stable expression cell line hOT7T175 was obtained by transfection of the expression plasmid pAK-rOT175 for animal cells into CHO/dhfr$^-$ cells, using CellPhect Transfection Kit (Amersham Pharmacia Biotech, Inc.). First, 240 µL of Buffer A (attached to CellPhect Transfection Kit) was added to 9.6 µg of plasmid DNA dissolved in 240 µL of distilled water followed by stirring. After the mixture was settled for 10 minutes, 480 µL of Buffer B (attached to CellPhect Transfection Kit) was added to the mixture, which was vigorously stirred to form liposomes containing the DNA. Then, $4 \times 10^5$ CHO/dhfr$^-$ cells (obtained from ATCC) were inoculated on a 60 mm Petri dish. After culturing the cells in Ham's F-12 medium (Nissui Seiyaku Co., Ltd.) supplemented with 10% fetal bovine serum (BIO WHITTAKER, Inc.) at 37° C. for 2 days in 5% carbon dioxide gas, 480 mL of the liposomes were dropwise added to the cells on the Petri dish. After culturing the cells at 37° C. for 6 hours in 5% carbon dioxide gas, the cells were washed twice with serum-free Ham's F-12 medium and 3 mL of 15% glycerol was added to the cells on the Petri dish followed by treatment for 2 minutes. The cells were again washed twice with serum-free Ham's F-12 medium followed by incubation in Ham's F-12 medium supplemented with 10% fetal bovine serum at 37° C. for 15 hours in 5% carbon dioxide gas. The cells were dispersed by trypsin treatment to recover from the Petri dish. The recovered cells were inoculated on a 6-well plate in $1.25 \times 10^4$ cells/well and incubation was initiated at 37° C. in Dulbecco's modified Eagle medium (DMEM) medium (Nissui Seiyaku Co., Ltd.) containing 10% dialyzed fetal bovine serum (JRH BIOSCIENCES, Inc.) in 5% carbon dioxide gas. The plasmid-transfected CHO transformants grew in the medium but the non-transfected cells gradually died, accordingly the medium was exchanged on Days 1 and 2 after the initiation of incubation to remove the cells died. Approximately 20 colonies of the CHO transformants that kept growing on Days 8 to 10 after the incubation were isolated. From the cells in these colonies, cells showing high reactivity with the ligand peptide metastin (hereinafter merely referred to as hOT7T175/CHO) were selected to provide for the following experiment.

The intracellular Ca ion level-increasing activity of the synthetic peptide in hOT7T175/CHO was determined using FLIPR (Molecular Devices, Inc.).

hOT7T175/CHO was subcultured in DMEM supplemented with 10% dialyzed fetal bovine serum (hereinafter abbreviated as dFBS) (hereinafter referred to as 10% dFBS/DMEM) and provided for the experiment. The hOT7T175/CHO was suspended in 10% dFBS-DMEM in $15 \times 10^4$ cells/ml. The suspension was inoculated on a 96-well plate for FLIPR (Black Plate Clear Bottom, Coster, Inc.) at 200 µl/well ($3.0 \times 10^4$ cells/200 µL/well), followed by incubation at 37° C. overnight in a 5% $CO_2$ incubator (hereinafter referred to as the cell plate). Then, 21 ml of HANKS/HBSS (9.8 g of HANKS, 0.35 g of sodium hydrogencarbonate, 20 ml of 1M HEPES; after adjusting the pH to 7.4 with 1N sodium hydroxide, the mixture was sterilized by filtration), 210 µl of 250 mM Probenecid and 210 µL of fetal bovine serum (FBS) (HANKS/HBSS-Probenecid-FBS) were mixed.

Furthermore, 2 vials of Fluo3-AM (50 µg/vial) were dissolved in 21 µL of dimethylsulfoxide and 21 µL of 20% Pluronic acid. The resulting solution was added to and mixed with 10 ml of the HANKS/HBSS-Probenecid-FBS described above. After the culture medium was removed, the mixture was dispensed onto the cell plate in 100 µl each/well, followed by incubation at 37° C. for an hour in a 5% $CO_2$ incubator (pigment loading). The peptide was dissolved in dimethylsulfoxide in $1 \times 10^{-3}$ M. The peptide solution was diluted with HANKS/HBSS containing 2.5 mM Probenecid, 0.2% BSA and 0.1% CHAPS. The dilution was then transferred to a 96-well plate for FLIPR (V-Bottom plate, Coster, Inc.) (hereinafter referred to as the sample plate). After completion of the pigment loading onto the cell plate, the cell plate was washed 4 times with wash buffer, which was prepared by adding 2.5 mM Probenecid to HANKS/HBSS, using a plate washer to leave 100 µL of the wash buffer after the washing. The cell plate and the sample plate were set in FLIPR and 0.05 ml of a sample from the sample plate was automatically transferred to the cell plate with the FLIPR device to promote the cell response. A change in the intracellular calcium ion level for 180 seconds was measured with passage of time. The intracellular Ca ion level-increasing activity [specific activity to Metastin (1-54)] is shown in TABLE 2.

TABLE 2

| Compound No. | Specific Activity |
|---|---|
| 708 | 12.8 |
| 709 | 9.8 |
| 710 | 7.2 |
| 712 | 8.9 |
| 713 | 3.7 |
| 714 | 0.7 |
| 715 | 1.6 |
| 716 | 3.6 |
| 717 | 1.0 |
| 718 | 2.6 |
| 719 | 3.8 |
| 720 | 0.8 |
| 721 | 1.1 |
| 722 | 2.2 |
| 723 | 2.0 |
| 724 | 1.4 |
| 725 | 2.7 |
| 726 | 3.1 |
| 727 | 1.5 |
| 728 | 3.2 |
| 730 | 4.1 |
| 731 | 8.8 |
| 732 | 3.2 |
| 734 | 2.3 |
| 735 | 3.4 |
| 736 | 2.4 |
| 737 | 3.0 |
| 738 | 1.4 |
| 739 | 1.6 |
| 740 | 1.1 |
| 742 | 2.3 |
| 743 | 3.4 |
| 744 | 2.4 |
| 745 | 3.0 |
| 746 | 2.2 |
| 747 | 2.6 |
| 748 | 0.4 |
| 749 | 0.5 |
| 750 | 1.0 |
| 754 | 3.1 |
| 755 | 3.5 |
| 756 | 2.4 |
| 757 | 2.7 |
| 758 | 1.8 |
| 759 | 1.9 |
| 760 | 1.7 |
| 763 | 6.4 |

TABLE 2-continued

| Compound No. | Specific Activity |
|---|---|
| 764 | 1.5 |
| 765 | 2.6 |
| 766 | 0.2 |
| 767 | 1.5 |
| 768 | 0.6 |
| 769 | 1.5 |
| 770 | 2.6 |
| 771 | 1.9 |
| 772 | 1.3 |
| 773 | 1.1 |
| 774 | 2.0 |
| 775 | 1.3 |
| 776 | 1.5 |
| 777 | 1.8 |
| 780 | 2.1 |
| 781 | 1.0 |
| 782 | 1.8 |
| 783 | 8.8 |
| 784 | 3.4 |
| 785 | 3.2 |
| 786 | 3.3 |
| 787 | 2.3 |
| 788 | 2.7 |
| 789 | 3.4 |
| 790 | 2.3 |
| 791 | 2.9 |
| 794 | 2.3 |
| 797 | 1.4 |
| 800 | 0.8 |
| 801 | 11.1 |
| 809 | 1.0 |
| 810 | 1.5 |
| 813 | 0.5 |
| 814 | 0.5 |
| 815 | 0.5 |
| 816 | 1.1 |
| 843 | 0.8 |
| 844 | 0.9 |
| 845 | 1.0 |
| 846 | 0.9 |
| 856 | 0.6 |
| 860 | 1.3 |
| 861 | 1.4 |
| 862 | 0.7 |
| 863 | 0.9 |
| 864 | 1.0 |
| 868 | 1.4 |
| 870 | 0.6 |
| 872 | 0.7 |
| 874 | 0.8 |
| 877 | 1.0 |
| 882 | 0.8 |
| 886 | 1.2 |
| 888 | 1.1 |
| 896 | 0.6 |
| 897 | 0.7 |
| 899 | 1.1 |

Test Example 2

Evaluation of Blood Testosterone Level Reducing Effect of Metastin Peptide Derivatives Using Mature Male Rats A metastin peptide derivative (hereinafter referred to as peptide) was dissolved in 50% DMSO aqueous solution (Otsuka Pharmaceutical Co., Ltd.) to prepare a peptide solution with a concentration of 0.03, 0.01 or 0.003 mM. This peptide solution was filled in five ALZET osmotic pumps (Model 2001, 0.2 ml in volume, release rate: 0.001 ml/hr, DURECT Corporation). The ALZET pumps filled with the peptide solution were implanted subcutaneously in 5. CD(SD)IGS male rats of 9 weeks old after birth (Charles River Japan, Inc.) on the back under ether anesthesia by one pump/animal. For negative control, 50% DMSO aqueous solution was filled in 5 ALZET osmotic pumps, which were similarly implanted in 5 male CD(SD)IGS rats (Charles River Japan, Inc.), respectively. These pump-implanted rats were fed for 6 days under normal feeding conditions. After weighing, the animal was decapitated to collect blood. After 0.03 ml/ml blood of aprotinin solution (Trasylol, Bayer) containing 0.1 g/ml EDTA.2Na was added to blood, the plasma was separated and recovered by centrifugation at 1,800×g for 25 min. From the plasma obtained, 0.05 ml was applied to radioimmunoassay (DPC.Total Testosterone Kit, Diagnostic Products Corporation) to measure the plasma testosterone level in each rat. The peptides are listed in TABLE 3, when the number of rats showing the testosterone level below the measurement limit (0.04 ng/ml of plasma level) in radioimmunoassay was 3 or more in the 5 rats receiving the peptides.

TABLE 3

| Compound No. |
|---|
| 720 |
| 721 |
| 723 |
| 726 |
| 727 |
| 732 |
| 734 |
| 738 |
| 739 |
| 742 |
| 744 |
| 745 |
| 746 |
| 750 |
| 755 |
| 756 |
| 757 |
| 758 |
| 759 |
| 763 |
| 765 |
| 767 |
| 773 |
| 775 |
| 776 |
| 787 |
| 788 |
| 797 |
| 814 |
| 856 |
| 870 |
| 872 |
| 874 |
| 877 |
| 882 |
| 888 |
| 896 |
| 897 |

INDUSTRIAL APPLICABILITY

According to the present invention, there are provided stable metastin derivatives having excellent biological activities (a cancer metastasis suppressing activity, a cancer growth suppressing activity, a gonadotropic hormone secretion stimulating activity, sex hormone secretion stimulating activity, etc.).

All patent applications, issued patents, publications, GenBank and other sequence reference numbers cited herein are incorporated by reference in their entirety.

The invention claimed is:

1. Ac-D-Tyr-Hyp-Asn-Thr-Phe-AzaGly-Leu-Arg(Me)-Trp-NH$_2$ or a salt thereof.

2. A medicament comprising the compound according to claim 1 or a salt thereof.

* * * * *

SEQUENCE LISTING

<160> NUMBER OF SEQ ID NOS: 41

<210> SEQ ID NO 1
<211> LENGTH: 54
<212> TYPE: PRT
<213> ORGANISM: Homo sapiens

<400> SEQUENCE: 1

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 2
<211> LENGTH: 162
<212> TYPE: DNA
<213> ORGANISM: Homo sapiens

<400> SEQUENCE: 2
ggtacttctc tgtctccgcc gccggaatct tctggttctc gtcagcagcc gggtctgtct      60
gctccgcact ctcgtcagat cccggctccg cagggtgctg ttctggttca gcgtgaaaaa     120
gacctgccga actacaactg gaactctttc ggtctgcgtt tc                         162

<210> SEQ ID NO 3
<211> LENGTH: 152
<212> TYPE: PRT
<213> ORGANISM: Mus musculus

<400> SEQUENCE: 3

Met Tyr Leu Arg Phe Gly Val Asp Val Cys Ser Leu Ser Pro Trp Lys
1               5                   10                  15

Glu Thr Val Asp Leu Pro Leu Pro Pro Arg Met Ile Ser Met Ala Ser
            20                  25                  30

Trp Gln Leu Leu Leu Leu Leu Cys Val Ala Thr Tyr Gly Glu Pro Leu
        35                  40                  45

Ala Lys Val Ala Pro Gly Ser Thr Gly Gln Gln Ser Gly Pro Gln Glu
    50                  55                  60

Leu Val Asn Ala Trp Glu Lys Glu Ser Arg Tyr Ala Glu Ser Lys Pro
65                  70                  75                  80

Gly Ser Ala Gly Leu Arg Ala Arg Arg Ser Ser Pro Cys Pro Pro Val
                85                  90                  95

Glu Gly Pro Ala Gly Arg Gln Arg Pro Leu Cys Ala Ser Arg Ser Arg
            100                 105                 110

Leu Ile Pro Ala Pro Arg Gly Ala Val Leu Val Gln Arg Glu Lys Asp
        115                 120                 125

Leu Ser Thr Tyr Asn Trp Asn Ser Phe Gly Leu Arg Tyr Gly Arg Arg
    130                 135                 140

Gln Ala Ala Arg Ala Ala Arg Gly
145                 150

<210> SEQ ID NO 4
<211> LENGTH: 456
<212> TYPE: DNA

<213> ORGANISM: Mus musculus

<400> SEQUENCE: 4

| | |
|---|---|
| atgtatctga gatttggcgt tgatgtctgc agcctgagtc cctggaagga gactgtagac | 60 |
| ctgccccttc ctcccagaat gatctcaatg gcttcttggc agctgctgct tctcctctgt | 120 |
| gtcgccacct atggggagcc gctggcaaaa gtgaagcctg atccacagg ccagcagtcc | 180 |
| ggaccccagg aactcgttaa tgcctgggaa aaggaatcgc ggtatgcaga gagcaagcct | 240 |
| gggtctgcag gctgcgcgc tcgtaggtcg tcgccatgcc cgccggttga gggccccgcg | 300 |
| gggcgccagc ggcccctgtg tgcctcccgc agtcgcctga tccctgcgcc ccgcggagcg | 360 |
| gtgctggtgc agcgggagaa ggacctgtcc acctacaact ggaactcctt cggcctgcgc | 420 |
| tacggcagga ggcaggcggc gcgggcagca cggggc | 456 |

<210> SEQ ID NO 5
<211> LENGTH: 156
<212> TYPE: PRT
<213> ORGANISM: Mus musculus

<400> SEQUENCE: 5

Met Tyr Leu Arg Phe Gly Val Asp Val Cys Ser Leu Ser Pro Trp Lys
1               5                   10                  15

Glu Thr Val Asp Leu Pro Leu Pro Pro Arg Met Ile Ser Met Ala Ser
            20                  25                  30

Trp Gln Leu Leu Leu Leu Leu Cys Val Ala Thr Tyr Gly Glu Pro Leu
        35                  40                  45

Ala Lys Val Ala Pro Leu Val Lys Pro Gly Ser Thr Gly Gln Gln Ser
    50                  55                  60

Gly Pro Gln Glu Leu Val Asn Ala Trp Glu Lys Glu Ser Arg Tyr Ala
65                  70                  75                  80

Glu Ser Lys Pro Gly Ser Ala Gly Leu Arg Ala Arg Arg Ser Ser Pro
                85                  90                  95

Cys Pro Pro Val Glu Gly Pro Ala Gly Arg Gln Arg Pro Leu Cys Ala
            100                 105                 110

Ser Arg Ser Arg Leu Ile Pro Ala Pro Arg Gly Ala Val Leu Val Gln
        115                 120                 125

Arg Glu Lys Asp Leu Ser Thr Tyr Asn Trp Asn Ser Phe Gly Leu Arg
    130                 135                 140

Tyr Gly Arg Arg Gln Ala Ala Arg Ala Ala Arg Gly
145                 150                 155

<210> SEQ ID NO 6
<211> LENGTH: 468
<212> TYPE: DNA
<213> ORGANISM: Mus musculus

<400> SEQUENCE: 6

| | |
|---|---|
| atgtatctga gatttggcgt tgatgtctgc agcctgagtc cctggaagga gactgtagac | 60 |
| ctgccccttc ctcccagaat gatctcaatg gcttcttggc agctgctgct tctcctctgt | 120 |
| gtcgccacct atggggagcc gctggcaaaa gtggcacctt ggtgaagcc tggatccaca | 180 |
| ggccagcagt ccggacccca ggaactcgtt aatgcctggg aaaaggaatc gcggtatgca | 240 |
| gagagcaagc ctgggtctgc agggctgcgc gctcgtaggt cgtcgccatg cccgccggtt | 300 |
| gagggccccg cggggcgcca gcggcccctg tgtgcctccc gcagtcgcct gatccctgcg | 360 |
| ccccgcggag cggtgctggt gcagcgggag aaggacctgt ccacctacaa ctggaactcc | 420 | ttcggcctgc gctacggcag gaggcaggcg gcgcgggcag cacggggc            468

<210> SEQ ID NO 7
<211> LENGTH: 130
<212> TYPE: PRT
<213> ORGANISM: Rattus sp.

<400> SEQUENCE: 7

Met Thr Ser Leu Ala Ser Trp Gln Leu Leu Leu Leu Cys Val Ala
1               5                   10                  15

Ser Phe Gly Glu Pro Leu Ala Lys Met Ala Pro Val Val Asn Pro Glu
            20                  25                  30

Pro Thr Gly Gln Gln Ser Gly Pro Gln Glu Leu Val Asn Ala Trp Gln
        35                  40                  45

Lys Gly Pro Arg Tyr Ala Glu Ser Lys Pro Gly Ala Ala Gly Leu Arg
    50                  55                  60

Ala Arg Arg Thr Ser Pro Cys Pro Val Glu Asn Pro Thr Gly His
65                  70                  75                  80

Gln Arg Pro Pro Cys Ala Thr Arg Ser Arg Leu Ile Pro Ala Pro Arg
                85                  90                  95

Gly Ser Val Leu Val Gln Arg Glu Lys Asp Met Ser Ala Tyr Asn Trp
            100                 105                 110

Asn Ser Phe Gly Leu Arg Tyr Gly Arg Arg Gln Val Ala Arg Ala Ala
        115                 120                 125

Arg Gly
    130

<210> SEQ ID NO 8
<211> LENGTH: 390
<212> TYPE: DNA
<213> ORGANISM: Rattus sp.

<400> SEQUENCE: 8
atgacctcgc tggcttcttg gcagctgctg cttctcctct gtgtggcctc ttttggggag      60
ccactggcaa aaatggcacc tgtggtgaac cctgaaccca caggccaaca gtccggaccc     120
caggaactcg ttaatgcctg gcaaaagggc ccgcggtatg cagagagcaa gcctggggct     180
gcaggactgc gcgctcgccg aacatcgcca tgcccgccgg tggagaaccc cacggggcac     240
cagcggcccc cgtgtgccac ccgcagtcgc ctgatccctg cgccccgcgg atcggtgctg     300
gtgcagcgcg agaaggacat gtcagcctac aactggaact cctttggcct cgctacggc     360
aggaggcagg tggcgcgggc ggcacggggc                                      390

<210> SEQ ID NO 9
<211> LENGTH: 398
<212> TYPE: PRT
<213> ORGANISM: Homo sapiens

<400> SEQUENCE: 9

Met His Thr Val Ala Thr Ser Gly Pro Asn Ala Ser Trp Gly Ala Pro
1               5                   10                  15

Ala Asn Ala Ser Gly Cys Pro Gly Cys Gly Ala Asn Ala Ser Asp Gly
            20                  25                  30

Pro Val Pro Ser Pro Arg Ala Val Asp Ala Trp Leu Val Pro Leu Phe
        35                  40                  45

Phe Ala Ala Leu Met Leu Leu Gly Leu Val Gly Asn Ser Leu Val Ile
    50                  55                  60

Tyr Val Ile Cys Arg His Lys Pro Met Arg Thr Val Thr Asn Phe Tyr

```
                65                  70                  75                  80
Ile Ala Asn Leu Ala Ala Thr Asp Val Thr Phe Leu Leu Cys Cys Val
                    85                  90                  95

Pro Phe Thr Ala Leu Leu Tyr Pro Leu Pro Gly Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Val Ser Ala Pro
                165                 170                 175

Val Leu Ala Leu His Arg Leu Ser Pro Gly Pro Arg Ala Tyr Cys Ser
                180                 185                 190

Glu Ala Phe Pro Ser Arg Ala Leu Glu Arg Ala Phe Ala Leu Tyr Asn
            195                 200                 205

Leu Leu Ala Leu Tyr Leu Leu Pro Leu Leu Ala Thr Cys Ala Cys Tyr
    210                 215                 220

Ala Ala Met Leu Arg His Leu Gly Arg Val Ala Val Arg Pro Ala Pro
225                 230                 235                 240

Ala Asp Ser Ala Leu Gln Gly Gln Val Leu Ala Glu Arg Ala Gly Ala
                245                 250                 255

Val Arg Ala Lys Val Ser Arg Leu Val Ala Ala Val Leu Leu Phe
            260                 265                 270

Ala Ala Cys Trp Gly Pro Ile Gln Leu Phe Leu Val Leu Gln Ala Leu
        275                 280                 285

Gly Pro Ala Gly Ser Trp His Pro Arg Ser Tyr Ala Ala Tyr Ala Leu
    290                 295                 300

Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
                325                 330                 335

Val Cys Pro Cys Ala Pro Arg Arg Pro Arg Arg Pro Arg Arg Pro Gly
            340                 345                 350

Pro Ser Asp Pro Ala Ala Pro His Ala Glu Leu His Arg Leu Gly Ser
        355                 360                 365

His Pro Ala Pro Ala Arg Ala Gln Lys Pro Gly Ser Ser Gly Leu Ala
    370                 375                 380

Ala Arg Gly Leu Cys Val Leu Gly Glu Asp Asn Ala Pro Leu
385                 390                 395

<210> SEQ ID NO 10
<211> LENGTH: 1194
<212> TYPE: DNA
<213> ORGANISM: Homo sapiens

<400> SEQUENCE: 10
atgcacaccg tggctacgtc cggacccaac gcgtcctggg gggcaccggc caacgcctcc      60
ggctgcccgg ctgtggcgc caacgcctcg acggcccag tcccttcgcc gcgggccgtg      120
gacgcctggc tcgtgccgct cttcttcgcg gcgctgatgc tgctgggcct ggtggggaac      180
tcgctggtca tctacgtcat ctgccgccac aagccgatgc ggaccgtgac caacttctac      240
atcgccaacc tggcggccac ggacgtgacc ttcctcctgt gctgcgtccc cttcacggcc      300
```

-continued

```
ctgctgtacc cgctgcccgg ctgggtgctg ggcgacttca gtgcaagtt cgtcaactac      360
atccagcagg tctcggtgca ggccacgtgt gccactctga ccgccatgag tgtggaccgc      420
tggtacgtga cggtgttccc gttgcgcgcc ctgcaccgcc gcacgccccg cctggcgctg      480
gctgtcagcc tcagcatctg ggtaggctct gcggcggtgt ctgcgccggt gctcgccctg      540
caccgcctgt cacccgggcc gcgcgcctac tgcagtgagg ccttccccag ccgcgccctg      600
gagcgcgcct tcgcactgta caacctgctg cgctgtacc tgctgccgct gctcgccacc      660
tgcgcctgct atgcggccat gctgcgccac ctgggccggg tcgccgtgcg ccccgcgccc      720
gccgatagcg ccctgcaggg gcaggtgctg cagagcgcg caggcgccgt gcgggccaag      780
gtctcgcggc tggtggcggc cgtggtcctg ctcttcgccg cctgctgggg ccccatccag      840
ctgttcctgg tgctgcaggc gctgggcccc gcgggctcct ggcacccacg cagctacgcc      900
gcctacgcgc ttaagacctg gctcactgc atgtcctaca gcaactccgc gctgaacccg      960
ctgctctacg ccttcctggg ctcgcacttc gacaggcct tccgccgcgt ctgcccctgc     1020
gcgccgcgcc gccccgccg ccccgccgg cccggaccct cggaccccgc agccccacac     1080
gcggagctgc accgcctggg gtcccacccg gcccccgcca gggcgcagaa gccagggagc     1140
agtgggctgg ccgcgcgcgg gctgtgcgtc ctggggagg acaacgcccc tctc           1194
```

<210> SEQ ID NO 11
<211> LENGTH: 396
<212> TYPE: PRT
<213> ORGANISM: Rattus sp.

<400> SEQUENCE: 11

```
Met Ala Ala Glu Ala Thr Leu Gly Pro Asn Val Ser Trp Trp Ala Pro
1               5                   10                  15

Ser Asn Ala Ser Gly Cys Pro Gly Cys Gly Val Asn Ala Ser Asp Gly
                20                  25                  30

Pro Gly Ser Ala Pro Arg Pro Leu Asp Ala Trp Leu Val Pro Leu Phe
            35                  40                  45

Phe Ala Ala Leu Met Leu Leu Gly Leu Val Gly Asn Ser Leu Val Ile
        50                  55                  60

Phe Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Thr Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Thr Val Ser Leu Ser Ile Trp Val Gly Ser Ala Ala Val Ser Ala Pro
                165                 170                 175

Val Leu Ala Leu His Arg Leu Ser Pro Gly Pro His Thr Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Leu Ala Thr Cys Ala Cys Tyr
    210                 215                 220
```

-continued

```
Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
            245                 250                 255

Val Arg Thr Lys Val Ser Arg Leu Val Ala Ala Val Leu Leu Phe
        260                 265                 270

Ala Ala Cys Trp Gly Pro Ile Gln Leu Phe Leu Val Leu Gln Ala Leu
        275                 280                 285

Gly Pro Ser Gly Ala Trp His Pro Arg Ser Tyr Ala Ala Tyr Ala Leu
    290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Gly Pro Gln Arg Gln Arg Pro His Ala Ser Ala
            340                 345                 350

His Ser Asp Arg Ala Ala Pro His Ser Val Pro His Ser Arg Ala Ala
        355                 360                 365

His Pro Val Arg Val Arg Thr Pro Glu Pro Gly Asn Pro Val Val Arg
    370                 375                 380

Ser Pro Ser Val Gln Asp Glu His Thr Ala Pro Leu
385                 390                 395

<210> SEQ ID NO 12
<211> LENGTH: 1188
<212> TYPE: DNA
<213> ORGANISM: Rattus sp.

<400> SEQUENCE: 12
atggccgcag aggcgacgtt gggtccgaac gtgagctggt gggctccgtc caacgcttcg      60
ggatgcccgg gctgcggtgt caatgcctcg gatgcccag gctccgcgcc aaggcccctg     120
gatgcctggc tggtgcccct gttttttcgct gccctaatgt tgctggggct agtcgggaac     180
tcactggtca tcttcgttat ctgccgccac aagcacatgc agaccgtcac caatttctac     240
atcgctaacc tggcggccac agatgtcact ttccttctgt gctgcgtacc cttcaccgcg     300
ctcctctatc cgctgcccac ctgggtgctg ggagacttca tgtgcaaatt cgtcaactac     360
atccagcagg tctcggtgca agccacatgt gccactttga cagccatgag tgtggaccgc     420
tggtacgtga ctgtgttccc gctgcgtgca cttcaccgcc gcactccgcg cctggccctg     480
actgtcagcc ttagcatctg ggtgggttcc gcagctgttt ccgccccggt gctggctctg     540
caccgcctgt cgcccgggcc tcacacctac tgcagtgagg cgtttcccag ccgtgccctg     600
gagcgcgctt tcgcgctcta caacctgctg gccctatacc tgctgccgct gctcgccacc     660
tgcgcctgct acggtgccat gctgcgccac ctgggccgcg ccgctgtacg ccccgcaccc     720
actgatggcg ccctgcaggg gcagctgcta gcacagcgcg ctggagcagt gcgcaccaag     780
gtctcccggc tggtgccgc tgtcgtcctg ctcttcgccg cctgctgggg cccgatccag     840
ctgttcctgg tgcttcaagc cctgggcccc tcgggggcct ggcaccctcg aagctatgcc     900
gcctacgcgc tcaagatctg ggctcactgc atgtcctaca gcaattctgc gctcaacccg     960
ctgctctatg ccttcctggg ttcccacttc agacaggcct ctgccgcgt gtgccctgc    1020 ggcccgcaac gccagcgtcg gccccacgcg tcagcgcact cggaccgagc cgcaccccat    1080
agtgtgccgc acagccgggc tgcgcaccct gtccgggtca ggaccccga gcctgggaac    1140 cctgtggtgc gctcgcccct cgttcaggat gaacacactg ccccactc                1188
```

<210> SEQ ID NO 13
<211> LENGTH: 396
<212> TYPE: PRT
<213> ORGANISM: Mus musculus

<400> SEQUENCE: 13

```
Met Ala Thr Glu Ala Thr Leu Ala Pro Asn Val Thr Trp Trp Ala Pro
1               5                   10                  15

Ser Asn Ala Ser Gly Cys Pro Gly Cys Gly Val Asn Ala Ser Asp Asp
            20                  25                  30

Pro Gly Ser Ala Pro Arg Pro Leu Asp Ala Trp Leu Val Pro Leu Phe
        35                  40                  45

Phe Ala Thr Leu Met Leu Leu Gly Leu Val Gly Asn Ser Leu Val Ile
    50                  55                  60

Tyr Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Ala Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Ala Val Ser Ala Pro
                165                 170                 175

Val Leu Ala Leu His Arg Leu Ser Pro Gly Pro Arg Thr Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Leu Ala Thr Cys Ala Cys Tyr
    210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Val Leu Leu Phe
            260                 265                 270

Ala Ala Cys Trp Gly Pro Ile Gln Leu Phe Leu Val Leu Gln Ala Leu
        275                 280                 285

Gly Pro Ser Gly Ala Trp His Pro Arg Ser Tyr Ala Ala Tyr Ala Val
    290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Cys Arg Gln Arg Gln Arg Arg Pro His Thr Ser Ala
            340                 345                 350

His Ser Asp Arg Ala Ala Thr His Thr Val Pro His Ser Arg Ala Ala
        355                 360                 365

His Pro Val Arg Ile Arg Ser Pro Glu Pro Gly Asn Pro Val Val Arg
    370                 375                 380
```

Ser Pro Cys Ala Gln Ser Glu Arg Thr Ala Ser Leu
385                 390                 395

<210> SEQ ID NO 14
<211> LENGTH: 1188
<212> TYPE: DNA
<213> ORGANISM: Mus musculus

<400> SEQUENCE: 14

| | | | | | |
|---|---|---|---|---|---|
| atggccaccg | aggcgacatt | ggctcccaat | gtgacctggt | gggctccgtc | caacgcttca | 60 |
| ggatgcccag | gctgcggtgt | caacgcctcg | gatgacccag | gctctgcgcc | aaggcccctg | 120 |
| gatgcctggc | tggttcccct | gttttttcgct | acactcatgt | tgcttgggct | ggtcggaaac | 180 |
| tcattggtca | tctacgttat | ctgccgccac | aagcacatgc | agacagttac | caacttctac | 240 |
| atcgctaacc | tggctgccac | agacgtcact | ttcctactgt | gctgcgtgcc | cttcaccgca | 300 |
| ctcctctacc | cgctgcccgc | ctgggtgctg | ggagacttca | tgtgcaaatt | cgtcaactac | 360 |
| atccagcagg | tctcggtgca | agccacatgt | gccactctga | cggccatgag | tgtggaccgc | 420 |
| tggtatgtga | ctgtgttccc | gctgcgtgca | cttcaccgcc | gcactccgcg | cctggccctg | 480 |
| gctgtcagcc | tcagcatctg | ggtggggtca | gcagctgtgt | ccgccccggt | gctggccctg | 540 |
| caccgcctgt | cgccagggcc | tcgcacctac | tgcagcgagg | cgtttcccag | ccgcgccctg | 600 |
| gagcgcgcct | tcgcgctcta | caacctgctg | gctctatatc | tgctgccgct | gctcgccacc | 660 |
| tgcgcctgct | acggcgccat | gctgcgccac | ctgggccgtg | cggctgtacg | ccccgcaccc | 720 |
| actgacggcg | ccctgcaggg | acagctgcta | gcacagcgcg | ccggagcagt | gcgcaccaag | 780 |
| gtctcccggc | tggtggccgc | tgtcgtcctg | ctcttcgccg | cctgctgggg | cccgatccag | 840 |
| ctgttcctgg | tgcttcaagc | cctgggcccc | tcggggggcct | ggcaccctcg | aagctatgcc | 900 |
| gcctacgcgg | tcaagatctg | ggctcactgc | atgtcctaca | gcaactcggc | gctcaatccg | 960 |
| ctgctctatg | ccttcctggg | ttcacacttc | agacaggcct | tctgccgcgt | gtgccctgc | 1020 |
| tgccggcaac | gccagcgccg | gccccacacg | tcagcgcact | cggaccgagc | tgcaactcac | 1080 |
| actgtgccgc | acagccgtgc | tgcgcaccct | gtgcggatca | ggagcccgga | gcctgggaac | 1140 |
| cctgtggtgc | gctcgccctg | cgctcagagt | gaacgcactg | cctcactc | | 1188 |

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 15

Lys Asp Leu Pro Asn Tyr Asn Trp Asn Ser Phe Gly Leu Arg Phe
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 16

```
Tyr Asn Trp Asn Ser Phe Gly Leu Arg Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 17

Asn Trp Asn Ser Phe Gly Leu Arg Phe
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 18

Trp Asn Ser Phe Gly Leu Arg Phe
1               5

<210> SEQ ID NO 19
<211> LENGTH: 45
<212> TYPE: DNA
<213> ORGANISM: Homo sapiens

<400> SEQUENCE: 19
aaggacctgc cgaactacaa ctggaactcc ttcggcctgc gcttc                45

<210> SEQ ID NO 20
<211> LENGTH: 30
<212> TYPE: DNA
<213> ORGANISM: Homo sapiens

<400> SEQUENCE: 20
tacaactgga actccttcgg cctgcgcttc                                 30

<210> SEQ ID NO 21
<211> LENGTH: 27
<212> TYPE: DNA
<213> ORGANISM: Homo sapiens

<400> SEQUENCE: 21
aactggaact ccttcggcct gcgcttc                                    27

<210> SEQ ID NO 22
<211> LENGTH: 24
<212> TYPE: DNA
<213> ORGANISM: Homo sapiens

<400> SEQUENCE: 22
tggaactcct tcggcctgcg cttc                                       24

<210> SEQ ID NO 23
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 23

Asn Thr Phe Gly Leu Arg Trp
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Decanoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 24

Asn Thr Phe Gly Leu Arg Trp
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 25

Xaa Asn Thr Phe Gly Leu Arg Trp
1               5

<210> SEQ ID NO 26
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 26

Xaa Asn Thr Phe Gly Leu Arg Trp
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[Bis-(2-Pyridylmethyl)aminomethyl]benzoyl-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Me)
<220> FEATURE:
<223> OTHER INFORMATION: C-term amidated

<400> SEQUENCE: 27

Phe Gly Leu Arg Trp
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Ureidobenzoyl-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Me)
<220> FEATURE:
<223> OTHER INFORMATION: C-term amidated

<400> SEQUENCE: 28
```

```
Phe Gly Leu Arg Trp
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Hyp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 29

Pro Asn Thr Phe Gly Leu Arg Trp
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(p-Hyroxyphenyl)propionyl-Hyp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 30

Pro Asn Thr Phe Gly Leu Arg Trp
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
```

```
<222> LOCATION: (7)..(7)
<223> OTHER INFORMATION: Arg(Me)
<220> FEATURE:
<223> OTHER INFORMATION: C-term amidated

<400> SEQUENCE: 31

Glu Asn Thr Phe Gly Leu Arg Trp
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (6)..(6)
<223> OTHER INFORMATION: AzaGly
<220> FEATURE:
<221> NAME/KEY: MOD_RES
<222> LOCATION: (8)..(8)
<223> OTHER INFORMATION: Arg(Me)
<220> FEATURE:
<223> OTHER INFORMATION: C-term amidated

<400> SEQUENCE: 32

Tyr Pro Asn Thr Phe Gly Leu Arg Trp
1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-AzaGly
<220> FEATURE:
<221> NAME/KEY: MOD_RES
<222> LOCATION: (3)..(3)
<223> OTHER INFORMATION: Arg(Boc2,Me)
<220> FEATURE:
<221> NAME/KEY: MOD_RES
<222> LOCATION: (4)..(4)
<223> OTHER INFORMATION: Trp(Boc)-Rink Amide MBHA

<400> SEQUENCE: 33

Gly Leu Arg Trp
1

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trt-Phe
<220> FEATURE:
<221> NAME/KEY: MOD_RES
```

```
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Boc2,Me)
<220> FEATURE:
<221> NAME/KEY: MOD_RES
<222> LOCATION: (5)..(5)
<223> OTHER INFORMATION: Trp(Boc)-Rink Amide MBHA

<400> SEQUENCE: 34

Phe Gly Leu Arg Trp
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Boc2,Me)
<220> FEATURE:
<221> NAME/KEY: MOD_RES
<222> LOCATION: (5)..(5)
<223> OTHER INFORMATION: Trp(Boc)-Rink Amide MBHA

<400> SEQUENCE: 35

Phe Gly Leu Arg Trp
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn(Trt)
<220> FEATURE:
<221> NAME/KEY: MOD_RES
<222> LOCATION: (2)..(2)
<223> OTHER INFORMATION: Thr(But)
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Boc2,Me)
<220> FEATURE:
<221> NAME/KEY: MOD_RES
<222> LOCATION: (7)..(7)
<223> OTHER INFORMATION: Trp(Boc)-Rink Amide MBHA

<400> SEQUENCE: 36

Asn Thr Phe Gly Leu Arg Trp
1               5
```

```
<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Asn(Trt)
<220> FEATURE:
<221> NAME/KEY: MOD_RES
<222> LOCATION: (2)..(2)
<223> OTHER INFORMATION: Thr(But)
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Boc2,Me)
<220> FEATURE:
<221> NAME/KEY: MOD_RES
<222> LOCATION: (7)..(7)
<223> OTHER INFORMATION: Trp(Boc)-Rink Amide MBHA

<400> SEQUENCE: 37

Asn Thr Phe Gly Leu Arg Trp
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Acp
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Thr(But)
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Boc2,Me)
<220> FEATURE:
<221> NAME/KEY: MOD_RES
<222> LOCATION: (8)..(8)
<223> OTHER INFORMATION: Trp(Boc)-Rink Amide MBHA

<400> SEQUENCE: 38

Xaa Asn Thr Phe Gly Leu Arg Trp
1               5

<210> SEQ ID NO 39
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Thr(But)
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Boc2,Me)
<220> FEATURE:
<221> NAME/KEY: MOD_RES
<222> LOCATION: (8)..(8)
<223> OTHER INFORMATION: Trp(Boc)-Rink Amide MBHA

<400> SEQUENCE: 39

Xaa Asn Thr Phe Gly Leu Arg Trp
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Ambz(4)-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Boc2,Me)
<220> FEATURE:
<221> NAME/KEY: MOD_RES
<222> LOCATION: (5)..(5)
<223> OTHER INFORMATION: Trp(Boc)-Rink Amide MBHA

<400> SEQUENCE: 40

Phe Gly Leu Arg Trp
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[Bis-(2-Pyridylmethyl)aminomethyl]benzoyl-Phe
<220> FEATURE:
<221> NAME/KEY: MOD_RES
<222> LOCATION: (2)..(2)
<223> OTHER INFORMATION: AzaGly
```

```
<220> FEATURE:
<221> NAME/KEY: MOD_RES
<222> LOCATION: (4)..(4)
<223> OTHER INFORMATION: Arg(Boc2,Me)
<220> FEATURE:
<221> NAME/KEY: MOD_RES
<222> LOCATION: (5)..(5)
<223> OTHER INFORMATION: Trp(Boc)-Rink Amide MBHA

<400> SEQUENCE: 41

Phe Gly Leu Arg Trp
1               5
```